US009255289B2

(12) United States Patent
Greene

(10) Patent No.: US 9,255,289 B2
(45) Date of Patent: Feb. 9, 2016

(54) GEOMETRIC PATTERNS AND LIPID BILAYERS FOR DNA MOLECULE ORGANIZATION AND USES THEREOF

(75) Inventor: Eric C. Greene, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 893 days.

(21) Appl. No.: 12/911,528

(22) Filed: Oct. 25, 2010

(65) Prior Publication Data
US 2011/0136676 A1 Jun. 9, 2011

Related U.S. Application Data

(63) Continuation-in-part of application No. PCT/US2009/041434, filed on Apr. 22, 2009.

(60) Provisional application No. 61/047,657, filed on Apr. 24, 2008, provisional application No. 61/116,815, filed on Nov. 21, 2008.

(51) Int. Cl.
| C40B 40/06 | (2006.01) |
| C40B 99/00 | (2006.01) |
| C40B 20/02 | (2006.01) |
| C40B 30/00 | (2006.01) |
| C40B 30/04 | (2006.01) |
| C12Q 1/68 | (2006.01) |
| B01J 19/00 | (2006.01) |
| B01L 3/00 | (2006.01) |

(52) U.S. Cl.
CPC ........... *C12Q 1/6837* (2013.01); *B01J 19/0046* (2013.01); *B01L 3/502761* (2013.01); *C12Q 1/6874* (2013.01); *B01J 2219/00317* (2013.01); *B01J 2219/00513* (2013.01); *B01J 2219/00529* (2013.01); *B01J 2219/00596* (2013.01); *B01J 2219/00608* (2013.01); *B01J 2219/00621* (2013.01); *B01J 2219/00637* (2013.01); *B01J 2219/00702* (2013.01); *B01J 2219/00722* (2013.01); *B01J 2219/00734* (2013.01); *B01L 2200/0663* (2013.01); *B01L 2400/0421* (2013.01); *B01L 2400/0487* (2013.01)

(58) Field of Classification Search
None
See application file for complete search history.

(56) References Cited

U.S. PATENT DOCUMENTS

| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 5,851,769 | A | 12/1998 | Gray et al. |
| 6,228,326 | B1 | 5/2001 | Boxer et al. |
| 6,593,090 | B2 * | 7/2003 | Connolly ............ 435/6.16 |
| 2003/0138973 | A1 * | 7/2003 | Wagner et al. ............ 436/518 |
| 2006/0057585 | A1 | 3/2006 | McAllister |
| 2008/0274905 | A1 | 11/2008 | Greene |

FOREIGN PATENT DOCUMENTS

| JP | 2006-078491 | 3/2006 |
| WO | WO-2006/088425 | 8/2006 |
| WO | WO-2007/041340 | 4/2007 |

OTHER PUBLICATIONS

Graneli, A., Yeykal, C. C., Prasad, T. K., and Greene, E. C. "Organized arrays of individual DNA molecules tethered to supported lipid bilayers,". Langmuir 22, pp. 292-299 (2006).
International Search Report and Written Opinion mailed on Oct. 6, 2009 for International Patent Applicatio No. PCT/US09/041434 filed on Apr. 22, 2009.
Japanese Office Action issued for JP 2011-506430, dated Nov. 30, 2012, 6 pages.
Aalfs, J.D. and R.E. Kingston, 2000. What does "Chromatin Remodeling" mean? TIBS. 25: p. 548-555.
Acharya, S., P.L. Foster, P. Brooks, and R. Fishel, 2003. The coordinated functions of the *E. coli* MutS and MutL proteins in mismatch repair. Mol Cell. 12: p. 233-246.
Adzuma, K., 1998. No sliding during homology search by RecA protein. The Journal of Biological Chemistry. 273(47): p. 31565-31573.
Aihara, H., Ito, Y., Kurumizaka, H., Yokoyama, S. & Shibata, T. (1999). The N-terminal domain of the human Rad51 protein binds DNA: structure and a DNA binding surface as revealed by NMR. Journal of Molecular Biology 290, 495-505.
Akerman, B. and Tuite, E. (1996) Single- and double-strand photocleavage of DNA by YO, YOYO and TOTO. Nucleic Acids Res, 24, 1080-1090.
Alani, E., 1996. The *Saccharomyces cerevisiae* Msh2 and Msh6 proteins form a complex that specifically binds to duplex oligonucleotides containing mismatched DNA base pairs. Molecular and Cellular Biology. 16(10): p. 5604-5615.
Albertorio, F., Diaz, A.J., Yang, T., Chapa, V.A., Kataoka, S., Castellana, E.T. and Cremer, P.S. (2005) Fluid and air-stable lipopolymer membranes for biosensor applications. Langmuir, 21, 7476-7482.
Alexeev, A. A., Mazin, A. V., and Kowalczykowski, S. C. (2003). Rad54 protein possesses chromatin-remodeling activity stimulated by the Rad51-ssDNA nucleoprotein filament. Nature Structural and Molecular Biology 10, 182-186.
Alexiadis, V., and Kadonaga, J. T. (2002). Strand pairing by Rad54 and Rad51 is enhanced by chromatin. Genes & Development 16, 2767-2771.
Allen, D.J., A. Makhov, M. Grilley, J. Taylor, R. Thresher, P. Modrich, and J. Griffith, 1997. MutS mediates heteroduplex loop formation by a translocation mechanism. The EMBO Journal. 16(14): p. 4467-4476.
Allewell, N. and V. Bloomfield, 1992. Teaching molecular biophysics at the graduate level. Biophysical Journal. 63: p. 1446-1449.
Amitani, I., Baskin, R. J., and Kowalczykowski, S. C. (2006). Visualization of Rad54, a chromatin remodeling protein, translocating on single DNA molecules. Molecular Cell 23, 143-148.

(Continued)

*Primary Examiner* — Catherine S Hibbert
*Assistant Examiner* — Channing S Mahatan
(74) *Attorney, Agent, or Firm* — Leason Ellis LLP

(57) ABSTRACT

The invention is related to nucleic acid arrays and methods of using nucleic acid arrays.

29 Claims, 106 Drawing Sheets
(87 of 106 Drawing Sheet(s) Filed in Color)

(56) References Cited

OTHER PUBLICATIONS

Assi, F., Jenks, R., Yang, J., Love, C., & Prentiss, M. (2002) *Journal of Applied Physics* 92, 5584-5586.
Axelrod, D. (1989) Total internal reflection fluorescence microscopy. Methods Cell Biol, 30, 245-270.
Banin, U., Bruchez, M., Alivisatos, A.P., Ha, T., Weiss, S. and Chemla, D.S. (1999) Evidence for a thermal contribution to emission intermittency in single CdSe/CdS core/shell nanocrystals. Journal of Chemical Physics, 110, 1195-1201.
Baumann, P. & West, S. C. (1998). Role of the human Rad51 protein in homologous recombination and double-stranded-break repair. Trends in Biochemical Sciences 23, 247-251.
Baumann, P., Benson, F. E. & West, S. C. (1996). Human Rad51 protein promotes ATP-dependent homologous pairing and strand transfer reactions in vitro. Cell 87, 757-766.
Baumann, P., Benson, F. E., Hajibagheri, N. & West, S. C. (1997) "Purification of human Rad51 protein by selective spermidine precipitation," Mutat. Res. 384, 65-72.
Bennink, M. L., Scharer, O. D., Kanaar, R., Sakata-Sogawa, K., Schins, J. M., Kanger, J. S., de Grooth, B. G. & Greve, J. (1999). Single-molecule manipulation of double-stranded DNA using optical tweezers: interaction studies of DNA with RecA and YOYO1. Cytometry 36, 200-208.
Bensimon, A., Simon, A., Chiffaudel, A., Croquette, V., Heslot, F. and Bensimon, D. (1994) Alignment and sensitive detection of DNA by a moving interface. Science, 265, 2096-2098.
Bensimon, D.; Simon, A. J.; Croquette, V.; Bensimon, A. (1995), "Stretching DNA with a Receding Meniscus: Experiments and Models," Physical Review Letters, 74, 4754-4757.
Benson, F. E., Stasiak, A. & West, S. C. (1994). Purification and characterization of the human Rad51 protein, an analogue of *E. coli* RecA. The EMBO Journal 13, 5764-5771.
Benson, F.E., P. Baumann, and S.C. West, 1998. Synergistic actions of Rad51 and Rad52 in recombination and DNA repair. Nature. 391: p. 401-404.
Berg, H. C. (1993) Random walks in biology (Princeton University Press, Princeton).
Berg, O.G., R.B. Winter, and P.H. von Hippel, 1981. Diffusion-driven mechanisms of protein translocation on nucleic acids. 1. Models and Theory. Biochemistry. 20: p. 6929-6948.
Bi, B., N. Rybalchenko, E.I. Golub, and C.M. Radding, 2004. Human and yeast Rad52 proteins promote DNA strand exchange. Proc Natl Acad Sci U S A. 101: p. 9568-9572.
Bianco, P. R., Tracy, R. B. & Kowalczykowski, S. C. (1998). DNA strand exchange proteins: a biochemical and physical comparison. Frontiers in Bioscience 3, d530-603.
Bianco, P.R., Brewer, L.R., Corzett, M., Balhorn, R., Yeh, Y., Kowalczyowski, S.C. and Baskin, R.J. (2001) Processive translocation and DNA unwinding by individual RecBCD enzyme molecules. Nature, 409, 374-378.
Black et al., "Structural determinants for generating centromeric Chromatin," Nature, vol. 430, pp. 578-582 (Jul. 2004).
Blackwell, L.J., D. Martik, K.P. Bjornson, E.S. Bjornson, and P. Modrich, 1998. Nucleotide promoted release of hMuts-alpha from heteroduplex DNA is consistent with an ATP-dependent translocation mechanism. The Journal of Biological Chemistry. 273(48): p. 32055-32062.
Bouchiat, C.; Wang, M. D.; Allemand, J.-F.; Strick, T.; Block, S. M.; Croquette, V.(1999) "Estimating the persistence length of a worm-like chain molecule from force-extension measurements," Biophysical Journal, 76, 409-413.
Bowers, J., P.T. Tran, A. Joshi, R.M. Liskay, and E. Alani, 2001. MSH-MLH complexes formed at a DNA mismatch are disrupted by the PCNA sliding clamp. Journal of Molecular Biology. 306: p. 957-968.
Bowers, J., T. Sokolsky, T. Quach, and E. Alani, 1999. A mutation in the MSH6 subunit of the *Saccharomyces cerevisiae* MSH2-MSH6 complex disrupts mismatch recognition. The Journal of Biological Chemistry. 274: p. 16115-16125.

Boxer, S. G. (2000) "Molecular transport and organization in supported lipid membranes," *Curr Opin Chem Biol* 4, 704-709.
Brewer, L.R., Corzett, M. and Balhorn, R. (1999) Protamine-induced condensation and decondensation of the same DNA molecule. Science, 286, 120-123.
Bruno, M., A. Flaus, C. Stockdale, C. Rencurel, H. Ferreira, and T. Owen-Hughes, 2003. Histone H2A/H2B dimer exchange by ATP-dependent chromatin remodeling activities. Molecular Cell. 12: p. 1599-1606.
Buchhop, S., M. Gibson, X. Wang, P. Wagner, H. Strzbecher, and C. Harris, Oct. 1, 1997. Interaction of p53 with the human Rad51 protein. Nucleic Acids Res. 25(19): p. 3868-74.
Bugreev, D. V. & Mazin, A. V. (2004). Ca2+ activates human homologous recombination protein Rad51 by modulating its ATPase activity. Proceedings of the National Academy of Sciences (USA) 101, 9988-9993.
Bugreev, D. V., Mazina, O. M., and Mazin, A. V. (2006). Rad54 protein promotes branch migration of Holliday junctions. Nature 442.
Bustamante, C., Bryant, Z. and Smith, S. (Jan. 23, 2003) Ten years of tension: single-molecule DNA mechanics. Nature, 421, 423-427.
Bustamante, C., S.B. Smith, J. Liphardt, and D. Smith, 2000. Single-molecule studies of DNA mechanics. Current Opinion in Structural Biology. 10: p. 279-285.
Bustamante, C.; Marko, J. F.; Siggia, E. D.; Smith, S. (1994) "Entropic elasticity of λ-phage DNA," Science, 265, 1599-1600.
Cazaux, C., Blanchet, J.-S., Dupuis, D., Villani, G., Defias, M. & Johnson, N. P. (1998). Investigation of the secondary DNA-binding site of the bacterial recombinase RecA. The Journal of Biological Chemistry 273, 28799-28804.
Chan, W.C.W. and Nie, S. (1998) Quantum dot bioconjugates for ultrasensitive nonisotopic detection. Science, 281, 2016-2018.
Cheezum, M.K., Walker, W.F. and Guilford, W.H. (2001) Quantitative comparison of algorithms for tracking single fluorescent particles. Biophysical Journal, 81, 2378-2388.
Chi, P., Kwon, Y., Seong, C., Epshtein, A., Lam, I., Sung, P., and Klein, H. L. (2006). Yeast recombination factor Rdh54 functionally interacts with the Rad51 recombinase and catalyzes Rad51 removal from DNA. The Journal of Biological Chemistry 281, 26268-26279.
Chi, P., Van Komen, S., Sehorn, M. G., Sigurdsson, S. & Sung, P. (2006). Roles of ATP binding and ATP hydrolysis in human Rad51 recombinase function. DNA Repair 5, 381-391.
Chou, S. Y., Krauss, P. R., & Renstrom, P. J. (1996) "Imprint Lithography with 25-nanometer resolution," *cience* 272, 85-87.
Cirillo, L.A. and K.S. Zaret, 2004. Preparation of defined mononucleosomes, dinucleosomes, and nucleosome arrays in vitro and analysis of transcription factor binding. Methods in Enzymology. 375: p. 131-158.
Cisse, I., Okumus, B., Joo, C., & Ha, T. (2007) "Fueling protein-DNA interactions inside porous nanocontainers," Proc Natl Acad Sci U S A 104, 12646-12650.
Clever, B., Interthal, H., Schmuckli-Maurer, J., King, J., Sigrist, M., and Heyer, W.-D. (1997). Recombinational repair in yeast: functional interactions between Rad51 and Rad54 proteins. The EMBO Journal 16, 2535-2544.
Conway, A. B., Lynch, T. W., Zhang, Y., Fortin, G. S., Fung, C. W., Symington, L. S. & Rice, P. (2004). Crystal Structure of a Rad51 filament. Nature Structural and Molecular Biology 11, 791-796.
International Search Report and Written Opinion issued for corresponding International Patent Application No. PCT/US2006/038131, mailed on Dec. 4, 2007. 12 pages.
Cox, M.M., 2001. Historical overview: searching for replication help in all the rec places. Proc Natl Acad Sci U S A. 98: p. 8173-8180.
Cox, M.M., 2003. The bacterial RecA protein as a motor protein. Annual Review of Microbiology. 57: p. 551-577.
Cremer, P. S. & Boxer, S. G. (1999), "Formation and spreading of lipid bilayers on planar glass supports," J. Phys. Chem. B 103, 2554-2559.
Cremer, P.S., et al., 1999. Writing and Erasing Barriers to Lateral Mobility onto Fluid Phospholipid Bilayers. Langmuir. 15: p. 3893-3896.

(56) References Cited

OTHER PUBLICATIONS

Crisona, N., et al., Nov. 15, 2000. Preferential relaxation of positively supercoiled DNA by *E. coli* topoisomerase IV in single-molecule and ensemble measurements. Genes Dev. 14(22): p. 2881-92.

Cromie, G. A., Connelly, J. C. & Leach, D. R. F. (2001). Recombination at double-strand breaks and DNA ends: conserved mechanisms from phage to humans. Molecular Cell 8, 1163-1174.

Crut, A., Géron-Landre, B., Bonnet, I., Bonneau, S., Desbiolles, P. and Escudé, C. (2005) Detection of single DNA molecules by multicolor quantum-dot end-labeling. Nucleic Acids Research, 33, e98.

Crut, A.; Lasne, D.; Allemand, J.-F.; Dahan, M.; Desbiolles, P., "Transverse fluctuations of single DNA molecules attached at both extremities to a surface," Physical Review E 2003, 67, 051910 1-6.

Davies, A., Masson, J., McIlwraith, M., Stasiak, A., Stasiak, A., Venkitaraman, A. & West, S. (Feb. 2001). Role of BRCA2 in control of the RAD51 recombination and DNA repair protein. Molecular Cell 7, 273-82.

Dimalanta, E. T., Lim, A., Runnheim, R., Lamers, C., Churas, C., Forrest, D. K., de Pablo, J. J., Graham, M. D., Coppersmith, S. N., Goldstein, S., et al. (2004) *Analytical Chemistry* 76, 5293-5301.

Dorigo, B., T. Schalch, K. Bystricky, and T.J. Richmond, 2003. Chromatin fiber folding: requirement for the histone H4 N-terminal tail. The Journal of Molecular Biology. 327: p. 85-96.

Doyle, P. S., Ladoux, B. & Viovy, J.-L. (2000). Dynamics of a tethered polymer in shear flow. Physical Review Letters 84, 4769-4772.

Dresser, M., Ewing, D., Conrad, M., Dominguez, A., Barstead, R., Jiang, H., and Kodadek, T. (1997). DMC1 functions in a *Saccharomyces cerevisiae* meiotic pathway that is largely independent of the RAD51 pathway. Genetics 147, 533-544.

Egelman, E. H. (2000), "A ubiquitous structural core," Trends in Biochemical Sciences 25, 183-184.

Egelman, E. H. (2001). Does a stretch DNA structure dictate the helical geometry of RecA-like filaments. Journal of Molecular Biology 309, 539-542.

Eggler, A., R. Inman, and M. Cox, Oct. 18, 2002. The Rad51-dependent pairing of long DNA substrates is stabilized by replication protein A. J Biol Chem. 277(42): p. 39280-8.

Empedocles, S.A., R. Neuhauser, K. Shimizu, and M.G. Bawendi, 1999. Photoluminescence from single semiconductor nanostructures. Advanced materials. 11(15): p. 1243-1256.

Essers, J., A.B. Houtsmuller, L. van Veelen, C. Paulusma, A.L. Nigg, A. Pastink, W. Vermeulen, J.H.J. Hoeijmakers, and R. Kanaar, 2002. Nuclear dynamics of Rad52 group homologous recombination proteins in response to DNA damage. The EMBO Journal. 21(8): p. 2030-2037.

Fernandez, J. M.; Li, H., (2004), "Force-clamp spectroscopy monitors the folding trajectory of a single protein," Science, 303, (5664), 1674-8.

Flaus, A., Martin, D. M. A., Barton, G. J., and Owen-Hughes, T. (2006). Identification of multiple distinct Snf2 subfamilies with conserved structural motifs. Nucleic Acids Research 34, 2887-2905.

Flores-Rozas, H., D. Clarck, and R.D. Kolodner, 2000. Proliferating cell nuclear antigen and Msh2p-Msh6p interact to form an active mispair recognition complex. Nature Genetics. 26: p. 375-378.

Folta-Stogniew, E., S. O'Malley, R.C. Gupta, K.S. Anderson, and C.M. Radding, 2004. Exchange of DNA base pairs that coincides with recognition of homology promoted by *E. coli* RecA protein. Molecular Cell. 15: p. 965-975.

Forkey, J.N., M.E. Quinlan, and Y.E. Goldman, 2000. Protein structural dynamics by single-molecule fluorescence polarization. Progress in Biophysics & Molecular Biology. 74: p. 1-35.

Fyodorov, D.V. and J.T. Kadonaga, 2003. Chromatin assembly in vitro with purified recombinant ACF and NAP-1. Methods in Enzymology. 371: p. 499-515.

Galkin, V.E., F. Esashi, X. Yu, S. Yang, S.C. West, and E.H. Egelman, 2005. BRCA2 BRC motifs bind Rad51-DNA filaments. Proc Natl Acad Sci U S A. 102(24): p. 8537-8542.

Glasmästar, K.; Larsson, C.; Höök, F.; Kasemo, B., (2002), "Protein adsorption on supported phospholipid bilayers," Journal of Colloid and Interface Science, (246), 40-47.

Gonda, D.K. and C.M. Radding, 1983. By searching processively RecA protein pairs DNA molecules that share a limited stretch of homology. Cell. 34: p. 647-654.

Gonzalez, C., 2001. Undergraduate research, graduate mentoring, and the University's mission. Science. 293: p. 1624-1626.

Gorbalenya, A. E., Koonin, E. V., Donchenko, A. P., and Blinov, V. M. (1988). A novel superfamily of nucleotide triphosphate-binding motif containing proteins which are probably involved in duplex unwinding in DNA and RNA replication and recombination. FEBS Letters 235, 16-24.

Gorman et al., "Dynamic basis for one-Dimensional DNA Scanning by the Mismatch Repair Complex Msh2-Msh6," Molecular Cell, vol. 28, pp. 359-370 (2007).

Gradia, S., D. Subramanian, T. Wilson, S. Acharya, A. Makhov, J. Griffith, and R. Fishel, 1999. hMSH2-hMSH6 forms a hydrolysis-independent sliding clamp on mismatched DNA. Molecular Cell. 3: p. 255-261.

Gradia, S., S. Acharya, and R. Fishel, 1997. The human mismatch recognition complex hMSH2-hMSH6 functions as a novel molecular switch. Cell. 91: p. 995-1005.

Gradia, S., S. Acharya, and R. Fishel, 2000. The role of mismatched nucleotides in activating the hMSH2-hMSH6 molecular switch. The Journal of Biological Chemistry. 275(6): p. 3922-3930.

Graneli, A., Yeykal, C. C., Robertson, R. B., and Greene, E. C. (2006b). Long-distance lateral diffusion of human Rad51 on double-stranded DNA. Proceedings of the National Academy of Sciences (USA) 103, 1221-1226.

Greene, E.C. and K. Mizuuchi, 2002. Direct observation of single MuB polymers: evidence for a DNA-dependent conformational change for generating an active target complex. Molecular Cell. 9: p. 1079-1089.

Greene, E.C. and K. Mizuuchi, 2002. Dynamics of a protein polymer: the assembly and disassembly pathways of the MuB transposition target complex. The EMBO Journal. 21: p. 1477-1486.

Greene, E.C. and K. Mizuuchi, 2002. Target immunity during Mu DNA transposition: transpososome assembly and DNA looping enhance efficient MuA-mediated disassembly of the MuB target complex. Molecular Cell. 10(6): p. 1367-1378.

Greene, E.C. and K. Mizuuchi, 2004. Visualizing the assembly and disassembly mechanisms of the MuB transposition targeting complex. The Journal of Biological Chemistry. 279: p. 16736-16743.

Greene, E.C. et al., "Direct Observation of Single MuB Polymers: Evidence for a DNA-Dependent Conformational Change for Generating an Active Target Complex," Molecular Cell, vol. 9, pp. 1079-1089, May 2002.

Gribnau et al., "Intergenic Transcription and Developmental Remodeling of Chromatin Subdomains in the Human b-globin Locus," Molecular Cell, vol. 5, pp. 377-386 (Feb. 2000).

Groves et al., "Electric Field-induced reorganization of two-component supported bilayer membranes," Proc. Natl. Acad. Sci USA, vol. 94, pp. 13390-13395 (Dec. 1997).

Groves et al., "Micropatterning Fluid Lipid Bilayers on Solid Supports," Science, vol. 275, pp. 651-653 (1997).

Groves, J. & Boxer, S. (Mar. 2002). Micropattern formation in supported lipid membranes. Acc Chem Res 35, 149-57.

Groves, J.T., et al., 1998. Substrate-membrane interactions: mechanisms for imposing patterns on a fluid bilayer membrane. Langmuir. 14: p. 3347-3350.

Guan, J. & Lee, L. J. Generating Highly ordered DNA nanostrand arrays, Proceedings of the National Academy of Sciences, USA 102, 18321-18325 (2005).

Gueroui, Z.; Place, C.; Freyssingeas, E.; Berge, B., "Observation by fluorescence microscopy of transcription on single combed DNA," Proc Natl Acad Sci U S A, 99, pp. 6005-6010 (2002).

Gupta, R. C., Bazemore, L. R., Golub, E. I. & Radding, C. M., "Activities of human recombination protein Rad51," Proceedings of the National Academy of Sciences (USA) 94, 463-468 (1997).

Gupta, R.C., E. Folta-Stogniew, S. O'Malley, M. Takahashi, and C.M. Radding, 1999. Rapid exchange of A:T base pairs is essential

(56) References Cited

OTHER PUBLICATIONS for recognition of DNA homology by human Rad51 recombination protein. Molecular Cell. 4: p. 705-714.

Gurrieri, S., Wells, K.S., Johnson, I.D. and Bustamante, C., "Direct visualization of individual DNA molecules by fluorescence microscopy: characterization of the factors affecting signal/background and optimization of imaging conditions using YOYO," Analytical Biochemistry, 249, pp. 44-53, (1997).

Guthhold, M., X. Zhu, C. Rivetti, G. Yang, N.H. Thomson, S. Kasas, H.G. Hansma, B. Smith, P.K. Hansma, and C. Bustamante, 1999. Direct observation of one-dimensional diffusion and transcription by *Escherichia coli* RNA polymerase. Biophys J. 77: p. 2284-2294.

Ha, "Single-molecule fluorescence methods for the study of nucleic acids," Current Opinion in Structural Biology, vol. 11, pp. 287-292 (2001).

Ha, T., "Structural Dynamics and processing of Nucleic Acid Revealed by Single-Molecule Spetroscopy," Biochemistry, 43, (14), 4055-63 (2004).

Ha, T., 2001. Single-molecule fluorescence resonance energy transfer. Methods. 25: p. 78-86.

Ha, T., Rasnik, I., Cheng, W., Babcock, H. P., Gauss, G. H., Lohman, T. M., & Chu, S. "Initiation and re-initiation of DNA unwinding by *Escherichia coli* Rep helicase," Nature 419, pp. 638-641 (2002).

Halford, S. and J. Marko, 2004. How do site-specific DNA-binding proteins find their targets? Nucleic Acids Res. 32(10): p. 3040-52.

Harada, Y., Funatsu, T., Murakami, K., Nonoyama, Y., Ishihama, A. & Yanagida, T. "Single-Molecule Imaging of RNA Polymeras_DNA Interactions in Real Time," Biophysical Journal 76, 709-715 (1999).

Hegner, M., Smith, S. B. & Bustamante, C. (1999). Polymerization and mechanical properties of single RecA-DNA filaments. Proceedings of the National Academy of Sciences (USA) 96, 10109-10114.

Henricksen, L.A., C.B. Umbricht, and M.S. Wold, 1994. Recombinant replication protein A: expression, complex formation, and functional characterization. The Journal of Biological Chemistry. 269(15): p. 11121-11132.

Heyer, W., Li, X., Rolfsmeier, M., and Zhang, X. "Rad54: the Swiss Army knife of homologous recombination?," Nucleic Acids Research, vol. 34, pp. 4115-4125 (Aug. 25, 2006).

Heyes, C. D., Groll, J., Möller, M., & Neienhaus, G. U. "Synthesis, patterning and applications of star-shaped poly(Ethylene glycol) biofunctionalized surfaces," Molecular Biosystems 3, 419-430 (2007).

Hohng, S. and Ha, T. (2004) Near-complete suppression of quantum dot blinking in ambient conditions. Journal of the American Chemical Society, 126, 1324-1325.

Howard-Flanders, P., West, S. C., Rusche, J. R. & Egelman, E. H. (1984). Molecular mechanisms of genetic recombination: the DNA-binding sites of RecA protein. Cold Spring Harbor Symp. Quant. Biol. 49, 571-580.

Hsieh, P., 2001. Molecular mechanisms of DNA mismatch repair. Mutation Research. 486: p. 71-87.

Jaskelioff, M., Van Komen, S., Krebs, J. E., Sung, P., and Peterson, C. L. (2003). Rad54p is a chromatin remodeling enzyme required for heteroduplex DNA joint formation with chromatin. The Journal of Biological Chemistry 278, 9212-9218.

Jeruzalmi, D., M. O'Donnell, and J. Kuriyan, 2002. Clamp loaders and sliding clamps. Current Opinion in Structural Biology. 12: p. 217-224.

Jiang, H., Xie, Y., Houston, P., Stemke-Hale, K., Mortensen, U. H., Rothstein, R., and Kodadek, T. (1996). Direct association between yeast Rad51 and Rad54 recombination proteins. The Journal of Biological Chemistry 271, 33181-33186.

Junop, M.S., G. Obmolova, K. Rausch, P. Hsieh, and W. Yang, 2001. Composite active site of an ABC ATPase: MutS uses ATP to verify mismatch recognition and authorize DNA repair. Mol Cell. 7: p. 1-12.

Kabata, H., Kurosawa, O., Arai, I., Washizu, M., Margarson, S. A., Glass, R. E., & Shimamoto, N. "Visualization of single molecules of RNA polymerase sliding along DNA," Science 262, 1561-1563 (1993).

Kabata, H., Okada, W., & Washizu, M. "Single-Molecule dynamics of the Eco RI Enzyme using stretched DNA: its application to In Situ sliding assay and optical DNA mapping," Jpn. J. Appl. Phys. 39, 7164-7171 (2000).

Kam, L.; Boxer, S. G., "Cell adhesion to protein-micropatterned-supported lipid bilayer membranes," J Biomed Mater Res 2001, 55, (4), 487-95.

Kanaar, R., Hoeijmakers, J. H. J. & van Gent, D. C. (1998). Molecular mechanisms of DNA double-strand break repair. Trends in Cell Biology 8, 483-489.

Kato, M., K. Yano, F. Matsuo, H. Saito, T. Katagiri, H. Kurumizaka, M. Yoshimoto, F. Kasumi, F. Akiyama, G. Sakamoto, H. Nagawa, Y. Nakamura, and Y. Miki, 2000. Identification of Rad51 alteration in patients with bilateral breast cancer. Journal of Human Genetics. 45: p. 133-137.

Keller, C.; Glasmästar, K.; Zhdanov, V.; Kasemo, B., "Formation of supported membranes from Vesicles," Phys Rev Lett; 5, 84, (23), pp. 5443-5446 (Jun. 2000).

Kelman, Z. and J. Hurwitz, 1998. Protein-PCNA interactions: a DNA-scanning mechanism? Trends in Biochemical Sciences. 23: p. 236-238.

Kelman, Z. and M. O'Donnell, 1995. Structural and functional similarities of prokaryotic and eukaryotic DNA polymerase sliding clamps. Nucleic Acids Research. 23(18): p. 3613-3620.

Kelman, Z., 1997. PCNA: structure, functions and interactions. Oncogene. 14: p. 629-640.

Khanna, K.K. and S.P. Jackson, 2001. DNA double-strand breaks: signaling, repair and the cancer connection. Nature Gentics. 27: p. 247-254.

Kiianitsa, K., Solinger, J. A., and Heyer, W.-D. (2006). Terminal association of Rad54 protein with the Rad51-dsDNA filament. Proceedings of the National Academy of Sciences (USA) 103, 9767-9772.

Kijas, A.W., B. Studamire, and E. Alani, 2003. msh2 separation of function mutations confer defects in the initiation steps of mismatch repair. Journal of Molecular Biology. 331: p. 123-138.

Kim, S., Blainey, P. C., Schroeder, C. M., & Xie, S. X. "Multiplexed single-molecule assay for enzymatic activity on flow-stretched DNA," Nature methods 4, 397-399 (2007).

Kinebuchi, T., Kagawa, W., Enomoto, R., Tanaka, K., Miyagawa, K., Shibata, T., Kurumizaka, H. & Yokoyama, S. (2004). Structural basis for octomeric ring formation and DNA interaction of the human homologous-pairing protein Dmc1. Molecular Cell 14, 363-374.

King, M.-C., Marks, J. H. & Mandell, J. B. (2003). Breast and Ovarian cancer risks due to inherited mutations in BRCA1 and BRCA2. Science 302, 643-646.

Klein H. L. (1997). RDH54, a RAD54 homologue in *Saccharomyces cerevisiae*, is required for mitotic diploid-specific recombination and repair for meiosis. Genetics 147, 1533-1543.

Kolodner, R.D. and G.T. Marsischky, 1999. Eukaryotic DNA mismatch repair. Current Opinion in Genetics and Development. 9: p. 89-96.

Kowalczykowski, S., 2000. Some assembly required. Nature Stuctural Biology. 7(12): p. 1087-1089.

Kowalczykowski, S.C., 2002. Molecular mimicry connects BRCA2 to Rad51 and recombinational DNA repair. Nature Structural Biology. 9(12): p. 897-899.

Kung, L.A., et al., 2000. Patterning Hybrid Surfaces of Proteins and Supported Lipid Bilayers. Langmuir. 16: p. 6773-6776.

Kurumizaka, H., Aihara, H., Kagawa, W., Shibata, T. & Yokoyama, S. (1999). Human Rad51 amino acid residues required for Rad52 binding. Journal of Molecular Biology 291, 537-548.

Laboratory Techniques in Biochemistry and Molecular Biology, vol. 24: Hybridization with Nucleic Acid Probes, P. Tijssen, ed. Elsevier, NY (1993).

Ladoux, B. & Doyle, P. S. (2000). Stretching tethered DNA chains in shear flow. Europhysics Letters 52, 511-517.

Ladoux, B., Quivy, J.P., Doyle, P., du Roure, O., Almouzni, G. and Viovy, J.L. (2000) Fast kinetics of chromatin assembly revealed by single-molecule videomicroscopy and scanning force microscopy. Proceedings of the National Academy of Sciences, USA, 97, 14251-14256.

(56) References Cited

OTHER PUBLICATIONS

Lau, P.J. and R.D. Kolodner, 2003. Transfer of the MSH2-MSH6 complex from proliferating cell nuclear antigen to mispaired bases in DNA. Journal of Biological Chemistry. 278: p. 14-17.

Lebofsky, R. & Bensimon, A., "Single DNA molecule analysis: Applications of molecular combing," Briefings in functional genomics and proteomics 1, pp. 385-396 (2003).

Leuba, S.H., M.A. Karymov, M. Tomschik, R. Ramjit, P. Smith, and J. Zlatanova, 2003. Assembly of single chromatin fibers depends on the tension in the DNA molecule: magnetic tweezers study. Proceedings of the National Academy of Sciences. 100: p. 495-500.

Lia, G., Praly, E., Ferreira, H., Stockdale, C., Tse-Dinh, Y. C., Dunlap, D., Croquette, V., Bensimon, D., and Owen-Hughes, T. (2006). Direct observation of DNA distortion by the RSC complex. Molecular Cell 21, 417-425.

Lin, J., et al. "Whole-Genome Shotgun Optical mapping of Deinococcus radiodurans," Science 285, 1558-1562 (1999).

Lisby, M. and R. Rothstein, Jun. 2004. DNA damage checkpoint and repair centers. Curr Opin Cell Biol. 16(3): p. 328-34.

Lisby, M., Barlow, J. H., Burgess, R. C., and Rothstein, R. (2004). Choreography of the DNA damage response: spatiotemporal relationships among checkpoint and repair proteins. Cell 118, 699-713, suppl pp. 1-9.

Lisby, M., U. Mortensen, and R. Rothstein, Jun. 2003. Colocalization of multiple DNA double-strand breaks at a single Rad52 repair centre. Nat Cell Biol. 5(6): p. 572-7.

Liu, Y., A.Z. Stasiak, J.-Y. Masson, M.J. McIlwraith, A. Stasiak, and S.C. West, 2004. Conformational changes modulate the activity of human Rad51 protein. Journal of Molecular Biology. 337: p. 817-827.

Luger et al., "Crystal structure of the nucleosome core particle at 2.8 A resolution," Nature vol. 389, pp. 251-260 (Sep. 1997).

Luger, K., T.J. Rechsteiner, A.J. Flaus, M.M.Y. Waye, and T.J. Richmond, 1997. Characterization of nucleosome core particles containing histone proteins made in bacteria. The Journal of Molecular Biology. 272: p. 301-311.

Marko, F. and E.D. Siggia, 1995. Stretching DNA. Macromolecules. 28: p. 8759-8770.

Masson, J.-Y., Stasiak, A. Z., Stasiak, A., Benson, F. E. & West, S. C. (2001). Complex formation by the human Rad51C and XRCC3 recombination repair proteins. Proceedings of the National Academy of Sciences (USA) 98, 8440-8446.

Masson, J.-Y., Tarsounas, M. C., Stasiak, A. Z., Stasiak, A., Shah, R., McIlwraith, M. J., Benson, F. E. & West, S. C. (2001). Identification and purification of two distinct complexes containing the five RAD51 paralogs. Genes & Development 15, 3296-3307.

Matsuo, Y. Sakane, I., Takizawa, Y., Takahashi, M., and Kurumizaka, H. (2006). Roles of the human Rad51 L1 and L2 loops in DNA binding. The FEBS Journal 273, 3148-3159.

Mazin, A., Alexeev, A., and Kowalczykowski, S. (2003). A novel function of Rad54 protein. Stabilization of the Rad51 nucleoprotein filament. The Journal of Biological Chemistry 278, 14029-14036.

Mazin, A., C.J. Bornarth, J.A. Solinger, W.D. Heyer, and S.C. Kowalczykowski, 2000. Rad54 protein is targeted to pairing loci by the Rad51 nucleoprotein filament. Molecular Cell. 6: p. 583-592.

Mazin, A., Zaitseva, E., Sung, P. & Kowalczykowski, S. (Mar. 1, 2000). Tailed duplex DNA is the preferred substrate for Rad51 protein-mediated homologous pairing. The EMBO Journal 19, 1148-56.

McIlwraith, M. J., et al., "RadA protein from Archaeoglobus fulgidus forms rings, nucleoprotein filaments and catalyses homologous recombination," Nucleic Acids Research 29, 4509-4517 (2001).

McIlwraith, M.J., E. Van Dyck, J.-Y. Masson, A.Z. Stasiak, A. Stasiak, and S.C. West, 2000. Reconstitution of the strand invasion step of double-strand break repair using human Rad51, Rad52 and RPA proteins. Journal of Molecular Biology. 304: p. 151-164.

Medintz, I.L., Uyeda, H.T., Goldman, E.R. And Mattoussi, H. (2005) Quantum dot bioconjugates for imaging, labeling and sensing. Nature Materials, 4, 435-446.

Meluh et al., "Cse4p is a component of the Core Centromere of Saccharomyces cerevisiae," Cell, vol. 94, pp. 607-613 (Sep. 1998).

Mendillo, M.L., D.J. Mazur, and R.D. Kolodner, 2005. Analysis of the interaction between the Saccharomyces cerevisiae MSH2-MSH6 and MLH1-PMS1 complexes with DNA using a reversible DNA end-blocking system. Journal of Biological Chemistry. 280: p. 22245-22257.

Meneghini et al., "Conserved Histone variant H2A.Z protects Euchromatin from the Ectopic Spread of Silent Heterochromatin," Cell, vol. 112, pp. 725-736 (Mar. 2003).

Michalet, X., F.F. Pinaud, L.A. Bentolila, J.M. Tsay, S. Doose, J.J. Li, G. Sundaresan, A.M. Wu, S.S. Gambhir, and S. Weiss, 2005. Quantum dots for live cells, in vivo imaging, and diagnostics. Science. 307: p. 538-544.

Mirshad, J. K. & Kowalczykowski, S. C. (2003). Biochemical characterization of a mutant RecA protein altered in DNA-binding loop 1. Biochemistry 42, 5945-5954.

Mizugushi et al., "ATP-Driven Exchange of Histone H2AZ Variant Catalyzed by SWR1 Chromatin Remodeling Complex," Science, vol. 303, pp. 343-348 (2004).

Modesti, M. and R. Kanaar, 2001. Homologous recombination: from model organism to human disease. Genome Biology. 2(5): p. 1014. 1-1014.5.

Morimatsu, K. & Horii, T. (1995). DNA-binding surface of RecA protein photochemical crosslinking of the first DNA binding site on the RecA filament. Eur. J. Biochem. 234, 695-705.

Morrison, C., Shinohara, A., Sonoda, E., Yamaguchi-Iwai, Y., Takata, M., Weichselbaum, R. R. & Takeda, S. (1999). The essential functions of human Rad51 are independent of ATP hydrolysis. Molecular and Cellular Biology 19, 6891-6897.

Muir, T.W., D. Sondhi, and P.A. Cole, 1998. Expressed protein ligation: a general method for protein engineering. Proceedings of the National Academy of Sciences. 95: p. 6705-6710.

Naryzhny, S.N., H. Zhao, and H. Lee, 2005. Proliferating cell nuclear antigen (PCNA) may function as a double homotrimer complex in the mammalian cell. Journal of Biological Chemistry. 280(14): p. 13888-13894.

Neuman, K.C., Abbondanzieri, E.A., Landick, R., Gelles, J. and Block, S.M. (2003) Ubiquitous transcriptional pausing is independent of RNA polymerase backtracking. Cell, 115, 437-447.

New, J.H., T. Sugiyama, E. Zaitseva, and S.C. Kowalczykowski, 1998. Rad52 protein stimulates DNA strand exchange by Rad51 and replication protein A. Nature. 391: p. 407-410.

Nirmal, M., Dabbousi, B.O., Bawendi, M.G., Macklin, J.J., Trautman, J.K., Harris, T.D. and Brus, L.E. (1996) Fluorescence intermittency in single cadmium selenide nanocrystals. Nature, 383, 802-804.

Nishinaka, T., A. Shinohara, Y. Ito, H. Yokoyama, and T. Shibata, 1998. Base pair switching by interconversion of sugar puckers in DNA extended by proteins of RecA-family: A model for homology search in homologous genetic recombination. Proc Natl Acad Sci U S A. 95: p. 11071-11076.

Obmolova, G., C. Ban, and W. Yang, 2000. Crystal structures of mismatch repair protein MutS and its complex with a substrate DNA. Nature. 407: p. 703-710.

Odom, T.W., et al., 2002. Generation of 30-50 nm Structures Using Easily Fabricated, Composite PDMS Masks. Journal of the American Chemical Society. 124: p. 12112-12113.

Odom, T.W., et al., 2002. Improved Pattern Transfer in Soft Lithography Using Composite Stamps. Langmuir. 18: p. 5314-5320.

Orelli, B. and D. Bishop, 2001. BRCA2 and homologous recombination. Breast Cancer Res. 3(5): p. 294-8.

Paques, F. and J.E. Haber, 1999. Multiple pathways of recombination induced by double-strand breaks in Saccharomyces cerevisiae. Microbiology and Molecular Biology Reviews. 63(2): p. 349-404.

Passy, S. I., Yu, X., Li, Z., Radding, C. M., Masson, J.-Y., West, S. C. & Egelman, E. H. (1999). Human Dmc1 protein binds DNA as an octomeric ring. Proceedings of the National Academy of Sciences (USA) 96, 10684-10688.

Pellegrini, L., Yu, D. S., Lo, T., Anand, S., Lee, M., Blundell, T. L. & Venkitaraman, A. R. (2002). Insights into DNA recombination from the structure of a RAD51-BRCA2 complex. Nature 420, 287-293.

Perkins, T.T., Dalal, R.V., Mitsis, P.G. and Block, S.M. (2003) Sequence-dependent pausing of single lambda exonuclease molecules. Science, 301, 1914-1918.

(56) References Cited

OTHER PUBLICATIONS

Petukhova, G., Stratton, S., and Sung, P. (1998). Catalysis of homologous DNA pairing by yeast Rad51 and Rad54 proteins. Nature 393, 91-94.
Petukhova, G., Sung, P., and Klein, H. (2000). Promotion of Rad51-dependent D-loop formation by yeast recombination factor Rdh54/Tid1. Genes & Development 14, 2206-2215.
Petukhova, G., Van Komen, S., Vergano, S., Klein, H., and Sung, P. (1999). Yeast Rad54 promotes Rad51-dependent homologous DNA pairing via ATP hydrolysis-driven change in DNA double helix conformation. The Journal of Biological Chemistry 274, 29453-29462.
Pinaud, F., Michalet, X., Bentolila, L.A., Tsay, J.M., Doose, S., Li, J.J., Iyer, G. and Weiss, S. (2006) Advances in fluorescence imaging with quantum dot bio-probes. Biomaterials, 27, 1679-1687.
Pluciennik, A. & Modrich, P. "Protein roadblocks and helix discontinuities are barriers to the initiation of mismatch repair," Proceedings of the National Academy of Sciences USA 104, 12709-12713 (2007).
Powell, S., Willers, H. & Xia, F. (Dec. 2002). BRCA2 keeps Rad51 in line. High-fidelity homologous recombination prevents breast and ovarian cancer? Molecular Cell 10, 1262-3.
Prasad et al., "A DNA-translocating Snf2 Molecular Motor: Saccharomyces cerevisiae Rdh54 Displays Processive Translocation and Extrudes DNA Loops," J. MOl. Biol., vol. 369, pp. 940-953 (2007).
Prasad, T. K., et al., "A DNA-Translocating Snf2 Molecular Motor: Saccharomyces cerevisiae Rdh54 display processive translocation and extrudes DNS Loops," J Mol Biol 369, 940-953 (2007).
Prasad, T. K., Yeykal, C., & Greene, E. C. "Visualizing the assembly of human Rad51 filaments on double-stranded DNA," Journal of Molecular Biology 363, 713-728 (2006).
Pugh, B. F. & Cox, M. M. (1988). General mechanism for RecA protein binding to duplex DNA. Journal of Molecular Biology 203, 479-493.
Qian, H., M.P. Sheetz, and E.L. Elson, 1991. Single particle tracking: analysis of diffusion and flow in two-dimensional systems. Biophysical Journal. 60: p. 910-921.
Quake, S.R., Babcock, H.P. and Chu, S. (151) The dynamics of partially extended single molecules of DNA. Nature, 388, 151-154, Jul. 10, 1997.
Raisner et al., "Histone Variant H2A.Z Marks the 5' ends of both Active and Inactive Genes in Euchromation," Cell, vol. 123, pp. 233-248 (Oct. 2005).
Raschle, M., Van Komen, S., Chi, P., Ellenberger, T., and Sung, P. (2004). Multiple interactions with the Rad51 recombinase govern the homologous recombination function of Rad54. The Journal of Biological Chemistry 279, 51973-51980.
Rasnik, I., et al., Feb. 13, 2004. DNA-binding orientation and domain conformation of the E. coli rep helicase monomer bound to a partial duplex junction: single-molecule studies of fluorescently labeled enzymes. J Mol Biol. 336(2): p. 395-408.
Rhoades, E., Gussakovsky, E., & Haran, G., "Watching proteins fold one molecule at a time," Proc Natl Acad Sci U S A 100, 3197-3202; correction p. 7418 (2003).
Rice, K. P., Eggler, A. L., Sung, P. & Cox, M. M. (2001). DNA pairing and strand exchange by the Escherichia coli RecA and yeast Rad51 proteins without ATP hydrolysis. The Journal of Biological Chemistry 276, 38570-38581.
Riehn et al., "Restriction mapping in nanofluidic devices," PNAS, vol. 102, pp. 10012-10016 (Jul. 2005).
Ristic, D., Modesti, M., van der Heijden, T., van Noort, J., Dekker, C., Kanaar, R. & Wyman, C. (2005). Human Rad51 filaments on double- and single-stranded DNA: correlating regular and irregular forms with recombination function. Nucleic Acids Research 33, 3292-3302.
Ristic, D., Wyman, C., Paulusma, C., and Kanaar, R. (2001). The architecture of the human Rad54-DNA complex provides evidence for protein translocation along DNA. Proceedings of the National Academy of Sciences (USA) 98, 8454-8460.
Sackmann, E., "Supported Membranes: Scientific and Practical Applications," Science, vol. 271, Jan. 5, 1996, pp. 43-48.

Saha, A., Wittmeyer, J., and Cairns, B. R. (2002). Chromatin remodeling by RSC involves ATP-dependent DNA translocation. Genes & Development 16, 2120-2134.
Saha, A., Wittmeyer, J., and Cairns, B. R. (2006). Chromatin remodeling: the industrial revolution of DNA around histones,. Nature Reviews Molecular Cell Biology 7, 437-447.
Salafsky, J.; Groves, J. T.; Boxer, S. G, "Architecture and function of membrane Proteins in planar supported bilayers: a study with photosynthetic reaction centers," Biochemistry, 35, 14773-14781 (1996).
Satchwell et al., "Sequence Periodicities in Chicken Nucleosome Core DNA," J. Mo; Biol, vol. 191, pp. 659-675 (1986).
Saxton, M.J. and K. Jacobson, 1997. Single-particle tracking: applications to membrane dynamics. Annual Reviews in Biophysics and Biomolecular Structure. 26: p. 373-399.
Schuler, B., "Single-Molecule Fluorescence Spectroscopy of Protein Folding," Chemphyschem, 6, (7), 1206-1220 (2005).
Schwartz et al., "Ordered Restriction Maps of Saccharomyces cerevisiae Chromosomes Constructed by Optical Mapping," Science, vol. 262, pp. 110-114(Oct. 1993).
Sehorn, M. S., Sigurdsson, S., Bussen, W., Unger, V. M. & Sung, P. (2004). Human meiotic recombinase Dmc1 promotes ATP-dependent homologous DNA strand exchange. Nature 429, 433-437.
Seidel, R., van Noort, J., van der Scheer, C., Bloom, J. G. P., Dekker, N. H., Dutta, C. F., Blundell, A., Robinson, T., Firman, K., and Dekker, C. (2004). Real-time observation of DNA translocation by the type I restriction modification enzyme EcoR124I. Nature Structural and Molecular Biology 11, 838-843.
Sekinger et al., "Intrinsic Histone-DNA Interactions and Low Nuclosome Density are important for preferential Accessibility of promoter regions in Yeast," Molecular Cell, vol. 18, pp. 735-748 (Jun. 2005).
Shan, Q., M. Cox, and R. Inman, Mar. 8, 1996. DNA strand exchange promoted by RecA K72R. Two reaction phases with different $Mg^{2+}$ requirements. J Biol Chem. 271(10): p. 5712-24.
Shimamoto, N., "One-Dimensional diffusion of Protein along DNA," The Journal of Biological Chemistry 274, 15293-15296 (1999).
Shin, D. S., Pellegrini, L., Daniels, D. S., Yelent, B., Craig, L., Bates, D., Yu, D. S., Shivji, M. K., Hitomi, C., Arvai, A. S., Volkmann, N., Tsuruta, H., Blundell, T. L., Venkitaraman, A. R. & Tainer, J. A. (2003). Full-length archaeal Rad51 structure and mutants: mechanisms for Rad51 assembly and control by BRCA2. The EMBO Journal 22, 4566-4576.
Shinohara, A., H. Ogawa, Y. Matsuda, N. Ushio, K. Ikea, and T. Ogawa, 1993. Cloning of human, mouse and fission yeast recombination genes homologous to RAD51 and recA. Nature Genetics. 4: p. 239-243.
Shinohara, M., Gasior, S. L., Bishop, D. K., and Shinohara, A. (2000). Tid1/Rdh54 promotes colocalization of Rad51 and Dmc1 during meiotic recombination. Proceedings of the National Academy of Sciences (USA) 97, 10814-10819.
Shinohara, M., Sakai, K., Shinohara, A., and Bishop, D. K. (2003). Crossover interference in Saccharomyces cerevisiae requires a TID1/RDH54 and DMC1-dependent pathway. Genetics 163, 1273-1286.
Shinohara, M., Shita-Yamaguchi, E., Buerstedde, J.-M., Shinagawa, H., Ogawa, H., and Shinhara, A. (1997). Characterization of the roles of the Saccharomyces cerevisiae RAD54 gene and homologue of RAD54, RDH54/TID1, in mitosis and meiosis. Genetics 147, 1545-1556.
Sigurdsson, S., K. Trujillo, B.W. Song, S. Stratton, and P. Sung, 2001. Basis for avid homologous DNA strand exchange by human Rad51 and RPA. The Journal of Biological Chemistry. 276(12): p. 8798-8806.
Sigurdsson, S., Van Komen, S., Petukhova, G., and Sung, P. (2002). Homologous DNA pairing by human recombination factors Rad51 and Rad54. The Journal of Biological Chemistry 277, 42790-42794.
Singleton, M. R., and Wigley, D. B. (2002). Modularity and Specialization in Superfamily 1 and 2 helicases. The Journal of Bacteriology 184, 1819-1826.
Singleton, S., R. Simonette, N. Sharma, and A. Roca, Dec. 2002. Intein-mediated affinity-fusion purification of the Escherichia coli RecA protein. Protein Expr Purif. 26(3): p. 476-88.
Smith, D.E., Babcock, H.P. and Chu, S. (1999) Single-polymer dynamics in steady shear flow. Science, 283, 1724-1727.

(56) References Cited

OTHER PUBLICATIONS

Smith, S. B et al., "Overstretching B-DNA: the Elastic Response of Individual double-Stranded and Single-Stranded DNA Molecules," Science, 271, pp. 795-799 (1996).
Solinger, J. A., and Heyer, W.-D. (2001). Rad54 protein stimulates the postsynaptic phase of Rad51 protein-mediated DNA strand exchange. Proceedings of the National Academy of Sciences (USA) 98, 8447-8453, Jul. 17, 2001.
Solinger, J. A., Kiianitsa, K., and Heyer, W.-D. (2002). Rad54, the Swi2/Snf2-like recombinational repair protein, disassembles Rad51:dsDNA filaments. Molecular Cell 10, 1175-1188.
Solinger, J.A., G. Lutz, T. Sugiyama, S.C. Kowalczykowski, and W.D. Heyer, 2001. Rad54 protein stimulates hteroduplex DNA formation in the synaptic phase of DNA strand exchange via specific interactions with the presynaptic Rad51 nucleoprotein filament. Journal of Molecular Biology. 307: p. 1207-1221.
Spies, M., Bianco, P.R., Dillingham, M.S., Handa, N., Baskin, R.J. and Kowalczyowski, S.C. (2003) A molecular throttle: the recombination hotspot χ controls DNA translocation by the RecBCD helicase. Cell, 114, 647-654.
St. John, P.M., et al., 1998. Diffraction-Based Cell Detection Using a Microcontact Printed Antibody Grating. Analytical Chemistry. 70: p. 1108-1111.
Stanford, N. P., M.D. Szczelkun, J.F. Marko, and S.E. Halford, 2000. One- and three-dimensional pathways for proteins to reach specific DNA sites. The EMBO Journal. 19(23): p. 6546-6557.
Stevens, B. C.; Ha, T. "Discrete and heterogeneous rotational dynamics of single membrane probe dyes in gel phase supported lipid bilayer,", Journal of Chemical Physics 2004, 120, 3030-3039.
Story, R. M., Weber, I. T. & Steitz, T. A. (1992). The structure of the *E. coli* recA protein monomer and polymer. Nature 355, 318-325.
Strick, T., V. Croquette, and D. Bensimon, Apr. 20, 2000. Single-molecule analysis of DNA uncoiling by a type II topoisomerase. Nature. 404(6780): p. 901-4.
Struhl K., "Naturally occuring poly(dA-dt) Sequences are upstream promoter elements for constitutive transcription in yeast," Proc. Natl. Acad. Sci. USA, vol. 82, pp. 8419-8423 (Dec. 1985).
Sturzbecher, H., B. Donzelmann, W. Henning, U. Knippschild, and S. Buchhop, Apr. 15, 1996. p53 is linked directly to homologous recombination processes via RAD51/RecA protein interaction. EMBO J. 15(8): p. 1992-2002.
Sugiyama, T., E.M. Zaitseva, and S.C. Kowalczykowski, 1997. A single-stranded DNA-binding protein is needed for efficient presynaptic complex formation by the *Saccharomyces cerevisiae* Rad51 protein. The Journal of Biological Chemistry. 272(12): p. 7940-7945.
Sung, N.S., J.I. Gordon, G.D. Rose, E.D. Getzoff, S.J. Kron, D. Mumford, J.N. Onuchic, N.F. Scherer, D.L. Sumners, and N.J. Kopell, 2003. Educating future scientists. Science. 301: p. 1485.
Sung, P., Krejci, L., Van Komen, S. and Sehorn, M.G. (2003) Rad51 recombinase and recombination mediators. The Journal of Biological Chemistry, 278, 42729-42732.
Swagemakers, S.M.A., J. Essers, J. de Wit, J.H.J. Hoeijmakers, and R. Kanaar, 1998. The human Rad54 recombinational DNA repair protein is a double-stranded DNA dependent ATPase. The Journal of Biological Chemistry. 273(43): p. 28292-28297.
Symington, L. S. (2002). Role of RAD52 epistasis group genes in homologous recombination and double-strand break repair. Microbiology and Molecular Biology Reviews 66, 630-670.
Tan, T. L. R., Kanaar, R., and Wyman, C. (2003). Rad54, a jack of all trades in homologous recombination. DNA Repair 2, 787-794.
Tanaka, M., Hermann, J., Haase, E., Fischer, M., & Boxer, S. G., "Frictional Drag and Electrical Manipulation of Recombinan Proteins in Polymer-Supproted Membranes," Langmuir 23, 5638-5644 (2007).
Tegenfeldt et al., "Micro- and nanofluidics for DNA analysis," Anal Bioanal Chem, vol. 378, pp. 1678-1692 (2004).
Thompson, R.E., D.R. Larson, and W.W. Webb, 2002. Precise nanometer localization analysis for individual fluorescent probes. Biophysical Journal. 82: p. 2775-2783.

Thomä, N. H., Czyzewski, B. K., Alexeev, A. A., Mazin, A. V., Kowalczykowski, S. C., and Pavletich, N. P. (2005). Structure of the SWI2/SNF2 chromatin-remodeling domain of eukaryotic Rad54. Nature Structural and Molecular Biology 12, 350-356.
Tokunaga, M., K. Kitamura, K. Saito, A.H. Iwane, and T. Tanagida, 1997. Single molecule imaging of fluorophores and enzymatic reactions achieved by objective-type total internal reflection fluorescence microscopy. Biochemical and biophysical research communications. 235: p. 47-53.
Tombline, G., Heinen, C. D., Shim, K.-S. & Fishel, R. (2002). Biochemical characterization of the human Rad51 protein: III. Modulation of DNA binding by adenosine nucleotides. The Journal of Biological Chemistry 277, 14434-14442.
Tsang, S.S., S.A. Chow, and C.M. Radding, 1985. Networks of DNA and RecA protein are intermediates in homologous pairing. Biochemistry. 24: p. 3226-3232.
Tsuzuki, T., Fujii, Y., Sakumi, K., Tominaga, Y., Nakao, K., Sekiguchi, M., Yoshimura, Y. & Morita, T. (1996). Targeted disruption of the Rad51 gene leads to lethality in embryonic mice. Proceedings of the National Academy of Sciences (USA) 93, 6236-6240.
Van Komen, S., Petukhova, G., Sigurdsson, S., Stratton, S., and Sung, P. (2000). Superhelicity-driven homologous DNA pairing by yeast recombination factors Rad51 and Rad54. Molecular Cell 6, 563-572.
VanLoock, M. S., Yu, X., Yang, S., Lai, A. L., Low, C., Campbell, M. J. & Egelman, E. H. (2003). ATP-mediated conformational changes in the RecA filament. Structure 11, 187-196.
Venkitaraman, A., 2002. Cancer susceptibility and the functions of BRCA1 and BRCA2. Cell. 108: p. 171-182.
Vivona, J.B. and Z. Kelman, 2003. The diverse spectrum of sliding clamp interacting proteins. FEBS Letters. 546: p. 167-172.
von Hippel, P.H. and O.G. Berg, 1989. Facilitated target location in biological systems. The Journal of Biological Chemistry. 264(2): p. 675-678.
Wang, M.D., Schnitzer, M.J., Yin, H., Landick, R., Gelles, J. and Block, S.M. (1998) Force and velocity measured for single molecules of RNA polymerase. Science, 282, 902-907.
Wang, Y. & Adzuma, K. (1996). Differential proximity probing of two DNA binding sites in the *Escherichia coli* recA protein using photo-cross-linking methods. Biochemistry 35, 3563-3571.
Wang, Z. & Sheetz, M. P., "One-dimensional diffusion on Microtubules of Particles Coated with Cytoplasmic Dynein and immunoglobulins," Cell Structure and Function 24, 373-383 (1999).
Washizu, M., Kurosawa, O., Arai, I., Suzuki, S., & Shimamoto, N., "Applications of Electrostatic Stretch-and Positioning of DNA," IEEE Trans. Ind. Appl. 31, 447-456 (1995).
Wei, Q.-H., Bechinger, C. & Leiderer, P. . "Single-file diffusion of Colloids in One-Dimensional Channels," Science 287, 625-627 (2000).
Weiss, S. (1999) Fluorescence spectroscopy of single biomolecules. Science, 283, 1676-1683.
West, S. C. (2003). Molecular views of recombination proteins and their control. Nature Reviews 4, 1-11.
Whitesides, G.M., E. Ostuni, S. Takayama, X. Jiang, and D.E. Ingber, 2001. Soft Lithography in Biology and Biochemistry. Annual Reviews in Biomedical Engineering. 3: p. 335-373.
Widom J., "Structure, Dynamics, and Function of Chromatin In Vitro," Annu. Rev. Biophys. Biomol. Struct., vol. 27, pp. 285-327 (1998).
Wieland et al., "Functional Complementation of Human Centromere Protein A (CENP-A) by Cse4p from *Saccharomyces cerevisiae*," Molecular and cellular Biology, vol. 24, pp. 6620-6630 (Aug. 2004).
Winter, R.B. and P.H. von Hippel, 1981. Diffusion-driven mechanisms of protein translocation on nucleic acids. 2. The *Escherichia coli* repressor-operator interaction: equilibrium measurements. Biochemistry. 20: p. 6948-6960.
Winter, R.B., O.G. Berg, and P.H. von Hippel, 1981. Diffusion-driven mechanisms of protein translocation on nucleic acids. 3. The *Escherichia coli* repressor-operator interaction: kinetic measurements and conclusions. Biochemistry. 20: p. 6961-6977.
Wittmeyer et al., "DNA Translocation and Nucleosome Remodeling Assays by the RSC Chromatin Remodeling Complex," Methods in Enzymology, vol. 377, pp. 322-343 (2004).

(56) References Cited

OTHER PUBLICATIONS

Wood, R.D., M. Mitchel, J. Sgouros, and T. Lindahl, 2001. Human DNA repair genes. Science. 291: p. 1284-1289.

Wu, Y., He, Y., Moya, I. A., Qian, X. & Luo, Y. (2004). Crystal structure of archaeal recombinase RadA: a snapshot of its extended conformation. Molecular Cell 15, 423-435.

Wu, Y., Qian, X., He, Y., Moya, I. A. & Luo, Y. (2005). Crystal structure of an ATPase-active form of Rad51 homolog from Methanococcus voltae. The Journal of Biological Chemistry 280, 722-728.

Xiao, J. and S.F. Singleton, 2002. Elucidating a key intermediate in homologous DNA strand exchange: structural characterization of the RecA-triple-stranded DNA complex using fluorescence resonance energy transfer. Journal of Molecular Biology. 320: p. 529-558.

Yang, S., Yu, X., Seitz, E. M., Kowalczykowski, S. C. & Egelman, E. H. (2001). Archaeal RadA protein binds DNA as both helical filaments and octomeric rings. Journal of Molecular Biology 314, 1077-1085.

Yao, N., J. Turner, Z. Kelman, P.T. Stukenburg, F. Dean, D. Shechter, Z.-Q. Pan, J. Hurwitz, and M. O'Donnell, 1996. Clamp loading, unloading and intrinsic stability of PCNA, beta and gp45 sliding clamps of human, *E. coli*, and T4 replicases. Genes to Cells. 1: p. 101-113.

Yildiz, A., J.N. Forkey, S.A. Mckinney, T. Ha, Y.E. Goldman, and P.R. Selvin, 2003. Myosin V walks hand-over-hand: single fluorophore imaging with 1.5-nm localization. Science. 300: p. 2061-2065.

Yoon, D., Y. Wang, K. Stapleford, L. Wiesm,ller, and J. Chen, (2004). P53 inhibits strand exchange and replication fork regression promoted by human Rad51. J Mol Biol. 336(3): p. 639-54.

Yoshikawa, Y., Hizume, K., Oda, Y., Takeyasu, K., Araki, S. and Yoshikawa, K. (2006) Protective effect of vitamin C against double-strand breaks in reconstituted chromatin visualized by single-molecule observation. Biophysical Journal, vol. 90; pp. 993-999.

Yoshina-Ishii, C.; Boxer, S. G. "Arrays of Mobile tethered vesicles on supported lipid bilayers,", J Am Chem Soc 2003, 125, (13), 3696-7.

Yu, X. & Egelman, E. H. (1997). The RecA hexamer is a structural homologue of ring helicases. Nature Structural Biology 4, 101-104.

Yu, X., Jacobs, S. A., West, S. C., Ogawa, T. & Egelman, E. H. (2001). Domain structure and dynamics in the helical filaments formed by RecA and Rad51 on DNA. Proceedings of the National Academy of Sciences (USA) 98, 8419-8424.

Yuan et al., "Genome-Scale Identification of Nucleosome Positions in *S. cerevisiae*," Science, vol. 309, pp. 626-630 (Jul. 2005).

Zaitseva, E. M., Zaitsev, E. N. & Kowalczykowski, S. C. (1999). The DNA binding properties of *Saccharomyces cerevisiae* Rad51 protein. The Journal of Biological Chemistry 274, 2907-2915.

International Search Report mailed on Jan. 30, 2014 for co-pending International Application No. PCT/US13/58641; 4 pages.

Dutta D et al. Selective tethering of ligands and proteins to a microfluidically patterned electroactive fluid lipid bilayer array. Langmuir. Jun. 15, 2010;26(12):9835-41.

Gorman J et al. Nanofabricated racks of aligned and anchored DNA substrates for single-molecule imaging. Langmuir. Jan. 19, 2010;26(2):1372-79.

Larsson C et al. Characterization of DNA immobilization and subsequent hybridization on a 2D arrangement of streptavidin on a biotin-modified lipid bilayer supported on SiO2. Anal Chem. Oct. 1, 2003;75(19):5080-7.

Visnapuu ML et al. The importance of surfaces in single-molecule bioscience. Mol Biosyst. May 2008;4(5):394-403, pp. 1-21.

\* cited by examiner

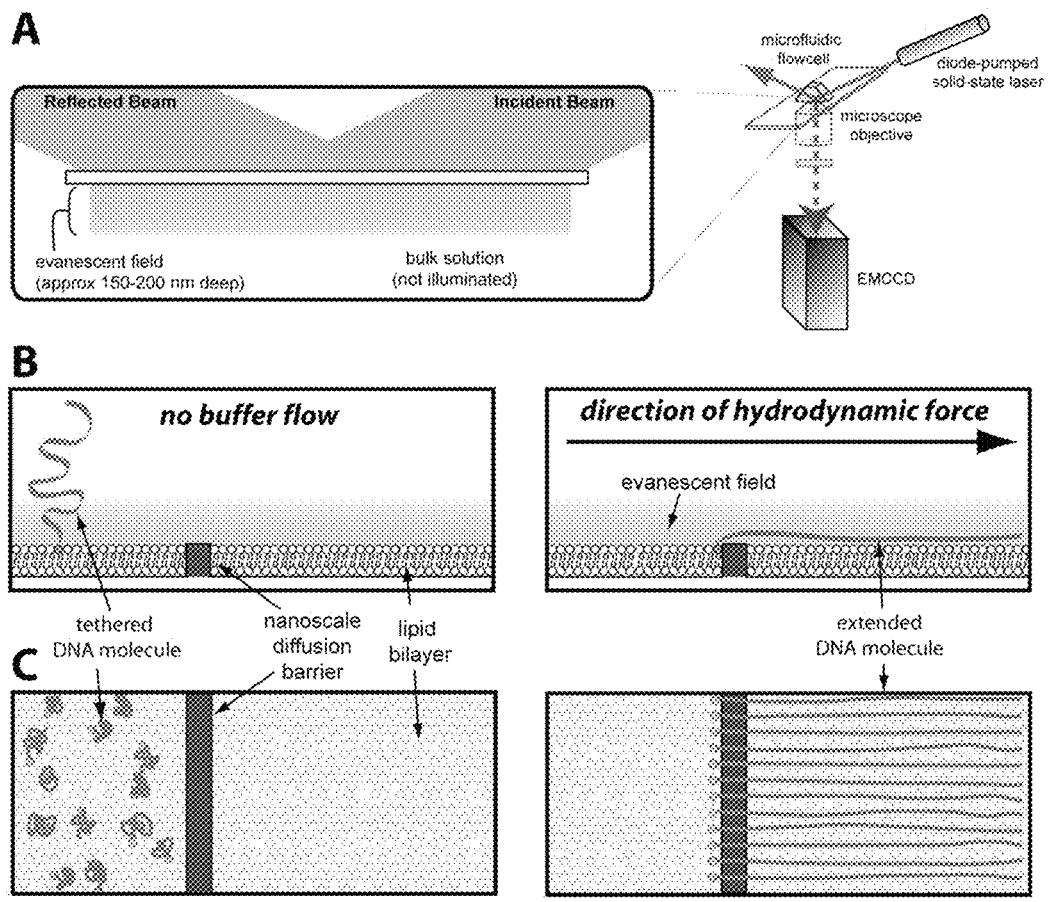
Figs. 1A-C

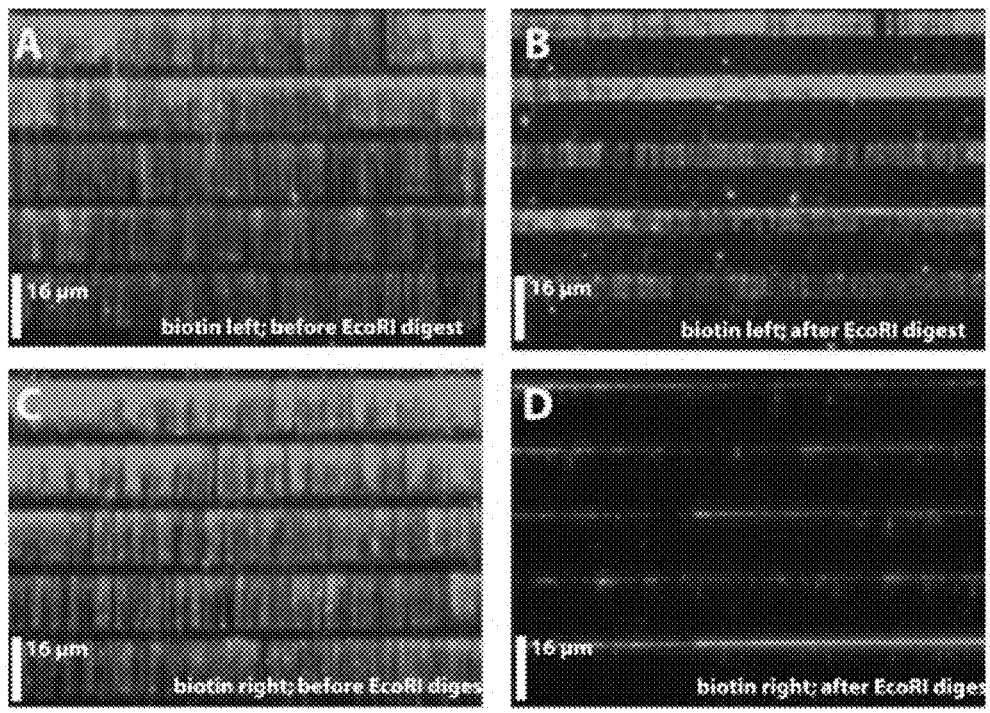
*Figs. 5A-D*

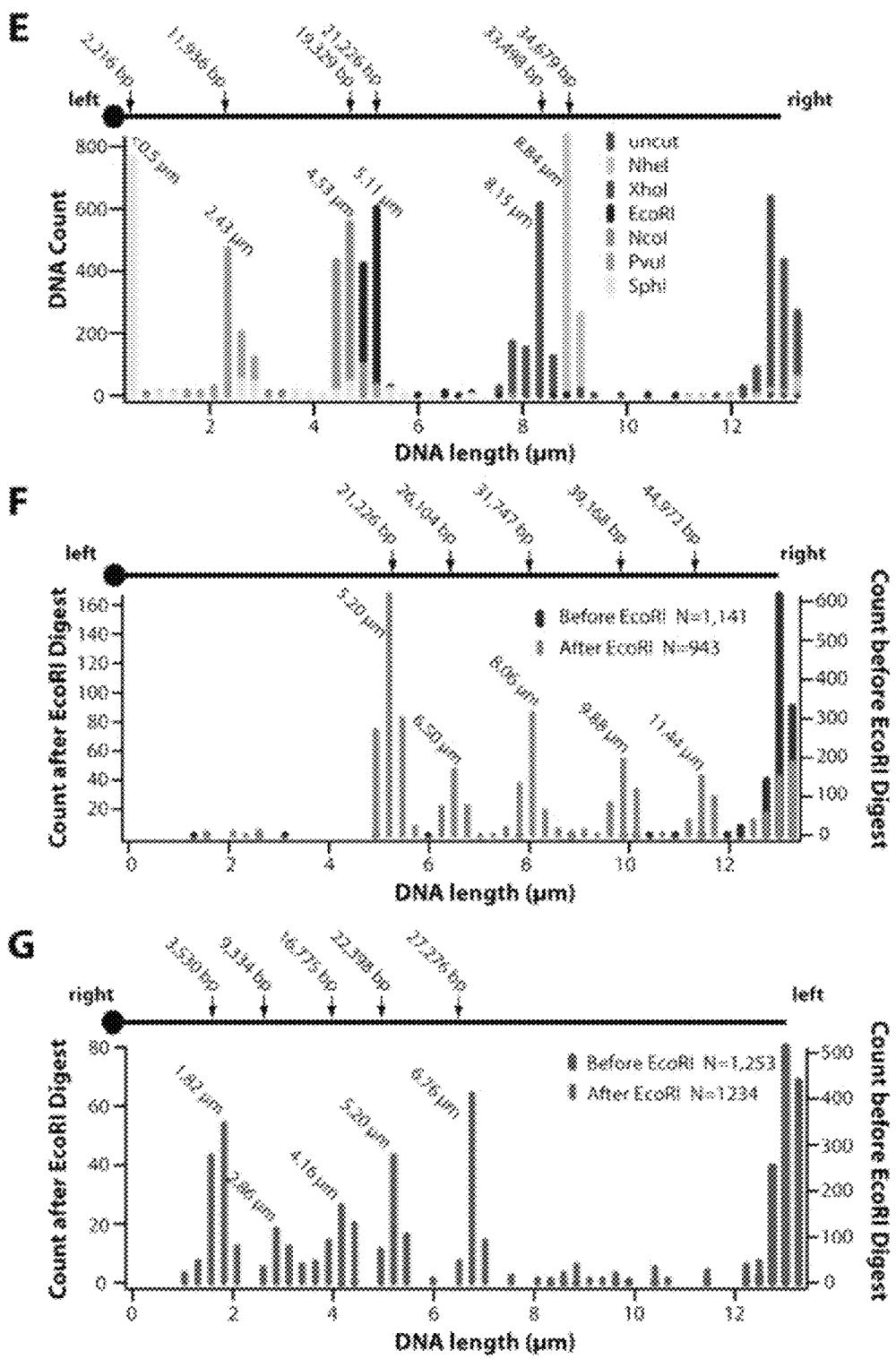
*Figs. 5E-G*

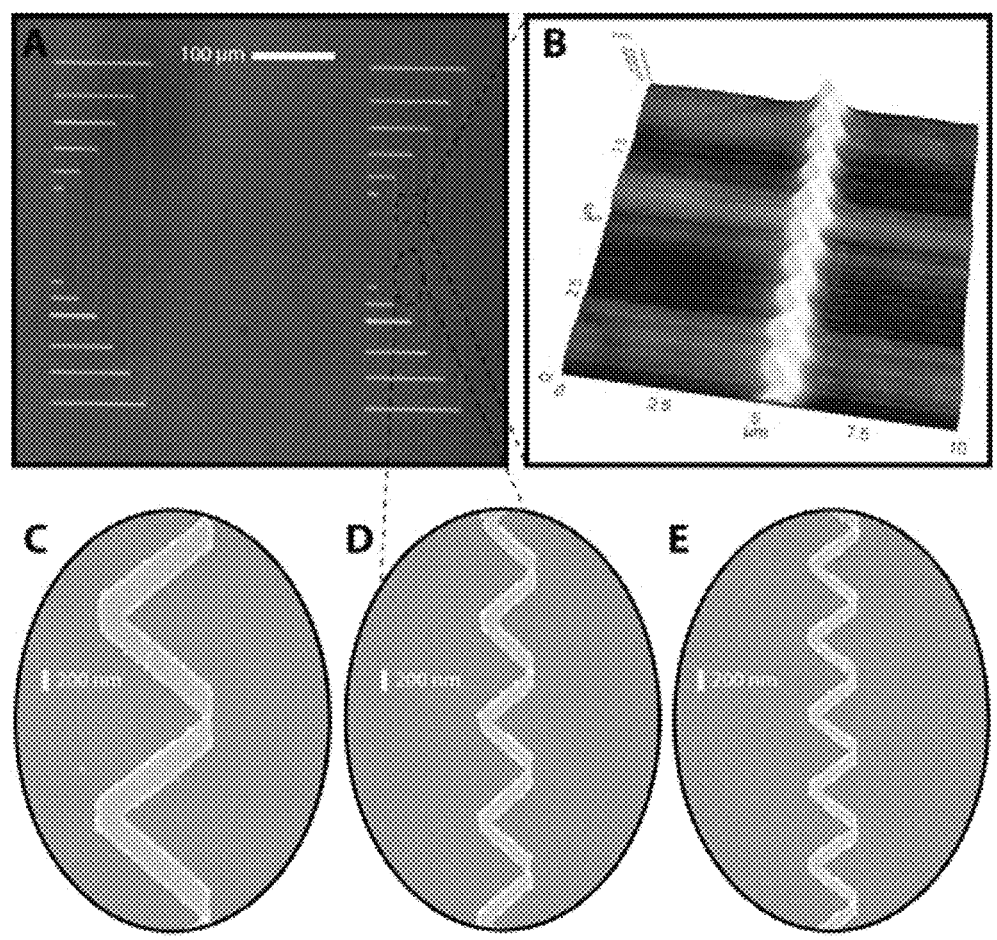
Figs. 7A-E

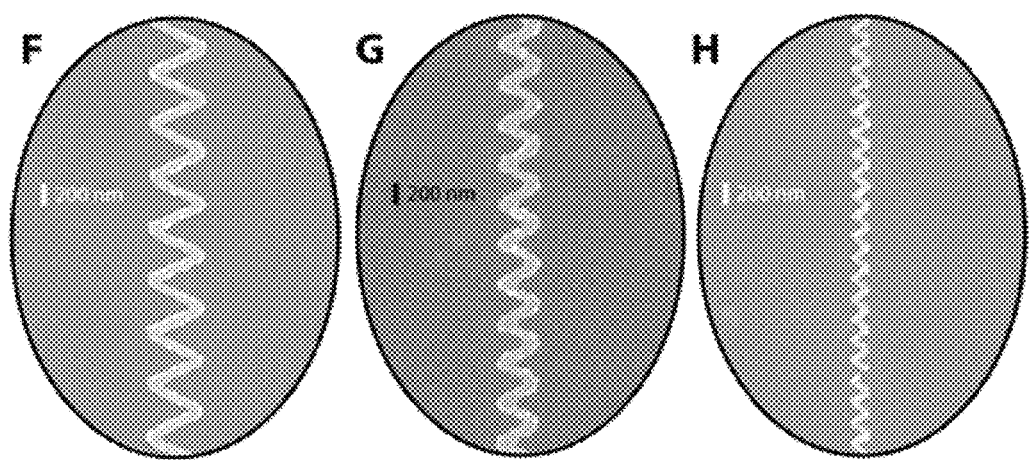
Figs. 7F-H

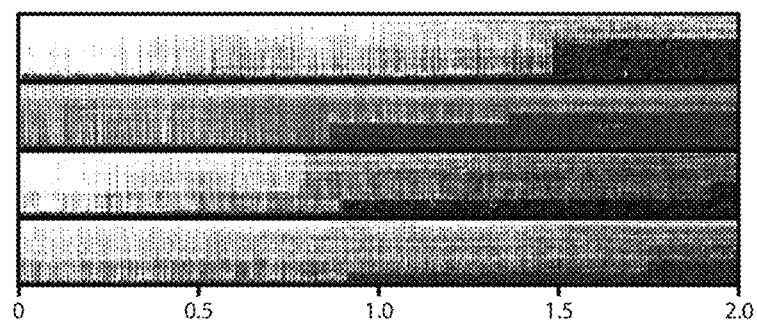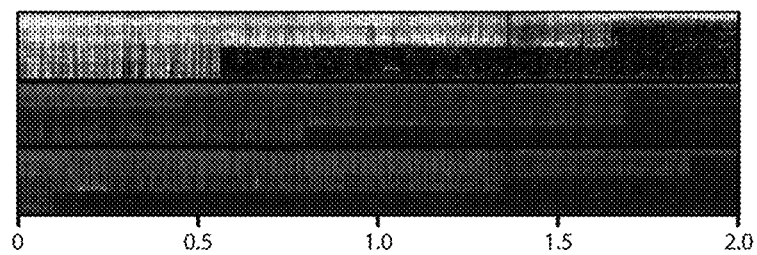
Fig. 10

"Double-tethered" Curtains of DNA

A. Current Design:

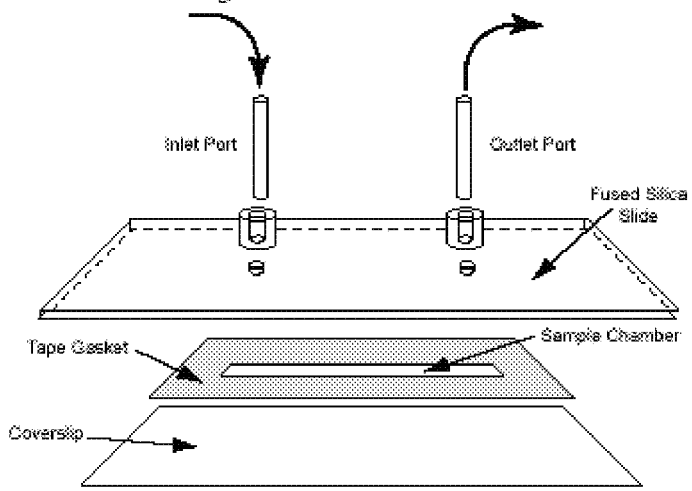

B. Alternative (future) design:

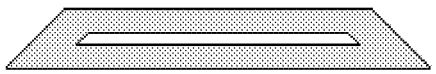

-replace tape gasket with polyethylene
(comprised a mixture of low and high density
polyethylene).
-the use of polyethylene will allow us to make a
stamping press that can be used to make the gaskets
from sheets of polyethylene.
-assemble flowcell and heat to just above the
melting point of the polyethylene, then cool to
seal the junction between the coverslip and
fused silica slide.

*Fig. 20*

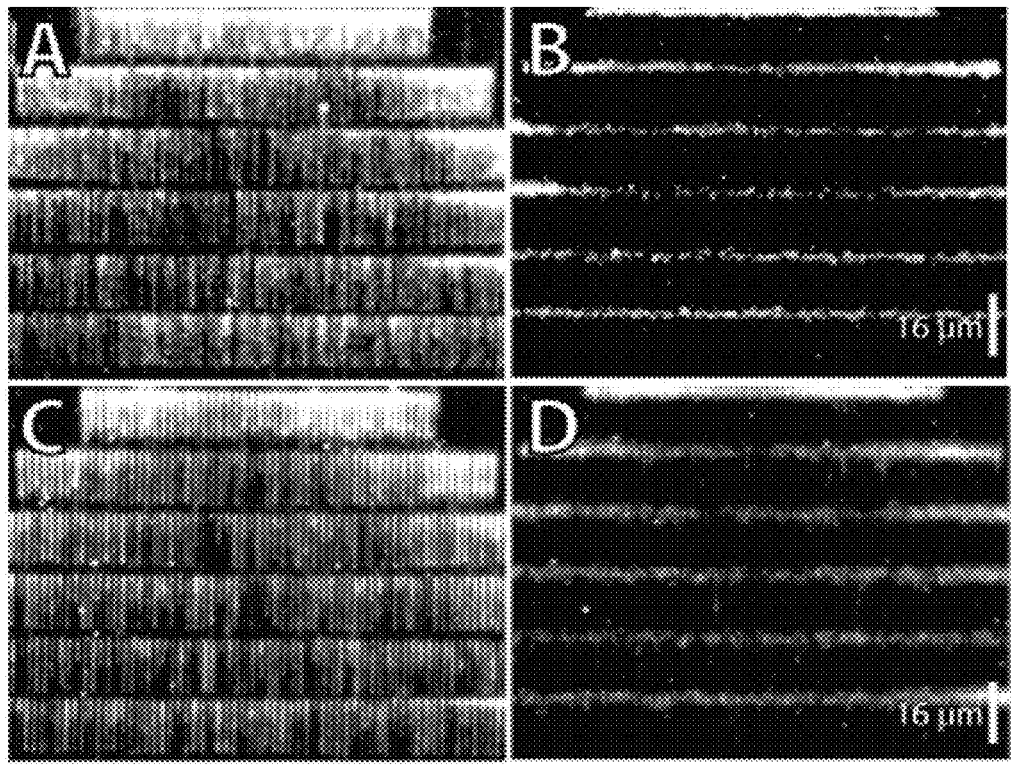
Figs. 24A-D

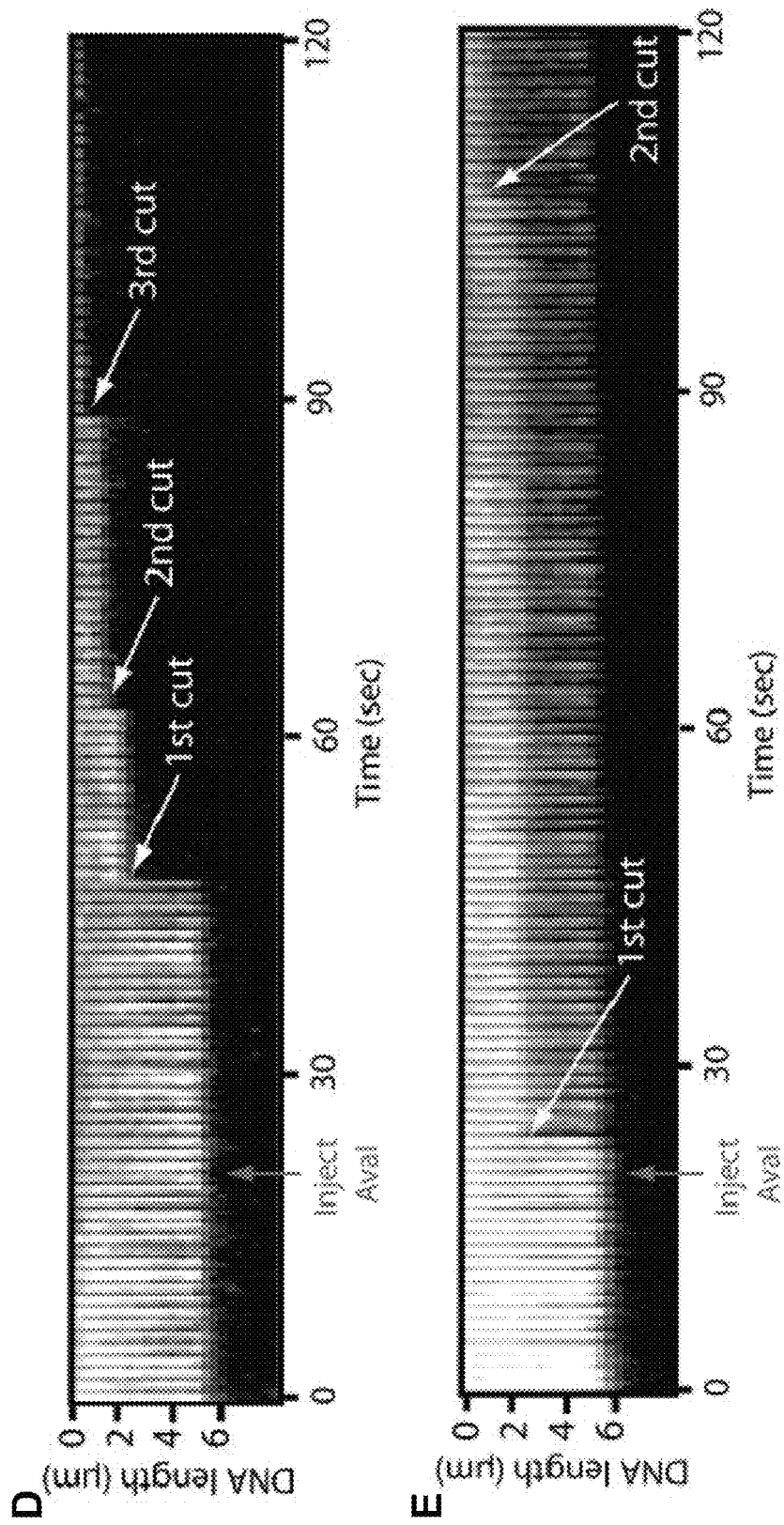
Figs. 26D-E

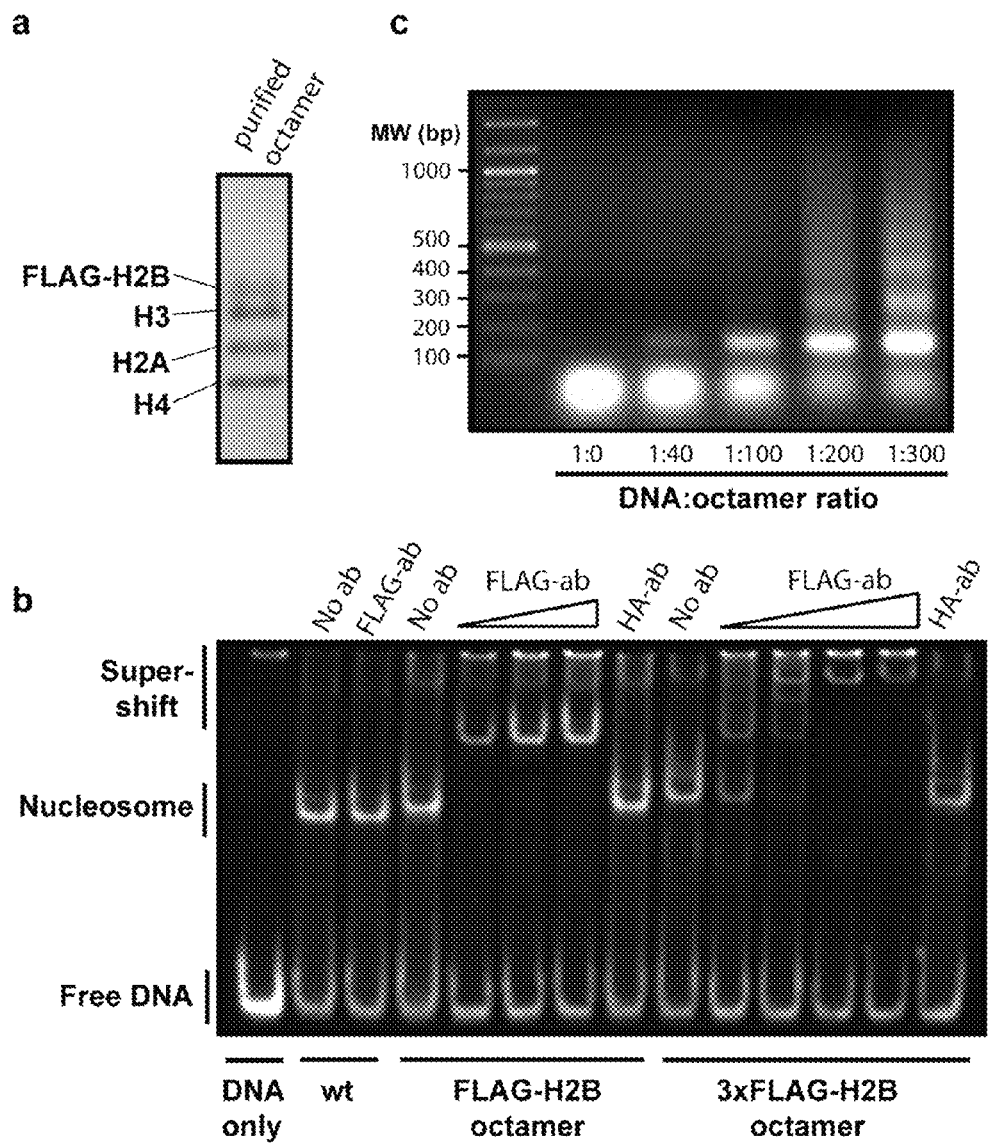
*Figs. 33A-C*

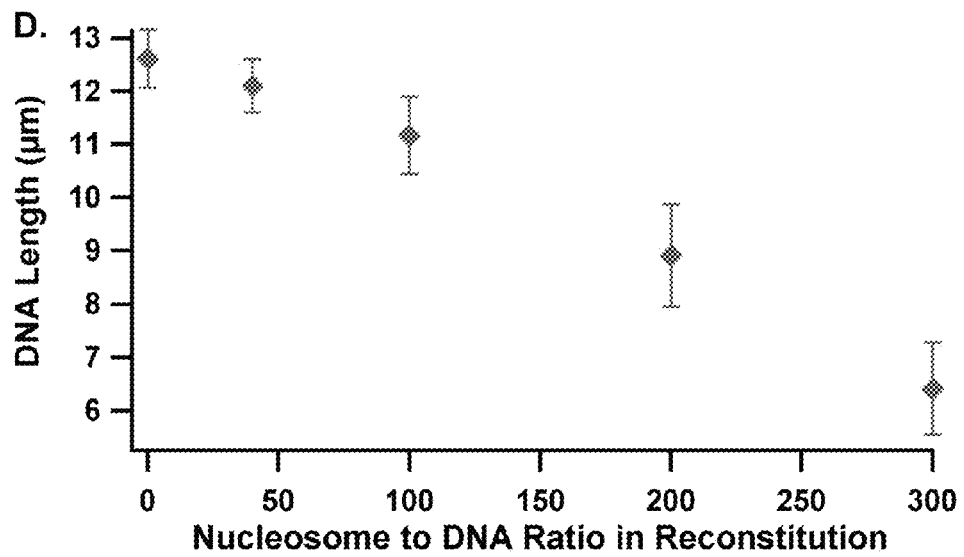
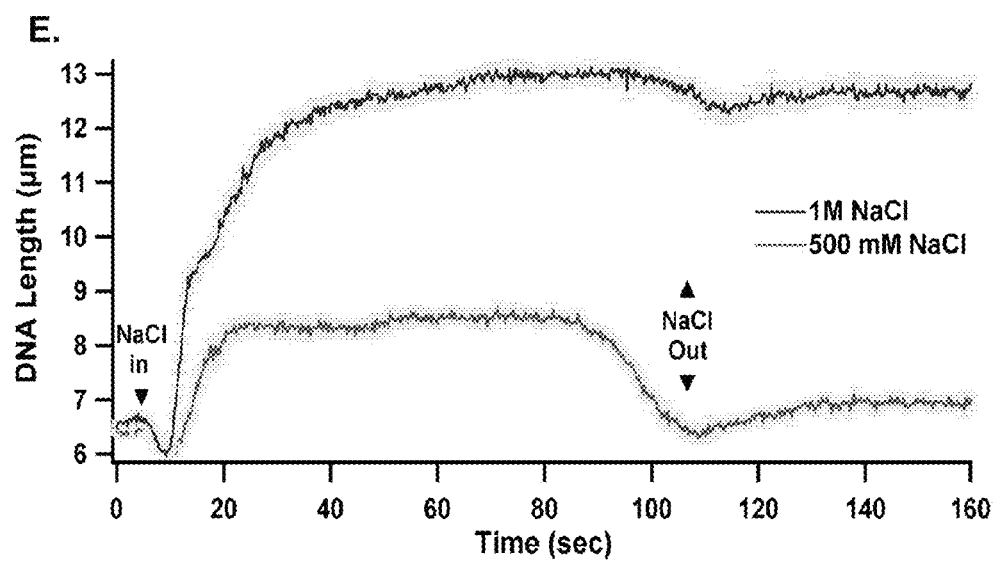
*Figs. 33D-E*

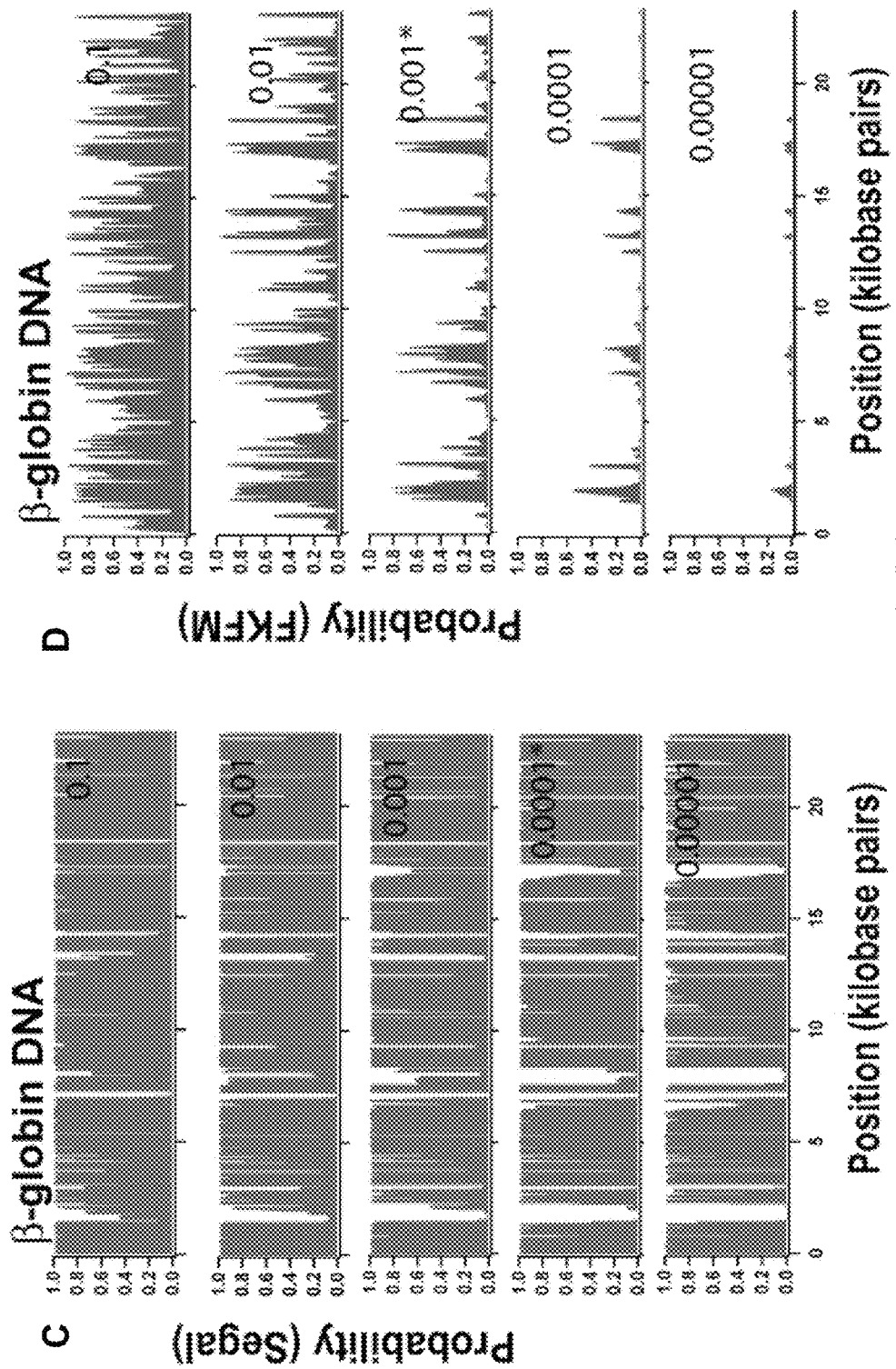
Figs. 34C-D

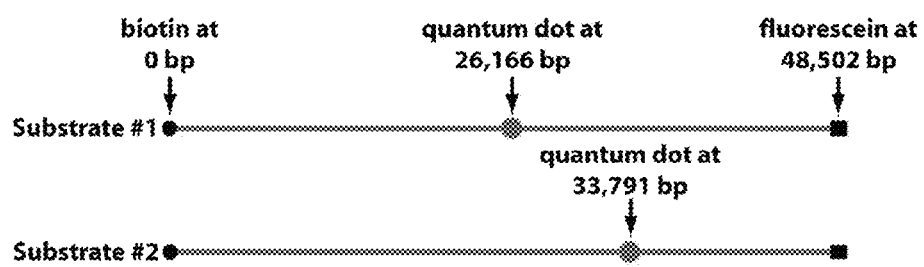
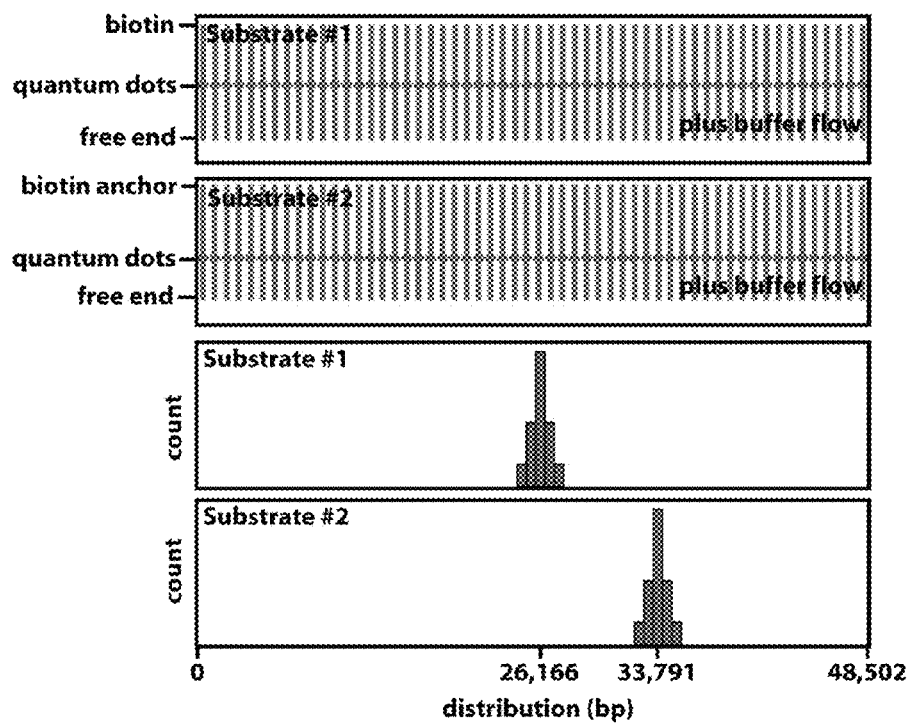
*Figs. 41A-B*

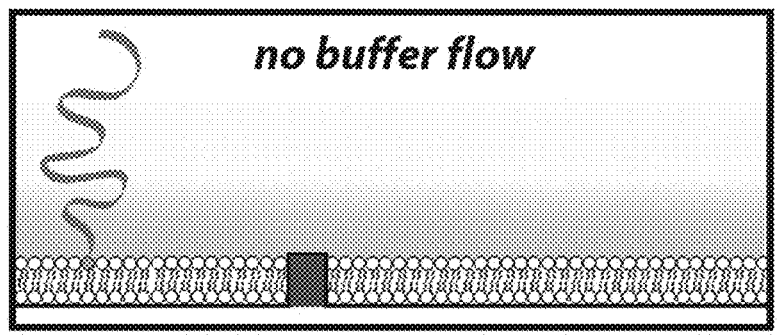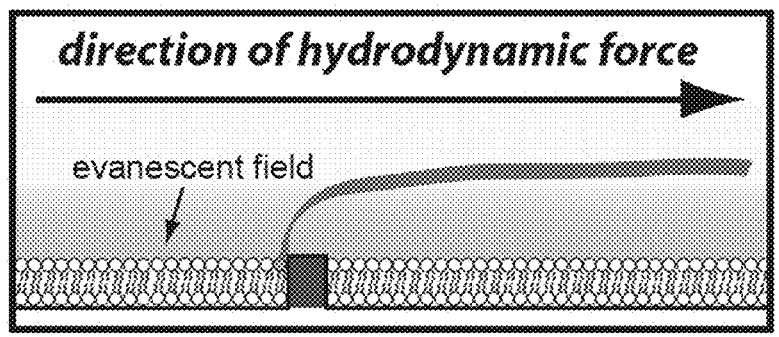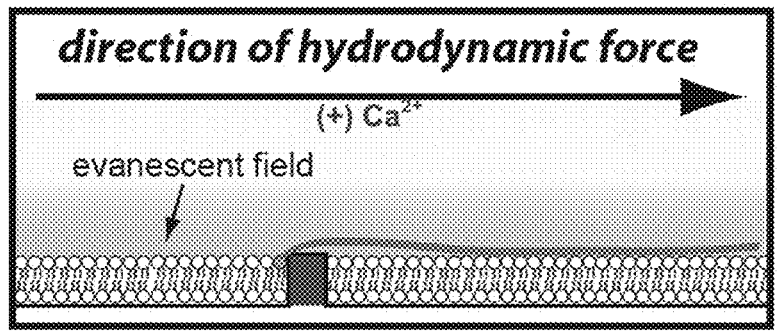
Fig. 43

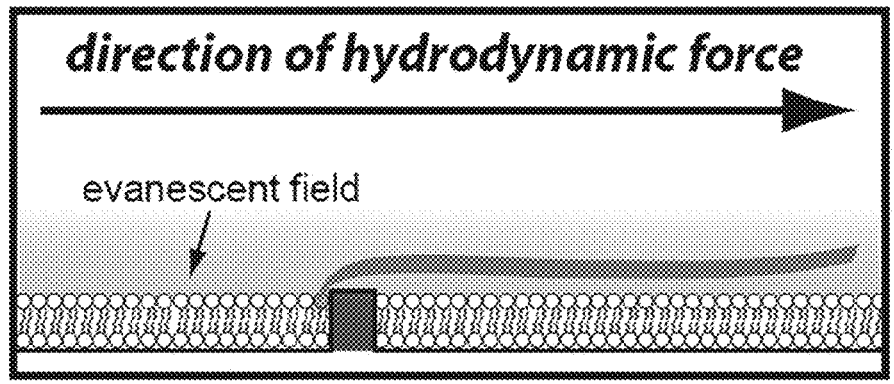
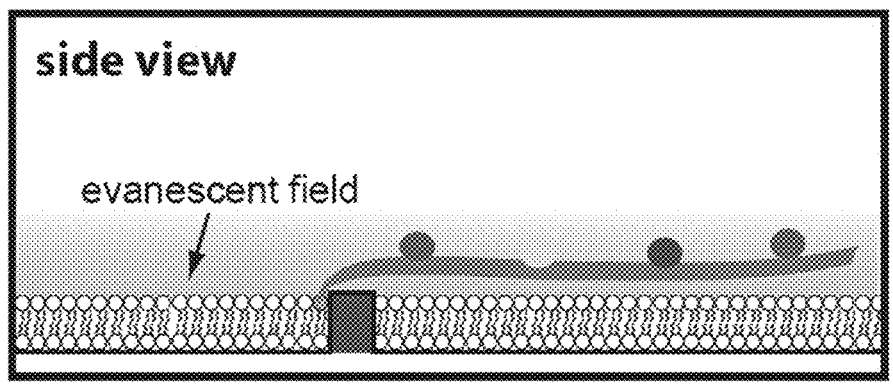
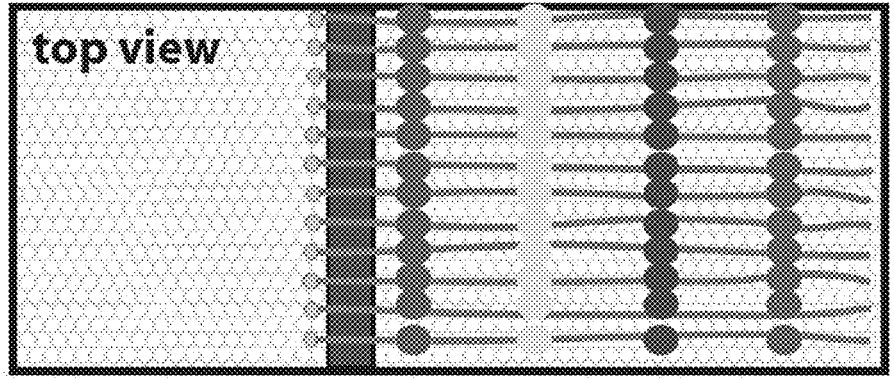
*Fig. 44*

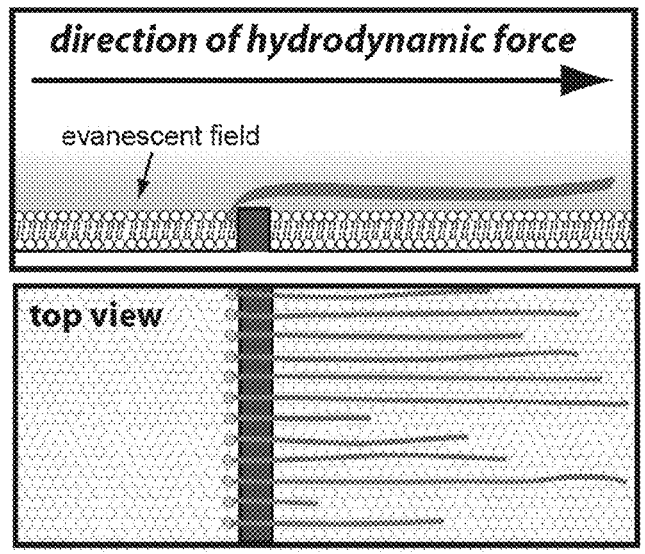
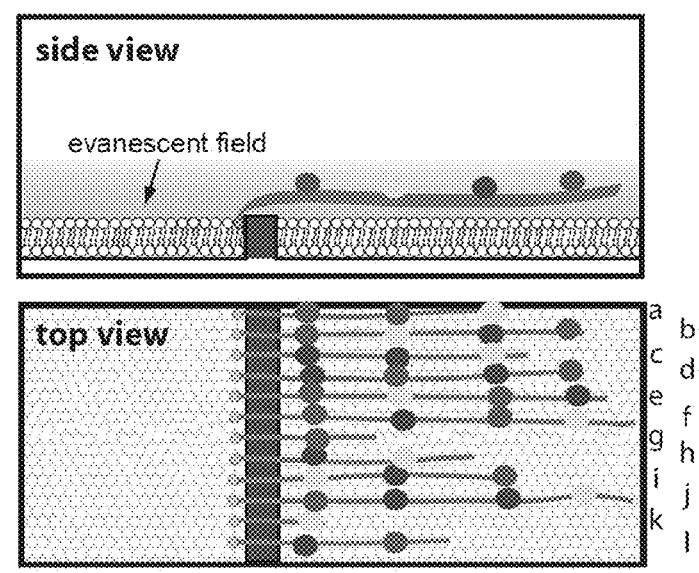
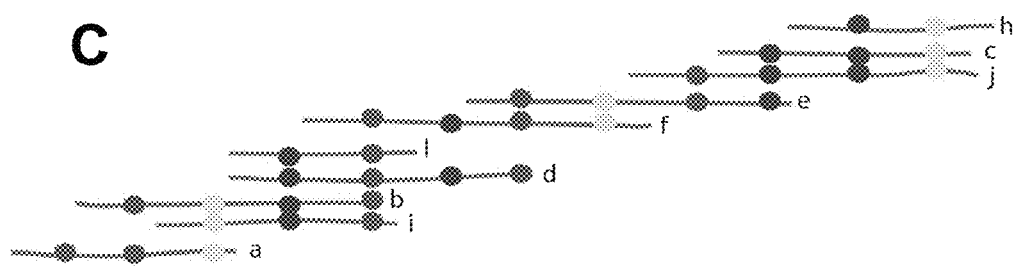
Fig. 45

1. Translocation
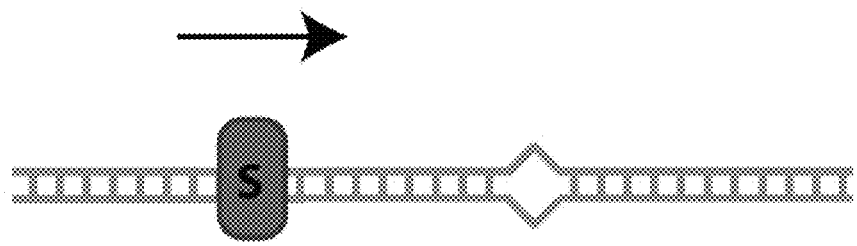
2. 1D-Diffusion
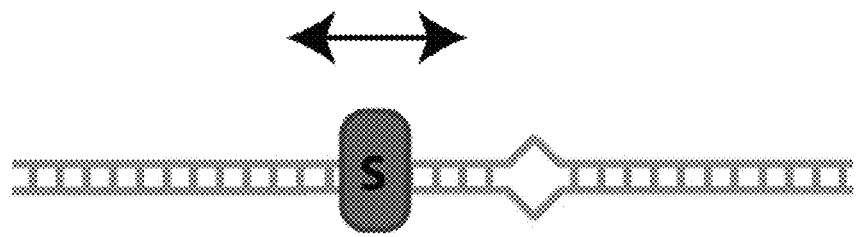
3. Random Collision
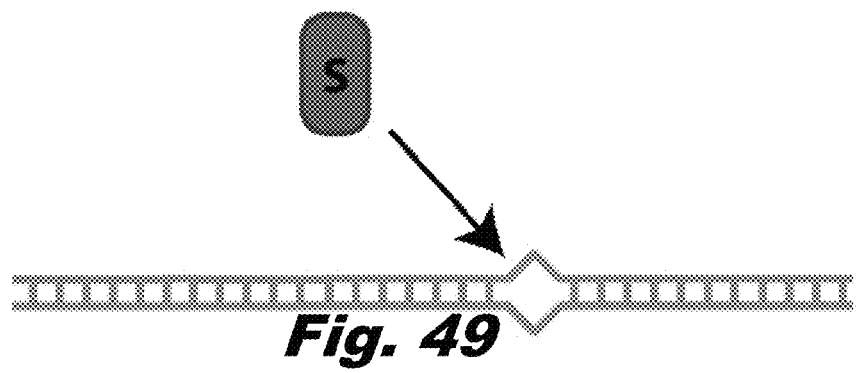
*Fig. 49*

1. Translocation
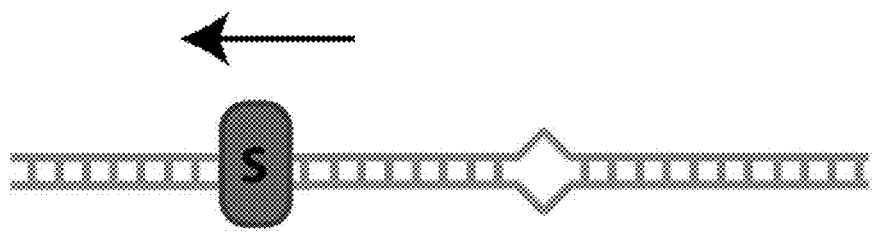
2. 1D-Diffusion
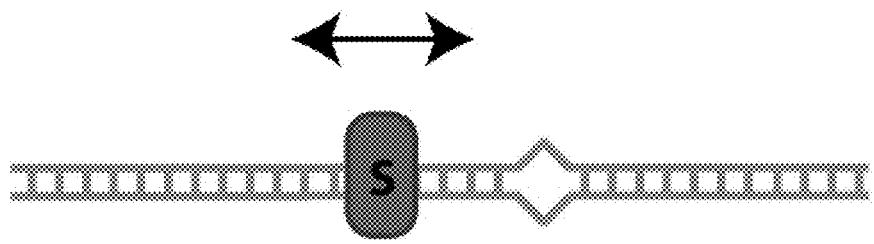
3. Stationary with DNA looping
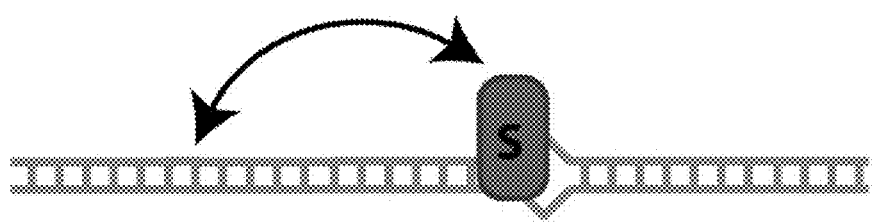
*Fig. 52*

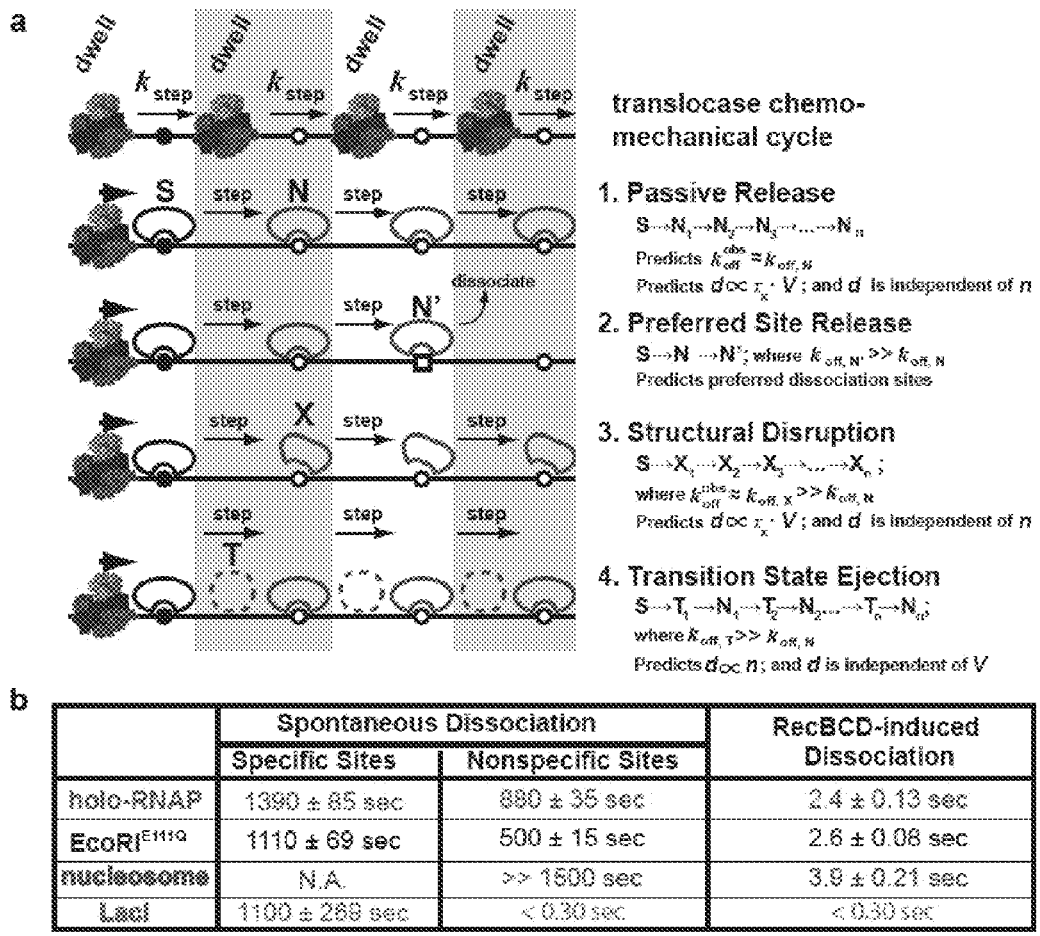
Figs. 66A-B

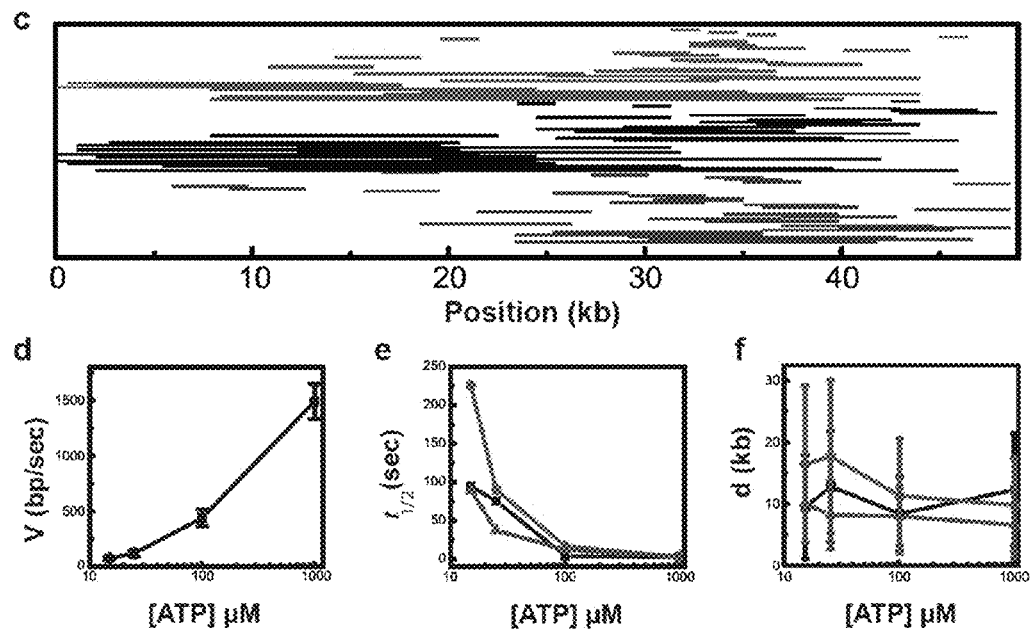
*Figs. 66C-D*

A.
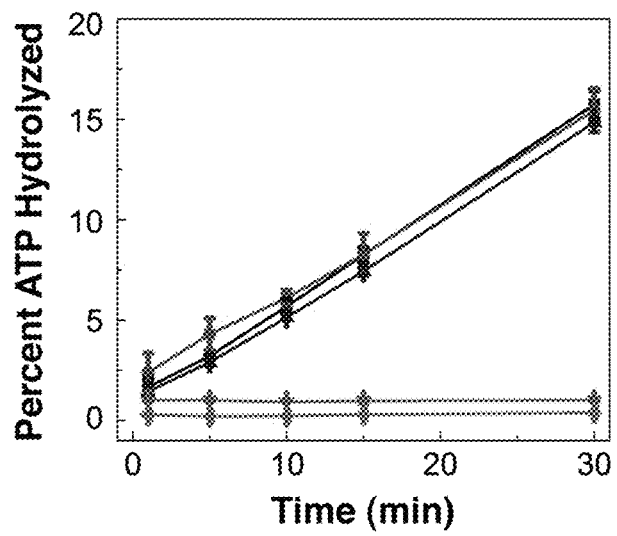
B.
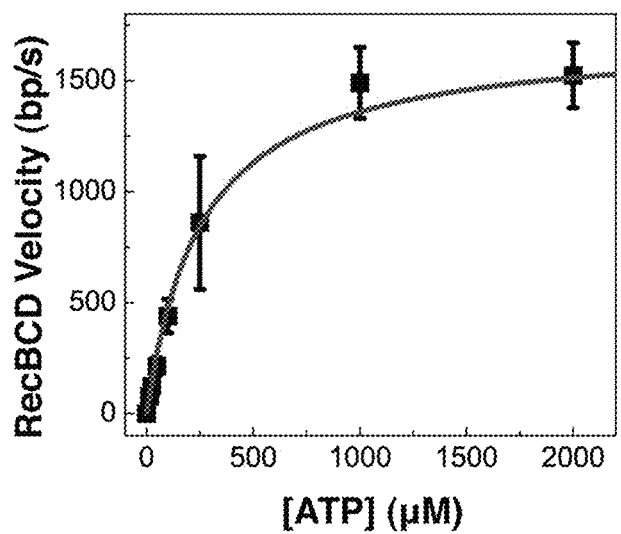
*Fig. 68*

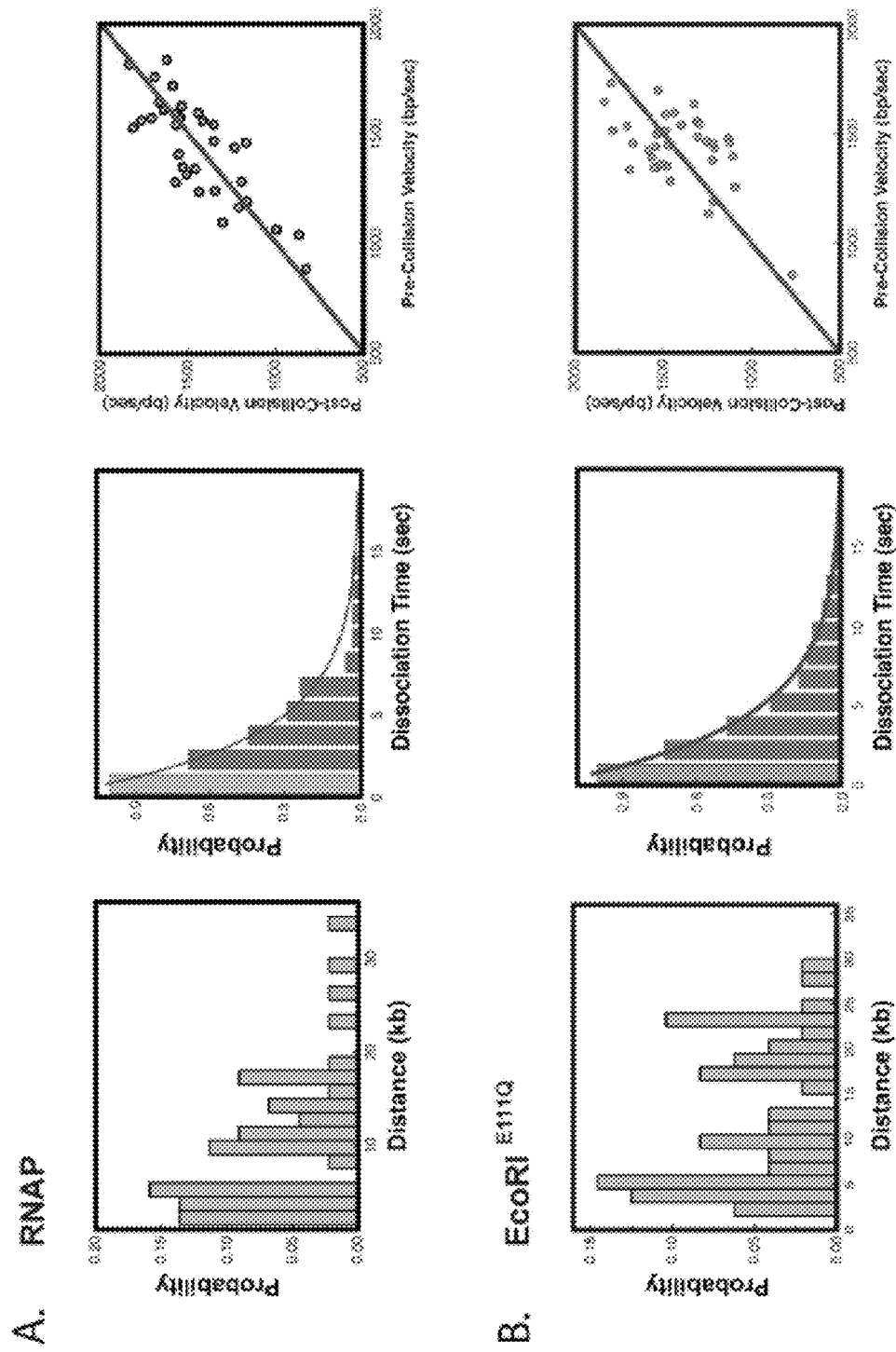
Figs. 70A-B

A.
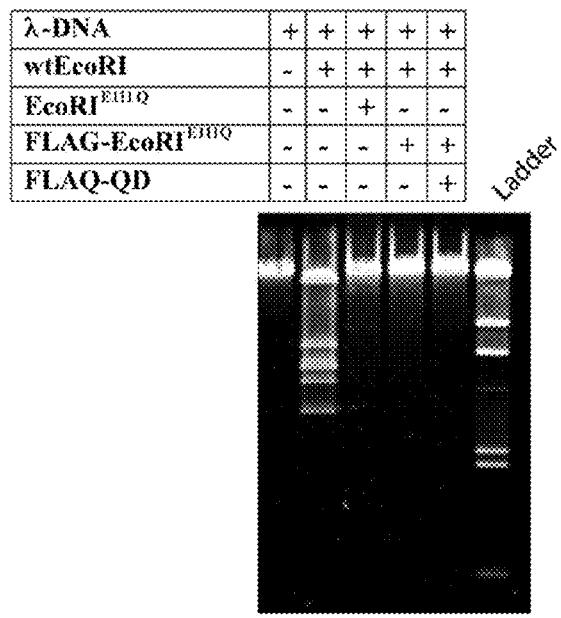
B.
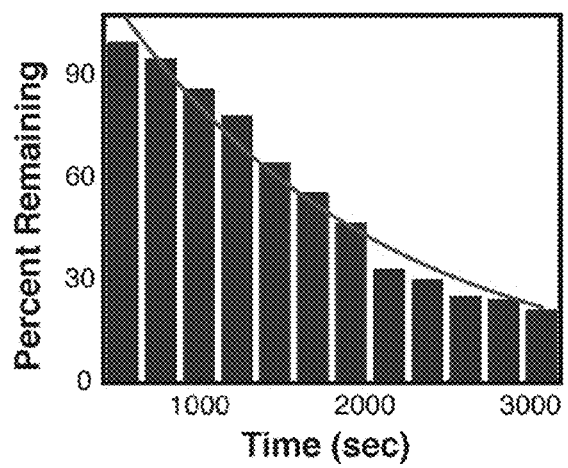
Fig. 74

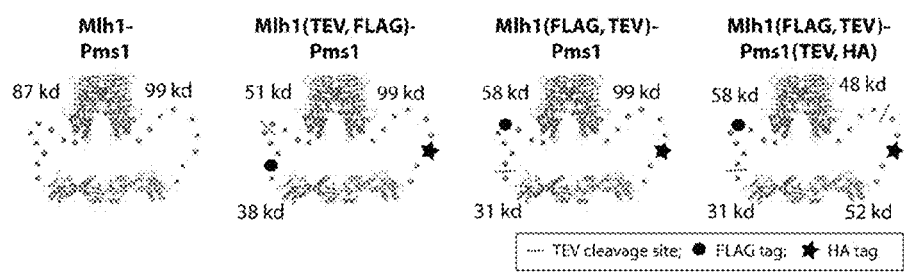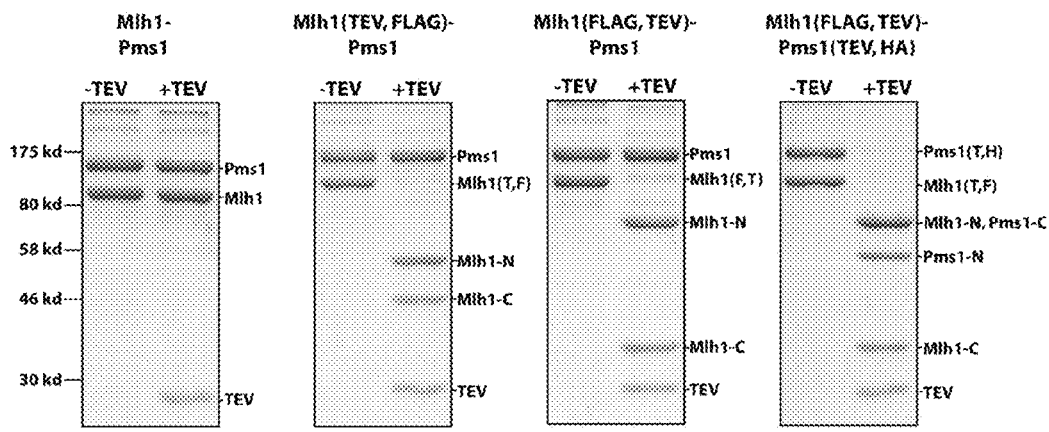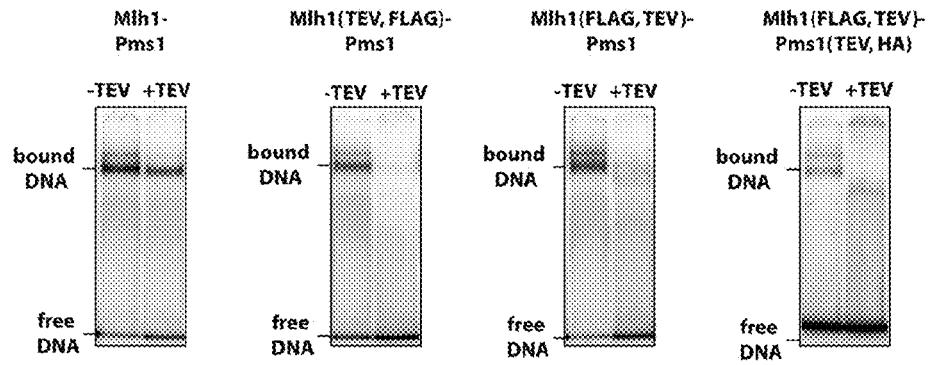
Fig. 86

GEOMETRIC PATTERNS AND LIPID BILAYERS FOR DNA MOLECULE ORGANIZATION AND USES THEREOF

This application is a continuation-in-part of International Application No. PCT/US2009/41434 filed on Apr. 22, 2009, which claims the benefit of priority of U.S. Ser. No. 61/047,657 filed on Apr. 24, 2008 and U.S. Ser. No. 61/116,815 filed on Nov. 21, 2008, the contents of each of which are hereby incorporated by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

GOVERNMENT INTERESTS

The work described herein was supported in whole, or in part, by National Institute of Health Grant Nos. PA-03-058, GM074739, GM082848. Thus, the United States Government has certain rights to the invention.

SEQUENCE LISTING

The instant application contains a Sequence Listing which has been submitted in ASCII format via EFS-Web and is hereby incorporated by reference in its entirety. Said ASCII copy, created on Nov. 23, 2010, is named 19240524.txt and is 10,165 bytes in size.

BACKGROUND OF THE INVENTION

Recent years have witnessed a dramatic increase in the use of technologies that allow the detailed interrogation of individual biological macromolecules in aqueous environments under near-native conditions. This increase can be attributed to the development and availability of highly sensitive experimental tools, such as atomic force microscopy (AFM), laser and magnetic tweezers, and fluorescence-based optical detection, all of which have all been used to study biological phenomena such as protein folding and unfolding, DNA dynamics, and protein-nucleic acid interaction.

SUMMARY OF THE INVENTION

The invention is based, in part, on the discovery that nucleic acid molecules can be disposed on a substrate and positionally aligned to allow analysis of individual nucleic acid molecules. Accordingly, in one aspect, the invention features an array that includes a substrate and nucleic acid molecules attached to the substrate. The nucleic acid molecules can be attached to the substrate by means of a linkage, e.g., a linkage between cognate binding proteins, e.g., neutravidin and biotin, or an antibody and antigen (e.g., anti-digoxigenin antibody and digoxigenin); or a crosslinking linkage, e.g., disulfide linkage or coupling between primary amines using gluteraldehyde. In some embodiments, the nucleic acid molecules are attached at one end. In some embodiments, the nucleic acid molecules are attached at both ends. In some embodiment, the nucleic acid molecule is reversibly attached to the lipid bilayer along its contour.

The array further includes a coating material, e.g., lipids, e.g., a lipid layer, e.g., a lipid bilayer, deposited onto the substrate. In one embodiment, the lipids are zwitterionic lipids. In one embodiment, polyethylene glycol (PEG) is added to the lipid bilayer. For example, 1%, 2%, 3%, 4%, 5%, 6%, 7%, 8%, 9%, 10%, 12% (w/w) or more of PEG can be included in the lipid bilayer.

The substrate can be, e.g., glass, fused silica ($SiO_2$), quartz, borosilicate glass, polydimethylsiloxane, polymerized Langmuir Blodgett film, functionalized glass, Si, Ge, GaAs, GaP, $SiO_2$, $SiN_4$, modified silicon, or a polymer (e.g., (poly)tetrafluoroethylene, (poly)vinylidenedifluoride, polystyrene, or polycarbonate). In one embodiment, the substrate is fused silica. The substrate can be, e.g., a disc, square, rectangle, sphere or circle. The substrate can be a suitable to be used in the methods described herein. In one embodiment, the substrate is a slide used for fluorescent microscopy.

The nucleic acid molecules can be, e.g., single stranded DNA, double stranded DNA, or RNA. The nucleic acid molecules can be about 10, 20, 30, 40, 50, 100, 150, 200, 500, 1000, 2000, 5000, 10000, 50000, 100000, 200000, or more nucleotides in length. The number of nucleic acid molecules that can be attached to the substrate can be determined by the size of the substrate and by the design of the array. In some embodiments, about 50, 100, 250, 500, 1000, 2000, 5000 or more nucleic acid molecules are attached to the substrate.

The nucleic acid molecules can be coupled to a label, e.g., a fluorescent label, e.g., YOYO1, or other fluorescent label described herein, or to a quantum dot.

In another aspect, the invention features an array that includes a substrate, a lipid bilayer disposed on the substrate, and nucleic acid molecules attached to the lipid bilayer by a linkage. In one embodiment, a polypeptide, e.g., neutravidin, is linked to the lipid head groups and a cognate polypeptide, e.g., biotin, is linked to the nucleic acid molecules. The nucleic acid molecules are attached to the lipid bilayer by a linkage between the neutravidin and the biotin. In some embodiments, the nucleic acid molecules are attached at one end. In some embodiments, the nucleic acid molecules are attached at both ends.

In one embodiment, the substrate further includes a diffusion barrier, e.g., a non-linear mechanical, chemical, or protein barrier, that prevents lipid diffusion. The diffusion barrier comprises a non-linear, geometric diffusion barrier. For example, the non-linear diffusion barrier can comprise a repetitive triangular wave producing a sawtooth pattern that repeats at nanometer-scale intervals, or a repetitive series of angles of varying degrees. The non-linear diffusion barrier can also comprise turns, bends, curves, or interruptions. In one embodiment, the barrier is non-linear over its entire length. In another embodiment, the barrier comprises at least one angle. In a further embodiment, the barrier comprises at least one angle less than about 180°. In another embodiment, the barrier comprises at least one angle of varying degrees. In some embodiments, the barrier comprises multiple angles of varying degrees. In another embodiment, the diffusion barrier is a non-linear, nanoscale barrier. A non-linear, mechanical barrier can be, e.g., a rough scratch or etch on the substrate, for example, wherein the scratch or etch is not linear. Protein barriers include, e.g., fibronectin. Protein barriers can be deposited onto a substrate, e.g., a substrate described herein, in well-defined patterns. Protein barriers can have a thickness of, e.g., 2, 3, 4, 5, 6, 7, 8, 9, 10, 15, 20 or more μm thick. In one embodiment, the barrier materials comprising a chemical barrier can comprise metals, such as chromium, aluminum, gold, titanium, platinum, osmium, or nickel. In another embodiment, the barrier materials can comprise metal oxides, such as aluminum oxide, or titanium oxide. In a further embodiment, the solid support comprises a geometric barrier, wherein the barrier is non-linear. In another embodiment, the barrier comprises a repetitive triangular wave. In other embodiments, the barrier forms a nanowell by connecting vertices of the non-linear, geometric barrier, while in some embodiments, the nanowell comprises a nanopore for entry of nucleic acids. In some embodiments, the non-linear, geometric barrier controls the lateral displacement of the nucleic acid molecule(s). The non-linear, geometric barrier can be generated by nanofabrication, for example, comprising electron-beam lithography or photolithographic techniques. For example, nanofabrication techniques that can lay down thin, 100 nm barriers of a metal, such as chromium, can be used.

In another aspect, the invention features an array that includes a substrate, a diffusion barrier described herein, a lipid bilayer disposed on the substrate, and nucleic acid molecules attached to the diffusion barrier by a linkage. In one embodiment, the diffusion barrier is coupled to a protein, e.g., biotin. A cognate protein, e.g., neutravidin, is then bound directly to the biotinylated diffusion barriers, and biotinylated nucleic acid molecules are attached to the diffusion barriers by binding to the cognate protein, e.g., neutravidin. In some embodiments, the nucleic acid molecules are attached at one end. In some embodiments, the nucleic acid molecules are attached at both ends.

In another aspect, the invention features a cell, e.g., a flowcell, e.g., a microfluidic flowcell, that includes an array described herein. The flowcell can be configured to allow a fluid to interact with the lipid bilayer, e.g., to flow over the lipid bilayer. In some embodiments, a substrate described herein further includes two openings, e.g., an inlet port and an outlet port. The cell, e.g., flowcell, includes the substrate, and a cover, e.g., a glass cover, e.g., a glass coverslip, adhesively attached at its perimeter to the substrate, creating a chamber between the substrate and the cover. The inlet port and the outlet port open into the chamber, allowing the application of a hydrodynamic force into the chamber and over the lipid bilayer deposited on the substrate. For example, a buffer can be forced through the inlet port into the chamber such that the buffer flows over the lipid bilayer and exits the chamber through the outlet port. In one embodiment, the flowcell further comprises a staging area, a bifurcated nanochannel, at least one pair of parallel channels, at least one pore, or a combination thereof. In another embodiment, the nucleic acid molecule of the invention is aligned along the non-linear, geometric barrier through application of a hydrodynamic force, an electrophoretic force, or a combination of the two forces.

In one embodiment, the nucleic acid molecules of the array are positioned into a desired orientation by application of a hydrodynamic force, an electrophoretic force, or combination of either, to the flowcell. For example, upon application of a hydrodynamic force to the flowcell, e.g., introduction of a buffer as described herein, the nucleic acid molecules are aligned in the direction of the hydrodynamic force. In embodiments in which the nucleic acid molecules are attached at one end, the hydrodynamic force results in the extension of the nonattached ends of the nucleic acid molecules in the direction of the flow of the hydrodynamic force. In embodiments in which the nucleic acid molecules are attached to the lipid heads of the lipid bilayer, the nucleic acid molecules will flow in the direction of the hydrodynamic force until the lipid head encounters a non-linear, geometric diffusion barrier, resulting in the extension of the nucleic acid molecule at a desired position in a desired orientation.

In one aspect, the invention provides a method for isolating a length-specific nucleic acid from a plurality of nucleic acids. The method comprises a) providing the microfluidic cell of the invention, wherein the attached nucleic acid molecule is a DNA molecule coupled to a fluorescent label that permits visualization of the DNA molecule; b) applying a first hydrodynamic or electrophoretic force perpendicular to the surface of the support to localize the attached DNA molecules to the nanowell; c) applying a second hydrodynamic or electrophoretic force tangential to the surface of the support to align the attached DNA molecules in a desired orientation within the pair of parallel channels; and d) visualizing the DNA molecule. In one embodiment, the method can optionally comprise applying continuously the second hydrodynamic or electrophoretic force tangential to the surface of the support.

In another aspect, the invention features a method for visualizing individual nucleic acid molecules. The method includes attaching nucleic acid molecules (coupled to a fluorescent label) to a substrate, to a lipid bilayer, or to a non-linear, geometric diffusion barrier, as described herein, to form an array. The array is then included in a flowcell, and the nucleic acid molecules are aligned in a desired orientation, as described herein. The arrays are then excited with a light source, e.g., a laser, at the excitation wavelength of the particular fluorescent label and the resulting fluorescence at the emission wavelength is detected. Detection of the fluorescence signal utilizes a microscope, e.g., a fluorescent microscope. In another embodiment, excitation and detection is mediated by Total Internal Reflection Fluorescence Microscopy (TIRFM), as described herein.

In another aspect, the invention features methods for analyzing the interactions between a nucleic acid and a polypeptide. The method includes, e.g., providing an array within a flowcell as described herein. The nucleic acid molecules can be aligned in a desired orientation by application of a hydrodynamic force, and the nucleic acid molecules can be visualized as described herein. A target polypeptide is then added to the flowcell, e.g., by being added to the buffer that mediates the hydrodynamic force across the array. In one embodiment, the target polypeptide is coupled to a fluorescent label that is different than the fluorescent label coupled to the nucleic acid molecule. The localization of the target polypeptide to the nucleic acid molecule can be visualized, and such localization is indicative of interaction between the target polypeptide and the nucleic acid molecule.

In one embodiment, the signals from the array are collected serially over time, allowing the movement of the target polypeptides on the nucleic acid molecules to be determined.

In one embodiment, the length of the nucleic acid molecules is determined before and after the addition of the polypeptide, wherein if the polypeptide causes the nucleic acid molecule to change length, e.g., shorten or lengthen, this indicates that the polypeptide causes a structural change in the nucleic acid molecule.

In another aspect, the invention features methods for identifying a nucleic acid sequence, e.g., a mutation in a nucleic acid sequence, that disrupts an interaction between a nucleic acid molecule and a polypeptide. The method includes providing a first array within a first flowcell as described herein. The first array contains a first population of identical nucleic acid molecules that are coupled to a first fluorescent label. The method also includes providing a second array within a second flowcell as described herein. The second array contains a second population of identical nucleic acid molecules that are coupled to a first fluorescent label. In another embodiment, the nucleotide sequence of the second population of nucleic acid molecules differs from the nucleotide sequence of the first population of nucleic acid molecules by at least one nucleotide. A polypeptide is then added to the flowcells, e.g., by being added to the buffer that mediates the hydrodynamic force across the arrays. In an embodiment of the invention, the polypeptide is coupled to a second fluorescent label, e.g., one that is different from the fluorescent label coupled to the nucleic acid molecules. The localization of the polypeptide to the nucleic acid molecules on the arrays can be visualized, and the localization of the polypeptide to the nucleic acid molecules of the first array, but not of the second array, is indicative that the nucleic acid molecules of the second array contain a nucleic acid sequence, e.g., a mutation, that disrupts the interaction between the nucleic acid molecules of the first array and the polypeptide.

In another aspect, the invention features methods for identifying an agent that disrupts the interaction of a polypeptide and a nucleic acid. The method includes, e.g., providing an array within a flowcell as described herein. The nucleic acid molecules (coupled to a first fluorescent label) can be aligned in a desired orientation by application of a hydrodynamic force, and the nucleic acid molecules can be visualized as described herein. A polypeptide is then added to the flowcell, e.g., by being added to the buffer that mediates the hydrodynamic force across the array. In another embodiment, the polypeptide is coupled to a fluorescent label that is different than the fluorescent label coupled to the nucleic acid molecule. In another embodiment, the polypeptide is a polypeptide that is known to bind to the nucleic acid molecules. The localization of the polypeptide to the nucleic acid molecule can be visualized. A candidate agent, e.g., a compound or drug, is then added to the flowcell, e.g., by being added to the buffer and whether the localization of the polypeptide can be visualized. An agent that causes loss of localization of the polypeptide anywhere along the length of the nucleic acid molecule is indicative of an agent that disrupts the interaction between the nucleic acid molecule and the polypeptide.

In another aspect, the invention features methods for sequencing a nucleic acid molecule. The method includes, e.g., providing a single stranded nucleic acid molecule, e.g., a single stranded DNA molecule. The single stranded nucleic acid molecule is mixed with DNA polymerase and a mix of fluorescently labeled nucleotide analogs, e.g., fluorescently labeled dNTPs. In another embodiment, each dNTP, e.g., dATP, dCTP, dGTP and dTTP, is coupled to a different fluorescent label. The mixture is reacted under conditions that allow the addition of the nucleotide analogs to the single stranded nucleotide molecules. The reacted nucleic acid molecules are then added to an array as described herein. The nucleic acid molecules can be aligned in a desired orientation by application of a hydrodynamic force, and the nucleic acid molecules can be visualized as described herein.

In one embodiment, the nucleic acid molecules are identical, and the sequence can be determined by parallel lines of color representing particular nucleotides across the array. In one embodiment, the nucleic acid molecules are different.

In another aspect, the invention features methods for high-throughput physical mapping of single DNA molecules, for example using restriction enzymes, hybridization with fluorescent proteins, or fluorescence in situ hybridization. In one embodiment, the method for mapping a nucleic acid molecule comprises (a) providing an array of the invention described herein, wherein the array comprises a plurality of heterogeneous nucleic acid molecules, and wherein the nucleic acid molecules are DNA molecules coupled to a first fluorescent label that permits visualization of the DNA molecules; (b) contacting a plurality of DNA probes to the DNA molecules, wherein each DNA probe is coupled to a fluorescent label that is not the first fluorescent label; (c) applying a hydrodynamic force or an electrophoretic force tangential to the surface of the support to align the DNA molecule in a desired orientation; and (d) visualizing the locations of binding of the DNA probes. In some embodiments, the plurality of nucleic acid molecules comprises heterogeneous nucleic acid molecules. In other embodiments, the plurality of nucleic acid molecules comprises identical (e.g., homogeneous) nucleic acid molecules. In further embodiments of the invention, the method further comprises: (e) contacting a restriction enzyme to the DNA molecule; (f) collecting the digested DNA molecule of interest; and (g) determining the changes in the length of the DNA molecule following the contacting step. The method can optionally comprise reversibly attaching the nucleic acid molecule along its contour to the lipid bilayer, for example by exposing the DNA molecules to a flowcell buffer contain an effective concentration of calcium. The DNA molecule can unattach itself from the lipid bilayer upon washing away the calcium present in the buffer. In one embodiment, the calcium concentration is at least about 0.5 mM, at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, at least about 10 mM, or at least about 10.5 mM.

In another aspect, the invention features a plurality of microfluidic flowcells described herein arranged in parallel. The plurality of flowcells can be used in parallel in any method described herein.

In another aspect, the invention features a diagnostic method that uses the arrays described herein for detecting a mutation in a nucleic acid. Detection can be achieved in a variety of ways including but not limited either through sequencing of the nucleic acids, or hybridization methods.

One aspect of the invention features methods for reversibly attaching a nucleic acid molecule along its contour to a lipid bilayer. The method comprises: (a) providing the array of claim 1, wherein the nucleic acid is a DNA molecule coupled to a first fluorescent label that permits visualization of the DNA molecule; (b) applying a hydrodynamic force or an electrophoretic force tangential to the surface of the support to align the DNA molecule in a desired orientation; (c) adding an effective concentration of $Ca^{2+}$ to the buffer flow; and (d) optionally washing away the $Ca^{2+}$ from the buffer. In one embodiment, the calcium concentration is at least about 0.5 mM, at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, at least about 10 mM, or at least about 10.5 mM.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-C is a diagram of lipid tethered DNA molecules aligned at a diffusion barrier. FIG. 1A shows a diagram of the total internal reflection fluorescence microscope (TIRFM) used to image single molecules of DNA. For imaging by TIRFM the long DNA molecules (48 kb) used in these studies must be extended parallel to the surface of the sample chamber in order to remain confined within the evanescent field. FIG. 1B-C depict the bilayer on the surface of a fused silica slide along with a barrier and the response of tethered DNA molecules to the application of a hydrodynamic force. The upper and lower panels in FIG. 1B-C depict views from the side and above, respectively. In the absence of buffer flow (FIG. 1B) the DNA molecules are tethered to the surface, but are not confined within the evanescent field, nor are they aligned at the barrier. As depicted FIG. 1C, when flow is applied, the DNA molecules are dragged through the bilayer until they encounter the diffusion barrier, at which point they will align with respect to one another and form a curtain of DNA molecules.

FIG. 2D shows an optical image at 10× magnification of a 2×3 series of barrier sets made of chromium deposited onto fused silica. The upstream and downstream areas are indicated and the arrow shows the direction that buffer would be flowing relative to the barrier patterns.

FIG. 3A shows an AFM image of a 10.5×10.5 μm area of fused silica with a 31 nm tall chromium barrier on the surface. An SEM image of a chromium barrier viewed from above is shown in FIG. 3B. The scale bars in FIG. 3B are divided into 100 nm increments. For comparison FIG. 3C-D show AFM and SEM images, respectively, of barriers made by manually etching the surface. The scale bars in FIG. 3D are divided into 5 μm increments. Note that the width of the manually etched barriers is comparable to the actual length of the λ-DNA molecules.

FIG. 4A shows the DNA molecules imaged at 60× magnification after they have been aligned at the barriers. The direction of buffer flow is from top to bottom and the dashed lines are to emphasize that this image comes from a surface with multiple barrier sets. There are approximately 805 DNA molecules in this single image (~150, 185, 185, 155, and 130 molecules in the $1^{st}$, $2^{nd}$, $3^{rd}$, $4^{th}$ and $5^{th}$ tiers, respectively). FIG. 4B shows the response of the DNA molecules immediately after stopping buffer flow. This shows that the molecules rapidly retract from the surface, leaving only their tethered ends within the evanescent field. In FIG. 4C, the DNA molecules have begun to diffuse away from the chromium barrier and FIG. 4D shows the same field of view immediately after buffer flow was resumed, causing the DNA molecules to realign at the barriers. FIGS. 4E-G show a 2×3 series of barrier sets viewed at 10× magnification with buffer flow on, without buffer flow, and then after resumed flow, respectively. The uneven fluorescence signal in the 10× image is due to heterogeneity in the evanescent field FIG. 5 depicts a physical mapping of a λ-DNA curtain. A curtain of λ-DNA tethered by the left ends of the molecules is shown before (FIG. 5A) and after (FIG. 5B) complete digestion with EcoRI, which yields a ~21 kb tethered product. FIGS. 5C-D show λ-DNA tethered by the right ends before and after digestion with EcoRI, which should yield a 3.5 kb tethered product. The images and histograms in FIG. 5E show the length distributions (measured from the barrier edge to the end of the DNA) of uncut λ-DNA tethered via the left end following a series of successive digests with Nhe I, Xho I, EcoRI, Nco I, Pvu I, and Sph I. The histograms in FIGS. 5F-G show the results of partial EcoRI digests with λ-DNA tethered by either the left or right ends, respectively. Fragments outside the peak values were due to either laser induced double-stranded breaks of the YOYO1 stained DNA or uncut DNA molecules.

FIG. 6A shows a simplified schematic of the TIRFM microscope and the illumination geometry used to generate the evanescent field. To make DNA curtains, the surface of a fused silica sample chamber is coated with a supported lipid bilayer and DNA molecules are anchored by one end to lipids within the bilayer. FIG. 6B shows an illustration of the surface viewed from the side in the presence and absence of buffer flow (right and left panels, respectively). Barriers engineered on the surface disrupt the bilayer and the DNA molecules accumulate against their edges when flow is applied. The pattern of the non-linear, geometric barrier is revealed when view from above FIG. 6C, and the DNA molecules load into the vertices of the adjacent triangles.

FIG. 7 are images of diffusion barriers with geometric nanowells. FIG. 7A shows an image of two barrier patterns in which parallel barriers are made in a sawtooth pattern to form geometric nanowells. This image was collected at 10× magnification after deposition of a supported lipid bilayer containing 0.1% rhodamine-DHPE (shown in red) and the barriers themselves appear black because they are not covered by lipids. FIG. 7B shows an AFM image of a 10×10 μm area of fused silica with a 20 nm tall chromium barrier with a representative non-linear, geometric pattern that repeats at 1-μm intervals. SEM images of chromium barriers viewed from above are shown in FIGS. 7C-H. The peak-to-peak distances of these patterns are 2000, 1000, 750, 500, 350, and 200 nm, for FIGS. 7C-H, respectively; SEM images are shown at the same magnification and a 200 nm scale bar is indicated in each for reference.

FIG. 10 are images of dynamic optical restriction mapping with EcoRI and BamHI. Kymograms shown in FIG. 10A-B show representative examples of real time restriction digests using either EcoRI alone or BamHI alone. The histograms below each set of kymograms represent the measured lengths of the DNA fragments observed during the course of each digest.

FIG. 13A shows a diagram of the total internal reflection fluorescence microscope (TIRFM) used to image single molecules of DNA. For imaging by TIRFM the long DNA molecules (48 kb) used in these studies must be extended parallel to the surface of the sample chamber in order to remain confined within the evanescent field. FIGS. 13B-C depict a cartoon illustration of the bilayer on the surface of a fused silica slide, and a single barrier set comprised of a linear barrier and a series of aligned pentagons separated by nanochannels. Also depicted is the response of tethered DNA molecules to the application of a hydrodynamic force. The magenta circles are the biotinylated ends and the red squares are the digoxigenin labeled ends of the DNA, respectively. The upper and lower panels in FIGS. 13B-C depict views from the side and above, respectively. In the absence of buffer flow (FIG. 13B) the DNA molecules are tethered to the surface, but are not confined within the evanescent field, nor are they aligned at the barrier. As depicted in FIG. 13C, when flow is applied, the DNA molecules are dragged through the bilayer until they encounter the linear diffusion barrier, at which point they will align with respect to one another and the DIG labeled ends become anchored to the antibody coated pentagons. DNA located between the linear barriers and the pentagons passes through the nanochannels and goes to the next available linear barrier in the pattern. The schematic in FIG. 13D highlights the variable spacing used between adjacent barrier sets within the overall pattern.

FIG. 14A shows a low magnification (20×) optical image from a section of a surface pattern with variable spacing between the different barrier sets. The distance between the first and second patterns was 100 μm, and the distance between the second and third patterns was 200 μm. A higher resolution optical image of a single barrier set collected at 100× magnification is shown in FIG. 14B and relevant pattern dimensions are indicated. An AFM image is show in FIG. 14C highlighting the height of the linear barriers and the pentagons, as well as the distance between these two barrier elements. An SEM image of a pattern with a single linear barrier and the arrayed pentagons is shown in FIG. 14D.

FIG. 15A shows an example of a double tethered curtain. The DNA molecules were stained with YOYO1 and anchored by one end to the lipid bilayer through a neutravidin-biotin interaction and anchored by the other end via an antibody-hapten linkage. Each vertical line in the region labeled "Double tethered DNA" corresponds to a single fluorescent DNA molecule. FIGS. 15B-C show examples with TIRFM images of DNA curtains aligned at the leading edge of a linear barrier before (upper panel) and after (lower panel) anchoring the second end of the molecules to the antibody coated pentagons through the brief application of a higher flow force. The flow rate used for initial alignment was 20 μl/min, and the flow rate used to anchor the second end of the DNA was 2-3 ml/min (as indicated). All images were taken in the absence of buffer flow. The experiments shown in FIGS. 15A-B used barriers and pentagons made with Ti—Au, DIG labeled DNA molecules and anti-DIG coated pentagons, whereas those shown in FIG. 15C used Cr barriers and pentagons, BrdU labeled DNA molecules, and anti-BrdU coated pentagons (as indicated). In all images, the locations of the linear barriers (L) and pentagons (P) are highlighted. The bright fluorescence signal located above the linear barriers comes from DNA molecules that are only anchored by the biotinylated end to the bilayer.

FIG. 17A shows an example of a double-tethered DNA curtain bound by QD labeled Mlh1-Pms1. The DNA is shown in green and the proteins are magenta. This image represents a single 100-millisecond image taken from a 1-minute video. FIG. 17B shows five representative kymograms made from individual DNA molecules from within FIG. 17A, as indicated with lower case letters and corresponding arrowheads.

FIG. 18A shows a diagram of the total internal reflection fluorescence microscope (TIRFM) used to image single molecules of DNA. For imaging by TIRFM the long DNA molecules (48 kb) used in these studies must be extended parallel to the surface of the sample chamber in order to remain confined within the evanescent field. FIGS. 18B-C depict a cartoon illustration of the bilayer on the surface of a fused silica slide, and a single barrier set comprised of a linear barrier and a series of aligned pentagons separated by nanochannels. Also depicted is the response of tethered DNA molecules to the application of a hydrodynamic force. The magenta circles are the biotinylated ends and the red squares are the digoxigenin labeled ends of the DNA, respectively. The upper and lower panels in FIGS. 18B-C depict views from the side and above, respectively. In the absence of buffer flow the DNA molecules are tethered to the surface, but are not confined within the evanescent field, nor are they aligned at the barrier. As depicted in FIG. 18C, when flow is applied, the DNA molecules are dragged through the bilayer until they encounter the linear diffusion barrier, at which point they will align with respect to one another and the DIG labeled ends become anchored to the antibody coated pentagons. DNA located between the linear barriers and the pentagons passes through the nanochannels and goes to the next available linear barrier in the pattern.

FIGS. 20A-B depicts designs for flowcells.

FIG. 21C shows a low magnification SEM image with a section of an arrayed pattern of rack elements. FIG. 21D shows a high magnification SEM image of a single rack pattern. A high magnification (100×) optical image of a single rack pattern is shown in FIG. 21E, and the linear barriers, pentagonal anchors, and channels between adjacent pentagons are all indicated. Also shown are color-coded arrowheads highlighting the orientation of the barriers relative to the direction of buffer flow from each of the two separate inlet channels. FIG. 21F shows an AFM image from the section a single rack along with a line profile illustrating the height of the metallic patterns

FIGS. 23A-B show an example of fluorescently tagged Msh2-Msh3 bound to curtains of DNA, before and after transiently pausing buffer flow, respectively. Proteins are shown in magenta and the DNA molecules in green. FIG. 23C shows a kymogram of Msh2-Msh3 binding distribution, and the positions of the proteins were measured as described.

FIG. 24A-D are photographic images that show DNA curtains with different separation distances. Panels FIGS. 24A-B show examples of DNA curtains assembled at barriers with 1000 nm spacing, in the presence of buffer flow and immediately after pausing flow, respectively. The molecules are 48.5 kb λ DNA stained with YOYO1. FIG. 24C-D show DNA curtains assembled at barriers with 1900 nm spacing, in the presence of buffer flow and immediately after pausing flow, respectively.

FIG. 26D is a photographic image that shows a real time AVaI restriction digest of a single DNA molecule loaded into a geometric nanowell, along with the corresponding graph of signal intensity taken from the indicated cross-section of the kymogram. The injection of AVaI is indicated with a green arrow and the individual DNA cleavage events are indicated with white arrows. Note that there are three AVaI cut sites in the 23 kb DNA, but only a subset are cut here because of the low concentration of enzyme injected. FIG. 26E is a photographic image that shows the results of the same AVaI digest when two DNA molecules are loaded into a single nanowell. Here the first cleavage event causes reduction, but not complete loss of the downstream YOYO1 signal.

FIG. 28A depicts the experimental design; full details of the nanofabrication and DNA curtain assembly can be found in Fazio et al (Langmuir. 24, 10524-10531 (2008)). YOYO1-stained DNA curtains (green) bound by QD-tagged nucleosomes are shown in FIG. 28B. The tethered end of each curtain is indicated as T1-T4, and arrows indicate the direction of flow. A kymogram illustrating five nucleosomes on one DNA molecule is shown in FIG. 28C. The nucleosomes disappear when flow is temporarily interrupted (red arrowheads), and reappear when flow is resumed (green arrowheads), verifying they are bound to the DNA and do not interact with the lipid bilayer. A longer kymogram collected without YOYO1 to avoid laser-induced photocleavage of the DNA is shown in FIG. 28D. Insets highlight 30-second windows where flow was transiently paused. Other signal gaps result from QD blinking. During a 25-minute observation 0.9% of the nucleosomes (5 of 580) moved and/or dissociated from the DNA, and the remaining 99.1% were stationary.

FIG. 31 shows the predicted and observed nucleosome distribution patterns on human β-globin DNA. FIG. 31A shows an overview of the 82-kb human β-globin locus, highlighting details of the 23-kb fragment (chr11 5,205,941-5,229,259) used in this study. Also shown are the in vivo nucleosome positions (purple) from Schones et al. (Cell. 132, 887-898 (2008)), and the ~7.2-kb deletion spanning most of the δ-globin gene and ~6-kb of upstream sequence found in Corfu δβ-thalassemia patients. Major ticks are at 1-kb intervals, and minor ticks are in 200-bp subdivisions. The nucleosome distribution patterns predicted by the Segal (magenta) and FKFM (green) models for the 23-kb fragment are shown in FIG. 31B, along with the observed patterns of nucleosome deposition determined by single-molecule imaging (blue). FIG. 31C are graphs that shows Pearson correlation analysis of the observed data for the β-globin locus compared results from the Segal (left panel) and FKFM models (right panel).

FIG. 32A shows examples of DNA that were labeled at the end or at an internal location with a single fluorescent QD. The DNA was stained with YOYO1 and is shown in green, and the QDs are shown in magenta. The top panels show images acquired during application of buffer flow to stretch the DNA, and the bottom panels show control images taken after transiently terminating buffer flow to verify that neither the DNA molecules nor the QDs were nonspecifically bound to the surface. End-labeled DNA substrates were made by annealing digoxigenin (DIG)-labeled oligonucleotides to the 12-nucleotide overhang at the right end of the λ-DNA. Internally labeled DNA substrates were constructed by treating biotinylated λ-DNA with the nicking enzymes Nb.BsmI and Nt.BstNBI (NEB) to generate nicks flanking a 16-bp region from 26,151-26,166 bps. A DIG-tagged oligonucleotide complementary the 16-bp gap was added to final concentration of 500 nM and incubated at 55° C. for 30 min to allow exchange. The reaction was cooled to room temperature followed by the addition of T4 DNA ligase. The DIG-tagged DNA substrates were assembled into DNA curtains, stained with YOYO1 and labeled with anti-DIG QDs. A histogram illustrating the locations of the engineered tags is shown in FIG. 32B. The data was collected under conditions identical to those of nucleosome position assay, and the positions of the tags were measured as described in the Methods. The internal tag was localized to within 37-bp of its actual position, and the end tag was localized to within 153-bp of its know position.

FIG. 33A-C are photographic images of blots representing the characterization of recombinant nucleosomes. FIG. 33A shows a Coomassie-stained SDS-PAGE of the purified histone octamer made with FLAG-H2B. For single molecule assays nucleosomes were assembled by 48.5-kb λ-DNA or 23-kb PCR fragment of the human β-globin locus made using the Expand 20 kb PLUS PCR system (Roche). The nucleosomes were assembled using salt dialysis (see below). The ratio of DNA to histone octamer was varied, and micrococcal nuclease assays were used to verify nucleosome assembly (FIG. 33B). FIG. 33C shows gel shift assays and antibody specificity controls using a smaller PCR fragment. The 280-bp DNA substrate containing a copy of the 601 nucleosome positioning sequence was prepared by PCR. Nucleosome assembly reactions contained 3 μg of DNA and 1.5 to 2-fold molar excess of histone octamer in 1.5 M NaCl, 10 mM Tris-Cl [pH 7.8], 1 mM EDTA. The reactions were dialyzed against a step-wise salt gradient (2 h at 1 M NaCl, 2 h at 0.8 M NaCl, 2 h at 0.6 M NaCl, 2 h at 0.4 M NaCl, and 12 h at 0.2 M NaCl) and nucleosome formation was verified by gel shift on 4% polyacrylamide. Antibody binding and specificity was also verified by gel shift after incubating 0.5-1 µg of nucleosomes with either anti-FLAG and anti-HA antibodies at 1:1 ratio for 15 minutes at 4° C.

FIG. 33D-E are graphs corresponding to the reconstitution of nucleosomes for single molecule imaging.

FIG. 34A contains predictions for λ-DNA at a range of concentration parameters as indicated at the top left corner of each panel. The prediction data set used for correlation measurements with experimental data is indicated with an asterisk (*).

FIG. 34B contains predictions for λ-DNA at a range of concentration parameters as indicated at the top left corner of each panel. The prediction data set used for correlation measurements with experimental data is indicated with an asterisk (*).

FIG. 34C-D demonstrates the predicted distributions at differing nucleosome concentrations. The Segal and FKFM algorithms contain concentration parameters for adjusting the nucleosome density on the DNA. FIG. 34C-D contains predictions for the β-globin DNA for each of the models at a range of concentration parameters as indicated at the top left corner of each panel. The prediction data sets used for correlation measurements with experimental data is indicated with an asterisk (*).

FIG. 35A-B show the Segal and FKFM predictions and the observed nucleosome positions divided into 758-bp bins for λ-DNA and the human β-globin DNA fragment, respectively.

FIG. 37A shows Coomassie-stained SDS PAGE of the reconstituted and purified histone octomers made with either H2AZ, Cse4, or Cse4/Scm3 (hexasomes), as indicated. Gel shift assays and antibody specificity controls using the 280-bp 601 PCR fragment are shown in FIG. 37B. Micrococcal nuclease footprint assays were used to verify nucleosome formation on λ-DNA FIG. 37C.

FIG. 39A shows a low magnification (20×) optical image from a section of a surface pattern with variable spacing between the different barrier sets. The distance between the first and second patterns was 100 µm, and the distance between the second and third patterns was 200 µm. A higher resolution optical image of a single barrier set collected at 100× magnification is shown in FIG. 39B and relevant pattern dimensions are indicated. An AFM image is show in FIG. 39C highlighting the height of the linear barriers and the pentagons, as well as the distance between these two barrier elements. An SEM image of a pattern with a single linear barrier (FIG. 39D) and the arrayed pentagons (FIG. 39E) is shown.

FIG. 40A shows an example of a single tethered curtain, in the absence (upper panel) and presence (lower panel) of buffer flow. FIG. 40B shows an example of a double-tethered DNA curtain in the absence of any buffer flow, illustrating that the DNA molecules remain extended even in the absence of continual hydrodynamic force. FIG. 40C shows the relative anchoring efficiency of the second DNA end as a function of the separation distance between the linear barrier and the polygon array, revealing a peak tethering efficiency corresponding to 13 µm, which is approximately equal to 80% extension of the DNA relative to its full contour length. FIG. 40D shows the percent of digoxigenin-labeled DNA that remains anchored after defined time intervals.

FIG. 41 is a schematic representation depicting a defined orientation of DNA molecules. This figure shows an example of two single tethered DNA curtains with a single DIG-Qdot tag marking the center of the DNA. FIG. 41A shows a schematic diagram of DNA substrates labeled with anti-DIG tagged quantum dots at two distinct positions. Substrate #1 is labeled at position 26,166 bp, and substrate #2 is labeled at position 33,791 bp. The ends of the DNA molecules are labeled with biotin and fluorescein, as indicated. FIG. 41B shows examples of single tethered DNA curtains made using either substrate #1 or substrate #2, and the locations of the biotin tag, the free DNA end, and the quantum dot tag are indicated. The lower panels show the measured distributions of the quantum dots tags for the two different substrates, highlighting the distinct locations.

FIG. 42A shows an example of a double-tethered DNA curtain bound by QD labeled Mlh1. The DNA is shown in green and the proteins are magenta. This image represents a single 100-millisecond image taken from a 1-minute video. FIG. 42B shows representative kymograms made from individual DNA molecules from within FIG. 42A, as indicated with lower case letters and corresponding arrowheads. FIG. 42C shows examples of DNA molecules that broke during the course of DNA collection, demonstrating that both the DNA and the bound proteins diffuse rapidly away from the surface.

FIGS. 43A-C are schematics that show reversible anchoring of DNA along its contour to a sample chamber surface.

FIGS. 44A-B are schematics that show non-destructive mapping of homogeneous DNA molecules.

FIGS. 45A-C are schematics that show non-destructive mapping of heterogeneous DNA molecules.

FIG. 49 is a schematic representing how Msh2-Msh6 survey DNA molecules.

FIG. 50A shows that biotinylated λ-DNA (48,502 bp) was tethered by both ends to solid anchor points on a microfluidic sample chamber surface otherwise coated with a lipid bilayer. Msh2-Msh6 was labeled with quantum dots (QDs) and injected into the sample chamber. FIG. 50B shows images of a YOYO1-stained DNA (green) bound by Msh2-Msh6 (magenta). When the DNA is broken, both it and the bound proteins diffuse away from the sample chamber surface.

FIG. 51A is a graph that shows representative MSD plots for four different Msh2-Msh6 complexes. FIG. 51B is a histogram of the diffusion coefficients calculated from the tracked proteins. This graph presents the cumulative information derived from 125 tracked complexes of Msh2-Msh6 in buffer containing 50 mM NaCl and either 1 mM ADP (N=97; shown in red) or 1 mM ATP (N=28; shown in blue). FIG. 51C shows a plot of the net displacement of Msh2-Msh6 from the origin after a 120 s period. FIG. 51D shows the range spanned by Msh2-Msh6 as it travels back and forth along the DNA over a 120 s period. FIG. 51E is a histogram of the apparent cumulative distance traversed by Msh2-Msh6 in 120 s. FIG. 51F is a histogram showing the average apparent velocities of the proteins calculated from the cumulative distance traveled divided by total time. The means and standard deviations for all plots were determined from Gaussian fits to the binned data.

FIG. 52 is a schematic representing mechanisms for activation of cleavage.

FIG. 54A shows an example of a kymogram showing one DNA molecule and the bound Msh2-Msh6. Arrowheads highlight the dissociation of Msh2-Msh6. FIG. 54B summarizes the behavior of 510 total Msh2-Msh6 complexes (from three separate experiments) after the injection of ATP into the sample chamber. "Distance traveled before dissociation" (x-axis) corresponds to the distance that Msh2-Msh6 moved prior to falling off the DNA. Dissociation events that occurred from internal positions on the DNA are colored red (N=149), and those that occurred at the end of the DNA molecules are colored blue (N=88).

FIG. 63A is a graph showing the distribution of QD-RNAP bound to λ-DNA. Locations of promoters are indicated; those facing left are shown blue, those facing right are red. The inset shows examples of YOYO1-stained λ-DNA (green) bound by RNAP (magenta). The tethered end of the DNA is on the left, and the free end of the DNA is on the right. FIG. 63B are kymograms of RecBCD colliding with RNAP core, holoenzyme, stalled elongation complex (EC), and stalled ECs chased with rNTPs. Gaps in magenta traces correspond to QD blinking. FIG. 63C is a graph showing the distribution of event types. FIG. 63D is a graph showing the racking data for collisions, with traces aligned at the collisions.

FIG. 64A is a histogram of EcoRI$^{E111Q}$ (upper panel, N=1481) and LacI (lower panel, N=700) bound to λ-DNA. The locations of the 5 EcoRI sites found in λ-DNA are indicated, along with examples of QD-EcoRI$^{E111Q}$ bound to YOYO1-stained λ-DNA (inset, upper panel), and examples of QD-LacI bound to the DNA (inset, lower panel) FIG. 64B is a kymogram showing RecBCD colliding with EcoRI$^{E111Q}$ or LacI (magenta), as indicated. FIG. 64C is a graph showing the distribution of event types for EcoRI$^{E111Q}$ and LacI. FIG. 64D is a graph showing the Tracking data for individual collisions.

FIG. 65A are kymograms showing RecBCD collisions with nucleosomes (magenta) that are labeled on either the H2A/H2B dimer or H3/H4 tetramer, as indicated. FIG. 65B is a graph showing the distribution of event types. FIG. 65C is a graph that shows tracking data illustrating collisions between RecBCD and nucleosomes.

FIG. 66 shows protein displacement mechanisms. FIG. 66A depicts models for protein displacement. FIG. 66B is a table showing spontaneous dissociation versus RecBCD-induced dissociation as determined from single exponential fits to dissociation data±s.d. Values for LacI nonspecific and RecBCD-induced dissociation represent upper bounds. Data are color-coded for each different protein, as indicated. FIG. 66C is a graph depicting representative sliding trajectories. Each line corresponds to the collision (right endpoint) and dissociation (left endpoint) for single proteins. FIG. 66D is a graph showing RecBCD velocity (mean±s.d.) at varying [ATP]. FIG. 66E is a graph showing protein $t_{1/2}$ at varying [ATP]. Error was ≤5.6% of the reported values. FIG. 66F is a graph showing pushing distances (mean±s.e.m.) at different ATP concentrations.

FIG. 67A is a schematic of experimental set-up. Bacteriophage λ-DNA (48,502 bp) was anchored by one end to a lipid bilayer through a biotin-streptavidin linkage and aligned within nanowells along the leading edge of a nanofabricated barrier to lipid diffusion through the application of hydrodynamic force. The distance between each nanowell was either 0.5-μm or 1.0-μm, which corresponds to the minimal separation distance between the adjacent DNA molecules within the curtain. RecBCD was loaded at the free DNA ends, excess protein flushed out, and translocation initiated by addition of 1 mM ATP (unless otherwise indicated). YOYO1 is ejected as the dsDNA is unwound and degraded, and the time-dependent decrease in DNA length provides a readout for RecBCD translocation. FIG. 67B is a representative example of a YOYO1-stained DNA curtain (with 1.0-μm nanowell spacing; top), examples of kymograms showing RecBCD translocation on λ-DNA with and without Chi (χ), as indicated (left panels), and representative tracking data that was used to determine translocation velocities (right panel). In these and all subsequent kymograms and traces the tethered end of the DNA is at the top, the free end is at the bottom, and buffer flow is from top to bottom. FIG. 67C is a histogram and FIG. 67D is a scatter plot of translocation velocities of RecBCD before and after Chi. The red line is shown as a reference with a slope of m=1.

FIG. 68 shows single molecule and bulk characterization of RecBCD. FIG. 68A is a graph of ATPase assays under single-molecule buffer conditions confirming that YOYO1 and the glucose oxidase oxygen scavenging system do not affect RecBCD activity (black squares: reactions without YOYO, blue triangles: with YOYO1, red circles: with YOYO1 and oxygen scavenging system, cyan: control without RecBCD, magenta: control without RecBCD but with YOYO1 and oxygen scavenging system). FIG. 68B is a graph of single-molecule measurement of the [ATP]-dependent RecBCD velocities at 37° C. The data is fit to a Michaelis-Menten curve with $V_{max}$ 1800±80 bp/sec and $K_m$=350±30 μM (red curve). The velocity at each ATP point is measured by fitting a histogram of at least sixty individual RecBCD traces to a Gaussian function and the error-bars correspond to the standard deviation of the fits.

FIG. 69A are salt-dependent histograms of holo-RNAP bound to λ-DNA. FIG. 69B is a histogram of core-RNAP bound to λ-DNA at 100 mM KCl. FIG. 69C is a graph of a heparin challenge of holo- and core-RNAP on DNA curtains. Over 95% of holo-RNAP remains bound after 8 minutes. The red line is a single exponential fit with a $t_{1/2}$3.4±0.03 sec (N=150). FIG. 69D is a graph of the half-life of holo-RNAP on λ-DNA promoter regions. The red line is a single exponential fit with a $t_{1/2}$23.2±1.42 min, N=58. FIG. 69E is a blot of transcription runoff assays confirm that epitope-tagged RNAP is fully active and that QDs do not inhibit activity. FIG. 69F is a graph of tracking data of individual QD-RNAPs transcribing λ-DNA in the curtain assay. Frames were acquired every 0.5 sec and smoothed with a 20 second sliding average filter. FIG. 69G is a blot of stalled elongation complexes were prepared on λ-DNA $p_L$ promoter and chased with cold rNTPs to assay transcription restart efficiency. As reported previously $G^{17}$, 100% of stalled complexes re-start transcription.

FIG. 70 is an analysis of collisions with RNAP, EcoRI$^{E111Q}$, and nucleosomes. FIG. 70A shows graphs of RNAP collisions. Left panel is a histogram of distances that RNAP holoenzyme was pushed by RecBCD. Middle panel is a graph of life times of RNAP after the collisions; blue bars represent roadblocks that were pushed along DNA, the grey bar includes lifetimes (≤1 sec) of directly ejected roadblocks, and the red line is a single exponential fit to the data. Right panel is a scatter plot showing the pre- and post-collision (while pushing RNAP) velocities of RecBCD. The red reference line has a slope of m=1. All data points fall on or near the reference line, and linear fit to the data yields a slope of m=0.994±0.02 ($R^2$=0.98), indicating no statistical difference in the velocity of RecBCD after the collisions (t-test, p=0.87). FIG. 70B shows graphs of EcoRI$^{E111Q}$ collisions. Left, middle, and right panels show EcoRI$^{E111Q}$ pushing distances, lifetime after the collisions, and a scatter plot with pre- and post-collision RecBCD velocities, respectively. All data points in the scatter plot fall on or near the reference line (m=1), and linear fit to the data yields a slope of m=1.0±0.02 ($R^2$=0.99), indicating no statistical difference in the velocity as a consequence of the collisions (t-test, p=0.55).

FIG. 72 are images showing the collision control experiments with different fluorescent tags. Robust sliding behavior was observed for: (FIG. 72A) RNAP tagged with Alexa Fluor 488 anti-FLAG antibodies, and 40-nm polystyrene fluorescent beads (conjugated with either anti-FLAG antibodies or streptavidin); (FIG. 72B) EcoRI$^{E111Q}$ tagged with either Alexa Fluor 488 anti-FLAG antibodies, or 40-nm polystyrene fluorescent beads conjugated with anti-FLAG antibodies; and (FIG. 72C) nucleosomes tagged with either Alexa Fluor 488 anti-FLAG antibodies, or 40-nm polystyrene fluorescent beads conjugated with anti-FLAG antibodies.

FIG. 73A is a kymogram of RecBCD pushing holo-RNAP on λ-DNA in a reversed orientation. FIG. 73B shows histograms of RecBCD translocation velocities as a function of ATP concentration. FIG. 73C shows kymograms of RecBCD colliding with QD-tagged holo-RNAP at 100 μM and 15 μM ATP concentration (as indicated). For experiments at 100 μM ATP, 0.2 sec frames were acquired every 0.4 seconds. Experiments at 15 μM ATP were conducted by acquiring 0.3 second frames every 1.3 seconds.

FIG. 74 shows the bulk and single molecule characterization of EcoRI$^{E111Q}$. FIG. 74A demonstrates QD-labeled EcoRI$^{E111Q}$ bound to λ-DNA protects all five cognate sites from digestion by wild-type EcoRI. FIG. 74B is a pgraph depicting the half-life of EcoRI$^{E111Q}$ on λ-DNA curtain cognate sites. The red line is a single exponential fit with a $t_{1/2}$18.5±1.07 minutes, N=102.

FIG. 75A shows LacI bound to the LacO region of λ-DNA and 98% of molecules dissociated from the DNA in the presence of 1 mM IPTG. FIG. 75B is a graph of the half-life of LacI on λ-DNA curtain LacO sites. The red line is a single exponential fit with a $t_{1/2}$11.5±0.3 seconds, N=79. FIG. 75C is a graph of the half-life of LacI on λ-DNA curtain LacO sites in the absence of IPTG. The red line is a single exponential fit with a $t_{1/2}$=1100±269 seconds, N=45.

FIG. 76A and FIG. 76B show scanning electron microscopy (SEM) images of typical etched barriers.

FIG. 78A is a schematic diagram of the DNA substrate labeled at each end with either biotin or FITC, as indicated, and labeled at an internal position with digoxigenin (DIG). The internal DIG tag was located 14,711 base pairs away from the biotinylated end of the DNA, and was labeled with an anti-DIG coated quantum dot (QD). FIG. 78B is a schematic representation of the expected location of the fluorescent QD (magenta dots) if the DNA molecules (green lines) are in the expected orientations (upper panel), the incorrect orientation (lower panel), or randomly distributed between the two possible orientations (lower panel). FIG. 78C shows an example of a double-tethered DNA curtain labeled at the internal position with the anti-DIG coated QDs; the upper panel shows a black and white image, and the lower panel shows a pseudo-colored version of the same image (the DNA is green and the QDs are magenta). Fluorescent points outside of the nanofabricated pattern represent QDs that are nonspecifically adsorbed to the bilayer. These are easily distinguished from those bound to DNA because they do not colocalize with the DNA molecules, and that are also free to diffuse in two dimensions, whereas those immobilized on the DNA are not. The patterns used in this image were made from Au (15-20 nm) with a thin (3-5 nm) Ti adhesion layer, and appear bright against a darker background. The location of each of the DNA bound QDs was determined by fitting the images to 2D Gaussian functions, as described (Prasad et al., J Mol Biol 2007, 369, 940-53), and the position data were then plotted as a histogram in FIG. 78D.

FIG. 79A is an illustration of some predicted structures for Mlh1-Pms1 based on structural and biochemical data[H17-H20]. The N-terminal domains (NTD), C-terminal domains (CTD), central pore, and linker arms are indicated. FIG. 79B is a diagram of the nanofabricated "rack" device used for making the double-tethered DNA curtains[H15]. The rack consists of linear barriers to lipid diffusion, which align the lipid-tethered DNA molecules, followed by an array of antibody-coated pentagons that provide immobile anchor points for the second end of the DNA. Pattern elements are ~20 nm tall, and the bilayer is ~5 nm thick. FIG. 79C is a photographic image of YOYO1-stained λ-DNA curtains (green; 48,502 bps) with and without QD-tagged Mlh1-Pms1 (magenta) in the top and bottom panels respectively. DNA-bound proteins were not detected in reactions using incorrect antibody-epitope pairs (not shown), and QDs alone did not bind DNA. FIG. 79D shows kymograms illustrating the motion of Mlh1-Pms1. The lower panel shows photo-cleavage (arrowhead) of a DNA during data collection. The proteins disappear from view when the DNA breaks, demonstrating that the proteins and DNA are not adsorbed to the bilayer.

FIG. 80A represents gel mobility shifts. Reactions contained 120 nM Mlh1-Pms1 and 60 nM 5'$^{32}$P-labeled 40-mer dsDNA. Antibodies were pre-incubated with Mlh1-Pms1, as indicated. FIG. 80B depicts nitrocellulose filter binding assays were performed with 100 pM 5'$^{32}$P-labeled 3 kb linear plasmid at the indicated concentrations of Mlh1-Pms1, and the percent bound DNA was determined by dividing the background subtracted counts measured for each filter by the total amount of DNA in the reactions. FIG. 80C shows the effects of antibodies and antibody-labeled QDs on the binding activity of Mlh1-Pms1 (20 nM) as determined by the nitrocellulose filter-binding assay.

FIG. 81A shows examples of MSD plots generated from tracking the motion of Mlh1-Pms1. FIG. 81B depicts diffusion coefficients derived from the MSD plots and categorized according into the different nucleotide conditions used for the measurements. Diamonds (♦) indicate the mean values, and the mean±standard deviations are color-coded (graph and inset; N≥25 for all reported diffusion coefficients). The cumulative diffusion coefficients for Mlh1-Pms1 and the previously measured values for Msh2-Msh6 are shown together for comparison[H14] and the upper boundaries for the theoretical diffusion coefficients based on models either with or without a rotational component are also shown[H14,H45]. FIG. 81C demonstrates diffusion coefficients for Mlh1-Pms1 determined at different concentrations of NaCl.

FIG. 82A is a kymogram of Mlh1-Pms1 (magenta) diffusing on a DNA molecule (unlabeled) anchored by both ends to the flowcell surface. Flow is cycled on and off as indicated. When flow is on Mlh1-Pms1 is pushed to the downstream anchored end of the DNA, but does not dissociate. FIG. 82B are kymograms of Mlh1-Pms1 dissociating from the free blunt ends (generated by SfoI digest) of single-tethered DNA molecules. FIG. 82C shows Mlh1-Pms1 (magenta) was bound to DNA (green) stained with YOYO1 and pushed repeatedly to the end of the molecule (as indicated) to verify that it did not dissociate. A DSB was introduced by laser illumination in the absence of flow. Upon breaking, the DNA retracts from the surface, as indicated by the sudden disappearance of the green signal. Flow was resumed to extend the broken DNA and push Mlh1-Pms1 towards the free end of the molecule. Mlh1-Pms1 immediately dissociates upon encountering the free DNA end (see inset). FIG. 82D shows Mlh1-Pms1 was bound to a looped DNA molecule (panel i), and slid along the arc formed by the DNA until stopping at the loop apex (panel ii). The protein remained at the DNA apex (panels iii-iv), but continued sliding down the DNA upon induction of a DSB (panel v), and immediately dissociated upon reaching the newly generated free end (kymogram vi), leaving behind the naked DNA (panel vii). FIG. 82E is a kymogram of Mlh1 bound to a double-tethered DNA molecule. In the absence of flow the proteins diffuse rapidly along the DNA, but when flow is applied they are pushed to the end of the DNA, and rapidly dissociate. Experiments in FIGS. 82A-E were collected from isolated DNA molecules, as described[H14]. The DNA in FIG. 82A, and FIG. 82B, was located with YOYO1, but the dye was removed prior to data acquisition to avoid unintentional photo-cleavage, and the experiments were conducted at 150 mM NaCl. The experiments in FIGS. 82C-E were conducted at 50 mM NaCl. In all cases, identical results were obtained ±1 mM ATP.

FIG. 83A depicts Mlh1-Pms1 (magenta) diffusing along a DNA bound by recombinant nucleosomes (green), and regions of overlapping signal are white. The nucleosomes were labeled with QDs either after conducting the Mlh1-Pms1 diffusion experiment (upper and middle panels), or before addition of Mlh1-Pms1 (lower panel). Examples of bypass and bounded diffusion are highlighted; identical results were obtained ±ATP. FIG. 83B shows Msh2-Msh6 (red) diffusing on a DNA molecule with unlabeled nucleosomes (green), and regions of overlap appear yellow. The upper and middle panels show results with unlabeled nucleosomes. The number designations (either 1 or 2) in the middle panel indicate number of QD-tagged Msh2-Msh6 molecules trapped in each region of the kymogram (6 total). The lower panel shows Msh2-Msh6 colliding with QD-labeled nucleosomes. See Supplemental Information for additional experimental details. FIG. 83C illustrates how the structures of Mlh1-Pms1 (left) and Msh2-Msh6 (right) may influence nucleosomal encounters[H18-H20,H24,H46]. The molecules are drawn to scale. The trajectory of the DNA leaving the nucleosome surface has been modified for illustrative purposes. Mlh1-Pms1 steps over the nucleosome (solid arrow). Nucleosome bypass by Msh2-Msh6 might occur by occasional hopping or 2D sliding (dashed arrows)[H8], but neither mechanism allows free mobility on a nucleosomal array.

FIG. 84A is a schematic overview of the experimental setup. A double-tethered DNA curtain (green) was prepared as described in the Materials and Methods. Streptavidin-QDs (Invitrogen; Magenta) were then anchored to the lipid bilayer, which contains a subset of biotinylated lipids, and videos were collected to determine if the anchored QDs could diffuse underneath the DNA. FIG. 84B is an image of the DNA curtain and QDs at the start of the experiment. FIG. 84C is an image showing numerous QD trajectories over an 82 second period and (FIG. 84D) eight examples of 2D particle tracking (blue or red traces) detailing movement of individual QDs as they diffuse underneath the DNA molecules. FIG. 84E depicts the final image from the data set. These results demonstrate that the anchored DNA molecules are far enough away from the surface of the microfluidic sample chamber to allow unhindered passage of a QD.

FIG. 86 shows TEV cleavage of Mlh1-Pms1 linker arms disrupts DNA-binding. FIG. 86A is a schematic overview of different TEV-containing Mlh1-Pms1 constructs. FIG. 86B is a photographic image of Coomassie-stained SDS-PAGE showing specificity of TEV cleavage for each of the different constructs. FIG. 86C depicts gel shift assays using a $^{32}$P-labeled oligonucleotide substrate±TEV cleavage. All of the proteins bind DNA before TEV cleavage, but treatment with TEV protease reduces or eliminates DNA binding activity in the bulk assay. Similarly, all of these protein constructs bound and diffused on DNA in the TIRFM assays, but we could detect no DNA binding activity in the TIRFM assays after TEV cleavage of the linker arms.

DETAILED DESCRIPTION OF THE INVENTION

Figure 1D:
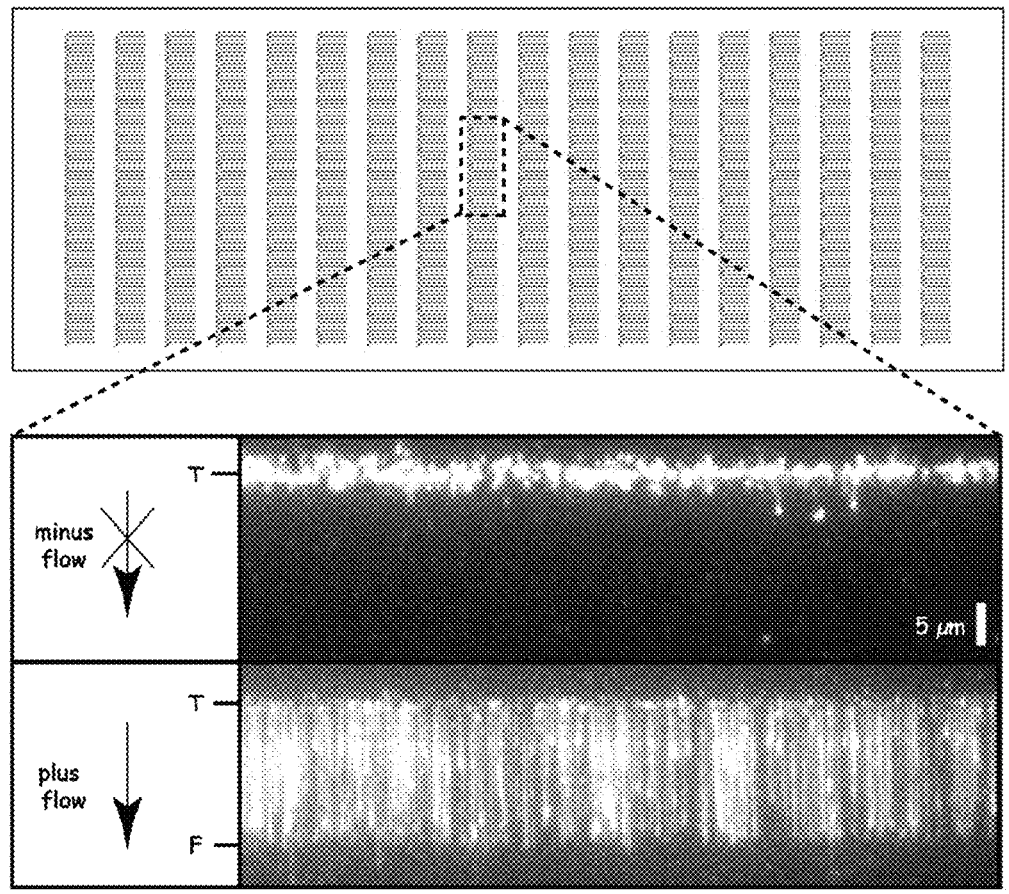
FIG. 1D is a schematic of a slide showing thousands of DNA molecules (upper panel) where in the presence of hydrodynamic force, DNA molecules are organized along the leading edge of a diffusion barrier.

The present invention is based in part on the discovery that nucleic acid molecules can be disposed on a substrate and positionally aligned along a non-linear, geometric diffusion barrier, e.g., a non-linear, geometric nanobarrier, to allow analysis of individual nucleic acid molecules. The methods and compositions described herein include a substrate, coating material, e.g., a lipid bilayer, and nucleic acid molecules attached directly to the substrate, attached to the substrate via a linkage, or attached to the lipid layer via a linkage. The nucleic acids are capable of interacting with their specific targets while attached to the substrate, and by appropriate labeling of the nucleic acid molecules and the targets, the sites of the interactions between the targets and the nucleic acid molecules can be derived. Because the nucleic acid molecules are positionally defined, the sites of the interactions will define the specificity of each interaction. As a result, a map of the patterns of interactions with nucleic acid molecules on the substrate is convertible into information on specific interactions between nucleic acid molecules and targets.

The invention is based in part on technologies useful for "high-throughput" single molecule research, which can be applied to a variety of systems involving protein-DNA interactions. For example, fluorescent nucleosomes have been reconstituted and it has been shown in the Examples below that DNA curtains can be used to define intrinsic energy landscapes. The invention is also based in part on assays that allow for directly visualization of 1-dimensional diffusion of proteins on DNA. For example, proteins involved in mismatch repair, such as Msh2-Msh6 and Mlh1-Pms1, both diffuse on DNA, but have different characteristics, suggesting that they travel along DNA via distinct mechanisms (see Examples discussed herein).

DEFINITIONS

As used herein, "geometric diffusion barriers", "geometric barriers", and "geometric barrier patterns" are non-linear, non-smooth diffusion barriers. For example, the non-linear, geometric diffusion barrier can comprise a repetitive series of angles of varying degrees. The non-linear, geometric diffusion barrier can also comprise turns, bends, curves, or interruptions. In one embodiment, the non-linear, geometric diffusion barrier is non-linear over its entire length. In another embodiment, the non-linear, geometric diffusion barrier comprises at least one angle. In a further embodiment, the barrier comprises at least one angle less than 180°. In another embodiment, the non-linear, geometric diffusion barrier comprises at least one angle of varying degrees. In some embodiments, the non-linear, geometric diffusion barrier comprises multiple angles of varying degrees. The non-linear, geometric barriers can also comprise, a repetitive non-linear, geometric shape, such as a repetitive triangular wave producing a sawtooth pattern, that repeats at nanometer-scale intervals (e.g., the interval is at least about 5 nm, at least about, 10 nm, at least about 20 nm, at least about 25 nm, at least about 30 nm, at least about 40 nm, 50 nm, at least about 100 nm, at least about 150 nm, at least about 200 nm, at least about 250 nm, at least about 300 nm, at least about 350 nm, at least about 400 nm, at least about 450, at least about 500 nm, at least about 600 nm, at least about 700 nm, at least about 750 nm, at least about 800 nm, at least about 900 nm, at least about 1000 nm, at least about 1500 nm, or at least about 2000 nm intervals). The vertex of each adjacent triangle of the repetitive triangular wave can form a nanoscale well within the non-linear, geometric barrier. This well can be referred to as a "geometric nanowell." The vertex of each adjacent triangle of the repetitive triangular wave can have peak-to-peak distances of at least about 50 nm, at least about 100 nm, at least about 150 nm, at least about 200 nm, at least about 250 nm, at least about 300 nm, at least about 350 nm, at least about 400 nm, at least about 450, at least about 500 nm, at least about 600 nm, at least about 700 nm, at least about 750 nm, at least about 800 nm, at least about 900 nm, at least about 1000 nm, at least about 1500 nm, or at least about 2000 nm.

Preparation of Substrate

Essentially, any conceivable substrate can be employed in the compositions and methods described herein. The substrate can be biological, nonbiological, organic, inorganic, or a combination of any of these, existing, e.g., as particles, strands, precipitates, gels, sheets, tubing, spheres, containers, capillaries, pads, slices, films, plates, or slides. The substrate can have any convenient shape, such as, e.g., a disc, square, sphere or circle. The substrate and its surface can form a rigid support on which to carry out the reactions described herein. The substrate can be, e.g., a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in is the art upon review of this disclosure. In some embodiments, the substrate is a made of $SiO_2$ and is flat.

In some embodiments, the substrate is coated with a linker to which the nucleic acid molecules attach. Such linkers can be, e.g., chemical or protein linkers. For example, the substrate can be coated with a protein such as neutravidin or an antibody.

In some embodiments, the substrate includes a diffusion barrier, e.g., a mechanical, chemical barrier, or protein barrier. Diffusion barriers can be prepared by applying barrier materials onto the substrate prior to deposition of the lipid bilayer; the bilayer then forms around the barriers. A mechanical barrier can be, e.g., a scratch or etch on the substrate, which physically prevents lipid diffusion.

In the case of a chemical barrier, the chemical nature of the barrier, and not its surface topography, is the primary factor in preventing lipid diffusion [Powell et al., (2002) *Molecular Cell*. 10: 1262-1263]. For example, a chemical barrier can comprise a metal, a metal oxide, or a combination thereof. In one embodiment, the metal comprises chromium, aluminum, gold, or titanium. In another embodiment, the metal oxide comprises chromium oxide, aluminum oxide, or titanium oxide. Barrier materials can be made that are similar to the thickness of the bilayer itself (e.g., 6-8 nm), or thinner than the bilayer.

Protein barriers can be deposited onto substrates, e.g., $SiO_2$ substrates, by a variety of methods. For example, protein barriers can be deposited in well-defined patterns by a process called microcontact printing [Kato et al., (2000). *Journal of Human Genetics*. 45:133-137; Davies, et al., (2001) *Molecular Cell*. 7: 273-282]. Microcontact printing uses a PDMS (poly[dimethylsiloxane]) template as a stamp for generating specific patterns on substrates. PDMS stamps can transfer proteins to a $SiO_2$ substrate in patterns with features as small as 1 µm, and thicknesses on the order of 5-10 nm [Kato et al., (2000). *Journal of Human Genetics*. 45:133-137; Davies, et al., (2001) *Molecular Cell*. 7: 273-282]. The PDMS stamps used for microcontact printing can be made, e.g., by soft-lithography as described in Davies, et al., (2001) *Molecular Cell*. 7: 273-282. Once made, the PDMS can be incubated with a solution of protein, dried, and then placed into contact with the substrate, e.g., $SiO_2$, resulting in transfer of the protein "ink" from the PDMS stamp to the substrate and yielding a pattern defined by the stamp design. For example, protein barriers can be made from fibronectin.

Figure 46:
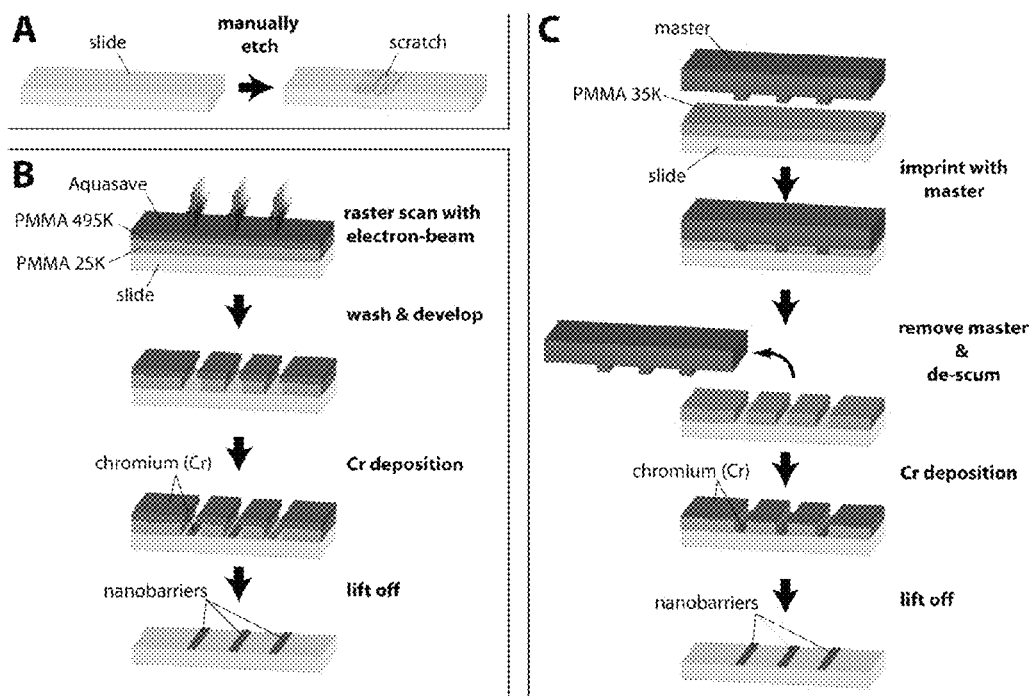
FIG. 46 is a schematic that shows formation of barriers either by etching methods (FIG. 46A) or by lithography techniques (FIG. 46B-C).

In one embodiment, electron-beam lithography can be used to engineer chromium barriers to lipid diffusion with nanometer (nm) scale features in order to make molecular curtains of DNA suspended above an inert bilayer. The shape of the barriers and the fluidity of the bilayer are used to direct the organization of the DNA into well-defined patterns in which all of the molecules are arranged in the same orientation and aligned with respect to one another. These barriers are simple and robust, they do not interfere with optical imaging of the fluorescent DNA molecules, and they can be precisely constructed at predefined locations on the surface of a microfluidic sample chamber. In another embodiment, the barriers can be generated as depicted in FIG. 46.

To the substrate is then attached a layer of a material. In one embodiment, the material is one that renders the substrate inert. For example, the material can be lipids, forming, e.g., a lipid bilayer. In another embodiment, the layer is made of zwitterionic lipids. A lipid bilayer can be deposited onto the substrate by applying liposomes to the substrate. Liposomes can be produced by known methods from, e.g., 1,2-dioleoyl-sn-glycero-3-phosphocholine (DOPC) or 0.5% biotin-phosphatidylethanolamine (biotin-PE) plus 99.5% DOPC (Avanti Polar Lipids, Alabaster, Ala.). In some embodiments, the lipid bilayer can include polyethylene glycol (PEG). For example, in embodiments where quantum dots are used to label nucleic acid molecules and/or polypeptides, PEG can be included in the lipid bilayer. PEG can also be included to make the surface of the bilayer inert to reagents added to the array.

Tethering Nucleic Acid Molecules

As described herein, the nucleic acid molecules can be attached to the substrate, to the lipid bilayer, or to the non-linear, geometric diffusion barrier, to form an array. The nucleic acid molecules can be attached by a linkage either at one end of the nucleic acid molecule or at both ends. For example, when a protein is coated on the substrate prior to the deposition of the lipid bilayer, the nucleic acid molecule can be linked to a cognate protein that binds to the protein coated on the substrate. In one embodiment, the substrate is coated with neutravidin and the nucleic acid molecule linker is biotin. Linkers can be added to the nucleic acid molecules using standard molecular biology techniques known to those of ordinary skill in the art.

Alternatively, the nucleic acid molecule can be linked to the lipid bilayer. In one embodiment, the lipid bilayer is deposited onto the substrate and a protein, e.g., neutravidin, is linked to the lipid head groups. Biotinylated nucleic acid molecules are then introduced, linking the nucleic acid molecules to the lipid bilayer.

In other embodiments, the nucleic acid molecules can be linked to the non-linear, geometric diffusion barriers. In one embodiment, the diffusion barrier is a protein, e.g., biotinylated bovine serum albumin (BSA), deposited on the substrate. Neutravidin is then bound directly to the biotinylated BSA protein barriers, and biotinylated nucleic acid molecules are linked to the biotinylated BSA protein barriers. Other known protein-cognate protein pairs can be used in the methods described herein. For example, antibodies, e.g., anti-digoxigenin antibodies, can be used as protein barriers and the cognate antigen, e.g., digoxigenin, linked to the nucleic acid molecule. In another embodiment, one end of the nucleic acid molecule is attached by a linkage, for example to the substrate or to a non-linear, geometric diffusion barrier. In a further embodiment, both ends of the nucleic acid molecule are attached by linkages, for example, to the substrate, to a non-linear, geometric diffusion barrier, or to a combination of the two surfaces. Double-tethered DNA substrates can be used for visualizing 1D diffusion For example, DNA molecules can be biotinylated at both ends. While a constant, moderate hydrodynamic flow force is applied, DNA is suspended above an inert lipid bilayer. The only interaction between the DNA and the surface is through the biotinylated ends of the molecule. For example, 80% extension of the DNA molecule corresponds to ~0.5 pN of force (e.g., where the DNA is not distorted).

Figure 13:
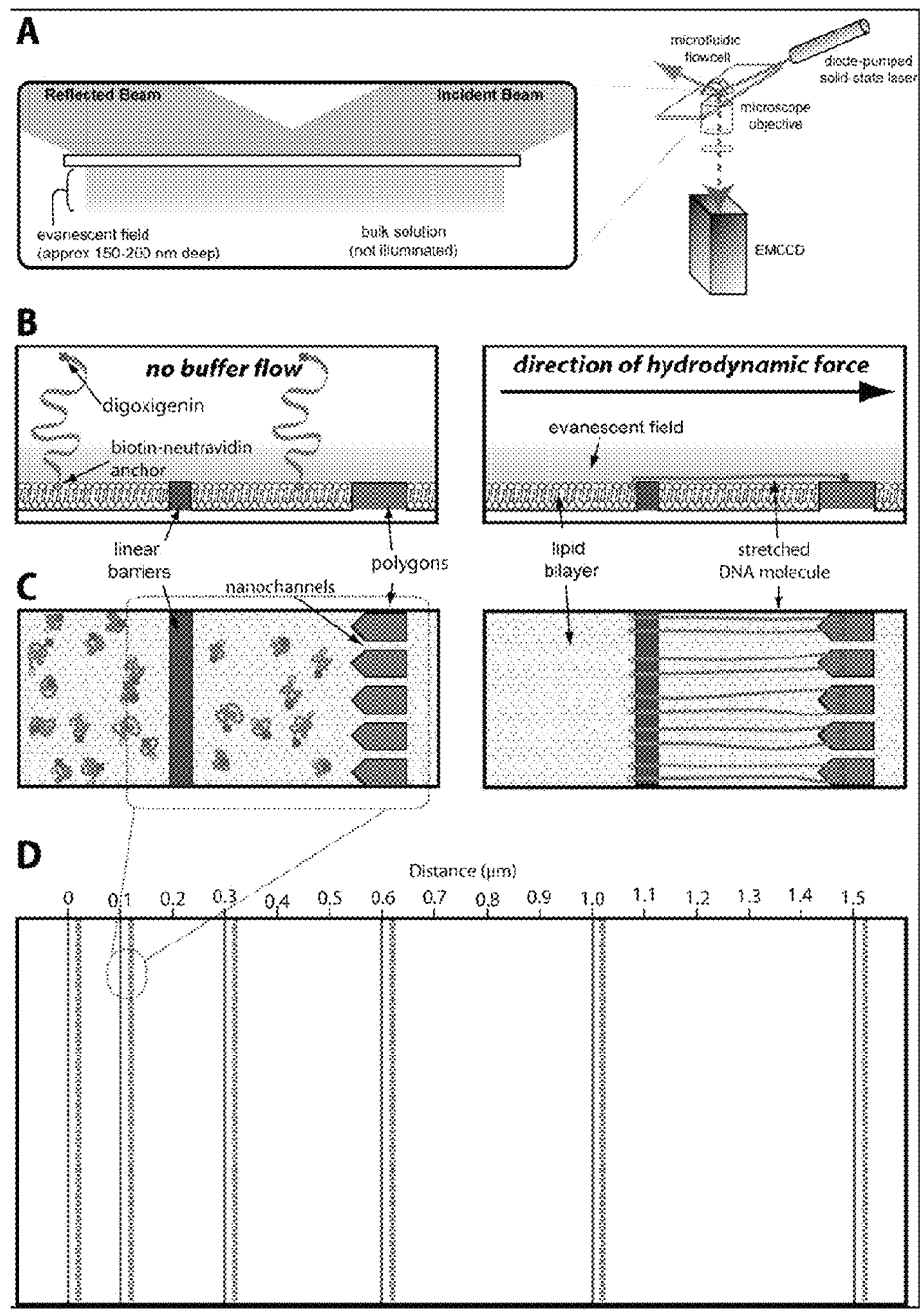
FIG. 13 is a schematic of a DNA rack design of lipid-tethered DNA molecules aligned at a diffusion barrier.
Figure 18:
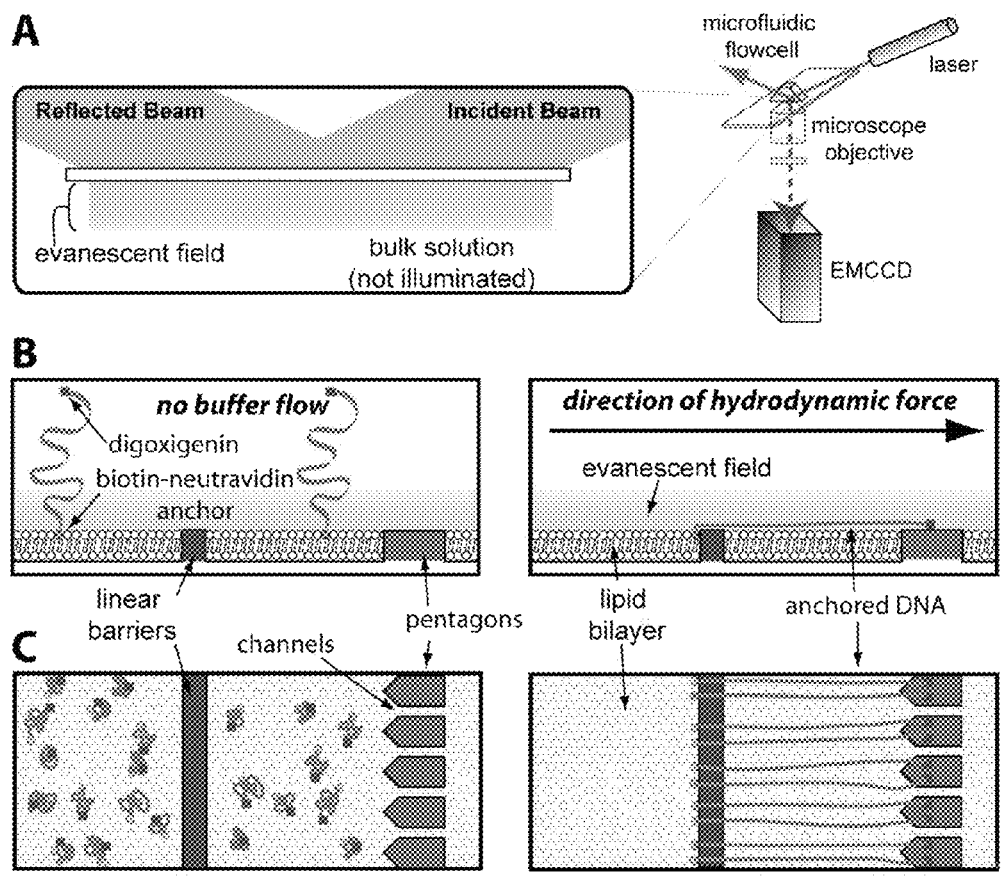
FIG. 18 is a schematic of a DNA rack design. Conceptual diagram of lipid-tethered DNA molecules aligned at a diffusion barrier.
Figure 21:
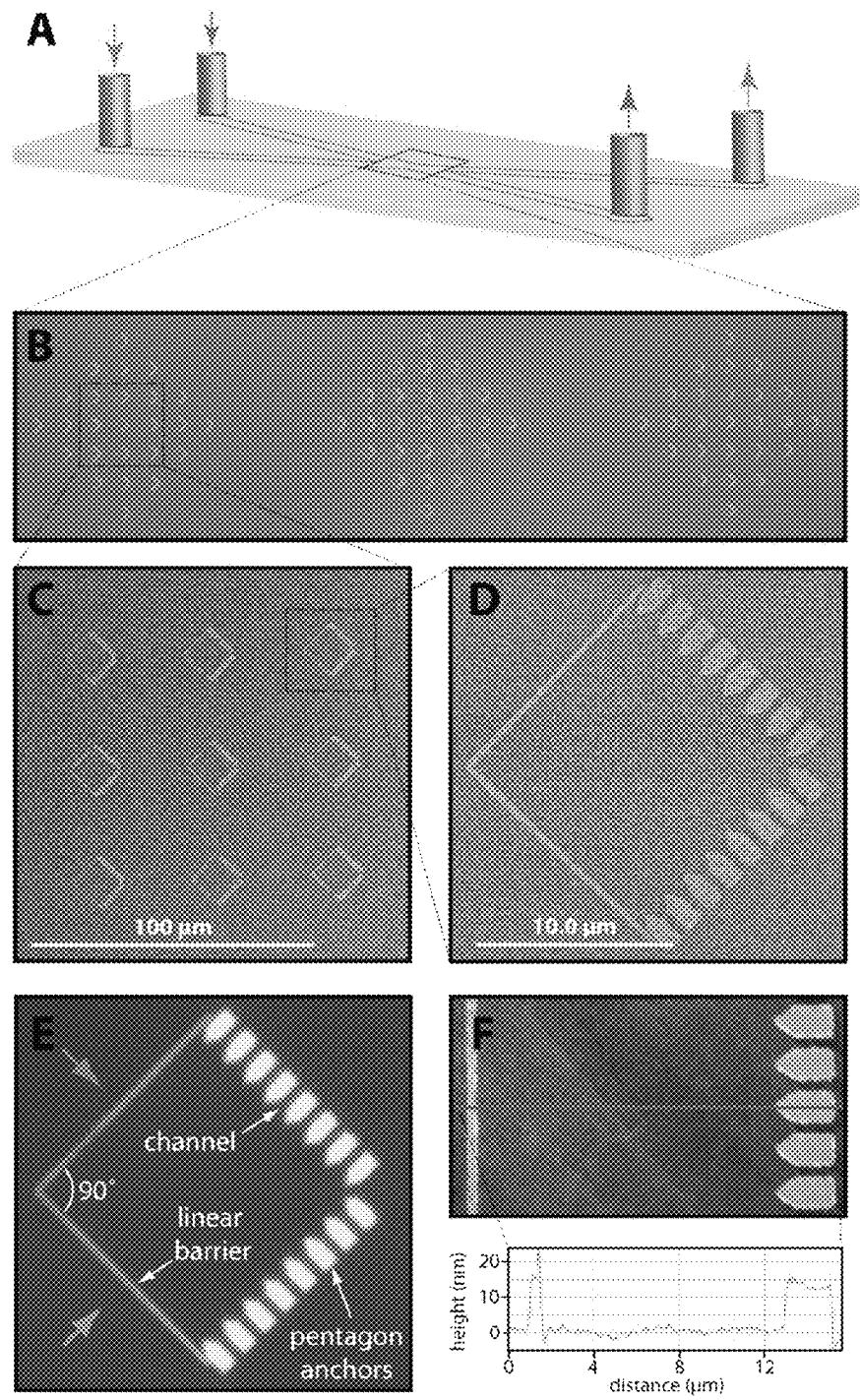
FIG. 21 depicts the design and fabrication of DNA racks. A flowcell with two orthogonal channels is shown in FIG. 21A and color-coded arrowheads indicate the two inlet ports along with the corresponding outlet ports. A low magnification (10×) optical image showing the 5×5 arrayed patterns of racks on the slide surface is shown in FIG. 21B. The patterns were located at the junction of the intersection buffer channels, as indicated. There were 25 of the 5×5 arrays on each slide, for a total of 625 individual DNA racks encompassing a surface area of 2 mm².

In some embodiments, attaching both ends of a nucleic acid molecule to the barriers, inert substrate, or a combination thereof, can generate a "rack," for example a DNA rack, as shown in FIGS. 13, 18, and 21. In some embodiments, the "rack" can be generated by reversibly anchoring the entire contour length of the nucleic acid molecule (e.g., a DNA molecule) to the lipid bilayer of an array described herein by exposing the nucleic acid molecules to an effective calcium concentration (for example, see FIG. 43C). In one embodiment, the calcium concentration is at least about 0.5 mM, at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, at least about 10 mM, or at least about 10.5 mM.

Labeling Nucleic Acid Molecules and Polypeptides

In another embodiment, the attached nucleic acid molecules and/or the interacting nucleic acid molecules or polypeptides are visualized by detecting one or more labels attached to the nucleic acid molecules or polypeptides. The labels can be incorporated by any of a number of means well known to those of skill in the art. The nucleic acid molecules on the array can be coupled to a nonspecific label, e.g., a dye, e.g., a fluorescent dye, e.g., YOYO1 (Molecular Probe, Eugene, Oreg.), TOTO1, TO-PRO, acridine orange, DAPI and ethidium bromide, that labels the entire length of the nucleic acid molecule. The nucleic acid molecules can also be labeled with Quantum dots, as described herein.

In another embodiment, the nucleic acid molecules, e.g., the nucleic acid molecules on the array or target nucleic acid molecules, can be coupled to a label at defined locations using known methods. The label can be incorporated during an amplification step in the preparation of the sample nucleic acids. For example, polymerase chain reaction (PCR) with labeled primers or labeled nucleotides will provide a labeled amplification product. The nucleic acid molecule is amplified in the presence of labeled deoxynucleotide triphosphates (dNTPs).

Alternatively, a label can be added directly to the nucleic acid molecule or to an amplification product after an amplification is completed. Means of attaching labels to nucleic acids include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the methods and compositions described herein include any composition detectable by spectroscopic, photochemical, biochemical, immunochemical, electrical, optical or chemical means. Useful labels include biotin for staining with labeled streptavidin conjugate, magnetic beads (e.g., Dynabeads™), fluorescent dyes (e.g., fluorescein, Texas red, rhodamine, green fluorescent protein, and the like, see, e.g., Molecular Probes, Eugene, Oreg.), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex) beads. Patents teaching the use of such labels include U.S. Pat. Nos. 3,817,837; 3,850,752; 3,939,350; 3,996,345; 4,277,437; 4,275,149; and 4,366,241.

In some embodiments, fluorescent labels are used. The nucleic acid molecules can all be labeled with a single label, e.g., a single fluorescent label. Alternatively, different nucleic acid molecules have different labels. For example, one nucleic acid molecule can have a green fluorescent label and a second nucleic acid molecule can have a red fluorescent label. Suitable chromogens which can be employed include those molecules and compounds that absorb light in a distinctive range of wavelengths so that a color can be observed or, alternatively, which emit light when irradiated with radiation of a particular wave length or wave length range, e.g., fluoresces.

A wide variety of suitable dyes are available, being primary chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers can be employed either by alone or, alternatively, in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes. oxacarbocyanine, marocyanine, 3-aminoequilenin, perylene, bisbenzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin. Individual fluorescent compounds that have functionalities for linking or that can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfon-atonaphthalene; N-phenyl 2-amino-6-sulfonatonaphthalene: 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl) palmitate; dansyl phosphatidylethanolamine; N,N'-dioctadecyl oxacarbocyanine; N,N'-dihexyl oxacarbocyanine; merocyanine, 4(3'pyrenyl)butyrate; d-3-aminodesoxy-equilenin; 12-(9'anthroyl)stearate; 2-methylanthracene; 9-vinylanthracene; 2,2'(vinylene-p-phenylene)bisbenzoxazole; p-bis [2-(4-methyl-5-phenyl-oxazolyl)]benzene; 6-dimethylamino-1,2-benzophenazin; retinol; bis(3'-aminopyridinium) 1,10-decandiyl diiodide; sulfona-phthylhydrazone of hellibrienin; chlorotetracycline; N(7-dimethylamino-4-methyl-2-oxo-3-chromenyl)maleimide; N-[p-(2-benzimidazolyl)-phenyl]maleimide; N-(4-fluoranthyl)-maleimide; bis (homovanillic acid); resazarin; 4-chloro-7-nitro-2,1, 3benzooxadiazole; merocyanine 540; resorufin; rose bengal; and 2,4-diphenyl-3(2H)-furanone.

The label can be a "direct label", i.e., a detectable label that is directly attached to or incorporated into the nucleic acid molecule. Alternatively, the label can be an "indirect label", i.e., a label joined to the nucleic acid molecule after attachment to the substrate. The indirect label can be attached to a binding moiety that has been attached to the nucleic acid molecule prior to attachment to the substrate. For a detailed review of methods of labeling nucleic acids and detecting labeled hybridized nucleic acids see M. Anderson's *Nucleic Acid Hybridization*, Springer Verlag, N.Y., (1999)) and Sambrook and Russell, *Molecular Cloning A Laboratory Manual*, Cold Spring Harbor Laboratory Press, NY ($3^{rd}$ edition, 2001).

Polypeptides can be visualized by coupling them to, e.g., fluorescent labels described herein, using known methods. Alternatively, other labels, such as Quantum dots (Invitrogen) can be used, as described herein.

Detecting Nucleic Acid Molecules and Polypeptides

As discussed above, the use of a fluorescent label is an embodiment of the invention. Standard procedures are used to determine the positions of the nucleic acid molecules and/or a target, e.g., a second nucleic acid molecule or a polypeptide. For example, the position of a nucleic acid molecule on an array described herein can be detected by the signal emitted by the label. In other examples, when a nucleic acid molecule on the array and a target nucleic acid molecule or polypeptide are labeled, the locations of both the nucleic acid molecules on the array and the target will exhibit significant signal. In addition to using a label, other methods can be used to scan the matrix to determine where an interaction, e.g., between a nucleic acid molecule on an array described herein and a target, takes place. The spectrum of interactions can, of course, be determined in a temporal manner by repeated scans of interactions that occur at each of a multiplicity of conditions. However, instead of testing each individual interaction separately, a multiplicity of interactions can be simultaneously determined on an array, e.g., an array described herein.

In certain embodiments, the array is excited with a light source at the excitation wavelength of the particular fluorescent label and the resulting fluorescence at the emission wavelength is detected. In certain embodiments, the excitation light source is a laser appropriate for the excitation of the fluorescent label.

Detection of the fluorescence signal can utilize a microscope, e.g., a fluorescent microscope. The microscope can be equipped with a phototransducer (e.g., a photomultiplier, a solid state array, or a ccd camera) attached to an automated data acquisition system to automatically record the fluorescence signal produced by the nucleic acid molecules and/or targets on the array. Such automated systems are known in the art. Use of laser illumination in conjunction with automated confocal microscopy for signal detection permits detection at a resolution of better than about 100 µm, better than about 50 µm, and better than about 25 µm.

The detection method can also incorporate some signal processing to determine whether the signal at a particular position on the array is a true positive or can be a spurious signal. For example, a signal from a region that has actual positive signal can tend to spread over and provide a positive signal in an adjacent region that actually should not have one. This can occur, e.g., where the scanning system is not properly discriminating with sufficiently high resolution in its pixel density to separate the two regions. Thus, the signal over the spatial region can be evaluated pixel by pixel to determine the locations and the actual extent of positive signal. A true positive signal should, in theory, show a uniform signal at each pixel location. Thus, processing by plotting number of pixels with actual signal intensity should have a clearly uniform signal intensity. Regions where the signal intensities show a fairly wide dispersion, can be suspect and the scanning system can be programmed to more carefully scan those positions.

Total Internal Reflection Fluorescence Microscopy

Total internal reflection fluorescence microscopy (TIRFM) is used to detect the nucleic acid molecules and polypeptides described herein. For TIRFM, a laser beam is directed through a microscope slide and reflected off the interface between the slide and a buffer containing the fluorescent sample. If the angle of incidence is greater than the critical angle [$\theta_c = \sin^{-1}(n_2/n_1)$; where $n_1$ and $n_2$ are the refractive indexes of the slide and aqueous samples, respectively], then all of the incident light is reflected away from the interface. However, an illuminated area is present on the sample side of the slide. This is called the evanescent wave, and its intensity decays exponentially away from the surface [Axelrod, D., (1989) *Methods Cell Biol.* 30:245-70; Forkey et al., (2000) *Progress in Biophysics & Molecular Biology.* 74:1-35]. For most applications the evanescent wave penetrates approximately 100 nm into the aqueous medium. This geometry reduces the background signal by several orders of magnitude compared to conventional fluorescence microscopy and readily allows the detection of single fluorescent molecules, because contaminants and bulk molecules in solution are not illuminated and do not contribute to the detected signal. [Forkey et al., (2000) *Progress in Biophysics & Molecular Biology.* 74:1-35]. By using TIRFM to visualize the arrays described herein, it is possible to simultaneously monitor hundreds of aligned DNA molecules within a single field-of-view.

The methods described herein use microfluidic flowcells composed of substrates that are rendered inert by deposition of a lipid bilayer as described herein. For example, DNA molecules can be suspended above an inert lipid bilayer. By applying a hydrodynamic force to the arrays described herein, the attached nucleic acid molecules are aligned in a desired orientation that is optimal for detection by, e.g., TIRFM. In one embodiment, a hydrodynamic force can be used to organize DNA molecules along the leading edge of a nanoscale diffusion barrier, for example a non-linear, geometric diffusion barrier. In another embodiment, an electrophoretic force can be used to organize DNA molecules along the edge of a barrier. Thousands of DNA molecules can be visualized in a single experiment using an array described herein. All molecules are physically aligned with one another.

A microfluidic flowcell that can be used in the methods described herein is depicted in FIG. 20. Generally, a substrate described herein is overlaid with a coverslip, e.g., a glass coverslip, to form a sample chamber, and the substrate contains an inlet port and an outlet port, through which a hydrodynamic force is applied. The hydrodynamic force can be mediated by, e.g., a buffer solution that flows over the lipid bilayer described herein. An exemplary microfluidic flowcell can be constructed from 76.2×25.4×1 mm (L×W×H) fused silica slides (ESCO Products, Oak Ridge, N.J.). Inlet and outlet holes can be drilled through the slides using, e.g., a diamond-coated bit (1.4 mm O.D.; Eurotool, Grandview, Mo.). A sample chamber can be prepared from a borosilicate glass coverslip (Fisher Scientific, USA) and, e.g., double-sided tape (~25 μm thick, 3M, USA) or a polyethylene gasket. Inlet and outlet ports can be attached using preformed adhesive rings (Upchurch Scientific, Oak Harbor, Wash.), and cured at 120° C. under vacuum for 2 hours. The dimensions of the exemplary sample chamber are 3.5×0.45×0.0025 cm (L×W×H). The total volume of the exemplary flowcell is ~4 μl. A syringe pump (Kd Scientific, Holliston, Mass.) is used to control buffer delivery to the sample chamber. This exemplary apparatus is not meant to be limiting, and one of skill in the art would appreciate modifications that could be made.

Figure 1E:
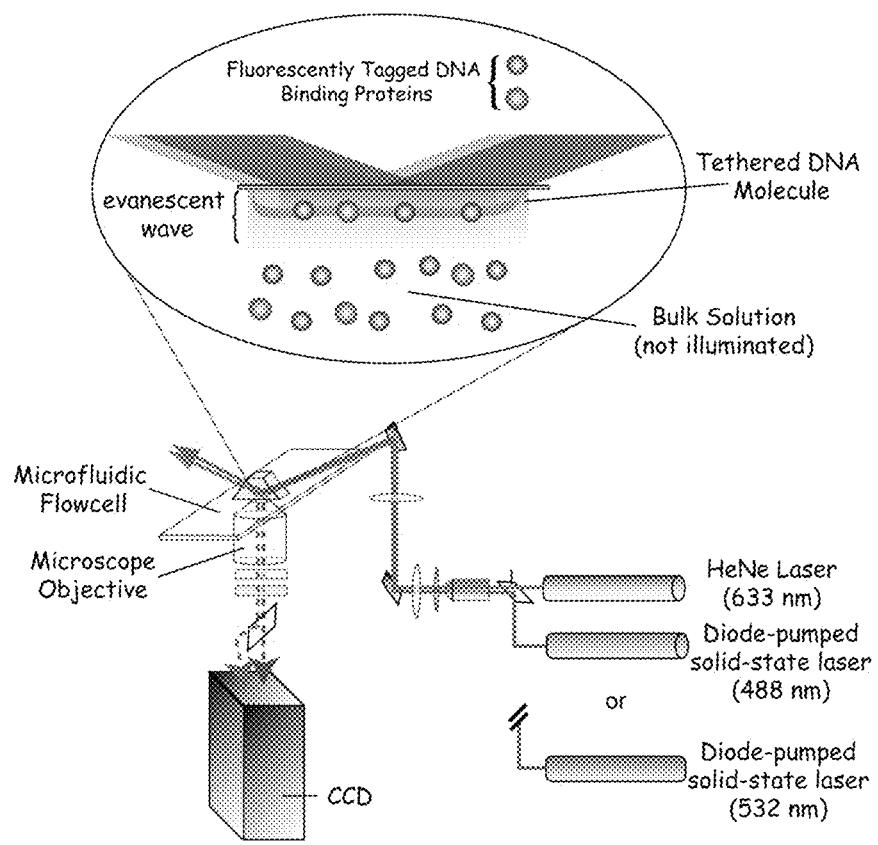
FIG. 1E is a schematic of an overview of a Total Internal Reflection Fluorescence Microscope (TIRFM).

A total internal reflection fluorescence microscope is depicted in FIG. 1E. An exemplary microscope is a modified Nikon TE2000U inverted microscope. [Groves, et al., (1998) *Langmuir* 14: 3347-3350] A 488 nm laser (Coherent Inc., Santa Clara, Calif.) and a 532 nm laser (CrystaLaser, Reno, Nev.) were focused through a pinhole (10 μm) using an achromatic objective lens (25×; Melles Griot, Marlow Heights, Md.), then collimated with another achromatic lens (f=200 mm). The beam was directed to a focusing lens (f=500 mm) and passed through a custom-made fused silica prism (J.R. Cumberland, Inc) placed on top of the flowcell. Fluorescence images were collected through an objective lens (100× Plan Apo, NA 1.4, Nikon), passed through a notch filter (Semrock, Rochester, N.Y.), and captured with a back-thinned EMCCD (Cascade 512B, Photometrics, Tucson, Ariz.). Image acquisition and data analysis were performed with Metamorph software (Universal Imaging Corp., Downington, Pa.). All DNA length measurements were performed by calculating the difference in y-coordinates from the beginning to the end of the fluorescent molecules. Diffusion estimates for the lipid-tethered DNA substrates were performed by manually tracking the tethered ends of four different molecules, and diffusion coefficients were calculated using: D=MSD/4t; where MSD (the mean square displacement) is the square of the average step size measured over time interval t (0.124 sec) [Kelman, Z., (1997) *Oncogene* 14:629-640.].

Methods for Visualizing Nucleic Acid Molecules and Polypeptides

The arrays described herein can be used to detect individual nucleic acid molecules, e.g., nucleic acid molecules coupled to a label. For example, an array can be constructed as part of a microfluidic flowcell described herein. The nucleic acid molecules, e.g., labeled nucleic acid molecules, can be attached to a substrate, to a lipid bilayer, or to a non-linear, geometric diffusion barrier, as described herein. Upon the application of hydrodynamic force, e.g., introduction of a buffer as described herein, the nucleic acid molecules are aligned in direction of the hydrodynamic force, with the nonattached ends of the nucleic acid molecules extending in the direction of the flow of the hydrodynamic force. Individual nucleic acid molecules on the array can be visualized before and/or after the application of the hydrodynamic force using, e.g., TIRFM as described herein.

In some embodiments, the interactions of nucleic acid molecules on the arrays with target polypeptides are determined. The nucleic acid molecules can be visualized before and/or after the application of a hydrodynamic force, as described herein. To visualize the interactions with target polypeptides, the polypeptides can be coupled to a label and introduced into the array, e.g., a microfluidic cell including the array, as a component of the buffer that mediates the hydrodynamic force. Individual nucleic acid molecules and individual target polypeptides can be visualized, e.g., by TIRFM as described herein, and interactions can be determined by colocalization of the signals from the nucleic acid molecules and the polypeptides. Such interactions can be further analyzed by collecting signals over a period of time. Such methods can be used to visualize, e.g., the movement of polypeptides along the length of individual nucleic acid molecules, as described herein.

Methods for High-Throughput Screening of Compounds

The methods and compositions described herein can be used to screen for compounds, e.g., drug compounds, that affect, e.g., disrupt, the interactions between nucleic acid molecules and polypeptides. For example, an array can be constructed as part of a microfluidic flowcell described herein. The nucleic acid molecules, e.g., labeled nucleic acid molecules, can be attached to a substrate, to a lipid bilayer, or to a non-linear, geometric diffusion barrier, as described herein. To visualize the interactions with target polypeptides, the polypeptides can be coupled to a label and introduced into the array, e.g., a microfluidic cell including the array, as a component of the buffer that mediates the hydrodynamic force. In some embodiments, the polypeptides are known to interact with the nucleic acid molecules, and the interactions are visualized as described herein. For example, the polypeptides can be proteins involved in DNA replication, recombination and/or repair. Candidate compounds can then be added to the array, e.g., as a component of the buffer that mediates the hydrodynamic force, and the effect of the compound on the interactions between individual nucleic acid molecules and the polypeptides can be visualized. Compounds that disrupt the interactions can be visually identified. Such methods can be automated.

For example, the methods described herein can be used to screen for therapeutic compounds to treat cancer, e.g., cancer of the breast, prostate, lung, bronchus, colon, rectum, urinary bladder, kidney, pancreas, oral cavity, pharynx, ovary, skin, thyroid, stomach, brain, esophagus, liver, cervix, larynx, soft tissue, testis, small intestine, anus, anal canal, anorectum, vulva, gallbladder, bones, joints, hypopharynx, eye, nose, nasal cavity, ureter, gastrointestinal tract; non-Hodgkin lymphoma, Multiple Myeloma, Acute Myeloid Leukemia, Chronic Lymphocytic Leukemia, Hodgkin Lymphoma, Chronic Myeloid Leukemia and Acute Lymphocytic Leukemia.

Methods for High-Throughput Sequencing of Nucleic Acid Molecules

The methods and compositions described herein can be used to sequence nucleic acid molecules. The arrays described herein can be constructed with identical nucleic acid molecules, e.g., single stranded DNA molecules, or with different nucleic acid molecules, e.g., single stranded DNA molecules. Before attaching the DNA molecules to the substrate, an oligonucleotide primer is annealed to the DNA molecules. Polymerase is then added along with the fluorescent dNTP mix. Such methods are known in the art. Fluorescent nucleotide analogs that do not terminate extension of the DNA strand are used. The DNA molecules are then attached to the substrate and the array is visualized as described herein.

The color of the nucleotide incorporated into the growing chain reveals the sequence of the DNA molecules. If all of the DNA molecules within the array are identical, then the incorporation of the first nucleotide during polymerization will yield a fluorescent line extending horizontally across the array. Subsequent nucleotide addition will also yield horizontal lines and the color of each line will correspond the DNA sequence. When sequencing different DNA molecules, the differences in DNA sequences are revealed as the incorporation of different fluorescent nucleotides across the array, rather than the lines of identical color seen when sequencing identical DNA molecules. In some embodiments, these methods are automated.

EXAMPLES

Examples are provided below to facilitate a more complete understanding of the present invention. The following examples illustrate the exemplary modes of making and practicing the present invention. However, the scope of the invention is not limited to specific embodiments disclosed in these Examples, which are for purposes of illustration only, since alternative methods can be utilized to obtain similar results.

Example 1

DNA Curtains and Nanoscale Curtain Rods: High-Throughput Tools for Single Molecule Imaging Single molecule visualization of protein-DNA complexes can reveal details of reaction mechanisms and macromolecular dynamics inaccessible to traditional biochemical assays. However, these techniques are often limited by the inherent difficulty of collecting statistically relevant information from experiments explicitly designed to look at single events. New approaches that increase throughput capacity of single molecule methods have the potential for making these techniques more readily applicable to a variety of biological questions involving different types of DNA transactions. Here we present a method for organizing DNA molecules into curtains along the leading edges of nanofabricated chromium barriers, which are located at strategic positions on a fused silica slide otherwise coated with a supported lipid bilayer. The individual molecules that make up the DNA curtains are visualized by total internal reflection fluorescence (TIRFM) allowing simultaneous imaging of thousands of perfectly aligned molecules. These DNA curtains present a robust and powerful experimental platform portending massively parallel data acquisition of individual protein-DNA interactions in real time.

Single-molecule techniques have revealed many insights into previously inaccessible aspects of biology and this field is now poised to profoundly impact the way that all biological macromolecules can be studied. However, many single-molecule methods suffer from disadvantages that limit their broader application, and meeting the oncoming challenges will require the development of more robust, user-friendly, high-throughput experimental platforms that can be readily applied to a broad range of biochemical systems.

For example, one common problem of many single molecule techniques is the requirement for the macromolecules under investigation be anchored to a solid support surface, which is unlike anything encountered within a cellular environment. It is essential to minimize nonspecific interactions with the surface that can perturb their biological properties. Traditional approaches for passivating surfaces have included nonspecific blocking agents (e.g. BSA or casein) or covalent modification with polyethylene glycol (PEG) (A1, A2). Nonspecific blocking proteins often do not work well enough to prevent surface adsorption of other molecules (A3). PEGylated surfaces are efficient at preventing nonspecific interactions between proteins or nucleic acids and the underlying surface, but PEG alone can not be sufficient in all cases. More recently, vesicle encapsulated reactions have been used in single molecule analysis (A4, A5). Vesicle encapsulation is a very promising approach that makes use of the native environment provided by lipid membranes, but has limited potential for biochemical experiments involving macromolecules that can not be confined within vesicles or those requiring successive addition of high-molecular weight components.

Single molecule techniques are also impeded by the difficulty of collecting statistically relevant information using procedures designed to image just one or at best a few molecules at any given time. This can be problematic when the reactions under investigation require the use of long DNA substrates, especially when the reactions themselves are inefficient and/or involve rare intermediates. Procedures for anchoring numerous, long DNA molecules to surfaces are present in the literature, and each has great potential for specific situations, but they also suffer from specific drawbacks with respect to biochemical applications. For example Bensimon et al., developed "DNA combing" (A6), which has evolved into a powerful tool (reviewed in (A7)). Combed DNA is anchored to a hydrophobic glass slide, and aligned with a receding air-water meniscus, yielding molecules adhered to the glass by multiple contact points and stretched ~150 percent beyond the length of normal B-DNA. The hydrophobic surfaces required for combing and the resulting distortion of the DNA can not be compatible with many proteins. In addition, while the combed DNA molecules are aligned along a common direction their ends are not aligned relative to one another nor is the orientation of the DNA defined with respect to its sequence. In another elegant approach, Kabata and colleagues reported that "belts" of λ-DNA could be stretched between two aluminum electrodes by dielectrophoresis, which they used to visualize the motion of RNAP and EcoRI by fluorescence microscopy (A8, A9). However the molecules in these belts are not oriented in the same direction with respect to their sequence, it remains unclear how the DNA links to the aluminum, and broader use of this technique has not been realized (A10). Recently, Guan and Lee have demonstrated that highly ordered arrays of DNA molecules can be stamped onto PDMS (polydimethyl siloxane) with an intriguing method based on molecular combing (A11). This technology is promising, but protein adsorption to unmodified PDMS can present a limitation for biochemical applications. Prentiss and colleagues have used an approach in which magnetic beads were linked to the free ends of DNA molecules anchored to a glass surface (A12). Kim et al., reported a similar approach, in which they anchored molecules of λ-DNA to a PEGylated surface and stretched the DNA with buffer flow (A13). In each of these examples they concurrently detect ~100-200 molecules, but required 10× magnification to expand the field-of-view, thus the overall density of the anchored DNA remained quite low (A13). Finally, Schwartz and co-workers have pioneered single DNA molecule optical mapping techniques (A14, A15), but these approaches may not be applicable for real time biochemical analysis of protein-DNA interactions.

To address these challenges we have developed "DNA curtains", which allow simultaneous imaging of on the order of one hundred individual DNA molecules within a single field-of-view (A16). Curtains are assembled by anchoring one end of a biotinylated DNA molecule to a lipid bilayer, which provides an inert environment compatible with a wide range of biological molecules (A17). The bilayer also permits long-range two-dimensional motion of the lipid-tethered DNA molecules. We have taken advantage of this mobility by using hydrodynamic force to organize the DNA molecules at microscale diffusion barriers, which are manually etched into the surface of the flowcell and oriented perpendicular to the direction of buffer flow. Lipids within the bilayer can not traverse the etched barrier (A18), therefore the lipid-tethered DNA molecules accumulate along the leading edges of these barriers (A16). A drawback of this approach is that manual etching greatly limits user control over the dimensions and locations of the microscale diffusion barriers. The etched barriers also compromise the quality of the optical surface, leading to problems such as light scattering, uneven alignment of DNA, nonspecific protein adsorption, inefficient coverage of the viewing area, and a high failure rate. Together these problems can undermine the use of DNA curtains for single-molecule biological research.

In this work, we use electron-beam lithography to engineer chromium barriers to lipid diffusion with nanometer (nm) scale features in order to make molecular curtains of DNA suspended above an inert bilayer. The shape of the barriers and the fluidity of the bilayer are used to direct the organization of the DNA into well-defined patterns in which all of the molecules are arranged in the same orientation and aligned with respect to one another. These barriers are simple and robust, they do not interfere with optical imaging of the fluorescent DNA molecules, and they can be precisely constructed at predefined locations on the surface of a microfluidic sample chamber. Using these nanoscale barriers we can concurrently image several hundred and even several thousand aligned DNA molecules in a single field-of-view. These uniform patterns of DNA provide a unique and powerful experimental platform enabling massively parallel data acquisition from thousands of individual molecules and offer a myriad of potential applications.

Results

Nanoscale Barriers to Lipid Diffusion.

The use of mechanical or chemical barriers to corral lipids within supported bilayers has been pioneered by S.G. Boxer and colleagues (A20). Inspired by these studies, we demonstrated that mechanical barriers to lipid diffusion can also be used to organize DNA molecules into curtains at defined locations on a fused silica surface (A16). We have shown that these curtains serve as a highly effective experimental platform for the study of protein-DNA interactions at the single molecule level (A21-23). The general principles behind this approach are outlined in FIG. 1. To make the curtains, DNA is first anchored by one end to a supported lipid bilayer coating the surface of the sample chamber (FIGS. 1B and 1C). In the absence of a hydrodynamic force the molecules are randomly distributed on the surface, but lie outside of the detection volume defined by the penetration depth of the evanescent field (~150-200 nm) (A24). Application of flow pushes the DNA through the sample chamber with one end anchored to the bilayer. The barriers are oriented perpendicular to the direction of flow at strategic locations in the path of the DNA (FIGS. 1B and 1C); this halts the movement of the molecules causing them to accumulate at the edges of the barriers where they are extended parallel to the surface, enabling visualization along their full contour length by TIRFM (A16).

Figure 2:
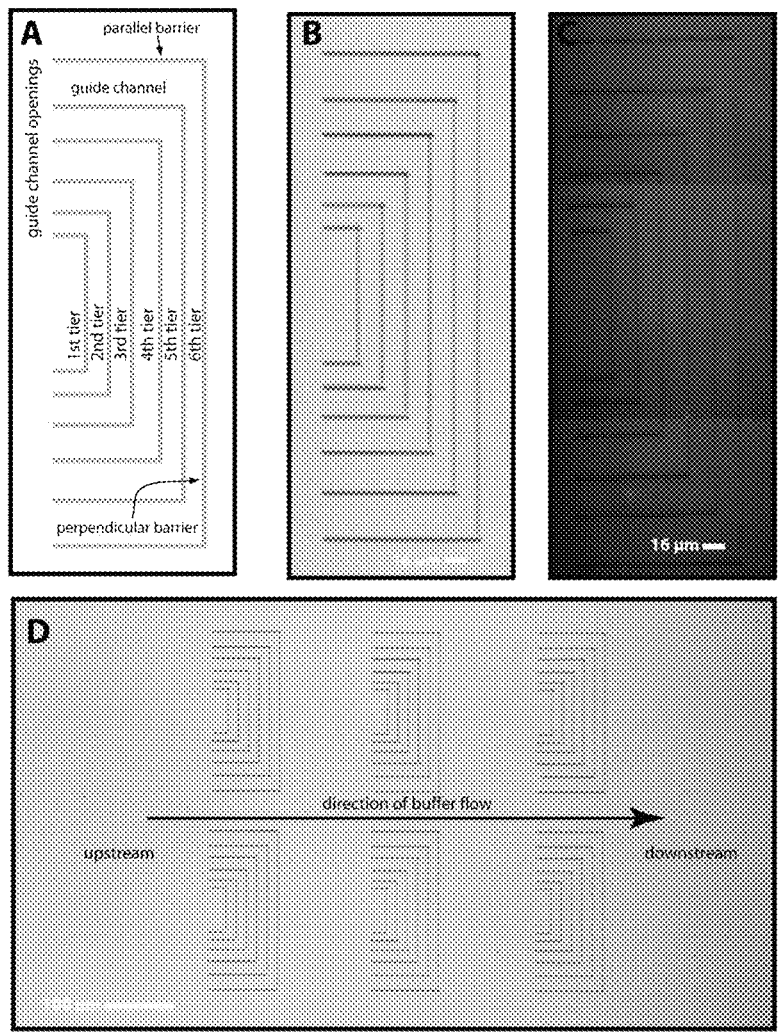
FIG. 2 is an image of patterned chromium diffusion barriers. The overall design of the desired barrier patterns is shown in FIG. 2A and the key features of the barriers are indicated. A magnified optical image of a single barrier set is shown in FIG. 2B and a composite fluorescence image of a barrier set after deposition of a bilayer containing 0.5% rhodamine-DHPE is shown in FIG. 2C.

In the past we used micrometer-scale diffusion barriers prepared by manually scoring the surface with a diamond-tipped scribe (A16, A19, A21-23). Manual etching is simple, yet inherently problematic because it is difficult to control. As an alternative we sought to apply lithographic techniques for generating precisely nanoscale patterned barriers that could be used to organize DNA molecules into curtains, making the most efficient use of available surface area. FIG. 2A shows a cartoon representation of a desired surface pattern comprised of an interlocking series of bracket-shaped barriers, and the important features of the design are indicated. Guide channels oriented parallel to the direction of flow ensure efficient capture of approaching DNA molecules tethered to the bilayer. Perpendicular barriers form the "curtain rods" against which the DNA molecules are aligned. The parallel barriers of the guide channels also prevent the molecules from sliding off the edges of the perpendicular barriers when buffer flow is transiently paused (see below). Collectively, these features can organize the tethered DNA molecules into curtains wherein all of the constituent molecules are aligned in the same orientation.

Figure 3:
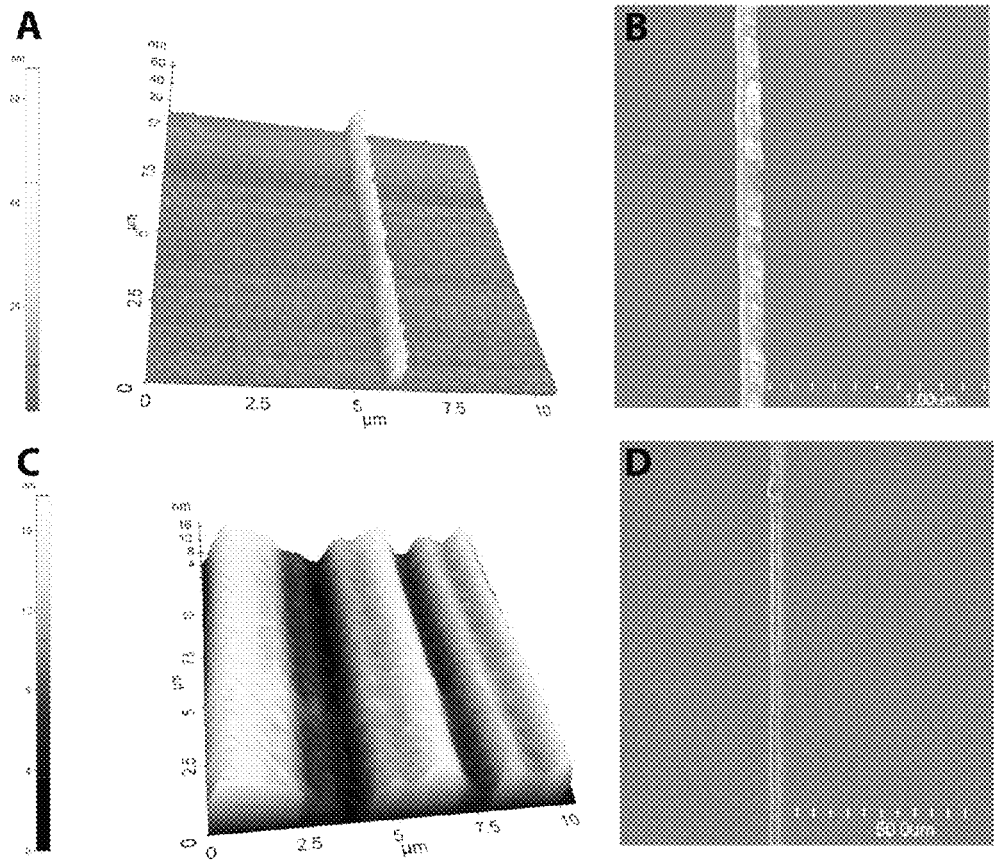
FIG. 3 are higher-magnification images for barrier characterization.

An optical image of a chromium barrier pattern with the afore-mentioned design elements prepared by direct-write electron beam (E-beam) lithography is shown in FIG. 2B. Fluorescence images of the same type of barrier collected at 60× magnification after deposition of a supported bilayer containing fluorescent lipids (0.5% rhodamine-DHPE), confirm that the lipids coat the fused silica, but that they do not cover the chromium barriers (FIG. 2C) (A20). The image in FIG. 2D shows a section of fused silica surface with a 2×3 series of chromium barrier sets. FIG. 3A shows an atomic force microscopy (AFM) image illustrating a representative single barrier that is 31 nm tall, and we have also made functional patterns with barriers ranging from 20.5 nm up to 173 nm. The height of the barriers is dictated by the amount of chromium evaporated onto the surface and can be accurately controlled as required for specific experimental needs. FIG. 3B shows a scanning electron microscopy (SEM) image of a parallel chromium barrier revealing a width 100±9 nm. As a point of comparison, FIGS. 3C-D show AFM and SEM images of manually etched barriers, respectively. In contrast to the highly uniform chromium barriers, the width of the etched barriers can be on the order of ~5-10 μm and they also have highly irregular topology, as previously reported (A18).

Assembly of DNA Curtains at Nanoscale Curtain Rods.

To assemble DNA curtains, biotinylated λ-DNA is tethered to the bilayer through tetravalent neutravidin that is in turn attached to a subset of lipids that have biotinylated head groups. The DNA molecules are pushed in the direction of the diffusion barriers through the application of a flow force. The initial application of buffer flow pushes the DNA into the barrier patterns where they accumulate at the ends of the guide channels. Once all of the molecules have accumulated within the barriers, flow is briefly terminated, allowing the molecules to diffuse freely within the bilayer. This step permits the DNA molecules to diffuse laterally within the bilayer so that they become evenly distributed along each of the barriers. The DNA molecules themselves are retained within the barrier set because flow is not stopped long enough to allow them to diffuse out of the guide channel openings. Flow can then be resumed to assess the distribution of the DNA, and if necessary this process is repeated at short intervals to achieve even disbursement of the DNA along the barrier edges (see Materials and Methods).

Figure 4:
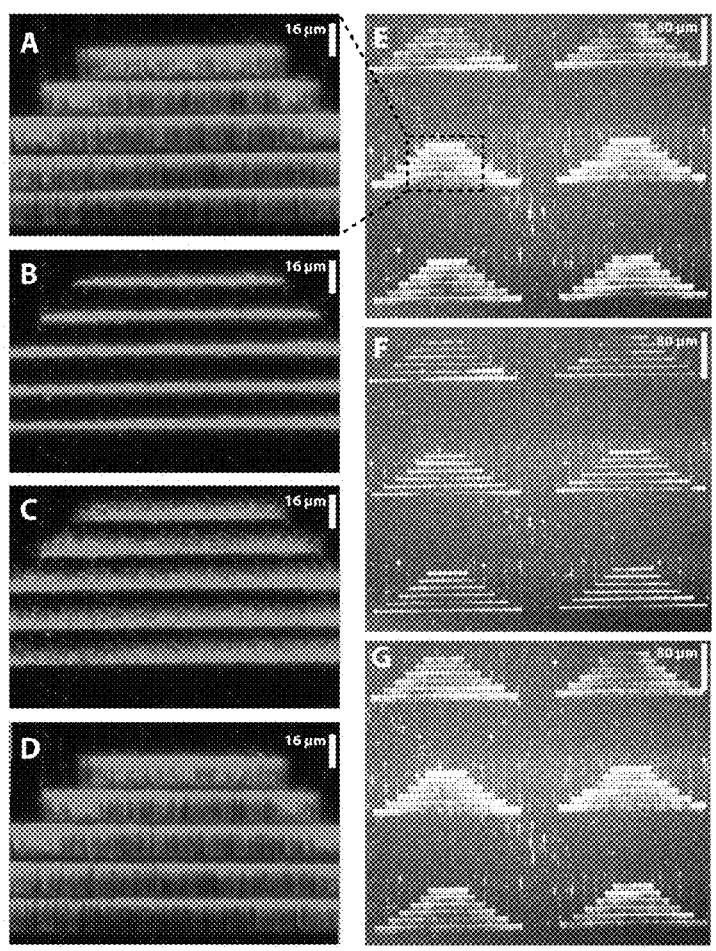
FIG. 4 are images of YOYO1-stained λ-DNA curtains assembled at the nano-scale diffusion barriers.

FIG. 4A shows an image with YOYO1 stained λ-DNA (48,502 bp) organized into curtains within a five-tiered barrier set. There are ~805 individual, molecules of λ-DNA in this field-of-view. When flow is transiently terminated, the DNA molecules diffuse up away from the surface and out of the evanescent field (FIG. 4B). This is a control used to verify that the DNA molecules are anchored by only one end to the sample chamber surface. Any molecules nonspecifically adsorbed to the surface will remain extended when flow is transiently paused and, if necessary, these molecules can be excluded from any further analysis. When flow is stopped for longer than a few seconds the anchored DNA molecules also begin to move away from the barrier edges, showing that they are not irreversibly anchored to the strips of chromium or otherwise immobilized to the surface (FIG. 4C). When flow is resumed the DNA molecules are pushed back into the diffusion barriers (FIG. 4D). If continuous buffer flow is maintained the λ-DNA molecules do not diffuse laterally, but rather remain in a single location along the barrier edge, ensuring that individual molecules can be readily tracked over time. However, shorter DNA fragments exhibit lateral diffusion when pushed against the barriers under the same flow conditions used for λ-DNA (see below).

FIGS. 4E-G show a 2×3 array of six-tiered barrier patterns containing λ-DNA curtains viewed at 10× magnification. There are roughly 1,000 of these 48.5 kb DNA molecules per barrier set and 6 sets of barriers, corresponding to a total content of at least 6,000 individual DNA molecules in this single field-of-view. The amount of DNA applied to the surface, the fraction of biotinylated lipid, the spacing between barrier sets, the number of barriers, and the width of the guide channel openings all dictate the total amount of DNA aligned at any given barrier. Any of these variables can be controlled to adjust the number of DNA molecules as needed.

Orientation Specificity and Optical Restriction Mapping of DNA Curtains.

The design of the curtains should yield DNA molecules all aligned with the same sequence orientation based upon the location of the biotin tag. If some fraction of the DNA is bound to the bilayer via its unlabeled end, then this second population of DNA will have reversed sequence orientation with respect to those molecules anchored via the biotin tag. Verifying the alignment is critical for future experiments meant to probe the sequence-dependent behavior of DNA bound proteins. λ-DNA has five EcoRI restriction sites located 21,226 bp, 26,106 bp, 31,747 bp, 39,168 bp and 44,972 bp from the left end of the molecules. If the molecules are in a given orientation, then complete EcoRI digestion of λ-DNA anchored by its left end will yield a tethered fragment of approximately 21 kb, and all of the downstream fragments will be washed from the sample chamber. Similarly, an EcoRI digestion of a curtain comprised of λ-DNA biotinylated at the right end should yield much smaller fragments corresponding to a final length of 3.5 kb. FIGS. 4A-D confirm these predictions, proving that all of the DNA molecules making up the curtain are tethered in the same orientation.

Optical restriction mapping has evolved into a powerful technique for the physical analysis of large DNA molecules (A14, A15, A25), and because the DNA curtains are organized with all of the molecules in a defined orientation they provide a very simple platform for mapping the locations of specific restriction sites. As shown in FIG. 5E, different combinations of single restriction sites can be easily mapped within the DNA curtain by successive introduction of the desired enzymes into the flowcell. In this example, the curtain was sequentially cut with NheI, XhoI, EcoRI, NcoI, PvuI, and SphI, and the observed lengths (μm) of the resulting DNA fragments were measured and plotted as a histogram to illustrate the location of the cleavage sites. As shown here, complete restriction digests leave behind tethered DNA fragments whose lengths correspond to the cleavage site closest to the biotinylated ends of the DNA, and any other downstream fragments are washed away. Complete restriction digests can only reveal single cleavage sites, and can not be used to map multiple, identical restriction sites throughout the DNA molecules. In contrast, a partial digest with one or more restriction enzymes should yield a population of discrete fragments whose lengths correspond to each of the restriction sites present in the DNA molecules. To verify this prediction, we preformed a partial EcoRI digest of curtains made with DNA molecules that were tethered by either the right or the left ends. The apparent lengths of the resulting DNA fragments were then measured and their distributions plotted as histograms (FIGS. 5F-G). This partial digest strategy was sufficient to identify all five EcoRI sites within the phage λ genome. Together these experiments demonstrate that the locations of restriction sites within large molecules can be rapidly identified via optical mapping of the DNA curtains.

The DNA fragment lengths reported above are indicated in microns, and represent an apparent, observed value rather than a direct measure of the actual contour length. To estimate the actual size of any DNA fragment in either microns or base pairs the observed contour length of the DNA in microns must be corrected for the fact that the molecules are not fully extended. The mean extension $\langle x \rangle /L$ of the DNA molecules examined in this study was approximately 0.80, corresponding to ≈0.6 pN of tension. A plot of all the different measured DNA fragment contour lengths in μm versus the known length of fully extended DNA fragments based on their size in either microns or base pairs can be used as a calibration curve to estimate the actual size of the DNA fragments. Although sufficient for estimating the number of base pairs in relatively large tethered DNA fragments, we note that this empirical relationship breaks down with shorter DNA molecules (≤9 kb), because the tension experienced by the DNA (and therefore the mean extended length) decreases as the molecules get shorter. For example, the SphI~2.2 kb fragments described above were too short to measure. In addition, smaller DNA fragments tend to diffuse laterally along the barrier edges, making it difficult count them directly. As consequence of these two effects, the observed lengths for the shorter fragments are just an approximation and the total number observed was based on the initial number of uncut DNA molecules. While measurements of these smaller fragment lengths is beyond the scope of this study, it should nevertheless be possible by including a rigorous analysis of signal intensity data and/or accommodating for effects of shear flow on extended polymers, and it can also be possible to restrict their lateral motion with alternative barrier designs.

Discussion

Here we apply nanolithography to engineer arrays of diffusion barriers, which are used to organize curtains of DNA on a surface coated with a supported lipid bilayer. With these tools we can visualize thousands of individual, perfectly aligned DNA molecules, all arranged in the exact same orientation, in real time using TIRFM. These nanofabricated DNA curtains offer numerous advantages that overcome some current limitations of single molecule DNA imaging. The method is simple and robust, the flowcells are reusable, the barriers themselves are highly uniform, and they do not compromise the optical quality of the fused silica or interfere with signal detection. In addition, the bilayer provides an inert environment closely resembling a cell membrane and is compatible with many biological macromolecules, ensuring that the DNA curtains can be used for imaging a range of biochemical systems (A17, A20).

Direct-write electron-beam lithography for nanofabricating barrier patterns offers tremendous reproducibility, accuracy, design flexibility, and is advantageous for prototyping devices. The key elements of the barrier design (barrier height, barrier width, barrier shape, barrier material, separation distance between adjacent barriers, guide channel shape or width, etc.) can all be adjusted to accommodate any desired substrate and/or experimental need with virtually no limitations on the overall pattern other than those spatial constraints imposed by the use of lithographic techniques. The shapes and dimensions of the barriers presented here were specifically constructed for visualizing λ-DNA molecules. For example, the parallel barriers within these sets are separated from one another by a distance of 16 μm to allow maximal surface coverage. Moreover, the design flexibility conferred by the use of nanolithography beckons the development of much more complex barrier elements to accommodate and/or manipulate any desired substrate.

Our primary intent was to generate new tools that facilitate massively parallel data collection for single molecule analysis of protein-DNA interactions, yet it is also apparent that the DNA curtains offer a myriad of other potential applications. For example, they enable rapid generation of physical maps of long DNA molecules, and we have demonstrated this with a series of optical mapping assays based on restriction endonuclease cleavage. Because these reactions are performed within a microfluidic sample chamber and DNA is only anchored by one end, collection of the liberated fragments in sufficient quantities for cloning and further analysis should prove straightforward. Similarly, these curtains can also be used to generate maps of binding sites for any DNA-binding protein of interest as long as it can be tagged with a fluorescent label. Finally, the perfect alignment of the DNA molecules within the curtains greatly facilitates data evaluation, and offers the future potential for automated image analysis.

Materials and Methods

Barrier Construction by E-Beam Lithography.

Fused silica slides were cleaned in NanoStrip solution (CyanTek Corp.) for 20 minutes, then rinsed with acetone and isopropanol and dried with $N_2$. The slides were spin-coated with a bilayer of polymethylmethacrylate (PMMA), molecular weight 25K plus 3% anisole, and 495K plus 1.5% in anisole (MicroChem), followed by a layer of Aquasave conducting polymer (Mitsubishi Rayon). Each layer was spun at 4000 rpm for 45 seconds using a ramp rate of 300 rpm/s. Patterns were written by E-beam lithography using an FEI Sirion scanning electron microscope equipped with a pattern generator and lithography control system (J. C. Nabity, Inc.). After the pattern was written the Aquasave was washed off with deionized water and the sample dried with $N_2$. Resist was developed using a 3:1 solution of isopropanol to methyl isobutyl ketone (MIBK) for 1 minute with ultrasonic agitation at 5° C. The substrate was then rinsed in isopropanol and dried with $N_2$. A thin layer of chromium was deposited using a Semicore electron beam evaporator. To effect lift-off, the coated substrate was submerged in a 65° C. acetone bath for 30 minutes, and then gently sonicated. Following lift-off, samples were rinsed with acetone to remove stray chromium flakes and dried with $N_2$. Barriers were imaged using a Hitachi 4700 scanning electron microscope and a PSIA XE-100 Scanning Probe Microscope in noncontact mode. Optical images of the barriers were taken with a Nikon Eclipse ME600 at either 10× or 20× magnification (as indicated).

Lipid Bilayers and DNA Curtains.

Flowcells and DNA curtains were constructed as previously described (A16). All lipids were purchased from Avanti Polar Lipids and liposomes were prepared as previously described. In brief, a mixture of DOPC (1,2-dioleoyl-sn-glycero-phosphocholine), 0.5% biotinylated-DPPE (1,2-dipalmitoyl-sn-glycero-3-phosphoethanolamine-N-(cap biotinyl)), and 8% mPEG 550-DOPE (1,2-dioleoyl-sn-glycero-3-phosphoethanolamine-N-[methoxy(polyethylene glycol)-550]). Liposomes were applied to the sample chamber for 30 minutes. Excess liposomes were flushed away with buffer containing 10 mM Tris-HCl (pH 7.8) and 100 mM NaCl. The flowcell was then rinsed with buffer A (40 mM Tris-HCl (pH 7.8), 1 mM DTT, 1 mM $MgCl_2$, and 0.2 mg/ml BSA) and incubated for 15 minutes. Neutravidin (660 nM) in buffer A was then injected into the sample chamber and incubated for 10 minutes. After rinsing thoroughly with additional buffer A, biotinylated λ-DNA (~10 pM) pre-stained with YOYO1 (1 dye per 600 base pairs) was injected into the sample chamber, incubated for 10 minutes, and unbound DNA was removed by flushing with buffer at 0.1 ml/min. For imaging, the buffers also contained 100 pM YOYO1 along with an oxygen scavenging system comprised of 1% (w/v) glucose, 60 mM β-mercaptoethanol, glucose oxidase (100 units/ml) and catalase (1,560 units/ml). Application of buffer flow caused the lipid-tethered DNA molecules to align along the leading edges of the diffusion barriers. The flow was stopped for 5 minutes allowing the DNA to diffuse towards the center of the barriers. The flow was started at 0.1 ml/min for 30 seconds and the flow on-off cycle was repeated 3-5 times until DNA curtains of even density formed along the diffusion barriers.

TIRFM.

The basic design of the microscope used in this study has been previously described (A19). The beam intensity at the face of the prism was ~10-15 mW. Images were detected with a back-illuminated EMCCD detector (Photometrics, Cascade 512B). TIRFM images were collected using a 60× water immersion objective lens (Nikon, 1.2 NA, Plan Apo) or a 10× objective (Nikon, 0.45 NA, Plan Apo), as indicated.

Restriction Enzymes.

For complete digests, 700 μl of the desired restriction enzyme in reaction buffer A (40 mM Tris-HCl (pH 7.8), 1 mM $MgCl_2$, 1 mM DTT, and 0.2 mg/ml BSA) plus 50 mM NaCl and 10 mM $MgCl_2$ was injected at 0.2 ml/min. All restriction enzymes were purchased from NEB and the amounts of enzymes used were as follows: NheI (100 units/ml); XhoI (100 units/ml); EcoRI (100 units/ml); NcoI (50 units/ml); PvuI (50 units/ml); and SphI (50 units/ml). Images of the DNA molecules were collected before the restriction enzyme injection and after all of the enzyme solution had flown through. For partial digests, the amount of EcoRI was reduced to 20 units/ml and 700 μl was injected at 0.4 ml/min.

REFERENCES

A1. Ha, T., Rasnik, I., Cheng, W., Babcock, H. P., Gauss, G. H., Lohman, T. M., & Chu, S. (2002) Initiation and re-initiation of DNA unwinding by the *Escherichia coli* Rep helicase. Nature 419, 638-641.

A2. Heyes, C. D., Groll, J., Möller, M., & Neienhaus, G. U. (2007) Synthesis, patterning and applications of star-shaped poly(ethylene glycol) biofunctionalized surfaces. Molecular Biosystems 3, 419-430.

A3. Rasnik, I., Myong, S., Cheng, W., Lohman, T. M., & Ha, T. (2004) DNA-binding orientation and domain conformation of the *E. coli* rep helicase monomer bound to a partial duplex junction: single-molecule studies of fluorescently labeled enzymes. J Mol Biol 336, 395-408.

A4. Rhoades, E., Gussakovsky, E., & Haran, G. (2003) Watching proteins fold one molecule at a time. Proc Natl Acad Sci USA 100, 3197-3202.

A5. Cisse, I., Okumus, B., Joo, C., & Ha, T. (2007) Fueling protein-DNA interactions inside porous nanocontainers. Proc Natl Acad Sci USA 104, 12646-12650.

A6. Bensimon, A., Simon, A., Chiffaudel, A., Croquette, V., Heslot, F., & Bensimon, D. (1994) Alignment and sensitive detection of DNA by a moving interface. Science 265, 2096-2098.

A7. Lebofsky, R. & Bensimon, A. (2003) Single DNA molecule analysis: applications of molecular combing. Briefings in functional genomics and proteomics 1, 385-396.

A8. Kabata, H., Kurosawa, O., Arai, I., Washizu, M., Margarson, S. A., Glass, R. E., & Shimamoto, N. (1993) Visualization of single molecules of RNA polymerase sliding along DNA. Science 262, 1561-1563.

A9. Kabata, H., Okada, W., & Washizu, M. (2000) Single-molecule dynamics of the EcoRI enzyme using stretched DNA: its application to in situ sliding assay and optical DNA mapping. Jpn. J. Appl. Phys. 39, 7164-7171.

A10. Washizu, M., Kurosawa, O., Arai, I., Suzuki, S., & Shimamoto, N. (1995) Application of electrostatic stretch-and-position of DNA. IEEE Trans. Ind. Appl. 31, 447-456.

A11. Guan, J. & Lee, L. J. (2005) Generating highly ordered DNA nanostrand arrays. Proceedings of the National Academy of Sciences, USA 102, 18321-18325.

A12. Assi, F., Jenks, R., Yang, J., Love, C., & Prentiss, M. (2002) Massively parallel adhesion and reactivity measurements using simple and inexpensive magnetic tweezers. Journal of Applied Physics 92, 5584-5586.

A13. Kim, S., Blainey, P. C., Schroeder, C. M., & Xie, S. X. (2007) Multiplexed single-molecule assay for enzymatic activity on flow-stretched DNA. Nature methods 4, 397-399.

A14. Dimalanta, E. T., Lim, A., Runnheim, R., Lamers, C., Churas, C., Forrest, D. K., de Pablo, J. J., Graham, M. D., Coppersmith, S. N., Goldstein, S., et al. (2004) A microfluidic system for large DNA molecule arrays. Analytical Chemistry 76, 5293-5301.

A15. Lin, J., Qi, R., Aston, C., Jing, J., Anantharaman, T. S., Mishra, B., White, O., Daly, M. J., Minton, K. W., Venter, J. C., et al. (1999) Whole-genome shotgun optical mapping of *Deinococcus radiodurans*. Science 285, 1558-1562.

A16. Granéli, A., Yeykal, C., Prasad, T. K., & Greene, E. C. (2006) Organized arrays of individual DNA molecules tethered to supported lipid bilayers. Langmuir 22, 292-299.

A17. Sackmann, E. (1996) Supported membranes: scientific and practical applications. Science 271, 43-48.

A18. Cremer, P. S. & Boxer, S. G. (1999) Formation and spreading of lipid bilayers on planar glass supports. J. Phys. Chem. B 103, 2554-2559.

A19. Granéli, A., Yeykal, C., Robertson, R. B., & Greene, E. C. (2006) Long-distance lateral diffusion of human Rad51 on double-stranded DNA. Proceedings of the National Academy of Sciences, USA 103, 1221-1226.

A20. Groves, J. & Boxer, S. (2002 March) Micropattern formation in supported lipid membranes. Acc Chem Res 35, 149-157.

A21. Gorman, J., Chowdhury, A., Surtees, J. A., Shimada, J., Reichman, D. R., Alani, E., & Greene, E. C. (2007) Dynamic basis for one-dimensional DNA scanning by the mismatch repair complex Msh2-Msh6. Mol Cell 28, 359-370.

A22. Prasad, T. K., Robertson, R. B., Visnapuu, M. L., Chi, P., Sung, P., & Greene, E. C. (2007) A DNA-translocating Snf2 molecular motor: *Saccharomyces cerevisiae* Rdh54 displays processive translocation and extrudes DNA loops. J Mol Biol 369, 940-953.

A23. Prasad, T. K., Yeykal, C., & Greene, E. C. (2006) Visualizing the assembly of human Rad51 filaments on double-stranded DNA. Journal of Molecular Biology 363, 713-728.

A24. Axelrod, D. (1989) Total internal reflection fluorescence microscopy. Methods Cell Biol 30, 245-270.

A25. Schwartz, D. C., Li, X., Hernandez, L. I., Ramnarain, S. P., Huff, E. J., & Wang, Y. K. (1993) Ordered restriction maps of *Saccharomyces cerevisiae* chromosomes constructed by optical mapping. Science 262, 110-114.

DNA Curtains Stained with YOYO1.

E-beam lithography was used to create chromium nanoscale barriers in a defined pattern on a fused silica slide. $\lambda$-DNA stained with YOYO1 was then assembled into curtains along the edges of the nanoscale barriers. Images were collected at 60× magnification at an acquisition rate of 10 frames per second and a time stamp is shown in the lower right corner. The movie begins with buffer flow on and the DNA extended. The flow is stopped showing that all of the DNA molecules diffuse away from the surface and the barrier edges. In the absence of flow the full length of the DNA can not be seen because it resides outside the excitation volume defined by the penetration depth of the evanescent field. Finally flow is resumed to re-extend the DNA.

Imaging YOYO1-Stained DNA Curtains at Lower Magnification.

Images were captured at 10× magnification and the full field-of-view shows a 2×3 array of barrier sets from the surface of a slide that had a 4×6 array of barriers (24 identical barrier patterns in total). The movie was collected at 10 frames per second and a time stamp is indicated in the lower right hand corner. The movie begins with buffer flow on and the DNA extended, then flow is stopped showing that the DNA diffuses away from the surface and the barrier edges, and finally flow is resumed to re-extend the DNA.

Example 2

Parallel Arrays of Geometric Nanowells for Assembling DNA Curtains with Controlled Lateral Dispersion The analysis of individual molecules is evolving into an important tool for biological research, and presents conceptually new ways of approaching experimental design strategies. However, more robust methods are required if these technologies are to be made broadly available within the biological research community. To help achieve this goal we have combined nanofabrication techniques with single-molecule optical microscopy for assembling and visualizing curtains comprised of thousands of individual DNA molecules organized at engineered diffusion barriers on lipid bilayer-coated surface. Here we present an important extension of this technology that implements non-linear, geometric barrier patterns comprised of thousands of nanoscale wells that can be loaded with single molecules of DNA. We show that these geometric nanowells can be used to precisely control the lateral distribution of the individual DNA molecules within curtains assembled along the edges of the engineered barrier patterns. The individual molecules making up the DNA curtain can be separated from one another by a user-defined distance dictated by the dimensions of the nanowells. We demonstrate the broader utility of these patterned DNA curtains in a real time restriction assay that we refer to as dynamic optical restriction mapping, which can be used to rapidly identify entire sets of cleavage sites within a large DNA molecule.

Advances in biology are often made possible only through the concurrent establishment of new technologies that bring together different scientific disciplines to achieve a common goal. This maxim has proven especially true for single-molecule research, where aspects of physics, chemistry, and biology have all provided invaluable contributions, which have led to the development of highly sensitive detection optics, robust fluorescent tags, and chemistries for anchoring individual molecules to surfaces. Taken together, these technological achievements have enabled new approaches for isolating, viewing and manipulating individual macromolecules while at the same time addressing important biological questions, and have opened new avenues of research, which have already revealed a wealth of new information. Nowhere is this more evident that in the study of nucleic acids and protein-nucleic acid interactions (B1-5). Yet even as these approaches are revealing more and more details of specific reaction mechanisms, broader implementation of the techniques remains hindered by their low throughput capacity and challenging technical nature; as a consequence most studies have been restricted to relatively simple model systems conducted in a handful of specialized laboratories.

In an effort to help make these techniques more broadly accessible we have integrated nanoscale engineering, microfluidics, and inert lipid bilayer-coated surfaces with optical microscopy to develop high-throughput methods for making curtains of DNA molecules that can be used for massively parallel data acquisition from thousands of individual protein-DNA complexes in real time using a robust experimental platform that is amenable to a wide variety of biological applications (B6, B7). These DNA curtains permit concurrent visualization of thousands of individual DNA molecules that are perfectly aligned with respect to one another and also enable real time detection of fluorescent proteins bound to the DNA (B8-11). However, a remaining limitation of this approach is the lack of control over the lateral separation between each of the molecules making up the DNA curtains. This can potentially present a problem, especially in instances where either implementation of the desired experiments or the subsequent data analysis is confounded by the presence of overlapping molecules within the curtain. In addition, while relatively large λ-DNA (48,502 bp) substrates remain at fixed lateral locations along the smooth chromium barriers as long as constant buffer flow is maintained, smaller DNA fragments exhibit significant lateral movement along the barriers. The lipid bilayers remain fluid at the edges of the chromium barriers (B12), and the observed mobility of the shorter DNA arises from slippage of the lipid anchors along the smooth barrier edges. This is especially problematic for single molecule data analysis because molecules targeted for investigation will inevitably slip along the barrier edge and collide with and/or bypass one another, making it extremely difficult to distinguish similar looking molecules from one another over periods longer than just a few seconds. Taken together, these complications can place significant design constraints on the experiments that can be conducted with DNA curtains, especially when using DNA substrates shorter in length than the phage λ genome.

In an effort to solve these problems we sought to develop new barrier designs that could control the positions of the molecules within the DNA curtain. Here we take advantage of the fact that lipid-tethered DNA molecules can slide along the barrier edges by demonstrating that simple non-linear, geometric barrier patterns made by nanolithography can be used to construct aligned DNA curtains with precisely controlled lateral displacement between the DNA molecules. These barriers consist of a repetitive triangular wave (sawtooth pattern) with nanometer-scale features, where the vertex of each adjacent triangle forms a tiny well, which we will refer to as geometric nanowells. We show that single molecules of DNA can be loaded into the nanowells and retained indefinitely for continued observation and analysis, so long as continuous buffer flow is maintained. The minimal separation distance between each of the DNA molecules within the curtain is defined by the distance between the adjacent nanowells within the non-linear, geometric barrier pattern, and the total number of DNA molecules within in each well is controlled by the amount of DNA applied to the surface. Although designed explicitly for single-molecule biochemical studies of protein-DNA interactions, DNA curtains made with these non-linear, geometric barrier patterns have a multitude of other potential applications. As an example of their broader utility, we use the DNA curtains made with geometric nanowells in a dynamic optical restriction mapping assay, which uses real time data collection to identify an entire set of specific cleavage sites within the phage λ genome in a reaction that takes under 2 minutes.

Materials and Methods

Barrier Construction by E-Beam Lithography.

Fused silica slides were cleaned in NanoStrip solution (CyanTek Corp, Fremont, Calif.) for 20 minutes, then rinsed with acetone and isopropanol and dried with $N_2$. The slides were spin-coated with a bilayer of polymethylmethacrylate (PMMA), molecular weight 25K and 495K, 3% in anisole (MicroChem, Newton, Mass.). Each layer was spun at 4,000 rpm for 45 seconds using a ramp rate of 300 rpm/s. Patterns were written by E-beam lithography using an FEI Sirion scanning electron microscope equipped with a pattern generator and lithography control system (J. C. Nabity, Inc., Bozeman, Mont.). Resist was developed using a 3:1 solution of isopropanol to methyl isobutyl ketone (MIBK) for 2 minutes with ultrasonic agitation at 5° C. The substrate was then rinsed in isopropanol and dried with $N_2$. A thin layer of chromium was deposited using a Semicore electron beam evaporator. To effect lift-off, the coated substrate was submerged in a 75° C. acetone bath for 30 minutes, and then gently sonicated. Following lift-off, samples were rinsed with acetone to remove stray chromium flakes and dried with $N_2$. Barriers were imaged using a Hitachi 4700 scanning electron microscope and a PSIA XE-100 Scanning Probe Microscope in noncontact mode. Optical images of the barriers were taken with a Nikon Eclipse ME600 at either 10× or 20× magnification (as indicated).

Lipid Bilayers and DNA Curtains.

The flowcells were assembled from fused silica slides (G. Finkenbeiner, Inc.) with chromium nanoscale diffusion barriers. Inlet and outlet ports were made by boring through the slide with a high-speed precision drill press equipped with a diamond-tipped bit (1.4 mm O.D.; Kassoy). The slides were cleaned by successive immersion in 2% (v/v) Hellmanex, 1 M NaOH, and 100% MeOH. The slides were rinsed with filtered sterile water between each wash and stored in 100% MeOH until use. Prior to assembly, the slides were dried under a stream of nitrogen and baked in a vacuum oven for at least 1 hour. A sample chamber was prepared from a borosilicate glass coverslip (Fisher Scientific) and double-sided tape (~25 μm thick, 3M). Inlet and outlet ports (Upchurch Scientific) were attached with hot-melt adhesive (SureBonder glue sticks, FPC Corporation). The total volume of the sample chambers was ~4 μl. A syringe pump (Kd Scientific) and actuated injection valves (Upchurch Scientific) were used to control sample delivery, buffer selection and flow rate. The flowcell and prism were mounted in a custom-built heater with computer-controlled feedback regulation to control the temperature of the sample from between 25-37° C. (±0.1° C.), as necessary.

DNA curtains were constructed as described (B7). All lipids were purchased from Avanti Polar Lipids and liposomes were prepared as previously described. In brief, a mixture of DOPC (1,2-dioleoyl-sn-glycero-phosphocholine), 0.5% biotinylated-DPPE (1,2-dipalmitoyl-sn-glycero-3-phosphoethanolamine-N-(cap biotinyl)), and 8% mPEG 550-DOPE (1,2-dioleoyl-sn-glycero-3-phosphoethanolamine-N-[methoxy(polyethylene glycol)-550]). Liposomes were applied to the sample chamber for 30 minutes. Excess liposomes were flushed away with buffer containing 10 mM Tris-HCl (pH 7.8) and 100 mM NaCl. The flowcell was then rinsed with buffer A (40 mM Tris-HCl (pH 7.8), 1 mM DTT, 1 mM $MgCl_2$, and 0.2 mg/ml BSA) and incubated for 15 minutes. Neutravidin (660 nM) in buffer A was then injected into the sample chamber and incubated for 10 minutes. After rinsing thoroughly with additional buffer A, biotinylated λ-DNA (10 pM) pre-stained with 1-2 nM YOYO1 was injected into the sample chamber, incubated for 10 minutes, and unbound DNA was removed by flushing with buffer at 0.1 ml/min. Application of buffer flow caused the lipid-tethered DNA molecules to align along the leading edges of the diffusion barriers. The flow was stopped for 5 minutes allowing the DNA to diffuse towards the center of the barriers. The flow was started at 0.1 ml/min for 30 seconds and the flow on-off cycle was repeated 3-5 times until DNA curtains of even density formed along the diffusion barriers.

TIRFM Imaging.

The basic design of the microscope used in this study has been previously described (B11). Briefly, the system is built around a Nikon TE2000U inverted microscope with a custom-made illumination system. A 488 nm, 200 mW diode-pumped solid-state laser (Coherent, Sapphire-CDHR) was used as the excitation source. The laser was attenuated as necessary with a neutral density filter and centered over the DNA curtain by means of a remotely operated mirror (New Focus). The beam intensity at the face of the prism was ~10-15 mW. Images were detected with a back-illuminated EMCCD detector (Photometrics, Cascade 512B). TIRFM images were collected using a 60× water immersion objective lens (Nikon, 1.2 NA Plan Apo), unless otherwise indicated.

Results

Design Strategy.

Figure 6:
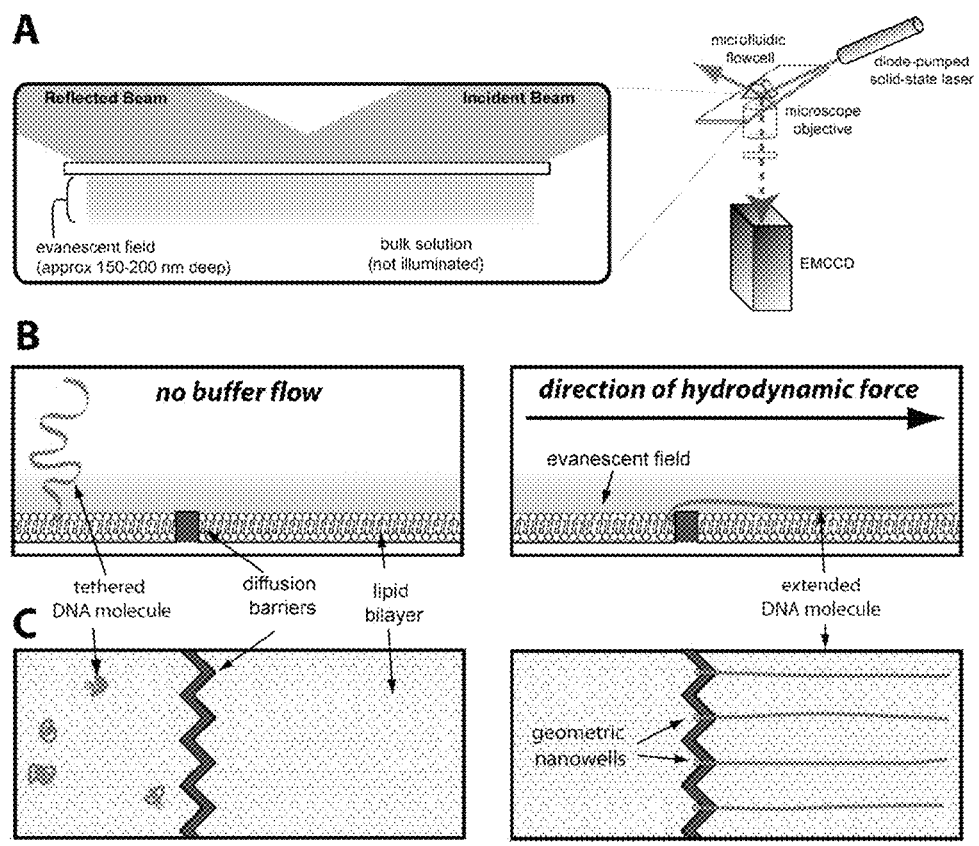
FIG. 6 represents a design strategy for geometric nanowells.
Figure 8:
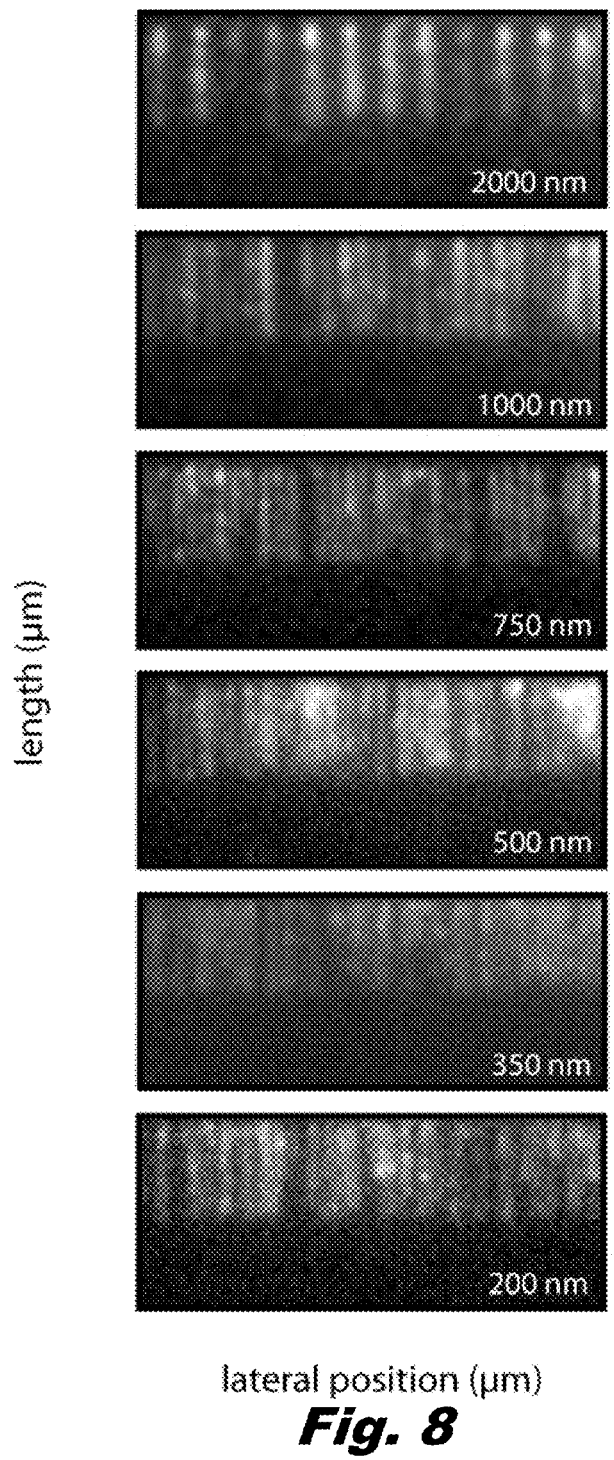
FIG. 8 represents DNA curtains with different separation distances. The different panels show examples of sections from YOYO1-stained DNA curtains prepared using non-linear, geometric barrier patterns with spacings of 2000, 1000, 750, 500, 350, and 200 nm, as indicated. Fluorescence cross-sections of the same curtains can be obtained. Intensity histograms from cross-section measurements can be generated.

We have shown that mechanical barriers to lipid diffusion can be used to organize DNA molecules into curtains that serve as a unique and effective experimental platform for the study protein-DNA interactions at the single molecule level (B6-11). The overall strategy for making DNA curtains is shown in FIG. 6. DNA molecules are first anchored by one end to a supported lipid bilayer coating the surface of the sample chamber and application of hydrodynamic force is used to push the lipid-tethered DNA molecules towards lipid diffusion barriers. Lipids within supported bilayers cannot traverse these mechanical barriers (B13-15). As a consequence, the barriers (curtain rods) also halt the forward movement of the DNA molecules, causing them to accumulate at the barrier edges where they extend into the evanescent field. As we have previously shown, molecules of λ-DNA (48.5 kb) can be assembled into curtains along these barrier edges and the molecules remain at fixed lateral locations (B6).

In contrast to the full-length λ phage genome, smaller DNA fragments diffuse laterally along the smooth barrier edges (see below). This is because the lipid bilayers remain fluid even at the barrier edges (B 12), and the tension exerted on the shorter DNAs by the hydrodynamic force is insufficient to overcome the tendency of the molecules to slide along the barriers. In addition, these chromium barriers are designed to be oriented exactly perpendicular to the flow force, and if they are misaligned by just a few degrees relative to the direction flow, then the smaller DNA molecules slip rapidly along the barrier edges. In light of these potential design flaws when used for smaller DNA substrates, we sought a new barrier design that could eliminate slippage of the molecules along the barrier edges. We reasoned that the locations of the DNA molecules along the barrier edges could be passively controlled by altering the shape of the barriers themselves. For example, because the DNA molecules can move along the smooth edges, then non-linear, geometric barrier patterns comprised of a simple, repetitive triangular wave would limit the mobility (FIG. 6B and FIG. 6C). This is because the hydrodynamic force exerted by the flowing buffer should push the DNA molecules into the vertex of each triangle with sufficient force to overcome any tendency of the molecules to move laterally within the bilayer (FIG. 6B). We refer to these triangular features as geometric nanowells (conceptually similar to the wells of a sequencing gel) because the DNA molecules loaded within each well would not be free to move laterally along the barrier, as long as a continuous flow force is maintained. In addition to eliminating lateral slippage, the peak-to-peak distance of the adjacent triangles within the patterns should dictate the minimal lateral separation of the DNA molecules that make up the curtain. For example, non-linear, geometric patterns that repeat at 500 nm intervals should yield DNA molecules separated from one another by 500 nm. The separation will be greater than 500 nm if some of the wells are not occupied, yet even in this case the distances should occur in defined increments divisible by 500 nm (i.e. 500, 1000, 1500, 2000 nm, etc.). If this were true, then these non-linear, geometric barrier patterns would confer precise control over the positioning of each individual DNA making up the curtain.

Examples of the non-linear, geometric barrier patterns tested here are shown in FIG. 7. We used electron-beam (E-beam) lithography to achieve these desired design features by engineering chromium barriers that were 100 nm wide and 30 nm tall arranged in a sawtooth pattern on a fused silica slide. FIG. 7A shows an optical image of a pair of barrier sets and once assembled into a flowcell the chromium barriers will be oriented perpendicular to the hydrodynamic force with the apex of each triangle pointing in the same direction that the buffer is flowing (as indicated in FIG. 6). FIG. 7B shows an AFM image of a non-linear, geometric barrier pattern with 1 μm peak-to-peak spacing and reveals a height of just 20 nm. Examples of SEM images of non-linear, geometric barriers with peak-to-peak distances of 2000, 1000, 750, 500, 350, and 200 nm are shown in FIG. 7C. These images demonstrate that we can use standard lithographic techniques to construct chromium barriers with precise non-linear, geometric patterns having nanometer scale features of our desired designs.

DNA Curtains with Defined Lateral Separation Between Molecules.

Figure 9:
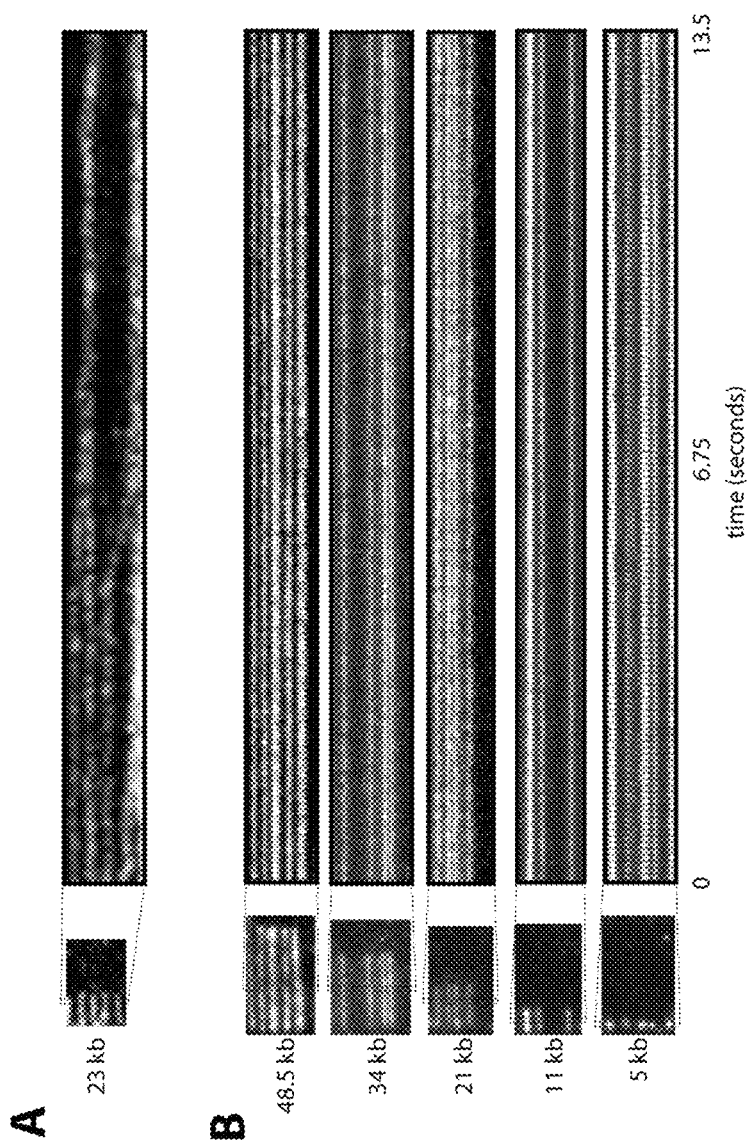
FIG. 9 shows that DNA slippage is eliminated with non-linear, geometric barrier patterns. The left panel in FIG. 9A shows a single 100-millisecond image of a section from a DNA curtain assembled at a smooth, linear barrier edge. The DNA molecules are comprised of a 20 kb PCR product stained with YOYO1. The right panel in FIG. 9A shows the kymogram spanning 13.5 seconds of a cross-section of the curtain (as indicated), which illustrates the lateral slippage of the DNA molecules. The left panels in FIG. 9B shows DNA curtains assembled at a non-linear, geometric barrier with 1-μm spacing. The lengths of the DNA molecules were 48.5, 34, 21, 11, and 5 kb, as indicated, and the fragments smaller than the 48.5 kb λ-DNA were generated by restriction digest of λ using W, X, Y, and Z. The right panels in FIG. 9B show 13.5 second kymograms demonstrating that the lateral motion of these DNA is eliminated with the non-linear, geometric barrier patterns.

If the DNA molecules within the curtains were in fact retained within the geometric nanowells, as we predicted, then the distance between the adjacent vertices of triangles within the pattern design should be reflected in the separation distance between the individual DNA molecules. FIG. 9 shows examples of DNA curtains made with non-linear, geometric barrier patterns with 2000, 1000, 750, 500, 350, and 200 nm separation between adjacent nanowells (FIG. 9A, left panels). As indicated above, these curtains are comprised of the 20 kb DNA that is fluorescently stained with the intercalating dye YOYO1. To verify that this design pattern yielded DNA molecules with the desired spacing we plotted signal intensity of the stained DNA versus its lateral location along the barrier edge, and these plots revealed peak-to-peak frequencies consistent with values from designs of the non-linear, geometric barrier patterns (FIG. 9A, middle panels). The 2000, 1000, 750, 500, 350, and 200 nm barriers yielded mean separation distances corresponding to the pattern designs. This data demonstrates that the non-linear, geometric barrier patterns prevent slippage of the DNA molecules along the non-linear, geometric diffusion barriers and also confirms that the distance between adjacent nanowells dictates the extent of lateral separation between individual molecules that make up the DNA curtain.

The number of DNA molecules that make up the curtains can be varied by modulating several different parameters, the simplest of which is the amount of DNA injected into the sample chamber (B6, B7). With these non-linear, geometric diffusion barrier patterns, if too much DNA is present, then multiple molecules of DNA will accumulate within each geometric nanowell. To avoid this problem these experiments were conducted with a relatively small amount of DNA, such that less than one DNA molecule should be found per nanowell. In other words, some of the nanowells will remain unoccupied, many of the wells will have a single DNA molecule, and some of the wells will have two (or more) molecules of DNA. This can be confirmed by measuring the fluorescence intensity of the DNA in each well, and those nanowells harboring two molecules will be twice as bright as those harboring just one, therefore allowing easy discrimination. FIG. 9B shows a histogram of total integrated intensity per DNA molecule, revealing a prominent peak, and a less prominent peak. In addition, a tally of the total number of geometric nanowells and the total number of DNA molecules within a barrier set. These values are also reflected in the fluorescence cross-sections shown in FIG. 9A, which provides further evidence that the number of DNA molecules loaded per nanowell can be controlled, and that any nanowells having more than one DNA can be readily identified based on signal intensity and discarded from further analysis if necessary.

DNA Molecules are Retained within the Geometric Nanowells.

As indicated above, DNA molecules aligned along smooth, linear chromium barriers can slip laterally along the barrier edges, and this effect can be very pronounced with shorter molecules of DNA. To illustrate this problem, a 20 kb PCR DNA fragment derived from the λ DNA was labeled with YOYO1 ((B16), and see Materials and Methods). These molecules were aligned along the edge of a smooth barrier and viewed over the course of 13.5 minutes. A kymogram illustrating the lateral locations of the DNA molecules over time was then generated from a cross-section of the curtain. As shown in FIG. 9A, the labeled ends of the molecules exhibited large movements consistent with lateral slippage of the DNA along the barrier edge even over periods spanning just a few seconds. DNA curtains made with non-linear, geometric barrier patterns are shown in FIG. 9B, along with the corresponding kymograms. In contrast to the movement observed with the smooth, linear barriers, the DNA molecules aligned at the non-linear, geometric patterns displayed absolutely no evidence of lateral slippage. Similar experiments with DNA molecules of sequentially shorter lengths revealed that the lateral movement of 34, 21, 11, and 5 kb DNA fragments was also eliminated with the non-linear, geometric barrier patterns (FIG. 9B). This data provided evidence indicating that the non-linear, geometric barrier patterns were highly effective at restricting movement of the DNA molecules along the barrier edges, further indicating that the molecules themselves were loaded into the geometric nanowells.

Dynamic Optical Restriction Mapping.

Using these non-linear, geometric barrier patterns permits studies of even relatively small DNA fragments by eliminating their lateral mobility along the barrier edges when maintained by a constant flow force. As we have previously shown, the design of the curtains also yields DNA molecules that are all aligned with the same sequence orientation based upon the location of the biotin tag at a specific end of the DNA (B6). As a consequence of this perfect alignment, restriction digest of the DNA molecules within the curtain yields identical, tethered fragments whose lengths correspond to the furthest upstream cleavage site (B6). Complete digests can not be used to identify multiple sites cleaved by the same restriction enzyme because the downstream DNA is flushed from the sample chamber as soon as the DNA is cleaved. However, partial restriction digests can be used to generate mixed populations of DNA molecules whose lengths reflect the distribution of cleavage sites throughout the DNA.

In principle, a complete restriction digest of the DNA can also reveal all of the fragments corresponding to each of these intermediate lengths, but only if the digest is viewed in real time and the cleavage rate is slower than the data acquisition frequency. In this case, following each individual cleavage event, the downstream fragment will be immediately flushed from the sample chamber by buffer flow, leaving behind the intact biotinylated fragment whose shortened length would correspond to the location of the cleavage site. This can happen repeatedly on the same DNA until that particular molecule is cleaved at the furthest upstream site relative to the anchored end of the DNA. The large number of DNA molecules that can be viewed with these DNA curtains makes it possible to detect all of the potential sites within the DNA, and the geometric nanowells prevent the DNA molecules from slipping back and forth after they are cleaved. Eventually all of the DNA molecules will be cut to a final length corresponding to the furthest upstream restriction site. We refer to this real time digest as dynamic optical restriction mapping and an example of such an assay is shown in FIG. 10. Here the DNA was digested with EcoRI and the digest was observed in real time. FIG. 10B shows the DNA before the digest and FIG. 10C shows the DNA after the digest was completed, which demonstrates that all of the DNA were eventually trimmed (corresponding to the 21 kb fragment) and confirming that all of the molecules were in the identical orientation. FIG. 10C shows examples of kymograms made from individual DNA molecules during the digestion reaction. These kymograms were selected because they provide examples where each of the five EcoRI sites can be identified. The total time required for this digest was just 30 seconds, and we anticipate that this time can be reduced significantly with further optimization. The length of the resulting fragments observed at the intermediate time points was measured and their distribution plotted as a histogram in FIG. 10D, which reveals all five of the EcoRI cuts sites in the λ phage genome. This assay is not possible with smooth, linear barrier designs because the DNA molecules start to rapidly slip back and forth as the fragment lengths become shorter and shorter, thus interfering with measurements of the same DNA molecule over time. Thus this real time dynamic optical restriction mapping assay is greatly facilitated when used in combination with the non-linear, geometric barrier patterns because the nanowells prevent the DNA molecules from moving as they get shorter and shorter during the digest.

Discussion

High-throughput approaches to single-molecule biochemistry have the potential to reveal numerous new details of reaction mechanisms and macromolecular dynamics, which were previously inaccessible to traditional ensemble approaches. In an effort to make these techniques more broadly applicable we have used nanoscale engineering to establish a high-throughput approach that we call DNA curtains, which facilitates massively parallel data acquisition from thousands of individual molecules viewed in real time. Here we have shown that non-linear, geometric barrier patterns can also be used to align curtains of DNA molecules tethered to a fluid lipid bilayer and that the geometry of the barriers dictates the lateral distance between the individual molecules that make up the curtains. We demonstrate that single molecules of DNA can be loaded into the geometric nanowells where they can be retained for further analysis and experimentation. This work brings the power of nanofabrication to bear on single-molecule biology by providing a very simple and robust means of controlling the lateral dispersion of DNA molecules assembled into a molecular curtain.

In our previous studies we demonstrated that DNA curtains are advantageous for analysis of protein-DNA interactions, in particular with systems that involve lateral movement of proteins along DNA (B8, B9). One complication of these experiments is that it is not always possible to irrefutably rule out the possibility that a protein under observation is interacting with two (or more) DNA molecules that are closely juxtaposed. Although the density of the DNA curtains can be decreased to help mitigate this issue, it still is not always possible to demonstrate that a specific protein under observation is bound to a particular DNA molecule. Moreover, while our DNA curtain assays have a demonstrated capability to enable massively parallel data acquisition, evaluation of the resulting data remains a challenge because automated image analysis programs can not readily distinguish two or more identical objects if they overlap to any significant extent. With the advent of the non-linear, geometric barrier patterns, these problems are eliminated, because the DNA molecules are maintained at fixed distances from one another and we can verify that only one molecule is loaded in a particular well based on the fluorescence intensity of the labeled DNA. Moreover, the non-linear, geometric patterns used here are extremely simple, yet highly effective at directing DNA molecules to defined locations on a surface. The ability to load and retain individual DNAs into geometric nanowells portends the future possibility of individually handling or isolating these single molecules, and we envision that the flexibility afforded by nanolithography will enable construction of intricate barrier patterns that can be used for even more complex manipulations of lipid anchored DNA molecules. While the primary motivation for this work remains development of robust, high-throughput tools for single-molecule optical detection of protein-DNA interactions, we envision that the DNA curtains and geometric nanowells have numerous potential applications pertaining to physical analysis of large DNA molecules. For example, a major aspect of genome research remains characterization of large DNA fragments, and numerous approaches have been developed for manipulating, analyzing and isolating these molecules (B17-21). We have shown that DNA curtains made up of these non-linear, geometric patterns can be used to generate optical restriction maps of the tethered DNA molecules, and because these assays are performed in the context of a microfluidic system the cleaved DNA fragments can easily be isolated for further analysis. This type of real time restriction digest imaging can be used for rapidly mapping the DNA molecules and the large numbers of molecules aligned in the curtains ensures acquisition of statistically relevant data from just a single run; we refer to this as dynamic optical restriction mapping. Finally, these perfectly ordered DNA substrates now offer the future potential for applying rigorous machine vision techniques for fully automated data analysis with little or no user intervention.

REFERENCES

B1. Bustamante, C., Bryant, Z., & Smith, S. B. (2003) *Nature* 421, 423-427.
B2. Cairns, B. R. (2007) *Nat Struct Mol Biol* 14, 989-996.
B3. Ha, T. (2001) *Curr Opin Struct Biol* 11, 287-292.
B4. Zlatanova, J. & van Holde, K. (2006) *Mol Cell* 24, 317-329.
B5. van Oijen, A. M. (2007) *Biopolymers* 85, 144-153.
B6. Fazio, T., Visnapuu, M.-L., Wind, S., & Greene, E. C. (2008) (submitted).
B7. Granéli, A., Yeykal, C., Prasad, T. K., & Greene, E. C. (2006) *Langmuir* 22, 292-299.
B8. Gorman, J., Chowdhury, A., Surtees, J. A., Shimada, J., Reichman, D. R., Alani, E., & Greene, E. C. (2007) *Mol Cell* 28, 359-370.
B9. Prasad, T. K., Robertson, R. B., Visnapuu, M. L., Chi, P., Sung, P., & Greene, E. C. (2007) *J Mol Biol* 369, 940-953.
B10. Prasad, T. K., Yeykal, C., & Greene, E. C. (2006) *Journal of Molecular Biology* 363, 713-728.
B11. Granéli, A., Yeykal, C., Robertson, R. B., & Greene, E. C. (2006) *Proceedings of the National Academy of Sciences, USA* 103, 1221-1226.
B12. Tsai, J., Sun, E., Gao, Y., Hone, J. C., & Kam, L. C. (2008) *Nano Lett* 8, 425-430.
B13. Boxer, S. G. (2000) *Curr Opin Chem Biol* 4, 704-709.
B14. Cremer, P. S. & Boxer, S. G. (1999) *J. Phys. Chem. B* 103, 2554-2559.
B15. Groves, J. & Boxer, S. (2002 March) *Acc Chem Res* 35, 149-157.
B16. Robertson, R. B., Prasad, T. K., Moses, D., Chowdhury, A., & Greene, E. C. (2008) (submitted).
B17. Bensimon, A., Simon, A., Chiffaudel, A., Croquette, V., Heslot, F., & Bensimon, D. (1994) *Science* 265, 2096-2098.
B18. Dimalanta, E. T., Lim, A., Runnheim, R., Lamers, C., Churas, C., Forrest, D. K., de Pablo, J. J., Graham, M. D., Coppersmith, S. N., Goldstein, S., et al. (2004) *Analytical Chemistry* 76, 5293-5301.
B19. Lebofsky, R. & Bensimon, A. (2003) *Briefings in functional genomics and proteomics* 1, 385-396.
B20. Lin, J., Qi, R., Aston, C., Jing, J., Anantharaman, T. S., Mishra, B., White, O., Daly, M. J., Minton, K. W., Venter, J. C., et al. (1999) *Science* 285, 1558-1562.
B21. Riehn, R., Lu, M. C., Wang, Y. M., Lim, S. F., Cox, E. C., & Austin, R. H. (2005) *Proceedings of the National Academy of Sciences USA* 102, 10012-10016.

Example 3

Diffusion Gated Nanowells for Trapping and Aligning Surface Anchored DNA Molecules We have previously demonstrated that we can use nanofabricated barriers to control lipid diffusion to align molecular curtains of DNA, which can be visualized by TIRF microscopy and used for physical analysis of the DNA molecules themselves or can serve as a tool for probing protein-DNA interactions. The advantages of this technology is that it permits these studies to be conducted at the single molecule level, but in a high throughput format that permits massively parallel data acquisition. However, one drawback of these prior barrier patterns is that they require the continuous application of a hydrodynamic (or electrophoretic) force to confine the mobility of the aligned DNA molecules. In the absence of this force the DNA molecules diffuse away from the barrier edge and making it difficult to probe biochemical interactions that involve the formation of DNA loops (e.g. the interactions between RNA polymerase bound to a promoter and a transcription factor bound to a distal enhancer element). To overcome this problem here we have developed a technology for aligning curtains of DNA wherein the constituent molecules are trapped at defined locations. This is accomplished using barriers patterns that contain long, narrow entry pores, which are used to guide single DNA molecules into individual geometric nanowells. In the absence of buffer flow the DNA molecules diffuse away from the lipid coated surface, but they can not escape the geometric nanowells over time scales ranging up to tens of minutes. These barrier designs are ideal for studying any protein-DNA interaction that involves the association of distal components bound along the same DNA chain.

Figure 11A:
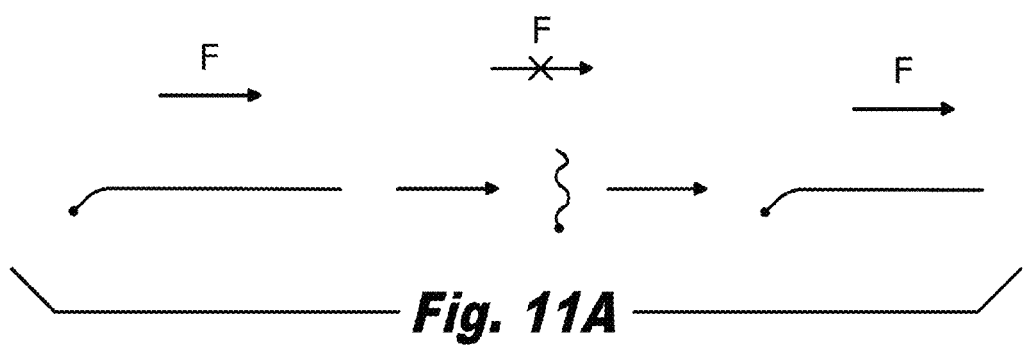
FIGS. 11A-D is a schematic of gated nanowells in the absence and presence of flow (F). Note that the drawings are not to scale, the dimensions of the barriers can be altered to accommodate specific experimental requirements, and the designs rely on nanofabrication techniques (such as electron-beam lithography).
Figure 11B:
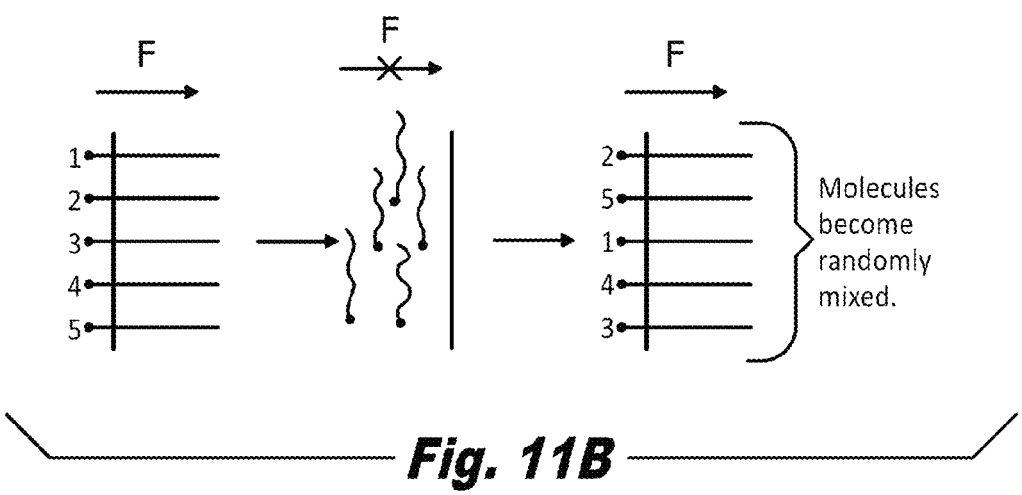
Figure 11C:
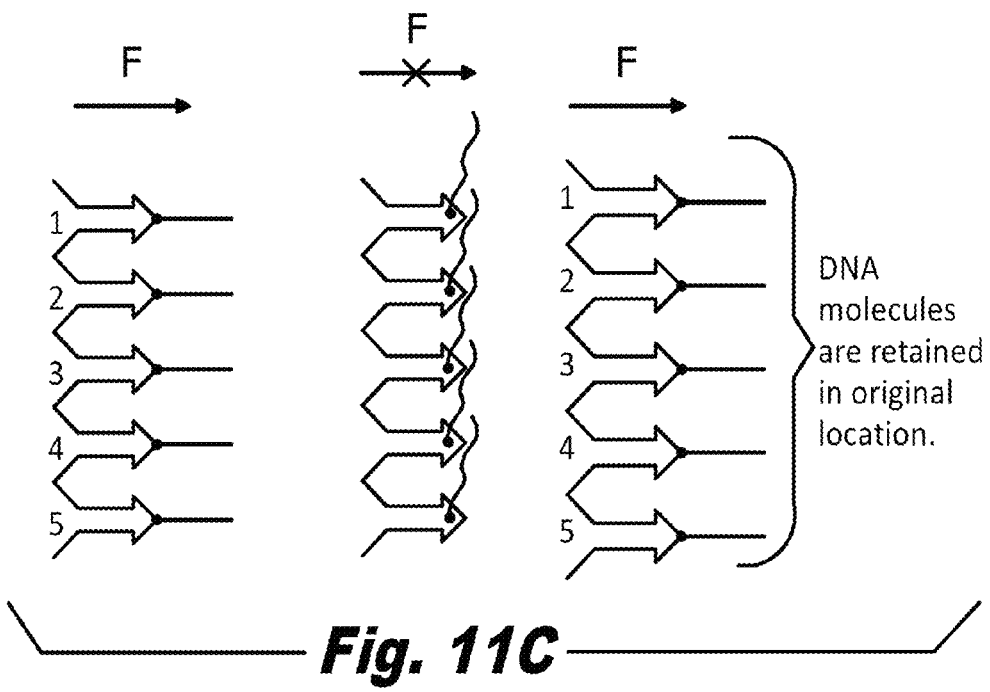
Figure 11D:
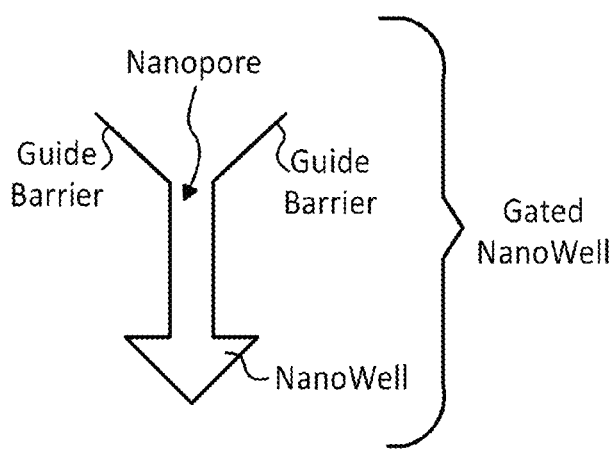

FIG. 11A illustrates the response of a surface tethered DNA molecule (shown in green throughout) to changes in applied buffer flow. When flow is maintained the DNA molecule can be stretched parallel to the surface and is maintained within the detection volume defined by the penetration depth of the evanescent field. When flow is paused the DNA diffuses up out of the field, permitting and long distance interactions (i.e. DNA looping) between distal locations along the contour length of the molecule. When flow is resumed the molecule can again be viewed along its full contour, allowing the assessment of any effects brought about by the DNA looping. FIGS. 11B-C show the consequences of transiently terminating buffer flow with a DNA curtain assembled at a normal linear diffusion barrier (barriers are shown in black) compared to a non-linear, geometric barrier comprised of gated nanopores. With a normal linear barrier edge, as shown in FIG. 11B, termination of flow allows DNA molecules to diffuse away from the surface, as described in FIG. 11A, but the DNA also diffuses away from the edge of the barrier itself. As a result, when flow is resumed the order of the DNA molecules along the edge is different compared to the order that existed before terminating buffer flow. In this example, the individual DNA molecules are numbered to emphasize that the order changes. This makes it extremely difficult or impossible to distinguish the molecules from one another before and after flow is transiently paused (i.e. if the molecules are all sequences, then one can not distinguish molecule #1 from any of the other four DNA molecules). In contrast, DNA molecules trapped and aligned with the gated geometric nanowells in FIG. 11C do not diffuse out of the individual nanowells when flow is terminated. This is because diffusion of the tethered DNA out of the nanowells comprising the non-linear, geometric barrier is inhibited by the long, narrow geometry of the nanopores. FIG. 11D highlights the details of the gated nanowells, including the guide channels used to direct the DNA into the nanopore entry channel, and the geometric nanowell residing at the end of the nanopore.

Uses: Trapping DNA for continuous analysis involving steps that necessitate the absence of buffer flow; Physical analysis of DNA looping; Analysis of protein-protein interactions that require DNA looping; and Will enable selective manipulation and isolation of single DNA molecules from within a more complex mixed population.

Example 4

Nanofabricated Racks for Aligning Curtains of Double-Tethered DNA Molecules

Figure 12A:
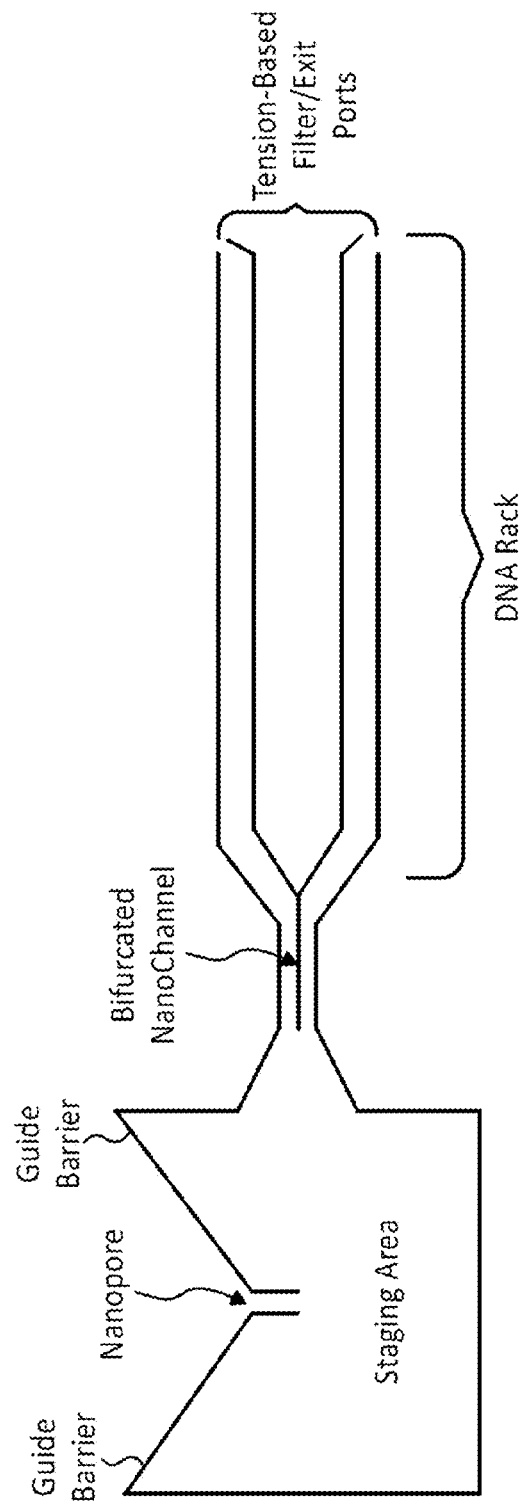
FIG. 12A is a schematic of the DNA rack for making curtains of double-tethered DNA. The diagram shows the overall design of the barriers elements that comprise the DNA rack. The guide channels are used to direct lipid-anchored molecules of DNA through a gated nanopore and into a staging area. Hundreds or thousands of DNA molecules will be loaded into the staging area, and once loaded these molecules will be pushed through a bifurcated nanochannel into the rack area. The tension-based filter/exit ports reside at the ends of these channels.
Figure 12B:
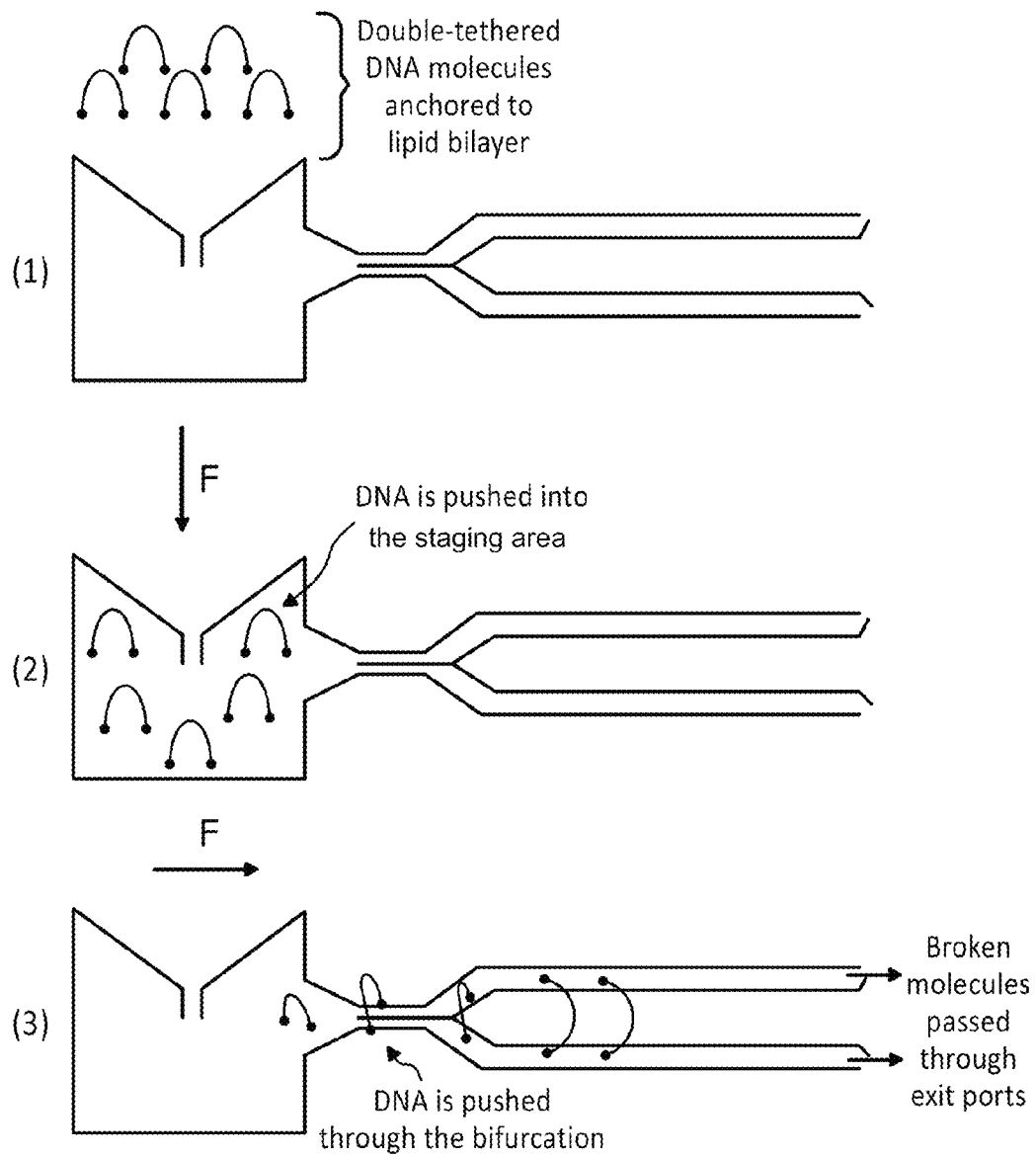
FIG. 12B is a schematic that shows how the rack is loaded with DNA. First, DNA molecules are anchored by both ends to a lipid bilayer coating the surface of the microfluidic sample chamber. Buffer flow is then used to push these molecules into the staging area, and once the staging area is loading with a sufficient number of DNA molecules buffer flow can be terminated. The DNA molecules are retained within the staging area because they can not readily diffuse back out through the gated nanopore. At this stage, a tangential force is applied (either buffer flow or electrophoretic) which pushes the DNA molecules though the bifurcated nanochannel (towards the right hand side in the drawing). DNA molecules will be passed through the exit ports and discarded in they are either (i) broken, (ii) too long, (iii) anchored by only one end, or (iv) have both anchored ends pass through the same side of the bifurcation. In contrast, DNA molecules will be retained within the rack if they are anchored to the bilayer by both ends, the ends of the individual molecules pass through separate sides of the bifurcation, and the DNA is longer then the distance separating the interior edges of the rack, but shorter than the length designated by the dimensions of the tension-based filter/exit ports. The dimension of the overall design can be adjusted to accommodate any desired DNA substrate

Here we present a combination of different non-linear, geometric barrier patterns that enable complex manipulation of DNA molecules that are anchored to a fluid lipid bilayer on the surface of a microfluidic sample chamber (see FIGS. 12A-B). The non-linear, geometric barrier elements include a nanopore-gated staging area, which is used to irreversibly capture linear DNA molecules that are anchored by both ends to the bilayer and pushed into the staging area using hydrodynamic force. Once captured, the DNA molecules are driven in the perpendicular direction using tangentially applied force generated either using buffer flow or an electric field. This pushed the DNA molecules to one side of the staging area where they encounter a bifurcated nanochannel that directs each end of the same DNA molecules down a pair of parallel channels (the DNA rack), which are separated by a user defined distance designed to stretch the double-tethered DNA molecules to a desired length. The exit ports at the ends of each channel are designed to retain any DNA using a tension-based selection while at the same time filtering out any broken molecules. Once the molecules are aligned within the rack they are maintained in a stretched configuration and can be visualized by TIRFM in the absence of either a flow or electrophoretic force. These aligned arrays of double-tethered DNA curtains offer an ideal high-throughput format for analyzing DNA molecules or protein-DNA interactions in the absence of a perturbing hydrodynamic force.

Uses: Any biochemical/biophysical studies of DNA or protein-DNA interactions that must be conducted in the absence of a perturbing hydrodynamic or electrophoretic force (for example, promoter-enhance interactions during transcription); Studies of one-dimensional diffusion and target site binding by proteins (i.e. visualizing where and how transcription factors or DNA repair proteins bind DNA); and Size selective fractionation of single DNA molecules (the rack elements can be designed to accommodate any desired DNA or even a range of different sized DNA molecules).

Example 5

Nanofabricated Racks of Aligned and Anchored DNA Molecules for Imaging Individual Protein-DNA Interactions Here we develop new strategies to construct curtains of DNA in which the substrates themselves are aligned with respect to one another and maintained in an extended configuration with both ends anchored to the surface of a microfluidic sample chamber that is otherwise coated with an inert lipid bilayer. This is accomplished through the use of nanofabricated racks of metallic barrier patterns with different functional elements, which together enable alignment and anchoring of hundreds of individual DNA molecules. Linear barriers to lipid diffusion are used to align the DNA, and antibody-coated pentagons provide solid anchor points for the free ends of the molecules. These double-tethered curtains of anchored DNA can be visualized using total internal reflection fluorescent microscopy under conditions that do not require the use of continuous buffer flow to stretch the DNA. This offers the potential for data acquisition without perturbing the behavior of the proteins under investigation through the application of an externally applied hydrodynamic force. We provide a proof-of-principle demonstration that these DNA racks can be used in a 1D diffusion assay that monitors the motion of the mismatch repair proteins along DNA.

Linear barriers to lipid diffusion are used to align the DNA, and antibody coated pentagons provide solid anchor points for the free ends of the molecules. These double-tethered curtains of anchored DNA can be visualized using total internal reflection fluorescent microscopy under conditions that do not require the use of continuous buffer flow to stretch the DNA. This offers the potential for data acquisition without perturbing the behavior of the proteins under investigation through the application of an externally applied hydrodynamic force. We provide a proof-of principle demonstration that these DNA racks can be used in a 1D diffusion assay that monitors the motion of the mismatch repair protein complex Msh2-Msh6 along DNA.

Dynamic interactions between proteins and DNA underlie many biological processes, and as such are the subject of intense investigation. Many laboratories are now tackling these problems using new experimental methods that enable the visualization of protein-DNA complexes at the single molecule level in real time, and the information garnered from these experiments is being used to build detailed mechanistic models of many different types of reactions. However, one major drawback of many single molecule techniques is that they are inherently designed to probe individual reactions, and as a consequence it can be challenging to gather statistically relevant data. This difficulty is often compounded by the fact that these experiments are often technically demanding. Therefore it is highly advantageous to establish new approaches that can increase throughput capacity of single molecule methods, and make these approaches both easier and more readily applicable to biological reactions involving different types of DNA transactions.

In an effort to help make these techniques more accessible we have integrated nanoscale engineering, microfluidics, and lipid bilayer-coated surfaces with single molecule optical microscopy to develop high-throughput methods for making molecular curtains comprised of thousands of individual DNA molecules (C1-3). A key aspect of these experimental platforms is that they take advantage of the fluid nature of lipid bilayers to control the organization of DNA molecules tethered to individual lipids (C4, C5). This is accomplished by first coating a sample chamber surface with a bilayer containing a small fraction of biotinylated head groups, and DNA molecules are then anchored by one end to the bilayer via a biotin-neutravidin linkage. These lipid-tethered DNA molecules are assembled into molecular curtains by pushing them to the leading edge of either micro- or nanoscale lipid diffusion barriers (for example, linear or non-linear, geometric barriers) through the application of a hydrodynamic force. In our initial studies we demonstrated that microscale barriers to lipid diffusion made by manually etching a fused silica surface with a diamond-tipped scribe could be used to align hundreds of lipid-tethered DNA molecules (C3). More recently we have established methods for fabricating barriers with nanoscale dimensions that allow for much more precise control over both the location and lateral distribution of the DNA molecules (C1, C2). These nanofabricated DNA curtains permit simultaneous visualization of thousands of individual DNA molecules that are perfectly aligned with respect to one another, and can be used for massively parallel data acquisition from thousands of individual protein-DNA complexes in real time using a robust experimental platform that is amenable to a wide variety of biological applications.

We have also shown that these DNA curtains are highly advantageous for studying protein-DNA interactions at the single molecule level, and we have applied these tools to biological systems such as chromatin remodeling, homologous DNA recombination, and post-replicative mismatch repair (C6-9). This experimental platform is especially applicable to the real time detection of fluorescent proteins bound to the DNA. However, these previous DNA curtains require the continuous application of a hydrodynamic force during data collection because just one end of the DNA is anchored to the lipid bilayer. If buffer flow is terminated the DNA does not remain stretched, and as a consequence it can not be visualized along its full contour length because it drifts outside of the detection volume defined by the penetration depth of the evanescent field. The need for buffer flow is not problematic for many types of measurements, however, it can potentially impact the behavior of bound proteins or protein complexes, and the magnitude of this impact can scale in proportion to the hydrodynamic radius of the molecules under observation. The influence of buffer flow is especially apparent during measurements involving proteins that slide on DNA by one-dimensional diffusion, because an applied flow force can strongly bias the direction that the sliding proteins travel along the DNA.

The need for buffer flow is not problematic for many types of measurements, however, it can potentially impact the behavior of bound proteins or protein complexes, and the magnitude of this impact can scale in proportion to the hydrodynamic radius of the molecules under observation. The influence of buffer flow is especially apparent during measurements involving proteins that slide on DNA by one-dimensional diffusion, because an applied flow force can strongly bias the direction that the sliding proteins travel along the DNA.

Here we sought to develop new procedures for making curtains of aligned DNA molecules that were held in an extended configuration anchored by both ends to the surface of a microfluidic sample chamber and suspended above an inert bilayer. To accomplish this we have developed new patterns of metallic barriers with distinctive functional elements. These metallic patterns incorporate both linear barriers to lipid diffusion and non-linear, geometric barriers comprising arrayed pentagons, and together these elements function to align and tether long molecules of DNA. The DNA molecules are first anchored by one end to a fluid lipid bilayer via a biotin-neutravidin interaction, and initially aligned with one another by using hydrodynamic force to push them into the linear barriers. The arrayed pentagons serve as solid anchor points positioned at a defined distance downstream from the linear barriers and are coated with antibodies directed against either digoxigenin or bromodeoxyuridine, which are covalently attached to the free ends of the DNA molecules. Importantly, once linked to the surface the DNA molecules are maintained in an extended state and confined within the detection volume defined by the penetration depth of the evanescent field, allowing for continuous observation along their full contour length, even in the absence of an applied hydrodynamic force.

Materials and Methods

Nanofabrication.

Fused silica slides were cleaned in NanoStrip solution (CyanTek Corp, Fremont, Calif.) for 20 minutes, then rinsed with acetone and isopropanol and dried with $N_2$. The slides were spin-coated with a bilayer of polymethylmethacrylate (PMMA), molecular weight 25K, 3% in anisole and 495K, 1.5% in anisole (MicroChem, Newton, Mass.), followed by a layer of Aquasave conducting polymer (Mitsubishi Rayon).

Each layer was spun at 4,000 rpm for 45 seconds using a ramp rate of 300 rpm/s. Polygon patterns for non-linear, geometric barriers and linear barriers were written by Ebeam lithography using an FEI Sirion scanning electron microscope equipped with a pattern generator and lithography control system (J. C. Nabity, Inc., Bozeman, Mont.). After patterning, Aquasave was rinsed off with deionized water. Resist was developed using a 3:1 solution of isopropanol to methyl isobutyl ketone (MIBK) for 1 minute with ultrasonic agitation at 5° C. The substrate was then rinsed in isopropanol and dried with $N_2$. A 15-20 nm layer of gold atop a 3-5 nm adhesion layer of either chromium or titanium was deposited using a Semicore electron beam evaporator. Liftoff was effected at 80° C. in a 9:1 ratio of methylene chloride to acetone. Alternatively, barriers were made out of just a 15-20 nm layer of chromium, as previously described. Following liftoff, samples were rinsed with acetone to remove stray chromium flakes and dried with $N_2$. Barriers were imaged using a Hitachi 4700 scanning electron microscope and a PSIA XE-100 Scanning Probe Microscope in noncontact mode. Optical images of the barriers were taken with a Nikon Eclipse ME600 at either 50× or 100× magnification (as indicated).

Lipid Bilayers and DNA Curtains.

The flowcells were assembled from fused silica slides (G. Finkenbeiner, Inc.) with chromium nanoscale diffusion barriers. Inlet and outlet ports were made by boring through the slide with a high-speed precision drill press equipped with a diamond-tipped bit (1.4 mm O.D.; Kassoy). The slides were cleaned by successive immersion in 2% (v/v) Hellmanex, 1 M NaOH, and 100% MeOH. The slides were rinsed with filtered sterile water between each wash and stored in 100% MeOH until use. Prior to assembly, the slides were dried under a stream of nitrogen and baked in a vacuum oven for at least 1 hour. A sample chamber was prepared from a borosilicate glass coverslip (Fisher Scientific) and double-sided tape (~25 µm thick, 3M). Inlet and outlet ports (Upchurch Scientific) were attached with hot-melt adhesive (SureBonder glue sticks, FPC Corporation). The total volume of the sample chambers was ~4 µl. A syringe pump (Kd Scientific) and actuated injection valves (Upchurch Scientific) were used to control sample delivery, buffer selection and flow rate. The flowcell and prism were mounted in a custom-built heater with computer-controlled feedback regulation to control the temperature of the sample from between 25-37° C. (±0.1° C.), as necessary. After each use, the slides were soaked in MeOH to remove the ports and tape, rinsed with water, washed briefly (15-20 minutes) with Nanostrip, and finally rinsed with water. This procedure was sufficient to clean the slide surfaces for reuse, and each slide could be used multiple times degrading the quality of the optical surface or the metallic patterns.

DNA curtains were constructed as described. All lipids were purchased from Avanti Polar Lipids and liposomes were prepared as previously described. In brief, a mixture of DOPC (1,2-dioleoyl-sn-glycero-phosphocholine), 0.5% biotinylated-DPPE (1,2-dipalmitoyl-sn-glycero-3-phosphoethanolamine-N-(cap biotinyl)), and 8-10% mPEG 550-PE (1,2-dioleoyl-sn-glycero-3-phosphoethanolamine-N-[methoxy (polyethylene glycol)-550]). The mPEG is does not affect bilayer formation or assembly of the DNA curtains, but rather serves to further passivated the surface against nonspecific adsorption of quantum dots (which we use in our studies of protein-DNA interactions). Liposomes were applied to the sample chamber in three injections of 200 µl followed by 5 minute incubations. Excess liposomes were flushed away with 1 ml of buffer A, which contained 10 mM Tris-HCl (pH 7.8) plus 100 mM NaCl, and the bilayer was incubated for an addition 30 minutes. Buffer A plus 25 µg/ml anti-DIG Fab (Roche) or anti-BrdU IgG (Sigma) was then injected into the sample chamber and incubated for 30 minutes. The sample chamber was then flushed with 1 ml of buffer B, which contained 40 mM Tris-HCl (pH 7.8), 1 mM DTT, 1 mM $MgCl_2$, and 0.2 µg/ml BSA, and incubated for an additional 5 minutes. 1 ml of buffer A containing Neutravidin (330 nM) was then injected into the sample chamber and incubated for 20 minutes. The flowcell was then rinsed with 3 ml of buffer B to remove any unbound Neutravidin. 1 ml of λ-DNA (20 pM) labeled at one end with biotin and at the other end with digoxigenin (see below) and pre-stained with 1-2 nM YOYO1 was injected into the sample chamber in five 200 µl aliquots, with a 2-3 minute incubation period following each injection. The DNA was then aligned at the linear barriers using a flow rate of 0.02 ml/min, and this rate was then increased to 2-3 ml/min to anchor the second end of the DNA molecules.

DNA substrates. The DNA substrates were made by ligating oligonucleotides to the 12 nucleotide overhangs at the end of the λ phage genome (48.5 kb). Ligation mixes (1 ml total volume) contained 4 nM λ DNA (Invitrogen), 1 µM biotinylated oligonucleotiode (5'-pAGG TCG CCG CCC [BioTEG]-3' [SEQ ID NO: 1]), 1 µM BrdU labeled oligonucleotide (or DIG labeled oligonucleotide; 5'-pGGG CGG CGA CCT [BrdU]-3' [SEQ ID NO: 2] or 5'-pGGG CGG CGA CCT [DIG]-3' [SEQ ID NO: 3]), and 1× ligase buffer (NEB). The reaction mix was warmed to 65° C. for 10 minutes and then cooled slowly to room temperature. After cooling, ligase was added (T4 DNA ligase (400 U/µl) or Taq ligase (40 U/µl); NEB) and the mixture was incubated overnight at 42° C. Reactions performed with T4 ligase were then heat inactivated at 65° C. for 10 minutes, and the ligated DNA products were purified over a Sephacryl S200HR column (GE Healthcare) run in 10 mM Tris-HCl (pH 7.8), 1 mM EDTA, plus 150 mM NaCl. The purified DNA was stored at −20° C.

For inserting a DIG labeled oligonucleotide complementary to position 26,151-26,166 on λ 500 ul of DNA (200 pM; labeled at the ends with biotin and BrdU (as described above)) was incubated for 2 h with the nicking enzymes Nb.BsmI and Nt.BstNBI (50 U each; NEB) at 55° C. in buffer containing 10 mM Tris-HCl (pH 7.8), 10 mM $MgCl_2$, 150 mM NaCl. 1 uM of oligonucleotide (5'-pCAT TCT TGA GTC CAA TTT TT[DIG]-3' (SEQ ID NO: 4)) was then added to the solution along with 10 mM EDTA and the mixture was incubated at 55° C. for 20 minutes and then allowed to slowly cool to room temperature over the course of an hour. ATP was added to a final concentration of 1 mM along with 2,000 units of T4 ligase and an additional 10 mM $MgCl_2$. The reaction was then incubated at room temp. for 90 min. Additional EDTA ($C_f$=20 mM) was added to the solution and the nicking enzymes and ligase were heat denatured at 80° C. for 20 minutes. This procedure was also used for concurrently inserting oligonucleotides at 26,151-26,166 and 33,779-33,791 in the same DNA.

For inserting an oligonucleotide at only position 33,779-33,791 on λ 500 ul DNA (200 pM; labeled at the ends with biotin and BrdU) was incubated for 2 h with the nicking enzyme Nt.BstNBI (50 U; NEB) at 55° C. in buffer containing 10 mM Tris-HCl (pH 7.8), 10 mM $MgCl_2$, 150 mM NaCl. The enzyme was heat denatured by incubation at 80° C. for 20 min. 1 µM of oligonucleotide (5'-pTTC AGA GTC TGA CTT TT[DIG]-3' [SEQ ID NO: 5]) was added to the solution and the mixture was incubated at 55° C. for 20 min., then cooled slowly to room temp. over the course of 1 h. ATP was then added to a final concentration of 1 mM along with 2,000 units of T4 ligase, and the reaction was incubated at room temp. for 90 min. The ligase was then heat denatured by incubation at 65° C. for 20 min.

TIRFM and 1D Diffusion Assays.

The microscope used in this study has been previously described (C3). In brief, the system is built around a Nikon TE2000U inverted microscope with a custom-made illumination system. A 488 nm, 200 mW diode-pumped solid-state laser (Coherent, Sapphire-CDHR) was used as the excitation source. The laser was attenuated as necessary with a neutral density filter and centered over the DNA curtain by means of a remotely operated mirror (New Focus). The beam intensity at the face of the prism was ~10-15 mW. Images were detected with a back-illuminated EMCCD detector (Photometrics, Cascade 512B). TIRFM images were collected using a 60× water immersion objective lens (Nikon, 1.2 NA Plan Apo), unless otherwise indicated.

Results

Design Elements of the DNA Rack.

We have previously demonstrated that mechanical barriers that disrupt the continuity of lipid bilayers can be used to construct molecular curtains of aligned DNA molecules (C1-3). We have also shown that these DNA curtains provide a unique and advantageous tool for studying protein-DNA interactions at the single molecule level when visualized by TIRFM. Here we expand on our previous work and demonstrate the development of new barrier elements, which we call DNA "racks", that can be used to make DNA curtains in which both ends of the molecules are anchored to the flowcell surface. An overview of the general design is presented in FIGS. 13 and 18 and utilizes a combination of two distinct pattern elements, as described below. To make the curtains, one end of the DNA is first anchored via a biotin-neutravidin interaction to a supported lipid bilayer coating the surface of the sample chamber (FIG. 13B and FIG. 13C). In the absence of a hydrodynamic force the molecules are randomly distributed on the surface, but lie primarily outside of the detection volume defined by the penetration depth of the evanescent field (~150-200 nm). Application of flow pushes the DNA through the sample chamber with one end remaining anchored to the bilayer. The first pattern elements are linear barriers to lipid diffusion, which are oriented perpendicular to the direction of flow at strategic locations in the path of the DNA (FIG. 13B and FIG. 13C); these linear barriers are designed to halt the movement of the lipid-tethered DNA molecules causing them to accumulate at leading edge of the barriers where they then extend parallel to the surface.

The second elements of the pattern are a series of arrayed pentagons (for example, a non-linear, geometric barrier) positioned behind the linear barriers and separated from one another by small nanochannels. The non-linear, geometric shape of the pentagons is intended to act as a funnel and direct any lipid-tethered DNA molecules through the nanochannels so that they do not accumulate at the leading edge of the pentagons, but rather are pushed along the surface until they encounter the next successive linear barrier in the pattern. The distance between the linear barriers and the pentagons is optimized for the length of the DNA to be used for the experiments. The pentagons themselves present a large surface that can be coated with antibodies directed against digoxigenin (DIG), which is covalently linked to the ends of the DNA opposite the ends bearing the biotin tag. When the DIG-coupled DNA end encounters the antibody-coated pentagons they should become immobilized, and the DNA should remain stretched parallel to the surface even when no buffer is being pushed through the sample chamber. The distance between each of the successive linear barriers should influence the density of aligned DNA because the total number of molecules anchored to the bilayer is directly proportional to the area encompassed by the bilayer upstream from each barrier. Varying the total distance between adjacent barrier sets on the flowcell surface should yield double-tethered DNA curtains of varying density, enabling the user to scan the surface for regions with an appropriate number of molecules for an experiment. Therefore the patterns were designed with separation distances of either 0.1, 0.2, 0.3, 0.4, or 0.5 μm between the adjacent sets of barriers (FIG. 13D).

Figure 14:
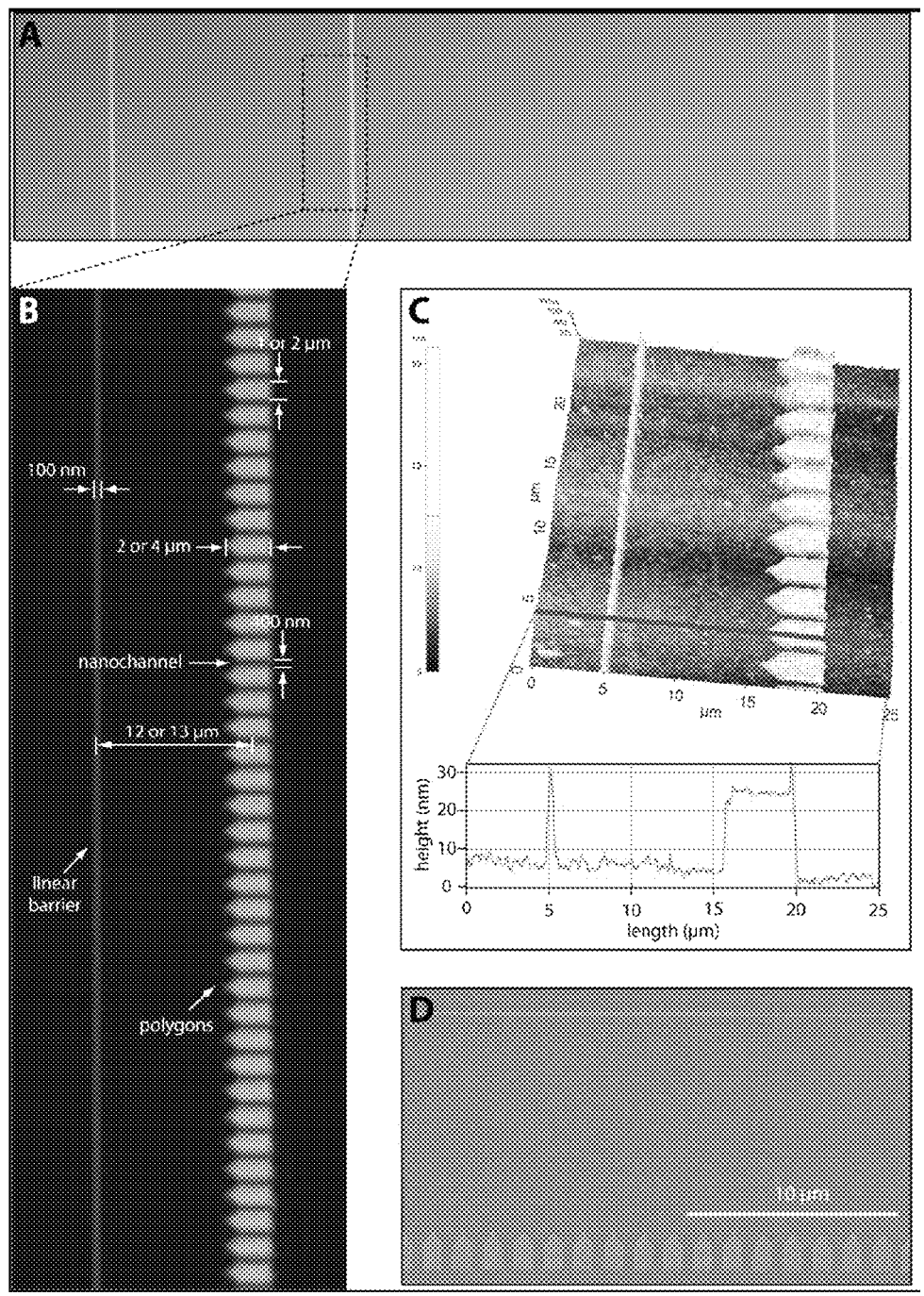
FIG. 14 depicts nanofabrication and characterization of the DNA rack elements.
Figure 19:
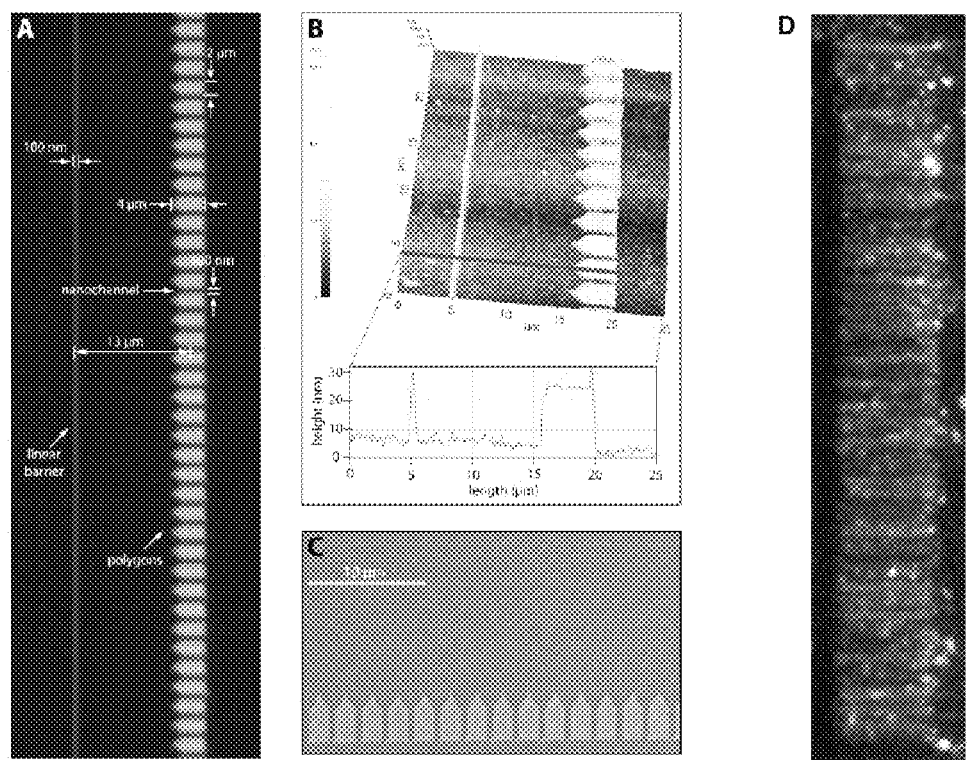
FIGS. 19A-D are images that show double tethered curtains of DNA.

FIGS. 14 and 19 show the characterization of a DNA rack made by Ebeam lithography and highlights specific features of the pattern geometry deemed critical for its function. FIG. 14A shows a low magnification optical image of the overall pattern design, indicating the variable spacing between the barrier sets within the pattern. A higher magnification optical image including the dimensions of critical pattern parameters is presented in FIG. 14B. FIG. 14C shows measurements of these parameters using atomic force microscopy (AFM). FIG. 14D shows characterization of the patterns with scanning electron microscopy (SEM). As demonstrated from these images, the height of the patterns elements was on the order of 20-25 nm, the width of the nanochannels was 500 nm, and the distance between the leading edge of the linear barriers and the center of the pentagon array was either 12 or 13 μm, as specified. This distance was specifically selected for use with λ-DNA, which is 48,502 base pairs with a fully extended contour length of approximately 16.5 μm, thus 11 to 13 μm would correspond to a mean extended length of ~70% to 80% that of the full contour length, respectively.

Assembly and Characterization of Double-Tethered DNA Curtains.

The overall design relies upon the selective, but nonspecific adsorption of antibodies to the exposed surface of the metallic pentagons, but the antibodies should not interact with the inert lipid bilayer. To assemble the DNA curtains, the surface of the flowcell was first coated with a lipid bilayer, as previously described, with the exception that BSA was omitted from all buffers used prior to deposition of the antibody. Once the bilayer was assembled on the surface, anti-DIG Fab fragments or anti-BrdU IgG was injected into the sample chamber where they were allowed to adhere nonspecifically to the exposed metal barriers. The antibodies could potentially bind both the linear barriers as well as the pentagons, but the very small surface area of the linear barriers should ensure selective adsorption of more antibody to the much larger pentagons. Following a brief incubation, the free Fab was rinsed from the flowcell and replaced with buffer containing 0.2 mg/ml BSA, which served as a nonspecific blocking agent to passivate any remaining exposed surfaces. DNA stained with the fluorescent intercalating dye YOYO1 was then injected into the sample chamber, incubated briefly without buffer flow, and then buffer flow was applied to push the anchored molecules into the linear barriers. Buffer flow was then terminated and the anchored DNA molecules imaged by TIRFM.

Figure 15:
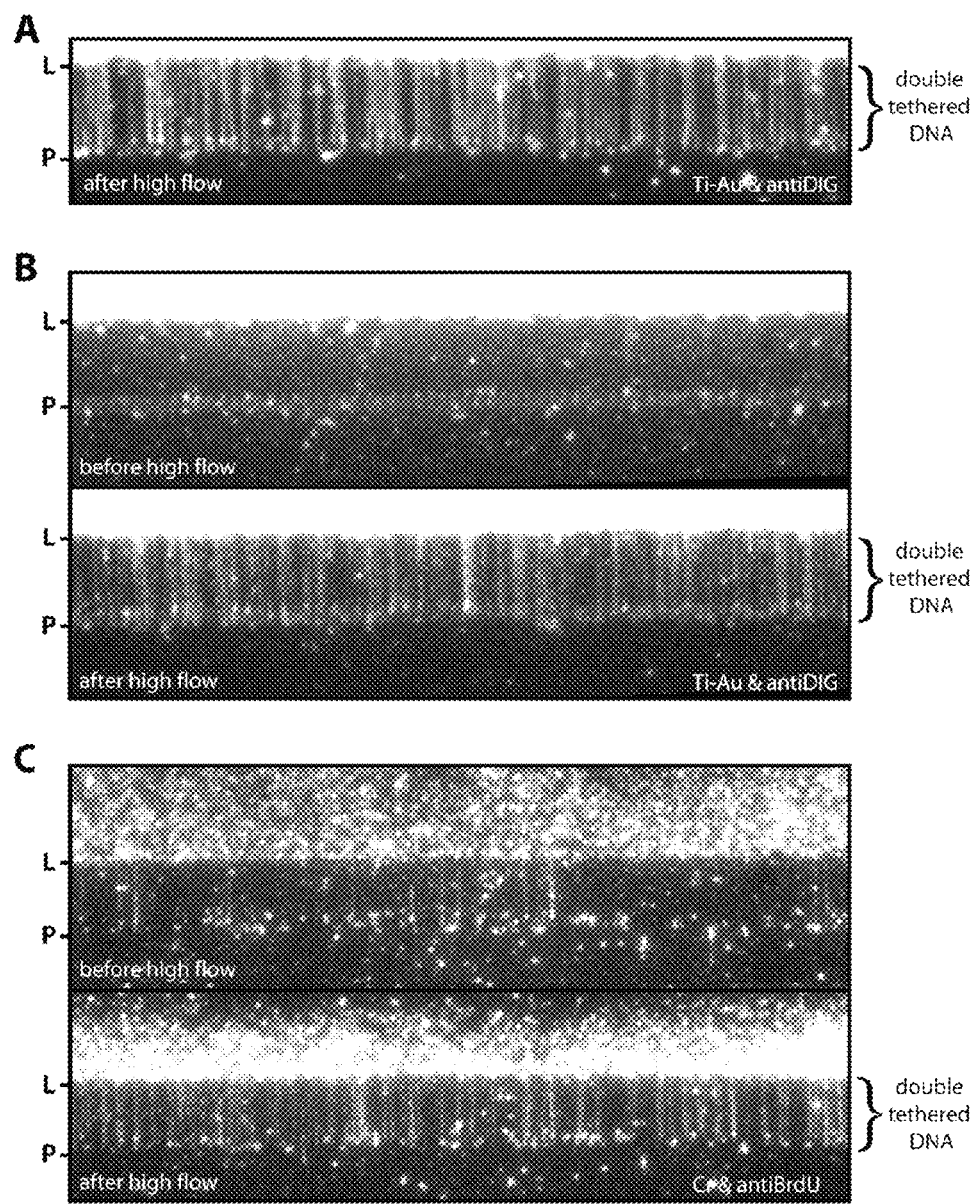
FIG. 15 depicts curtains of double-tethered DNA.

As shown in FIG. 15A, this procedure yielded curtains of DNA molecules that remained fully extended and visible even though no buffer was flowing through the sample chamber. Any DNA molecules that failed to become anchored by the DIG labeled end remained near the linear barriers, but only the ends of the molecules could be observed rather than their full contour lengths. These single-tethered DNA molecules gradually diffused away from the barrier edges and could also be pushed away from the barrier edge simply by reversing the direction of buffer flow (FIG. 15), but the double-tethered DNA molecules remained anchored to their original locations, providing additional conformation that the molecules making up the curtain are anchored in the desired configuration. The number of DNA molecules at each of the different barrier locations was proportional to the distance between the adjacent linear barriers. Similar results were obtained with DNA that was end-labeled with a single bromodeoxyuridine (BrdU) and pentagons coated with anti-BrdU antibodies (see below), although the BrdU anchored DNA ends had a greater tendency to dissociate from the pentagons. Finally, control experiments verified that the presence of both the DIG labeled and the Fab fragments were necessary for efficiently anchoring both ends of the DNA.

If the DNA anchored between the barriers was nonspecifically adhered to the sample chamber surface along its contour length, rather than suspended above the inert bilayer, then introduction of a double-stranded break should not cause the molecules to retract from the surface. In contrast, if the DNA were only anchored by the biotin and DIG-tagged ends as designed and suspended above the bilayer, then a double strand break in the strands should cause the molecules to retract away from the surface. When DNA molecules randomly break they can immediately retract from the surface as they diffuse out of the evanescent field and disappear from view. DNA molecules can only interact with the sample chamber surface through their anchored ends, and cannot interact nonspecifically with the lipid bilayer.

Defined Orientation of the DNA.

Figure 16:
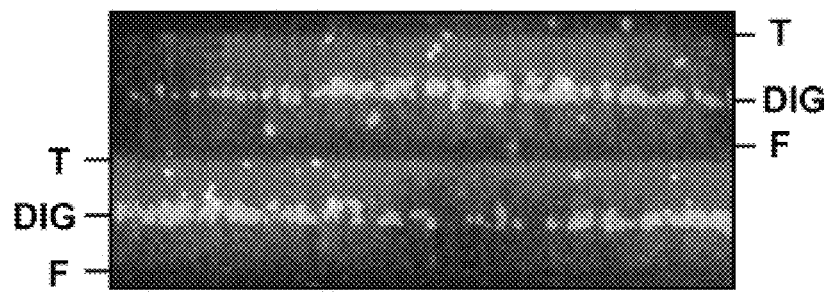
FIG. 16 shows the defined orientation of DNA molecules. This figure shows an example of two single tethered DNA curtains with a single DIG-Qdot tag marking the center of the DNA. This needs to be repeated with a double tethered curtain to provide verification that the molecules are all in the same orientation.

The differential chemistries used to anchor the two ends of the DNA was predicted to define the orientation of the DNA molecules within the curtains. Specifically, the biotinylated end should be anchored at the edge of the linear barrier and the other end should be at the pentagons, and based on this design all of the molecules should be in the exact same orientation. If the DNA molecules were aligned as expected, then a fluorophore located at a single specific site within the DNA and offset from its center should appear as a fluorescent "line" spanning the DNA curtain. The line should be oriented perpendicular to the long axis of the extended DNA molecules and should coincide precisely with the know location of the fluorescent tag. In contrast, if the DNA molecules were randomly oriented, then the fluorescent tags should appear as two lines demarking each of the two possible orientations of the DNA. To confirm that the DNA was oriented correctly, the molecules were labeled at the free ends with BrdU, and labeled at a specific internal position with DIG. The internal labels were made using an oligonucleotide replacement strategy wherein (see Materials and Methods). Experiments with DNA curtains anchored by a single end confirmed that the fluorescent tags were present at a single location within the DNA molecules as dictated by the sequences of the oligonucleotides. The double-tethered curtains were then assembled using pentagons coated with anti-BrdU antibodies, and after assembly the DIG tags with labeled with anti-DIG coated Qdots. As shown in FIG. 16, the anti-DIG Qdots were all aligned with one another, confirming the orientation of the DNA molecules.

Imaging Proteins Sliding on the DNA.

The primary motivation for development of these double-tethered DNA curtains was for use in experiments designed to visualize motion of proteins along DNA. We have previously demonstrated that the protein complex Msh2-Msh6 can diffuse in one-dimension along duplex DNA (C6) (see also FIGS. 50, 51, 52, 53, 54, and 55). Msh2-Msh6 is an essential component of the post-replicative mismatch repair machinery and is responsible for locating and initiating repair of biosynthetic DNA replication errors. Our initial studies with Msh2-Msh6 relied upon DNA molecules that were tethered by either end to neutravidin nonspecifically absorbed to a fused silica surface that was otherwise coated with a lipid bilayer.

With this approach we would obtain only 10-30 DNA molecules per flowcell that were suitable for making diffusion measurements. These double tethered DNA molecules were randomly distributed and had to be manually located before use by visually scanning the entire surface, making these 1D-diffusion measurements technically demanding. As shown above, using the engineered surfaces we can now visualize thousands of molecules per flowcell. Here we demonstrate that these anchored curtains of DNA are suitable for visualizing protein-DNA interactions.

Figure 17:
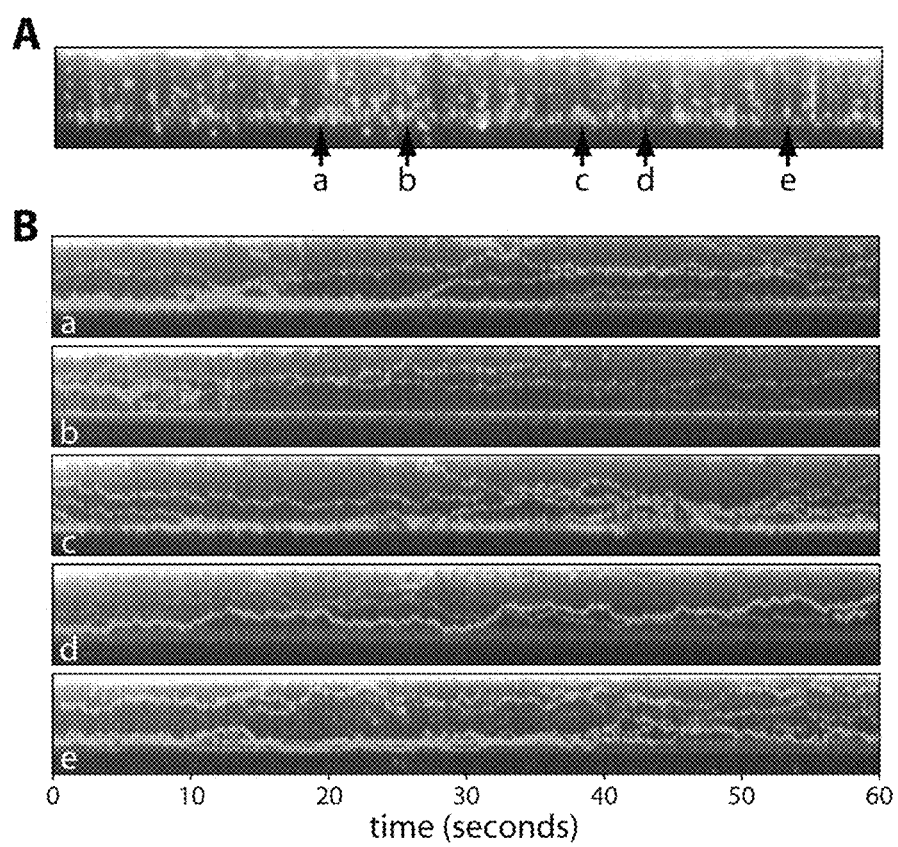
FIG. 17 depicts use of DNA racks to visualize 1D protein diffusion.

For these experiments we used the mismatch repair protein complex Mlh1-Pms1, and it was labeled with a single quantum dot via a FLAG epitope tag that was engineered into the Mlh1 subunit. The labeled proteins were injected into a flowcell containing a curtain of double tethered DNA molecules and videos were collected over a 60-second period. As shown in FIG. 17A, we could readily detect binding of Mlh1-PMs1 to the DNA molecules that were aligned and anchored on the surface. There were approximately 100 DNA molecules and 250 DNA-bound proteins observed in this single field of view, illustrating the improvement of this approach compared to our previous technique for making double tethered DNA molecules. The proteins bound to the DNA rapidly diffused along the DNA molecules, and this motion was revealed in kymograms made from representative examples of molecules within the DNA curtains (FIG. 17B). As with the naked DNA molecules, the protein-bound DNA molecules also retracted from view when the DNA strands were broken, verifying that there were no nonspecific interactions with the surface.

See also FIGS. 56, 57, 58, 59, 60, 61 and 62 for additional studies pertaining to double tethered curtains used to visualize Mlh1 diffusion as well as the diffusion of the Mlh1-Pms1 complex.

Discussion

Here we used direct-write Ebeam lithography to nanofabricate arrays of diffusion barriers followed by pentagonal anchor points, which together utilize different functional features to anchor curtains of DNA by both ends on the surface of a microfluidic sample chamber. We refer to these patterned surfaces as DNA "racks" because the DNA is stretched out and anchored to the flowcell surface where they can be viewed by TIRFM. An important aspect of these devices is that the fused silica surface is coated with a supported lipid bilayer, and the DNA molecules are suspended above this bilayer, ensuring that they are maintained within an inert microenvironment compatible with a range of biological molecules. We have demonstrated that these tools can be used along with wide-field TIRF microscopy to visualize hundreds of individual, perfectly aligned DNA molecules, all of which are arranged in the same orientation and anchored by both ends to the sample chamber surface. As with our previous nanofabricated devices, this new approach is simple and robust, the flowcells are reusable, the barriers themselves are uniform, and they do not compromise the optical quality of the fused silica or interfere with signal detection.

As a first conceptual demonstration of the utility of these DNA racks we show here that they can be used to image 1D-diffusion of DNA binding proteins. Our previous approach to these experiments relied upon DNA that was randomly anchored to a surface via biotin-neutravidin interactions, which yielded no more than 1-3 molecules of DNA per field-of-view, and there were just ~10-30 double-tethered DNA molecules present over the entire surface of the flowcell. Moreover, in our prior studies, the orientation of the DNA could not be defined because the molecules were anchored with a biotin located at either end of the DNA. Therefore the molecules were randomly oriented on the flow-cell surface, making it difficult to locate and compare different DNA molecules to one another in order to dissect sequence specific events. While this original approached proved useful for our initial studies, it was tedious and remained challenging to collect sufficient data for thorough analysis. As demonstrated here, we are now able to visualize on the order of one hundred DNA molecules per field-of-view, thousands of molecules are present on the surface of a flowcell, and all of these DNA molecules are aligned in the exact same orientation, which will make 1D diffusion measurements and molecule-to-molecule comparisons straightforward for future work.

REFERENCES

C1. Fazio, T., Visnapuu, M. L., Wind, S., & Greene, E. C. (2008) DNA curtains and nanoscale curtain rods: high-throughput tools for single molecule imaging. Langmuir 24, 10524-10531.
C2. Visnapuu, M. L., Fazio, T., Wind, S., & Greene, E. C. (2008) Parallel arrays of geometric nanowells for assembling curtains of DNA with controlled lateral dispersion. Langmuir 24, 11293-11299.
C3. Granéli, A., Yeykal, C., Prasad, T. K., & Greene, E. C. (2006). Langmuir 22, 292-299.
C4. Sackmann, E. (1996) Supported membranes: scientific and practical applications. Science 271, 43-48.
C5. Groves, J. & Boxer, S. (2002 March) Micropattern formation in supported lipid membranes. Acc Chem Res 35, 149-157.
C6. Gorman, J., Chowdhury, A., Surtees, J. A., Shimada, J., Reichman, D. R., Alani, E., & Greene, E. C. (2007) Dynamic basis for one-dimensional DNA scanning by the mismatch repair complex Msh2-Msh6. Mol Cell 28, 359-370.
C7. Granéli, A., Yeykal, C., Robertson, R. B., & Greene, E. C. (2006) Long-distance lateral diffusion of human Rad51 on double-stranded DNA. Proceedings of the National Academy of Sciences, USA 103, 1221-1226.
C8. Prasad, T. K., Robertson, R. B., Visnapuu, M. L., Chi, P., Sung, P., & Greene, E. C. (2007) A DNA-translocating Snf2 molecular motor: *Saccharomyces cerevisiae* Rdh54 displays processive translocation and extrudes DNA loops. J Mol Biol 369, 940-953.
C9. Prasad, T. K., Yeykal, C., & Greene, E. C. (2006). Journal of Molecular Biology 363, 713-728.

Example 6

Assessing Mechanisms of Msh2-Msh6 and Mlh1-Pms1 Mobility Along Arrays of Intersecting DNA Molecules During postreplicative mismatch repair (MMR), proteins must communicate information over long distances along the DNA helix. Without being bound by theory, evidence from bulk biochemical studies deminstrates this communication occurs predominantly through mechanisms involving motion of proteins along DNA. Consistent with this, we have used single molecule optical microscopy to demonstrate that the MMR proteins Msh2-Msh6 and Mlh1-Pms1 can both travel along DNA via a mechanism most consistent with sliding. Neither the bulk biochemical studies nor our single molecule observations could completely rule out other mechanisms, such as hopping, jumping and/or intersegmental transfer. Here we have devised an assay that enables us to determine whether Msh2-Msh6 and/or Mlh1-Pms1 can travel along DNA while employing one or more of these alternative mechanisms. This new assay relies upon nanofabricated metallic structures for arranging individual DNA molecules into crisscrossed patterns suspended above the surface of a microfluidic sample chamber otherwise coated with a lipid bilayer. We used these substrates to determine whether or not Msh2-Msh6 and/or Mlh1-Pms1 could transfer directly from one strand of DNA to another as the proteins slid past the junctions between intersecting DNA molecules.

MMR is conserved from bacteria to man. MMR involves various proteins, such as MutSα (which comprises Msh2-Msh6), MutLα (which comprises Mlh1-Pms1), ExoI, RPA, PCNA, pol δ, of which MutSα and MutLα will be discussed herein. Defects in this process result in 100-1000× increase in mutation frequency. For example, defects in MMR is associated with a cancer-prone syndrome, hereditary nonpolyposis colorectal cancer (HNPCC). Up to 90% of HNPCC cases are due to mutations in MSH2 or MLH1.

Figure 48:
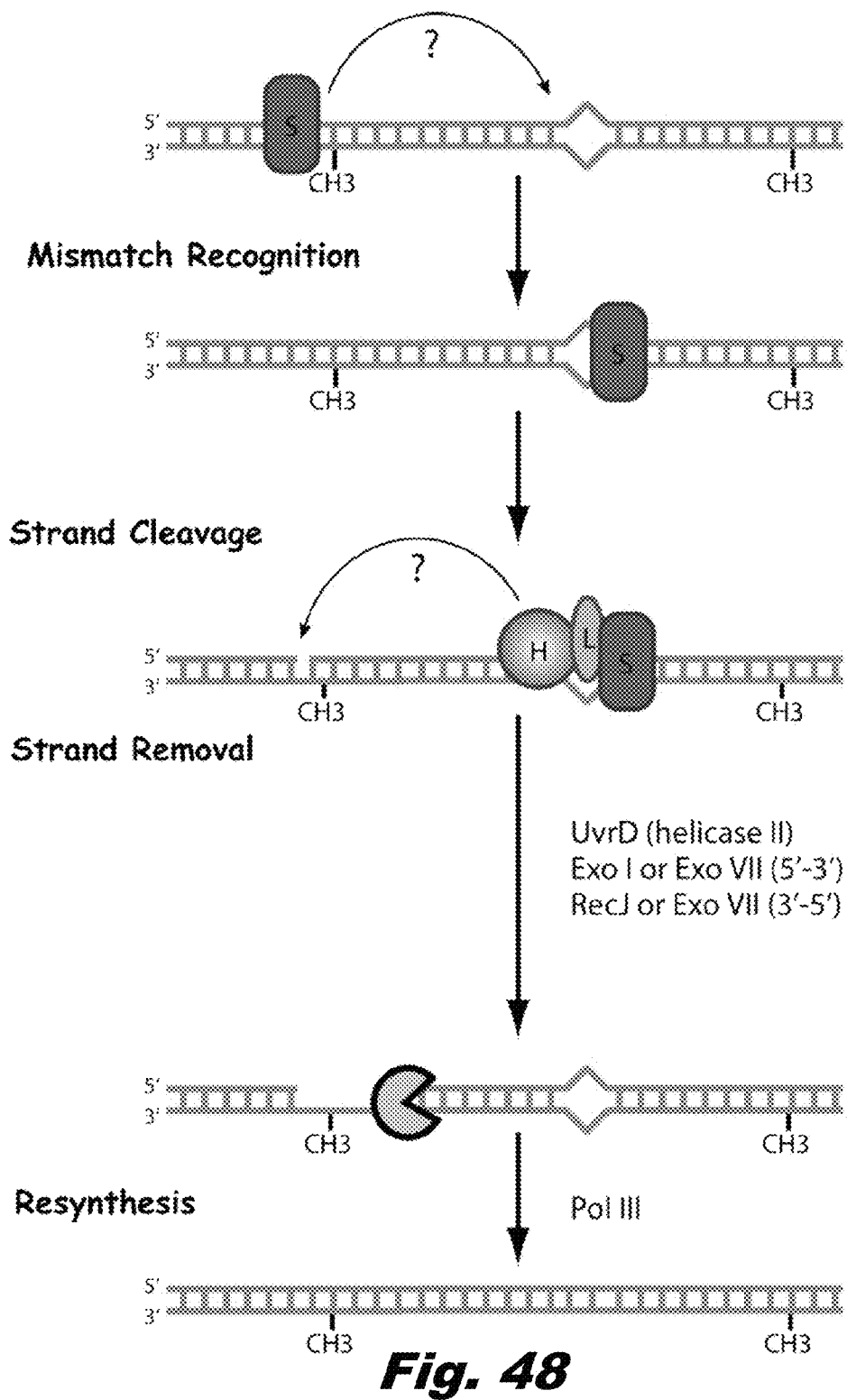
FIG. 48 is a schematic representing an overview of post-replicative mismatch repair.
Figure 50:
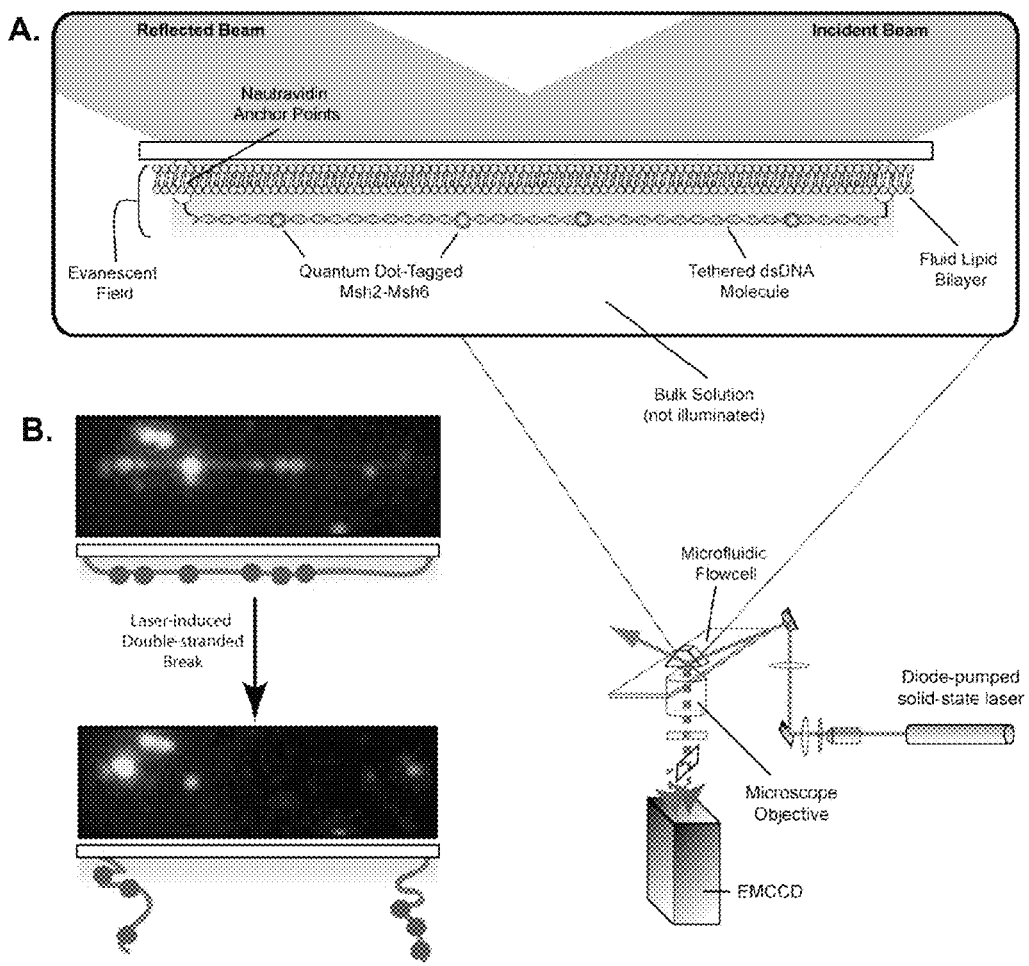
FIG. 50 represents a TIRFM-based experimental design for probing the dynamics of protein-DNA interactions at the single molecule level.
Figure 51:
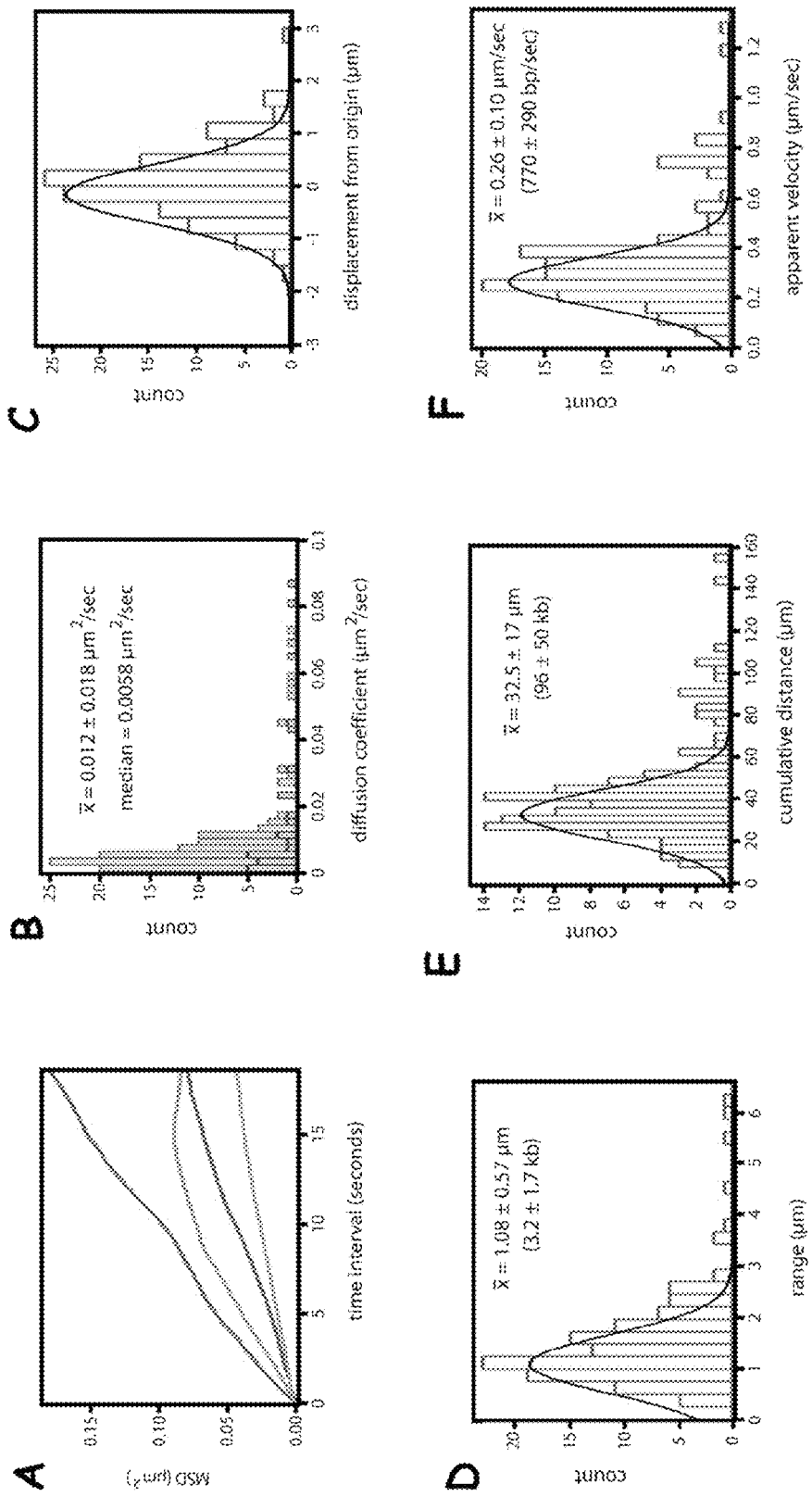
FIG. 51 shows graphs representing general Characteristics of Msh2-Msh6 diffusion.
Figure 53:
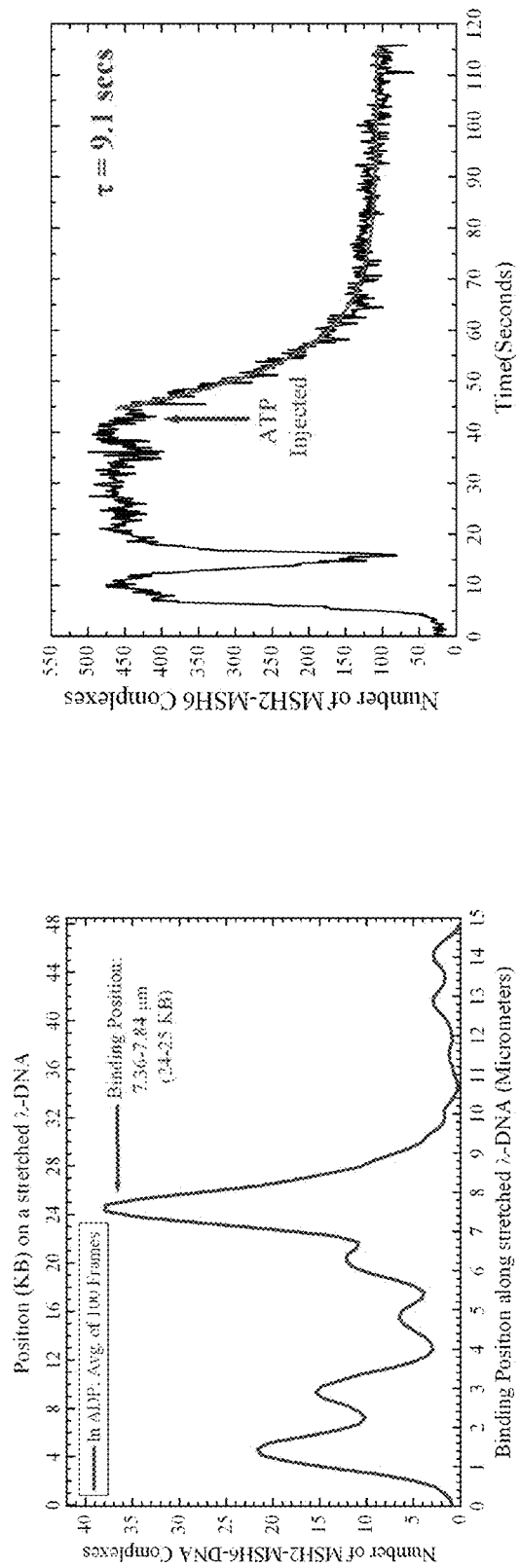
FIG. 53 shows graphs representing High-throughput single-molecule analysis of Msh2-Msh6.
Figure 54:
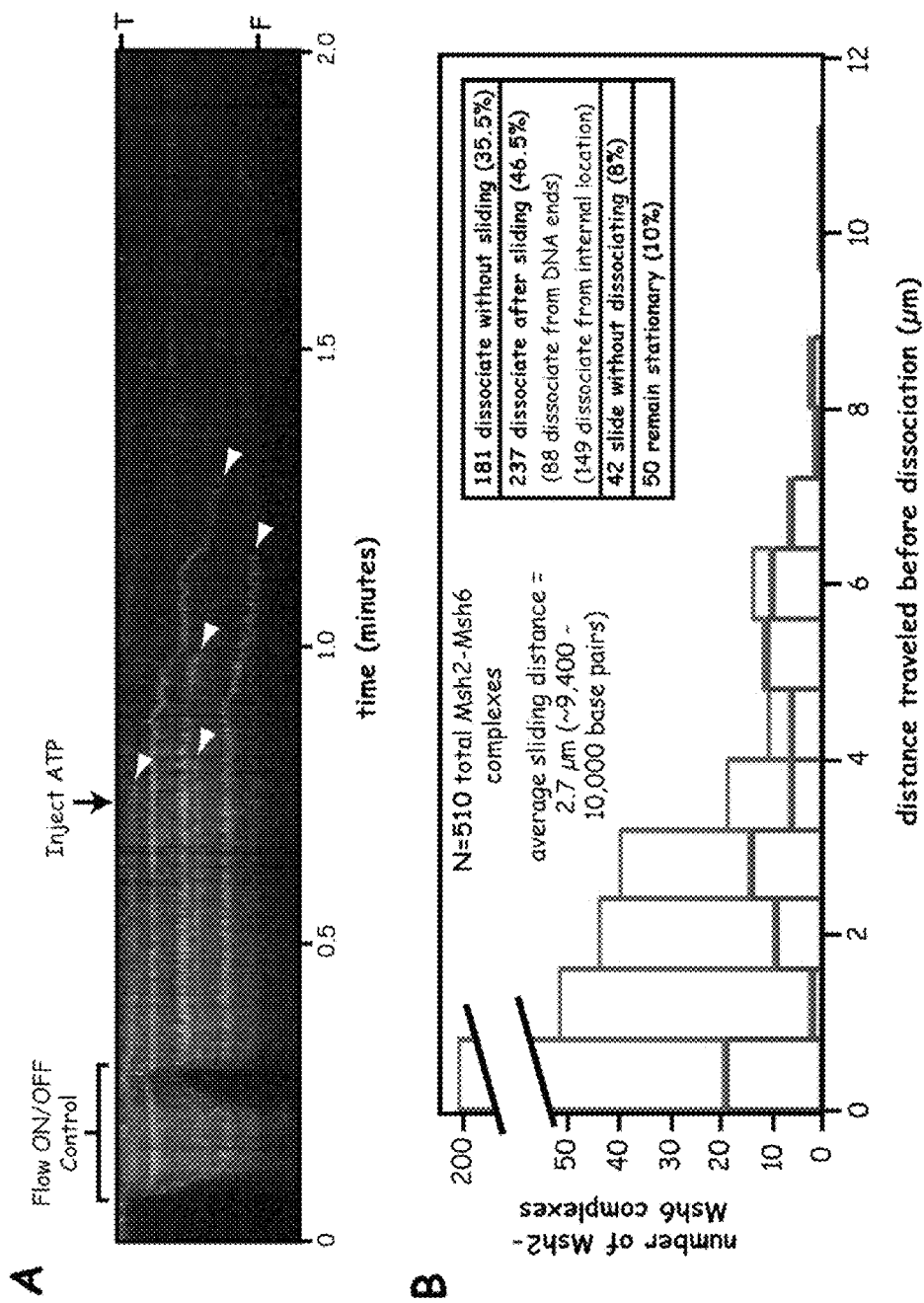
FIG. 54 shows ADP/ATP exchange-mediated dissociation can occur from internal locations and from DNA ends.
Figure 55:
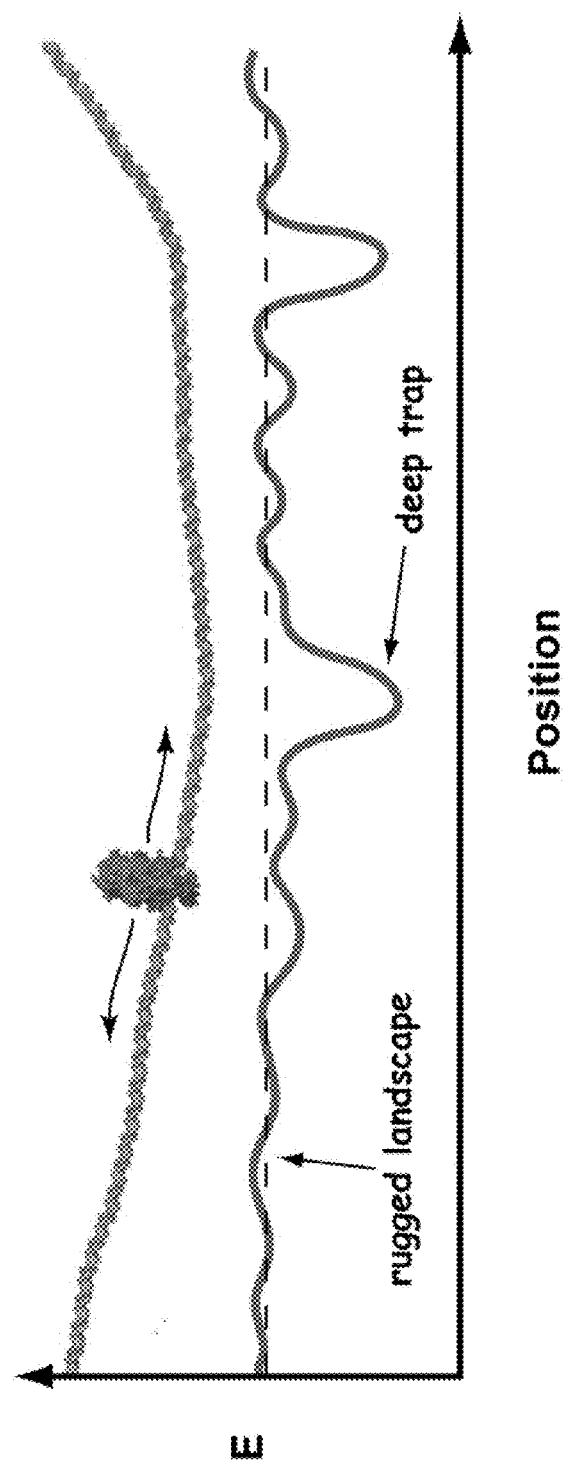
FIG. 55 depicts a model for DNA scanning by Msh2-Msh6. The biophysical model depicts interactions between Msh2-Msh6 (magenta) and DNA substrates (cyan). Below the DNA is an energy landscape describing its bending propensity (Vlahovicek et al., 2003), wherein the minima in the landscape correlate with regions that are either intrinsically bent or highly flexible. Positions corresponding to deep depressions in the landscape (e.g., lesions or nicks) will interact favorably with the diffusing protein, and the depth of the energy minima will dictate how long the protein remains at any given site. Proteins that locate deep traps can escape in a reaction driven by the exchange of ADP for ATP.
Figure 56:
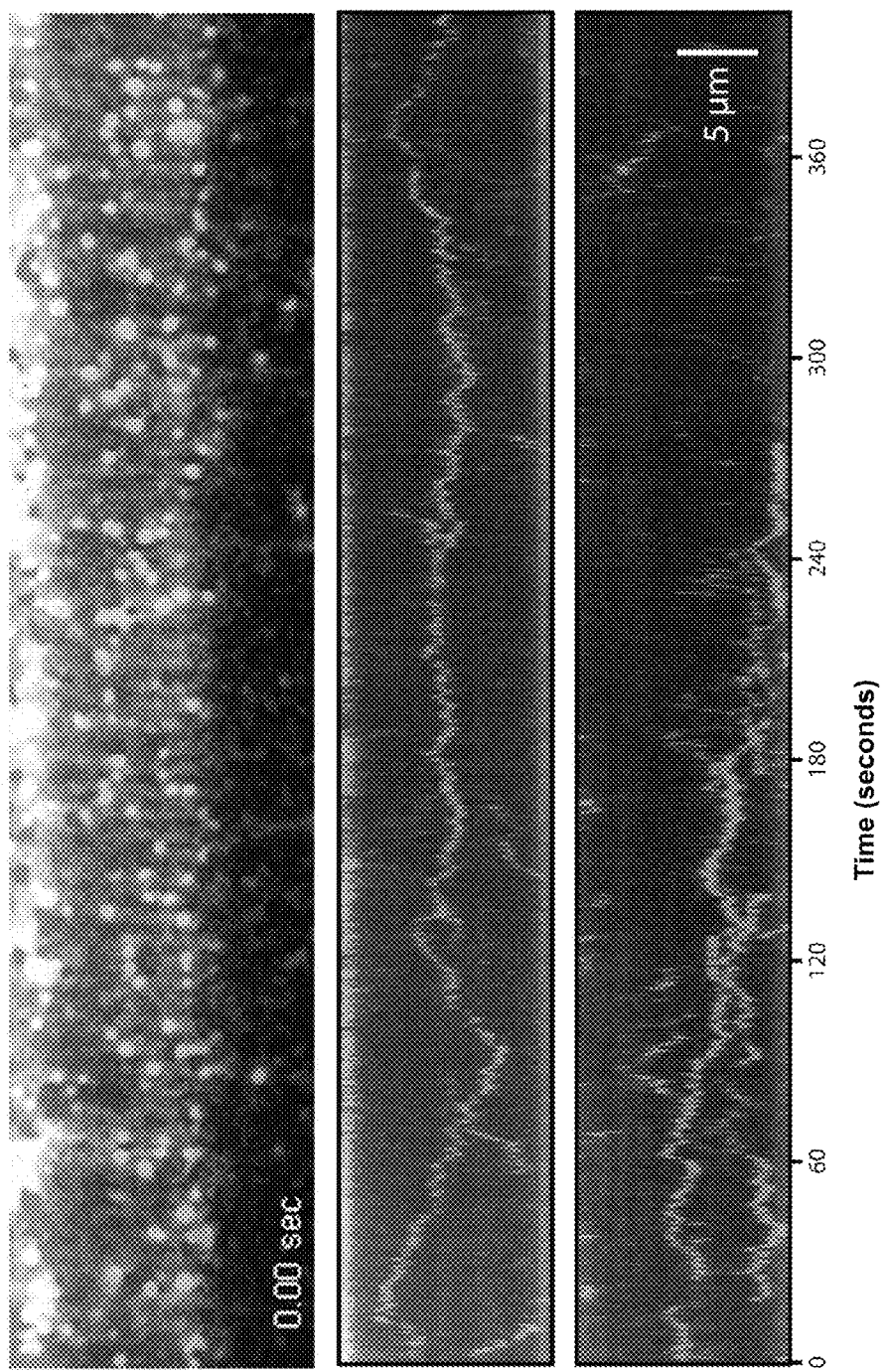
FIG. 56 shows a photographic image of an example of a double DNA tethered curtain used to visualize the diffusion of Mlh1-Pms1.
Figure 57:
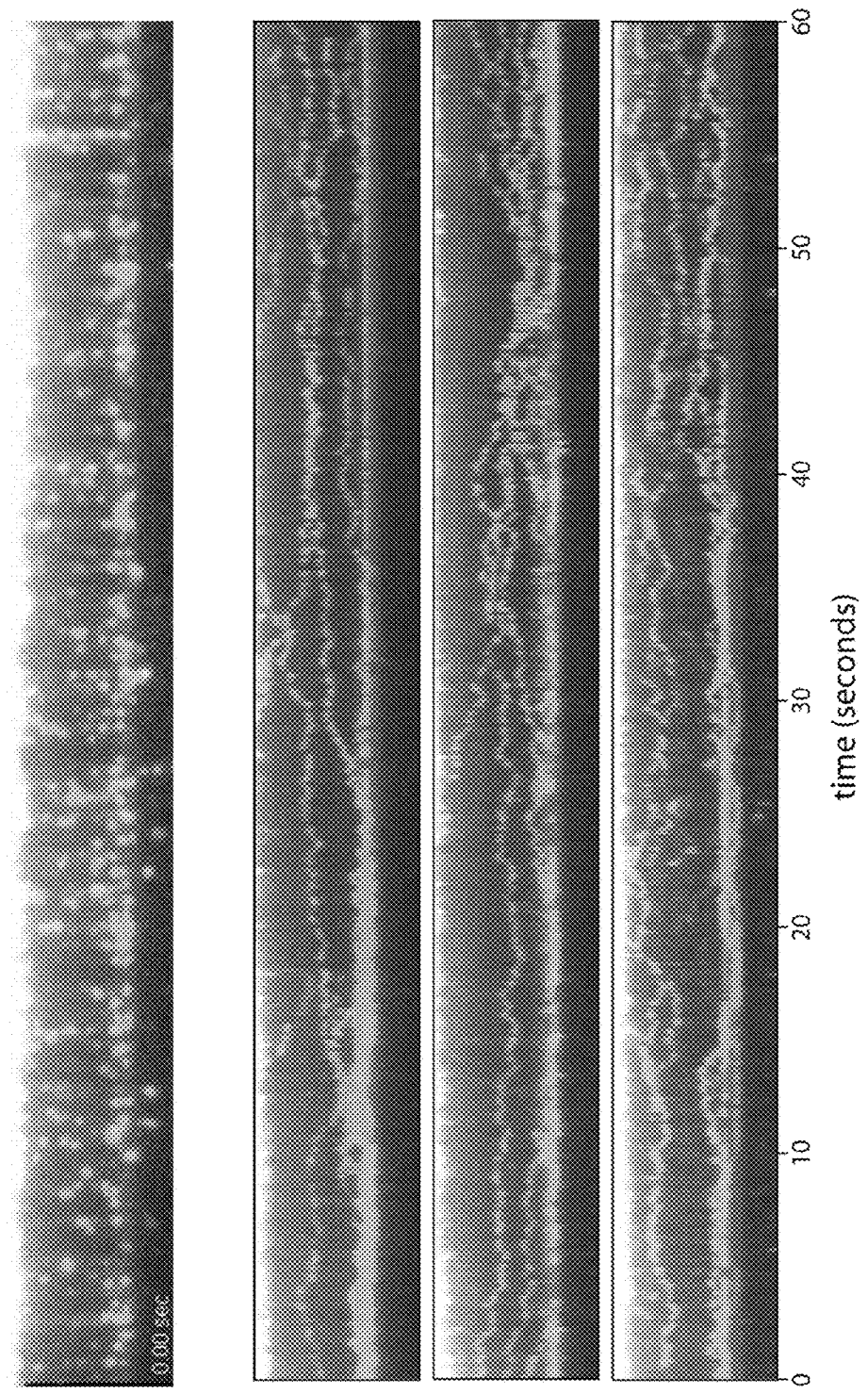
FIG. 57 shows a photographic image of an example of a double DNA tethered curtain used to visualize the diffusion of Mlh1.
Figure 58A:
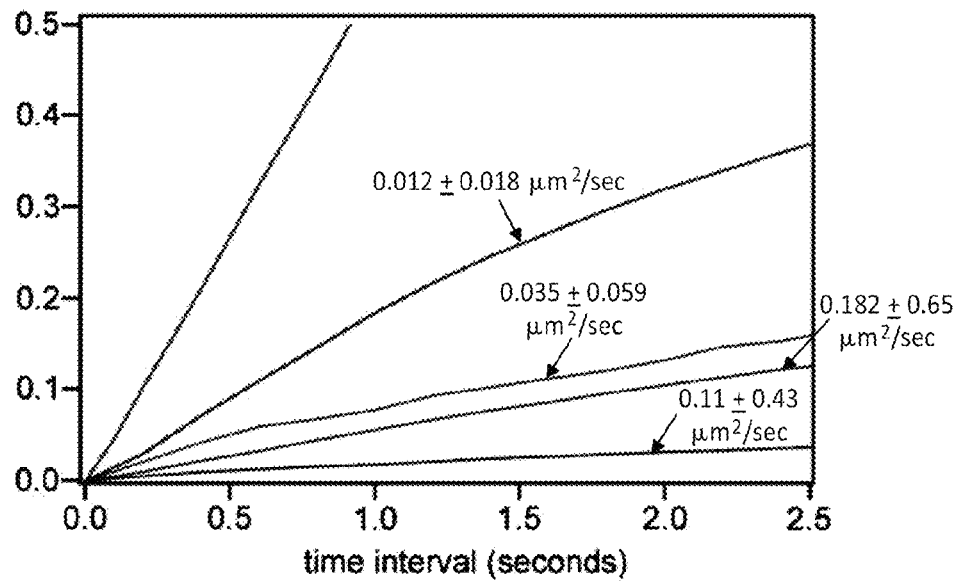
FIGS. 58A-B show graphs representing that Mlh1-Pms1 diffuses on DNA and travels faster than Msh2-Msh6.
Figure 58B:
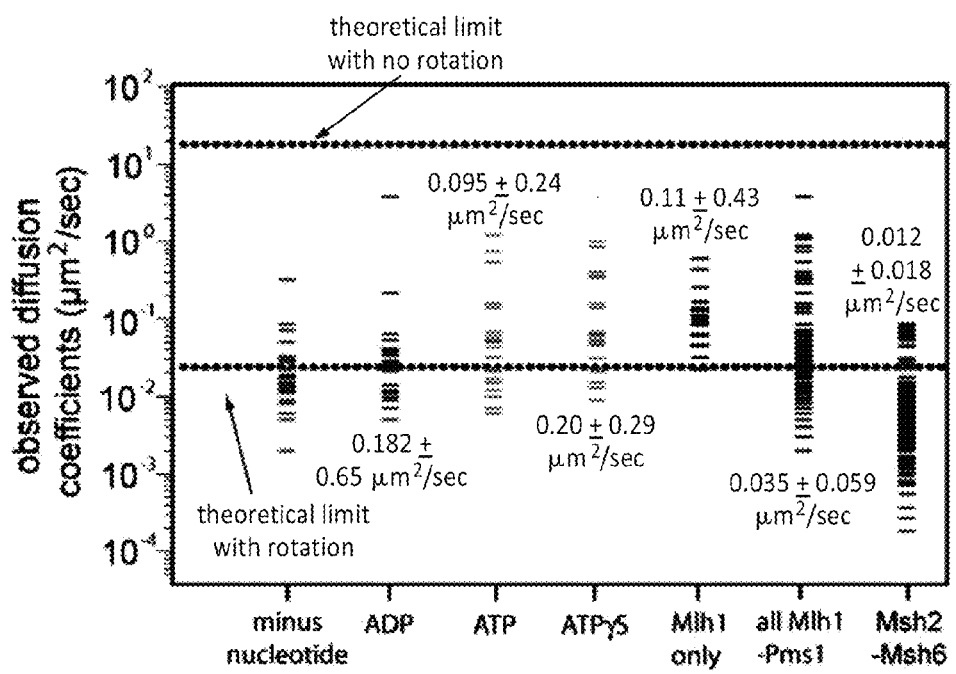
Figure 59:
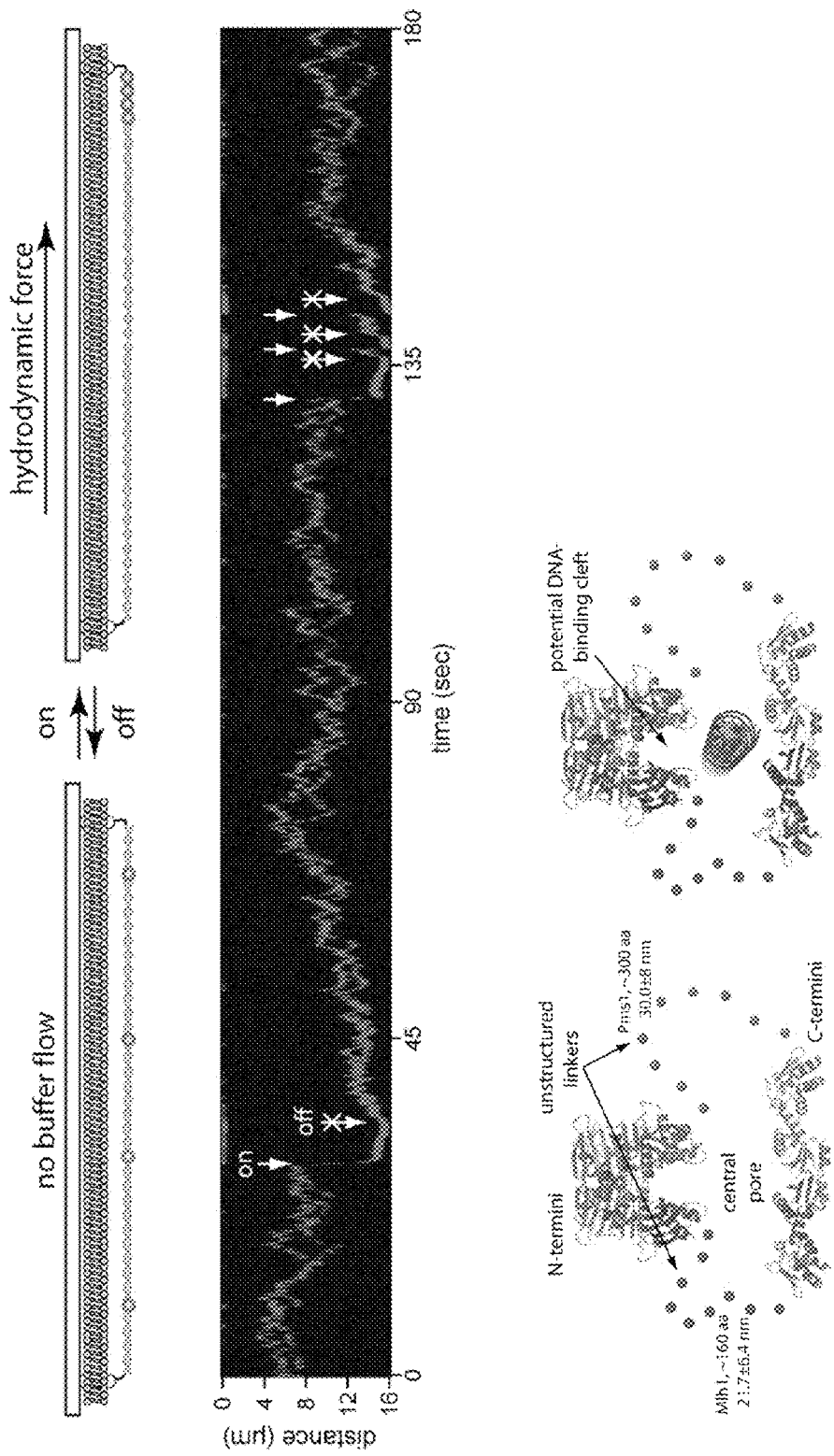
FIG. 59 is an illustration and photographic image that show that Mlh1-Pms1 does not dissociate from blocked DNA ends.
Figure 60:
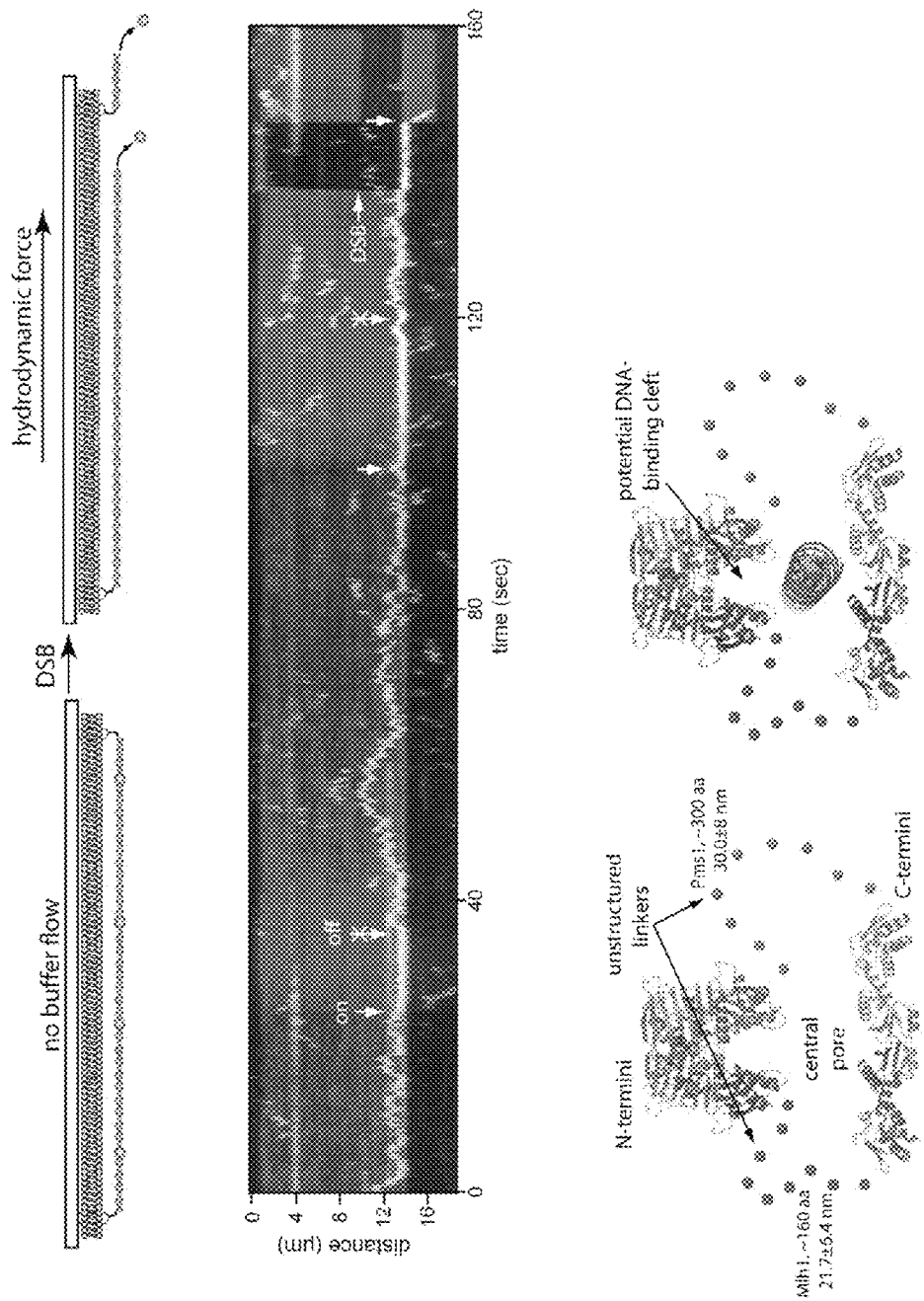
FIG. 60 is an illustration and photographic image that show that Mlh1-Pms1 does dissociate from free DNA ends.
Figure 61:
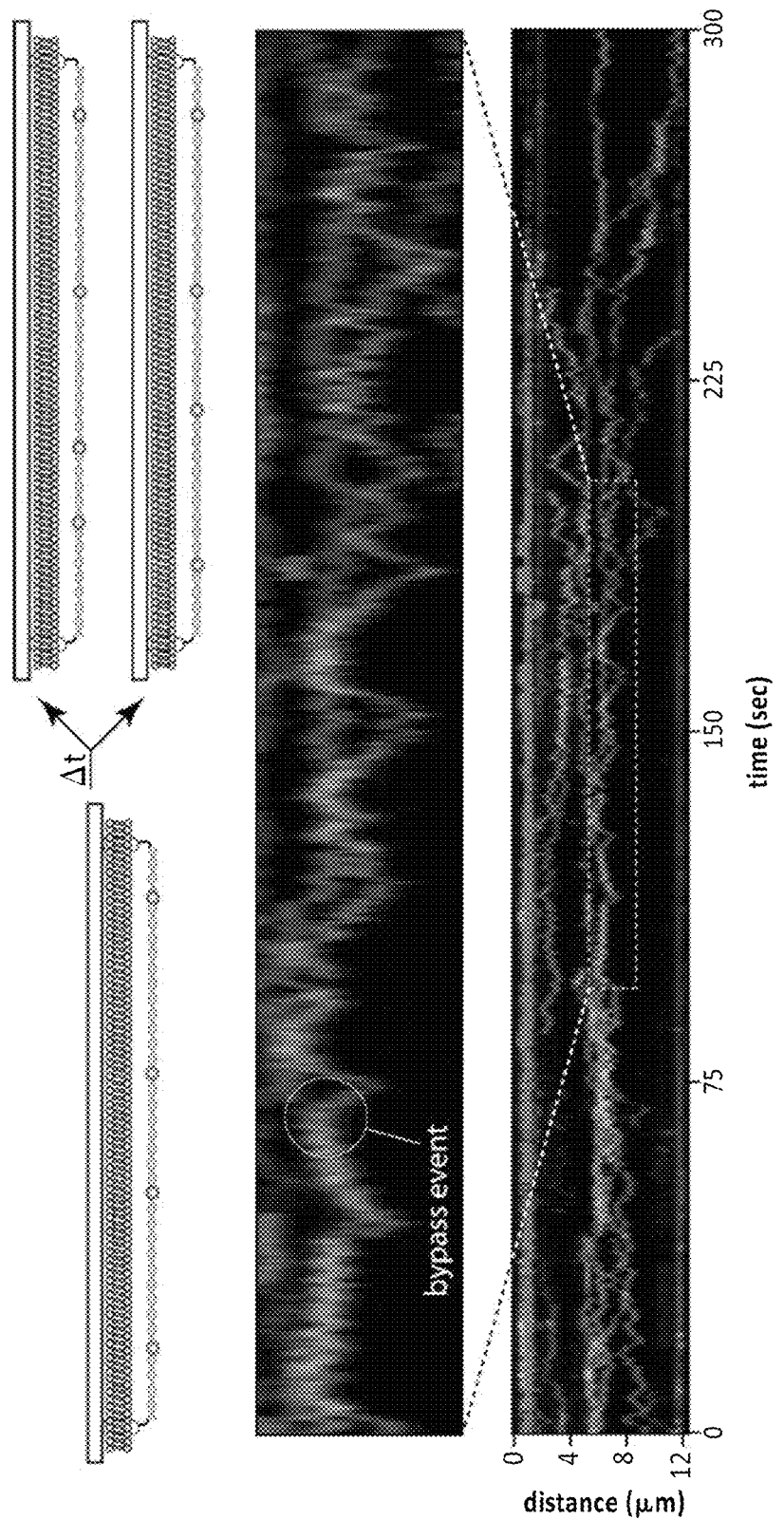
FIG. 61 is an illustration and photographic images that show that Mlh1-Pms1 complexes can bypass each other.
Figure 62:
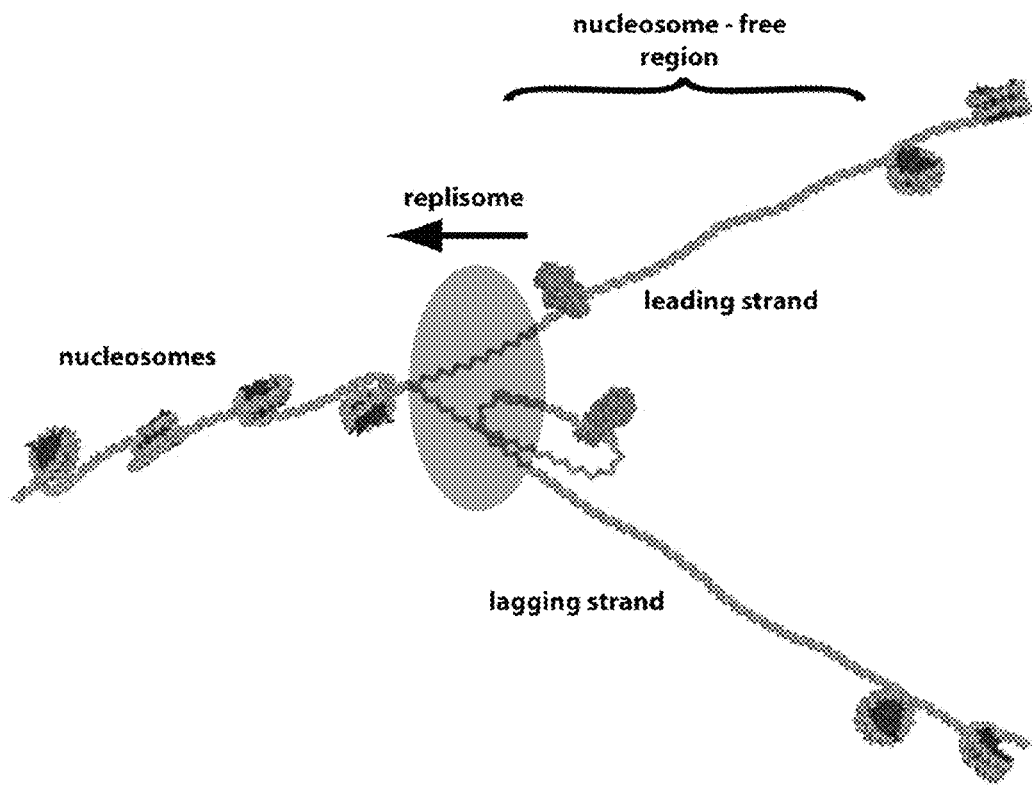
FIG. 62 is a schematic representation showing how an Msh2-Msh6 complex can scan the genome.

Biochemical reactions involving genomic transactions often require proteins to communicate regulatory information over long distances along a DNA strand. Postreplicative mismatch repair (MMR) is an evolutionarily biochemical pathway requiring protein-mediated signaling over long distances of DNA during the repair of replication errors (see for example, FIG. 48). MMR has been most studied in *E. coli* where the proteins MutS, MutL, and MutH promote the initiation of strand-specific repair by taking advantage of the transiently unmethylated state of the newly synthesized daughter DNA. MutS binds mismatched DNA and together with MutL activates the MutH nicking endonuclease. This leads to cleavage of the daughter strand at the nearest hemi-methylated dGATC, which serves as a strand discrimination signal enabling distinction between the parental DNA and the error-containing daughter strand. The nick generated by MutH provides an entry point for other proteins that complete downstream steps of the pathway. The stand discrimination signals can be located up to ~2 kb away from the mismatch and still elicit repair in reconstituted in vitro systems. Moreover, once removal of the daughter strand ensues, the excision machinery stops only after it has bypassed the original location of the mispaired base. These findings highlight that communication along the DNA helix is necessary to coordinate mismatch binding with events at the distal strand discrimination signal, and the proteins involved must keep track of which strand is which throughout the entire process.

In eukaryotes, MMR involves up to eleven different proteins, including Msh2-Msh6 (MutSα) and Mlh1-Pms1 (MutLα), both of which are necessary for the initial stages of the repair reaction. Cancer-associated mutations can be mapped to the MSH and MLH genes, indicating the importance of these proteins in genome maintenance. Msh2-Msh6 in a heterodimer comprised of two MutS homologs, and is necessary for initial mismatch recognition and binding. Mlh1-Pms1 interacts with Msh2-Msh6 after mismatch recognition and is thought to coordinate downstream steps in the repair pathway. ATP-binding and hydrolysis can provoke conformational changes in Mlh1-Pms1 necessary to regulate these protein-protein interactions. Homologs of MutH are not found in eukaryotes, but Mlh1-Pms1 itself is a latent endonuclease that is activated in the presence of Msh2-Msh6, PCNA, RFC, mismatched DNA, and ATP. This endonuclease activity is necessary for processing the daughter DNA strand during repair. How the daughter stand is identified remains unclear because the strand discrimination signals in eukaryotes are unknown. Pre-existing nicks between adjacent Okazaki fragments in the lagging strand or the 3' hydroxyl present on the leading strand of replication-restart intermediates can participate in strand discrimination, again highlighting the need for long distance communication along the DNA helix. Structures of MutL family members can be found in Guarné et al. ((2004) EMBO J. 23: 4134-4135) and in Kosinski et al. ((2005) Journal of Molecular Biology. 351: 895-909).

It is necessary for the MMR proteins to communicate information between the lesion and the distal strand discrimination signal. The mechanism by which this communication occurs has been the subject of intensive investigation. Accumulating evidence supports the idea that 1D diffusion is an integral aspect of MMR protein function (see FIG. 49). In support of this, we have visualized Msh2-Msh6 at the single molecule level using total internal reflection fluorescence microscopy (TIRFM) and demonstrated that the protein can rapidly diffuse in one dimension along DNA. We have also demonstrated that Mlh1-Pms1 can also diffuse on DNA, and it travels an order of magnitude faster that Msh2-Msh6. Lateral movement of these proteins can contribute to lesion recognition, post-recognition steps necessary for locating strand discrimination signals, and/or processing of the daughter DNA strand. From a mechanistic perspective the diffusion appears to occur via a sliding mechanism wherein the proteins travel while remaining engaged with bound DNA strand. However, we could not unambiguously rule out jumping, hopping, and/or intersegmental transfer, all of which potential mechanisms enabling a protein to passively travel along DNA without need for a high-energy cofactor. A common aspect of these mechanisms is that they each must invoke an intermediate state in which the proteins are either partially or fully disengaged from the DNA substrate, and therefore capable of establishing interactions with a second DNA site. Consequently hopping, jumping, and/or intersegmental transfer can allow direct transfer of a protein from one DNA strand another. In contrast, a protein traveling along DNA purely via a sliding mechanism would be incapable of directly transferring from one DNA to the next because the protein must by definition remain engaged with the substrate as it is moving.

To determine whether Msh2-Msh6 and Mlh1-Pms1 traveled along DNA via sliding or whether hopping, jumping, and/or intersegmental transfer contributed to the observed motion we sought to directly visualize proteins on two intersecting DNA molecules to ask whether the proteins could transfer directly from one strand to the next. This was accomplished using nanofabricated patterns of crisscrossed DNA molecules that were suspended above an inert lipid bilayer and anchored to the surface of a microfluidic sample chamber. We then used single molecule optical microscopy to visualize the movements of individual fluorescent proteins as they traversed the intersecting DNA molecules. We reasoned that any events involving direct transfer of proteins between DNA molecules would be apparent as abrupt 90° turns in the protein motion coinciding with the intersecting junctions of the DNA. The existence of such events would provide an unambiguous readout arguing that mechanism of protein movement involved a 3D component wherein the originally bound DNA was released. In contrast, the absence of protein transfer between crossed DNA strands at the junction points would argue strongly that the observed lateral motion was a pure sliding mechanism wherein the proteins remained in continuous, uninterrupted contact with the DNA.

Results

Design and Fabrication of Crisscrossed DNA Patterns.

Experiments using catenated plasmids have been used to probe protein-mediated communication between distal DNA sites, and elegant examples of these studies have included promoter-enhancer interactions, restriction endonucleases, and site-specific recombination. We sought to devise an experiment using intersecting molecules of DNA in a format compatible with single molecule imaging. The design strategy for engineering crisscrossed patterns of DNA suspended above an inert lipid bilayer is illustrated in FIG. 21. The approach for making arrays of intersecting DNA molecules relied upon a combination of hydrodynamic force and diffusion barriers (such as non-linear, geometric nanoscale diffusion barriers) to control the organization of DNA molecules anchored by one end to a lipid bilayer via a biotin-neutravidin connection. A key feature of the current design is that the different pattern elements are organized into squares wherein two adjacent sides are comprised of linear barriers, and the other two sides are non-linear, geometric barriers made up of arrayed pentagons. The patterns are placed at the center of a four-channel flowcell such that each of the linear barriers is oriented perpendicular to one of the two buffer inlet channels. The linear elements serve as diffusion barriers, which cannot be traversed by the lipids within the bilayer. Arrays of pentagons are positioned downstream from the linear barriers and serve as solid attachment points for the other end of the DNA. The pentagons are nonspecifically coated with antibodies directed against digoxigenin, which is covalently attached to the free ends of the DNA. When the lipid-tethered DNA molecules are pushed into the linear diffusion barriers, they extend parallel to the surface and the DIG-labeled free end of the DNA then binds the antibodies adsorbed to the exposed pentagon surfaces. The triangular faces of the pentagons are designed to funnel DNA into the channels between each adjacent pentagon to minimize accumulation of DNA molecules within the interior of the square patterns.

FIGS. 21B-E show examples of SEM (scanning electron microscopy), optical, and AFM (atomic force microscopy), images of patterns made with thin layers of gold (Au) deposited on a fused silica surface by Ebeam lithography. The dimensions of critical pattern parameters are indicated. The linear barrier elements were about 100 nm wide. The pentagons were 2 µm in length and 1 µm in width, and each pentagon was separated from its nearest neighbors by channels that were 400 nm in width. The height of the different metallic elements was about 20-25 nm, and the distance between the leading edge of the linear barrier elements and the center of the arrayed pentagons was 12 µm. This distance was specifically selected for use with $\lambda$-DNA (48,502 bp, 16.5 µm), such that the anchored molecules would be extended to ~70-80% of their full length, depending upon where the ends were anchored within the pentagons. This distance was chosen so as not to stretch the DNA beyond its natural length and avoid deformation of the B-form geometry. Moreover, we have previously conducted 1D diffusion experiments with both Msh2-Msh6 and Mlh1-Pms1 using DNA stretched to the same extent.

Figure 22:
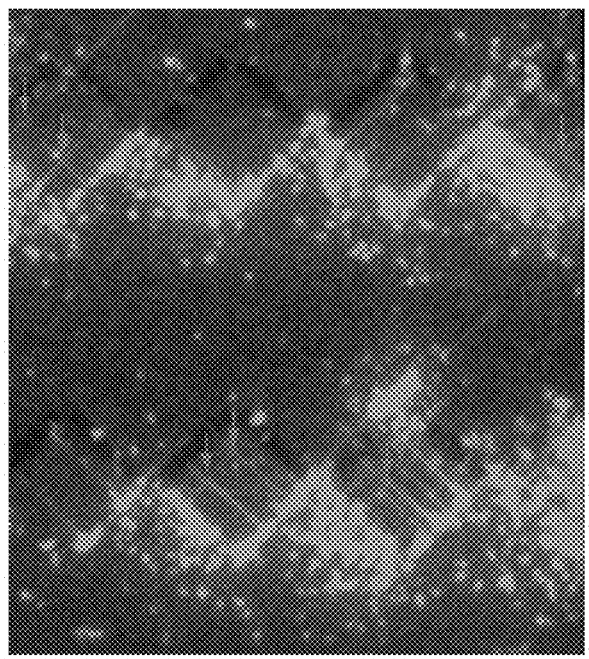
FIG. 22 depicts crisscrossed patterns of DNA. This image contains examples of crisscrossed DNA molecules. The DNA (green) is stained with YOYO1 and the junction points between the DNA molecules are marked with red arrowheads.

Assembly of the crisscrossed DNA curtains involved the sequential addition of different components to achieve the desired substrate configuration. First, the surfaces of the flowcell were first coated with a lipid bilayer containing a small fraction (0.5%) of biotinylated lipid. The inert bilayer covers the exposed fused silica, but can not form over the gold surface patterns, leaving the metallic surfaces exposed to solution. Anti-DIG Fab fragments were then injected into the sample chamber, and incubated for a brief period, allowing them to adhere to any surfaces not protected by the lipid bilayer. The large surface area of the pentagons relative to the much smaller linear barriers ensures that the pentagons are selectively coated with more antibodies. The sample chamber surface was then blocked with buffer containing BSA, and neutravidin was coupled to the bilayer to provide a mobile attachment point for the DNA. Finally λ-DNA labeled at one end with biotin and at the other end with digoxigenin was injected into the sample chamber and pushed into the linear barrier elements. Once the molecules encounter the linear barriers, they stretch out and the free ends adhered to the pentagons. FIG. 22 shows examples of YOYO1 stained DNA molecules that were aligned and anchored to the metallic racks. One end of the DNA was linked to the lipid bilayer through a biotin-neutravidin connection, and the other end of the DNA was labeled with digoxigenin (DIG) and coupled to the pentagons via nonspecifically adsorbed anti-DIG Fab fragments. No buffer was flowing during image acquisition, confirming that the DNA molecules were anchored by both the biotinylated and digoxigenin labeled ends. As shown here, the anchored DNA molecules are oriented at 90° relative to one another ensuring that they are in close physically proximity only at the intersecting points.

Lateral Motion of Msh2-Msh6 Along DNA does not Involve a 3D Component.

We have previously shown that Msh2-Msh6 can travel along DNA by 1D diffusion and that the observed motion is consistent with a mechanism involving a rotational component wherein the proteins continually track the phosphate backbone. In addition, we have demonstrated that this motion appears to involve continuous contact between Msh2-Msh6 and the phosphate backbone with no obvious evidence that the linear motion included any hops or jumps along the DNA.

Mlh1-Pms1 can (or Cannot) Directly Transfer Between Crossed DNA Molecules.

Our previous work has shown that Mlh1-Pms1 can also slide along DNA, but travels roughly an order of magnitude more rapidly than Msh2-Msh6, suggesting that these two protein complexes move via fundamentally distinct mechanisms. The structures of these two protein complexes is also strikingly different. Msh2-Msh6 is a compact heterodimeric complex that engages DNA through close contact with the phosphate backbone. Mlh1-Pms1 has N- and C-terminal domains separated by long linker arms that are thought to encircle DNA. Interestingly, bulk biochemical experiments have revealed that Mlh1-Pms1 binds tightly and nonspecifically to DNA, with a strong preference for circular substrates, and does not dissociate over time scales spanning several minutes. However, despite the apparent tight binding affinity, Mlh1-Pms1 can transfer to a competitor DNA in solution, suggesting that the addition of excess competitor DNA provokes dissociation from the initial bound substrate.

Methods

Proteins.

HA-tagged Msh2-Msh6 and FLAG-tagged Mlh1-Pms1 were purified from *S. cerevisiae* as previously described. The protein complexes were labeled with quantum dots (Invitrogen) conjugated to either anti-HA or anti-FLAG, as appropriate. The epitope-tagged proteins are fully functional for MMR in vivo, and the labeled proteins retained wild-type DNA binding activities in gel shift and filter-binding assays, as previously described.

Nanofabrication.

Fused silica slides were cleaned in NanoStrip solution (CyanTek Corp, Fremont, Calif.) for 20 minutes, then rinsed with acetone and isopropanol and dried with $N_2$. The slides were spin-coated with a bilayer of polymethylmethacrylate (PMMA), molecular weight 25K, 3% in anisole and 495K, 1.5% in anisole (MicroChem, Newton, Mass.), followed by a layer of Aquasave conducting polymer (Mitsubishi Rayon). Each layer was spun at 4,000 rpm for 45 seconds using a ramp rate of 300 rpm/s. Polygon patterns and linear elements forming the non-linear "V" non-linear, geometric barriers were written by Ebeam lithography using an FEI Sirion scanning electron microscope equipped with a pattern generator and lithography control system (J. C. Nabity, Inc., Bozeman, Mont.). After patterning, Aquasave was rinsed off with deionized water. Resist was developed using a 3:1 solution of isopropanol to methyl isobutyl ketone (MIBK) for 1 minute with ultrasonic agitation at 5° C. The substrate was then rinsed in isopropanol and dried with $N_2$. A 15-20 nm layer of gold atop a 3-5 nm adhesion layer of either chromium or titanium was deposited using a Semicore electron beam evaporator. Liftoff was effected at 80° C. in a 9:1 ratio of methylene chloride to acetone. Following liftoff, slides were rinsed with acetone and dried with $N_2$. Barriers were imaged using a Hitachi 4700 scanning electron microscope and a PSIA XE-100 Scanning Probe Microscope in noncontact mode. Optical images of the barriers were collected with a Nikon Eclipse ME600.

Assembly of Crisscrossed DNA.

The flowcells were assembled from fused silica slides (G. Finkenbeiner, Inc.) with chromium nanoscale diffusion barriers. Inlet and outlet ports were made by boring through the slide with a high-speed precision drill press equipped with a diamond-tipped bit (1.4 mm O.D.; Kassoy). The slides were cleaned by successive immersion in 2% (v/v) Hellmanex, 1 M NaOH, and 100% MeOH. The slides were rinsed with filtered sterile water between each wash and stored in 100% MeOH until use. Prior to assembly, the slides were dried under a stream of nitrogen and baked in a vacuum oven for at least 1 hour. A sample chamber was prepared from a borosilicate glass coverslip (Fisher Scientific) and double-sided tape (~25 μm thick, 3M). Inlet and outlet ports (Upchurch Scientific) were attached with hot-melt adhesive (SureBonder glue sticks, FPC Corporation). The total volume of the sample chambers was ~4 μl. A syringe pump (Kd Scientific) and actuated injection valves (Upchurch Scientific) were used to control sample delivery, buffer selection and flow rate. The flowcell and prism were mounted in a custom-built heater with computer-controlled feedback regulation to control the temperature of the sample from between 25-37° C. (±0.1° C.), as necessary. After each use, the slides were soaked in MeOH to remove the ports and tape, rinsed with water, washed briefly (15-20 minutes) with Nanostrip, and finally rinsed with water. This procedure was sufficient to clean the slide surfaces for reuse, and each slide could be used multiple times degrading the quality of the optical surface or the metallic patterns.

DNA curtains were constructed as described. All lipids were purchased from Avanti Polar Lipids and liposomes were prepared as previously described. In brief, a mixture of DOPC (1,2-dioleoyl-sn-glycero-phosphocholine), 0.5% biotinylated-DPPE (1,2-dipalmitoyl-sn-glycero-3-phosphoethanolamine-N-(cap biotinyl)), and 8% mPEG 550-DOPE (1,2-dioleoyl-sn-glycero-3-phosphoethanolamine-N-[methoxy (polyethylene glycol)-550]). The mPEG is does not affect bilayer formation or assembly of the DNA curtains, but rather serves to further passivated the surface against nonspecific adsorption of quantum dots (which we use in our studies of protein-DNA interactions). Liposomes were applied to the sample chamber for 30 minutes. Excess liposomes were flushed away with buffer containing 10 mM Tris-HCl (pH 7.8) and 100 mM NaCl. The flowcell was then rinsed with buffer A (40 mM Tris-HCl (pH 7.8), 1 mM DTT, and 1 mM $MgCl_2$) and incubated for 15 minutes. Buffer A plus 30 μg/ml anti-DIG Fab (Roche) was then injected into the sample chamber and incubated for 20 minutes. The sample chamber was then flushed with buffer A plus and 0.2 mg/ml BSA for 5 minutes. Neutravidin (330 nM) in buffer A was then injected into the sample chamber and incubated for 20 minutes. After rinsing thoroughly with additional buffer A plus 0.2 mg/ml BSA, λ-DNA (15-20 pM) labeled at one end with biotin and at the other end with digoxigenin and pre-stained with 1-2 nM YOYO1 was injected into the sample chamber, incubated for 10 minutes, and unbound DNA was removed by flushing with buffer at 0.1 ml/min. Application of buffer flow caused the lipid-tethered DNA molecules to align along the leading edges of the diffusion barriers.

TIRFM and Data Analysis.

The basic design of the microscope used in this study has been previously described. In brief, the system is built around a Nikon TE2000U inverted microscope with a custom-made illumination system. For this study, a 488 nm, 200 mW diode-pumped solid-state laser (Coherent, Sapphire-CDHR) was used as the excitation source. The laser was attenuated as necessary and centered over the DNA curtain by means of a remotely operated mirror (New Focus). The beam intensity at the face of the prism was ~10-15 mW. Images were detected with a back-illuminated EMCCD detector (Photometrics, Cascade 512B). TIRFM images were collected using a 60× water immersion objective lens (Nikon, 1.2 NA Plan Apo), unless otherwise indicated.

Example 7

Visualizing Protein-DNA Interactions with Nanofabricated DNA Curtains

Restriction Enzymes and Msh2-Msh3.

For complete digests, 700 μl, of the desired restriction enzyme in reaction buffer A (40 mM Tris-HCl (pH 7.8), 1 mM MgCl2, 1 mM DTT, and 0.2 mg/ml BSA) plus 50 mM NaCl and 10 mM MgCl2 was injected at 0.2 mL/min. All restriction enzymes were purchased from NEB and the amounts of enzymes used were as follows: NheI (100 units/ml); XhoI (100 units/ml); EcoRI (100 units/ml); NcoI (50 units/ml); PvuI (50 units/ml); and SphI (50 units/ml). Images of the DNA molecules were collected before the restriction enzyme injection and after all of the enzyme solution had flown through. For partial digests, the amount of EcoRI was reduced to 20 units/ml and 700 μl was injected at 0.4 mL/min.

Msh2-Msh3 was purified as described in Surtees, J. A.; Alani, E. J. Mol. Biol. 2006, 360, 523-536 and TIRFM experiments with Msh2-Msh3 were performed essentially as described for our previously published experiments with Msh2-Msh6 (Gorman, J. et al. Mol. Cell. 2007, 28, 359-370). In brief, HA tagged Msh2-Msh3 was incubated with anti-HA antibody conjugated quantum dots at 1:2 protein:quantum dot ratio for 15 min in Buffer A plus 50 mM NaCl. 50 μL, of 1.5 nM quantum dot tagged Msh2-Msh3 was then injected at 0.1 mL/min to allow efficient binding. The flow rate was increased to 0.4 mL/min for data collection, and the binding distributions were quantitated as described (Prasad, T. K.; Robertson, R. B.; Visnapuu, M. L.; Chi, P.; Sung, P.; Greene, E. C. J. Mol. Biol. 2007, 369, 940-953).

Figure 23:
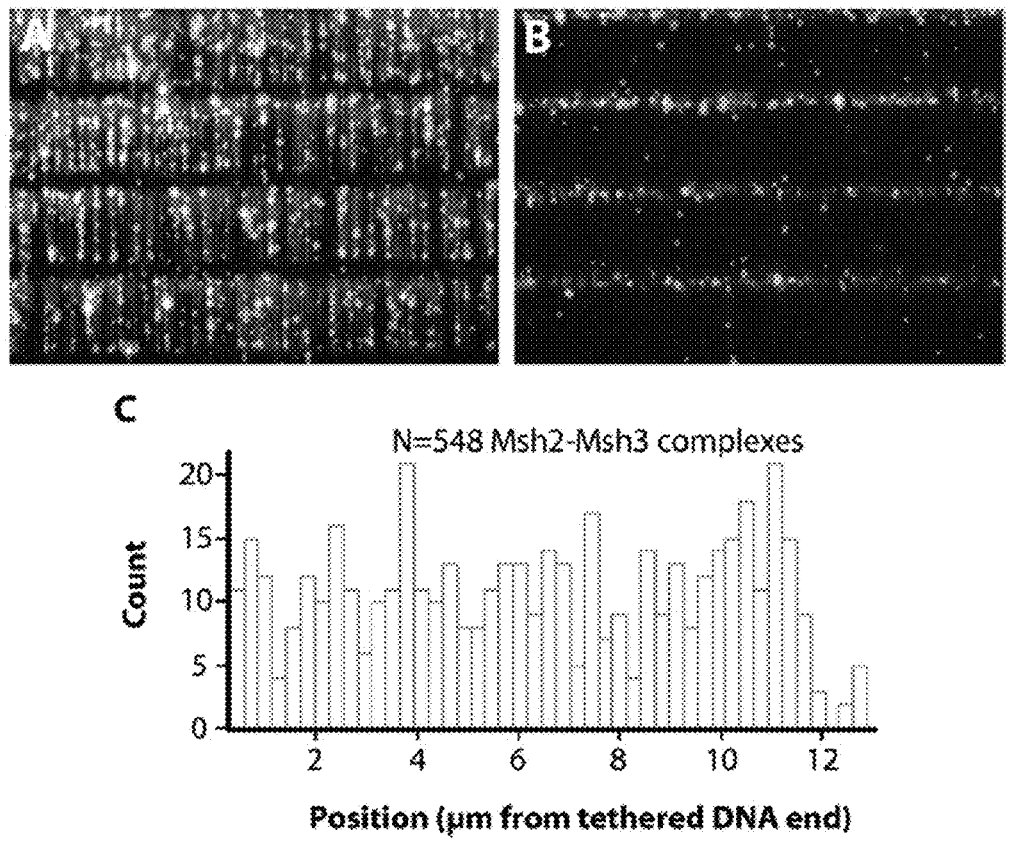
FIG. 23 depicts protein binding distributions measured with nanofabricated DNA curtains.

These DNA curtains are useful for analysis of protein-DNA interactions at the level of individual molecules, and are capable of providing statistically relevant information in a single experimental run. To demonstrate this utility, we examined the binding distribution of Msh2-Msh3, a protein complex that is involved in postreplicative mismatch repair of small insertion/deletion loops and DNA processing during genetic recombination (Surtees, J. A.; Alani, E. J. Mol. Biol. 2006, 360, 523-536; Langston, L. D.; Symington, L. S. EMBO J. 2005, 24, 2214-2223) For this experiment recombinant Msh2-Msh3 bearing an HA epitope tag on Msh2 was labeled with anti-HA tagged quantum dots (Gorman, J.; Chowdhury, A.; Surtees, J. A.; Shimada, J.; Reichman, D. R.; Alani, E.; Greene, E. C. Mol. Cell 2007, 28, 359-370). The tagged proteins were then injected into a sample chamber containing DNA curtains, and the unbound proteins were removed by buffer flow. The DNA molecules and remaining bound proteins were then viewed in the presence and absence of buffer flow (FIG. 23A and FIG. 23B). This transient pause in buffer flow is used as a control to verify that the observed proteins are bound only to the DNA and are not bound to the flowcell surface (compare FIG. 23, panels A and B). As shown in FIG. 23A and FIG. 23C, Msh2-Msh3 bound to the curtains of λ-DNA, but did not display any favored regions or sites for undamaged, homoduplex DNA substrates. There are 226 individual DNA molecules and 548 complexes of Msh2-Msh3 in this single field-of-view collected at 60× magnification, highlighting the statistical power of this approach for viewing single protein-DNA complexes.

Example 8

DNA Curtains with Defined Lateral Separation Between Molecules

FIG. 24A-D shows representative examples of YOYO1-stained DNA curtains assembled at a non-linear, geometric diffusion barrier pattern with either 1000 nm spacing (FIG. 24A-B) or 1900 nm spacing (FIG. 24C-D) between the adjacent geometric nanowells. In the presence of buffer flow the DNA molecules are extended along the surface, but when flow is terminated they diffuse out of view, verifying that they are not nonspecifically adsorbed to the bilayer. These images demonstrate that the non-linear, geometric barriers patterns can be used to prepare DNA curtains, and also shows that the distance between the DNA molecules is influenced by the spacing constraints of the nanowells (compare FIG. 24A and FIG. 24C). If the DNA molecules within the curtains were in fact retained within the geometric nanowells, as we predicted, then the distance between the adjacent vertices of triangles within the pattern design should be reflected in the separation distance between the individual DNA molecules.

Figure 24E:
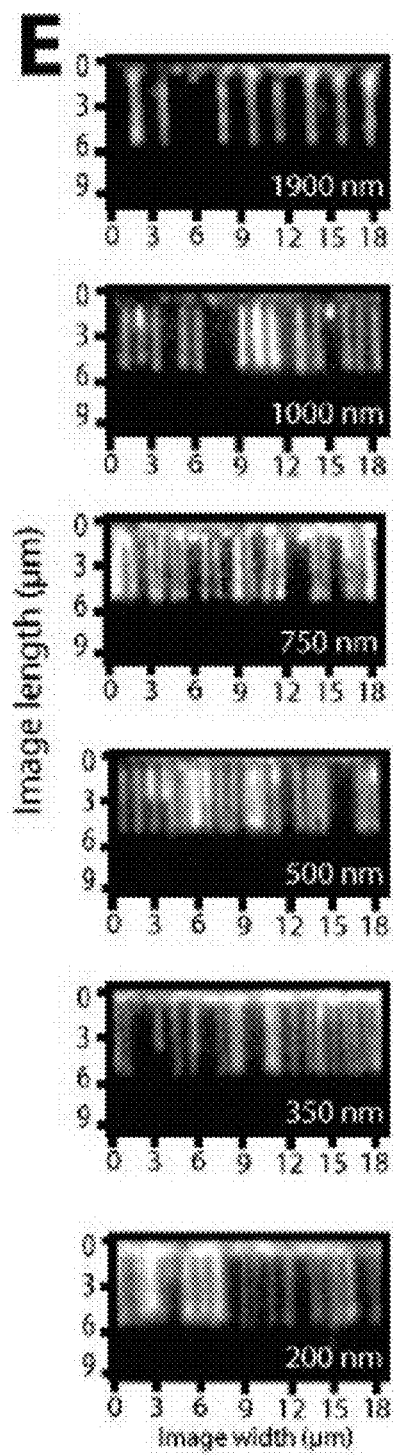
FIG. 24E is a series of photographic images that show DNA curtains with different separation distances. These show examples of sections from YOYO1-stained DNA curtains prepared using non-linear, geometric barrier patterns with spacings of 1900, 1000, 750, 500, 350, and 200 nm, as indicated. The DNA molecules used here are 23 kb PCR products derived from the human β-globin locus.
Figure 24F:
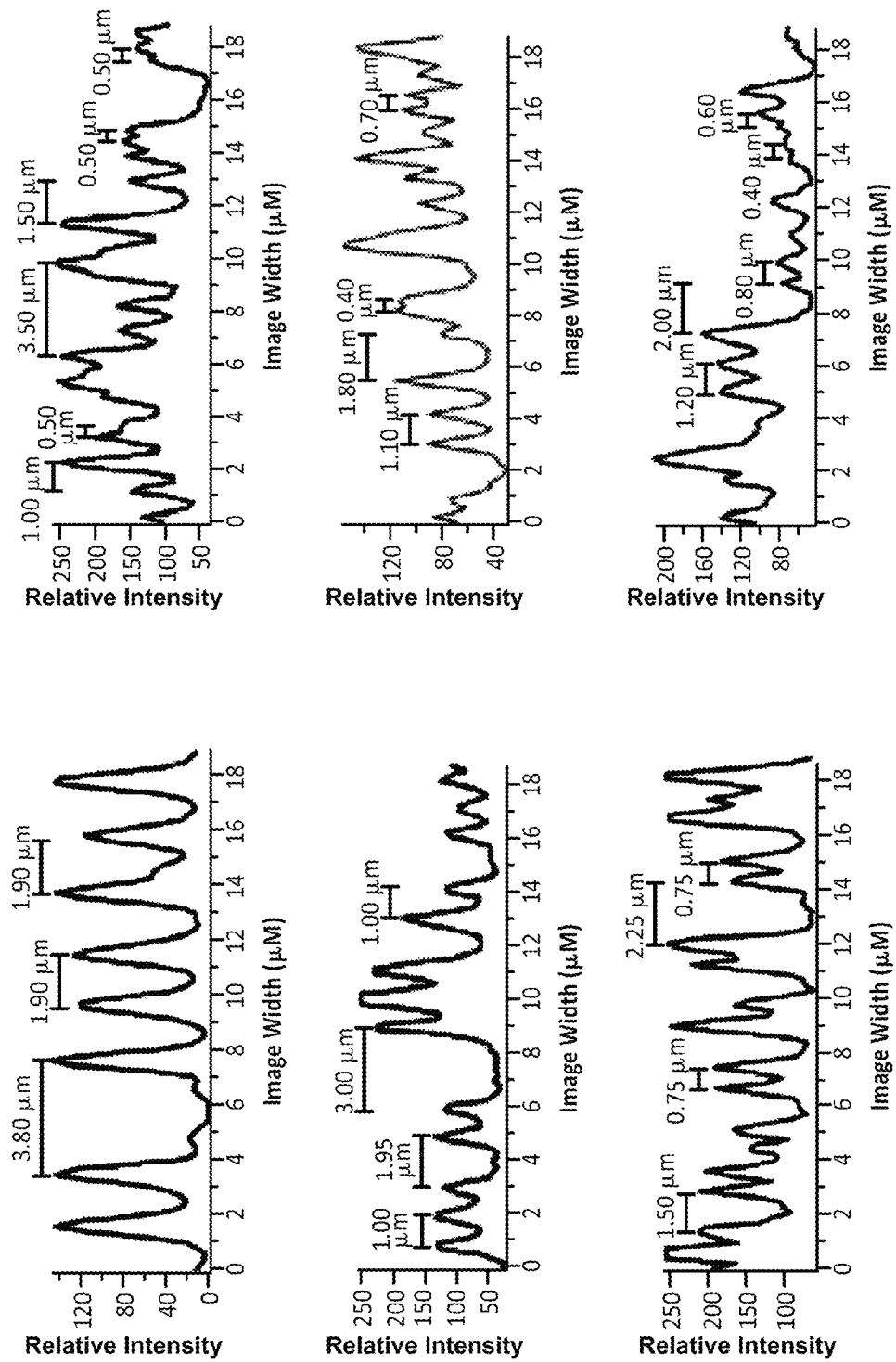
FIG. 24F shows graphs of fluorescence cross-sections of the same curtains described in FIGS. 24A-E and the distances between some representative examples of adjacent DNA peaks are indicated in micrometers. These images were collected from single flow cells containing different sets of nanowell barriers with the indicated spacing.
Figure 24G:
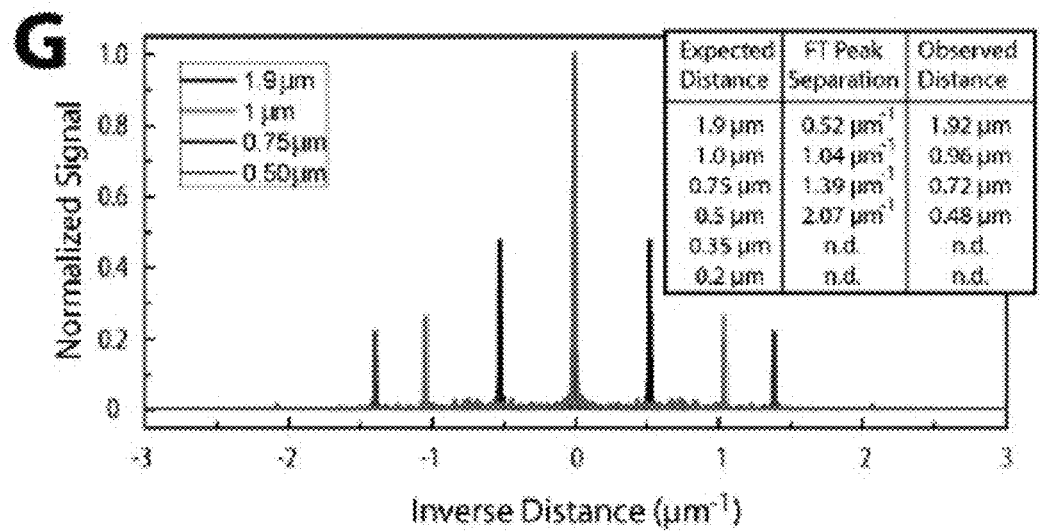
FIG. 24G is a graph that shows a normalized power spectrum of Fourier Transforms from cross-sections of DNA curtains made using non-linear, geometric barrier patterns with spacings of 1900, 1000, 750, and 500 nm. Note that the optical resolution was insufficient to perform this analysis on the 350 and 200 nm barrier patterns. Values for a given distance based on the barrier design, the peak separation found by the FT analysis, and the corresponding observed separation distance are all indicated (inset).

FIG. 24E highlights examples of DNA curtains made with non-linear, geometric barrier patterns with 1900, 1000, 750, 500, 350, and 200 nm separation between adjacent nanowells. These curtains are comprised of the 23 kb DNA that is fluorescently stained with the intercalating dye YOYO1. To verify that this design pattern yielded DNA molecules with the desired spacing we plotted signal intensity of the stained DNA versus its lateral location along the barrier edge, and these plots confirmed peak-to-peak distances consistent with values from designs of the non-linear, geometric barrier patterns (FIG. 24F). The 1900, 1000, 750, 500, 350, and 200 nm barriers yielded separation distances corresponding to the pattern designs. For the geometric nanowells with 1900, 1000, 750, 500, and 350 nm spacing, we could resolve the distances between DNA molecules loaded into adjacent wells. For the 200 nm nanowells spacing it was not possible to resolve DNA molecules loaded into adjacent wells because the closely spaced molecules led to overlapping fluorescence signal. However, at lower concentrations of DNA, we were able to confirm that the observed spacing between the DNA molecules occurred in intervals divisible by 200 nm (FIG. 24F, lower panel), indicating that the 200 nm nanowells were functioning. Similarly, we used Fourier transform (FT) analysis to verify the distribution patterns of the DNA within the curtains. As shown in FIG. 24G, the peak-to-peak separation of the power spectrum from the FT correlated to within 5% of the expected values based on the designs of the non-linear, geometric barrier patterns. Taken together, these data demonstrate that the distance between adjacent nanowells dictates lateral separation between individual molecules that make up the DNA curtain.

Figure 25:
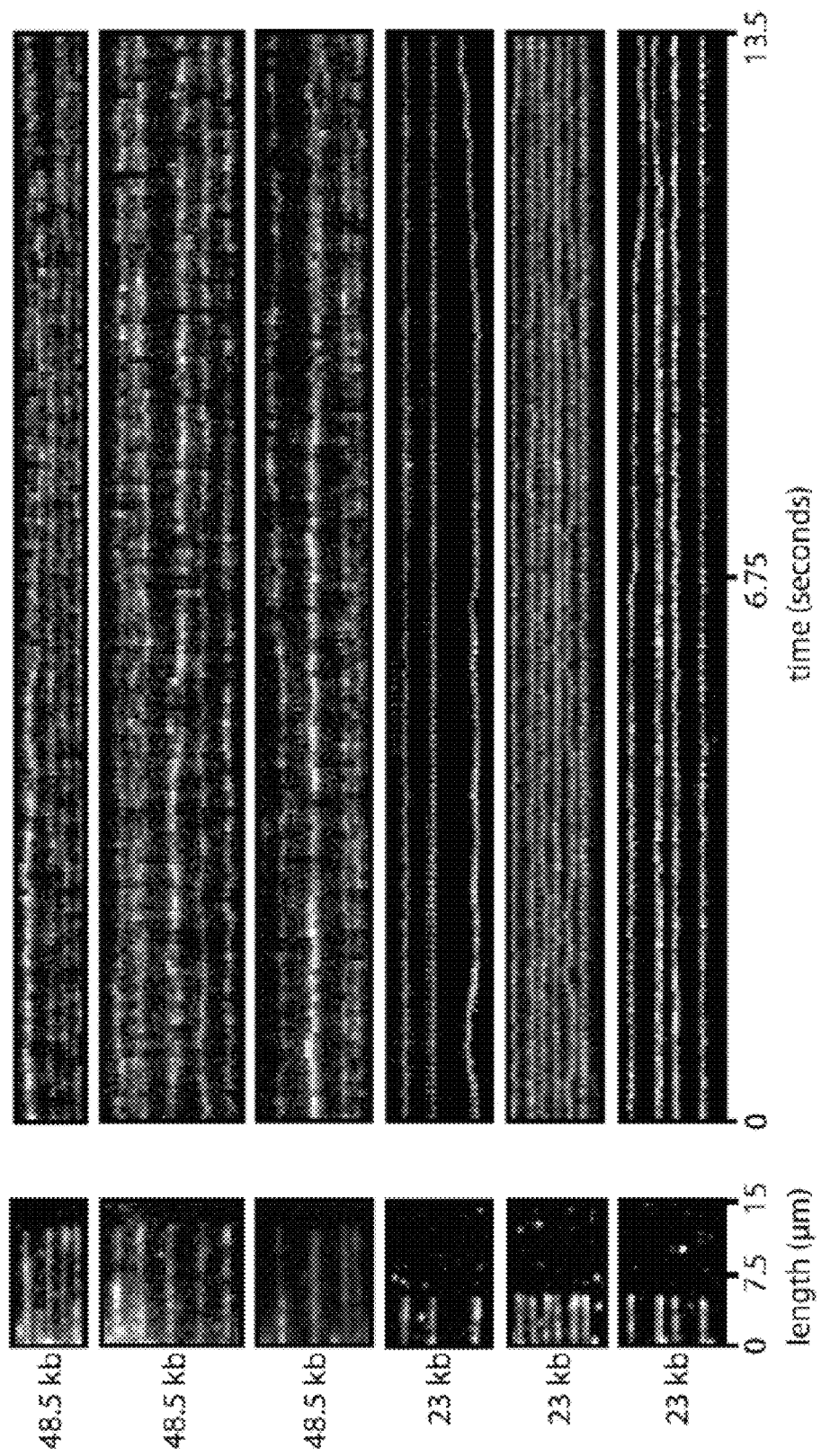
FIG. 25 is a photographic image that shows single 100-ms images of a section from different DNA curtains assembled at a smooth barrier edge. The YOYO1 stained molecules are comprised of either 48.5 kb λ DNA or a 23 kb PCR product, as indicated. The right panels show kymograms of cross-sections from the same images spanning a duration of 13.5 s, illustrating the lateral slippage of the DNA molecules along the barrier edges. DNA slippage is eliminated with non-linear, geometric barrier patterns, as shown in FIG. 9B.

As indicated above, DNA molecules aligned along smooth, linear chromium barriers can slip laterally along the barrier edges, and this effect becomes more pronounced with shorter molecules of DNA. To illustrate this problem, either 48.5 kb λ DNA or a 23 kb PCR DNA fragment derived from the human β-globin locus was labeled with YOYO1 (see Materials and Methods in Example 2) and these molecules were aligned along the edge of a smooth barrier. Kymograms illustrating the lateral locations of the DNA molecules over a period of 13.5 s were then generated from a cross-section of the curtain. As shown in FIG. 25, the fluorescently labeled molecules exhibited movement consistent with lateral slippage of the DNA along the barrier edge even over periods spanning just a few seconds. In addition, quantification of the lateral motion (position variance divided by time) of the DNA molecules aligned along the smooth barrier edges yielded a broad range of values with a mean of $1.6\times10^{-3}\pm2.1\times10^{-3}$ µm$^2$/s. DNA curtains made using non-linear, geometric barrier patterns with 500 nm spacing are shown in FIG. 9B, along with the corresponding kymograms. In contrast to the movement observed with the smooth barriers, the λ DNA molecules aligned at the non-linear, geometric patterns displayed absolutely no evidence of lateral slippage over the same 13.5 s period. Similar experiments with DNA molecules of sequentially shorter lengths revealed that the lateral movement of 34, 21, 11, and 5 kb DNA fragments was also eliminated with the non-linear, geometric barrier patterns (FIG. 9B). Quantification of the lateral motion of these DNA molecules yielded values of just 2.00×10-6 (1.73×10-6 µm2/s, demonstrating that the DNA was effectively immobilized. These DNA molecules remained stationary even over much longer periods spanning tens of minutes and this was true for each of the different barrier dimensions. This data provides evidence indicating that the non-linear, geometric barrier patterns effectively restricted lateral movement of the DNA molecules along the barrier edges.

Figures 26A, 26B:
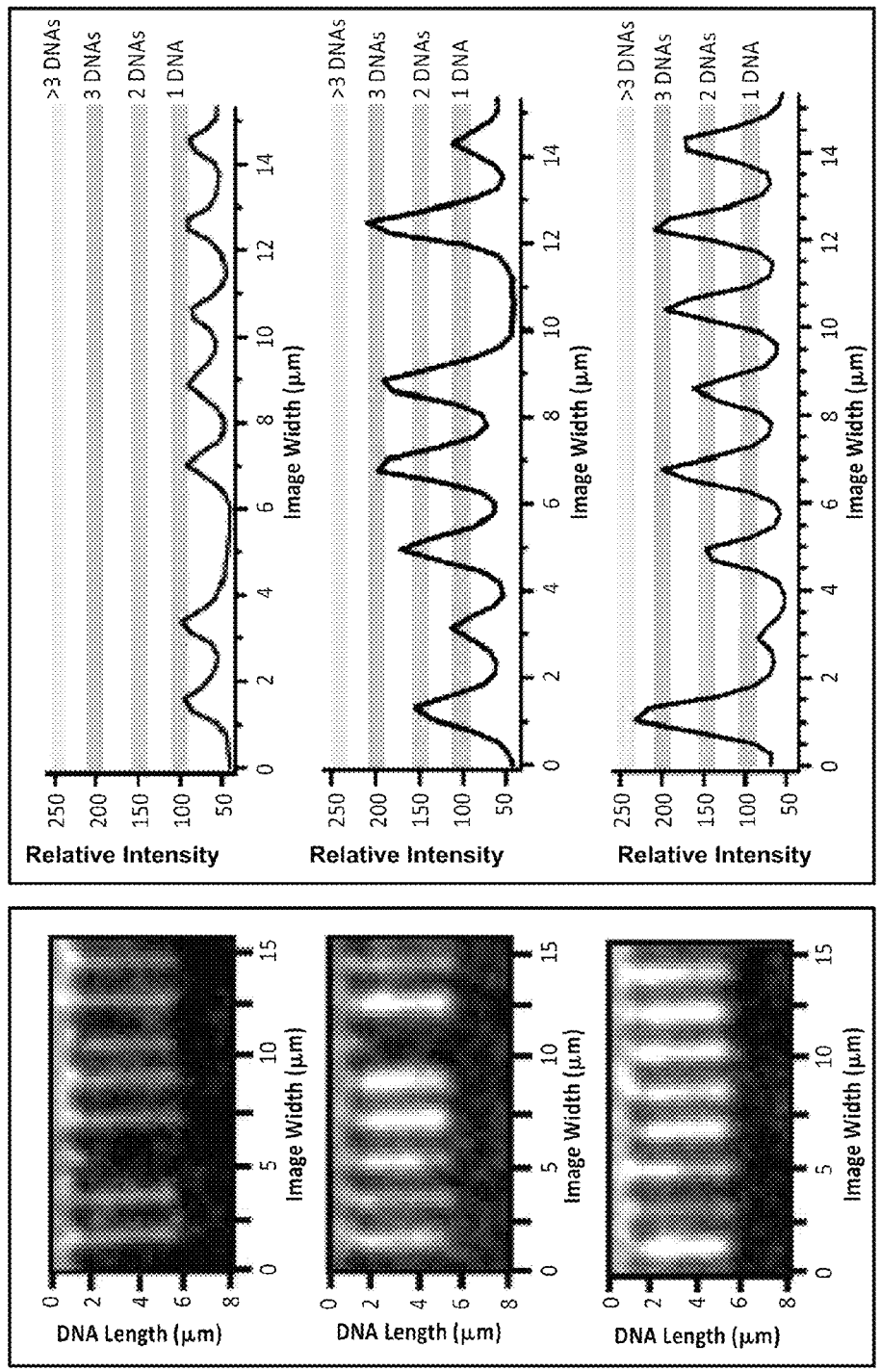
FIG. 26A provides photographic images that show examples of DNA curtains assembled with different DNA densities at barriers with 1.9 μm spacing between the nanowells. Fluorescence cross-sections of the same images are shown in FIG. 26B and the colored bars highlight the relative fluorescence signal intensity (in arbitrary units) observed for different numbers of DNA loaded per nanowell, either 1, 2, 3, and >3 DNAs as indicated. This summarizes the loading of single DNA molecules into the nanowells.
Figure 26C:
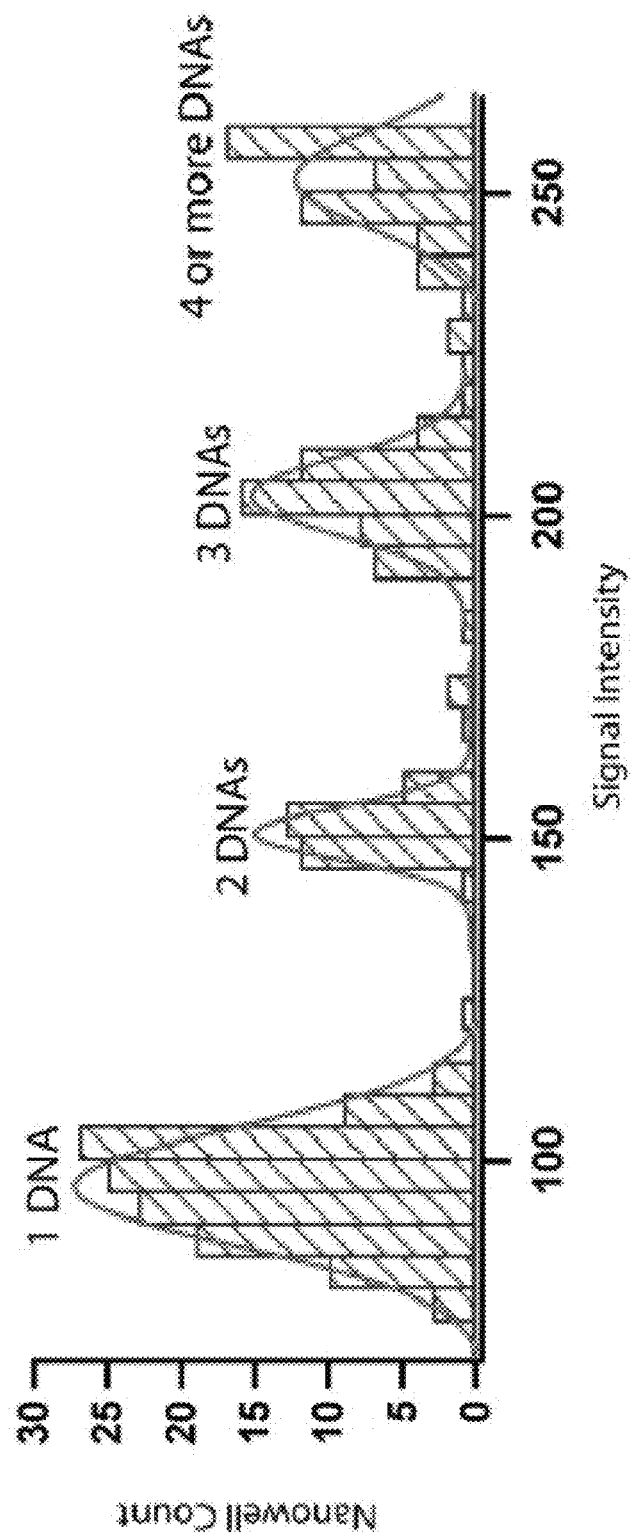
FIG. 26C is a histogram that shows the distribution of DNA occupancy within the nanowells. Under the conditions used here, 44% of the nanowells were loaded with a single DNA molecule.

FIG. 26A shows sections of YOYO1-stained DNA curtains with differing amounts of DNA assembled at barriers with 1900 nm spacing between the adjacent geometric nanowells. These three images were collected from a single barrier set, as the design of the barriers themselves effectively provides a gradient of differing DNA concentrations. This occurs because the guide channel openings that direct the tethered DNA molecules to the nanowell-containing barriers are all similar widths, whereas the different tiers within the barrier set get incrementally wider. Fluorescence cross-sections of the DNA molecules are shown in FIG. 26B and the relative signal intensity corresponding to the different numbers of DNA molecules are indicated by the horizontal bars. Single DNA molecules were readily identified because they exhibited the lowest observed relative signal intensity (compare the upper, middle and lower panels in FIG. 26A-B). Nanowells with multiple DNA molecules were also readily identified because they exhibited a clear incremental increase in the relative signal intensity consistent with 1 or more additional DNA molecules (compare the upper, middle, and lower panels in FIG. 26B). FIG. 26C shows a histogram of the number of DNA molecules per nanowell, demonstrating that under the conditions used for assembling the DNA curtains most of the nanowells (44%) contained only one molecule of DNA, whereas 8% had no DNA, 13% had 2 DNA molecules, 18% had 3 DNA molecules, and 17% had 4 or more molecules of DNA.

To further confirm the assignment of the lowest relative signal intensity as arising from just one DNA, the DNA molecules were partially digested in real time with very low concentrations of the restriction endonuclease AVaI (FIG. 26D-E, and see below). If just one DNA molecule is present in a nanowell, then stochastic cleavage events will coincide with the complete and near instantaneous loss of any DNA downstream from the corresponding cleavage site because the YOYO1-stained DNA fragment liberated by the AVaI cut will be washed away by buffer flow. In contrast, if multiple DNA molecule are present in a single nanowell, then a single stochastic cleavage event by AVaI will not yield instantaneous loss of all downstream signal, but rather will result in a decease in signal intensity downstream of the cleavage site corresponding to loss of just one DNA molecule. As shown in FIG. 26D, when a single DNA is loaded in the nanowell cleavage by the restriction enzyme leads to immediate loss of the corresponding downstream DNA fragment. In contrast, when multiple DNA molecules are present in a nanowell (FIG. 26E; in this example there are two molecules in the nanowell), cleavage by the restriction enzyme results in an incremental decrease in the downstream signal because just one of the DNA molecules is cut over the course of the digest. The results from these partial restriction digests confirmed that the lowest YOYO1 fluorescence signal corresponds to just one molecule of DNA.

Example 9

Dynamic Optical Restriction Mapping

Figure 27A:
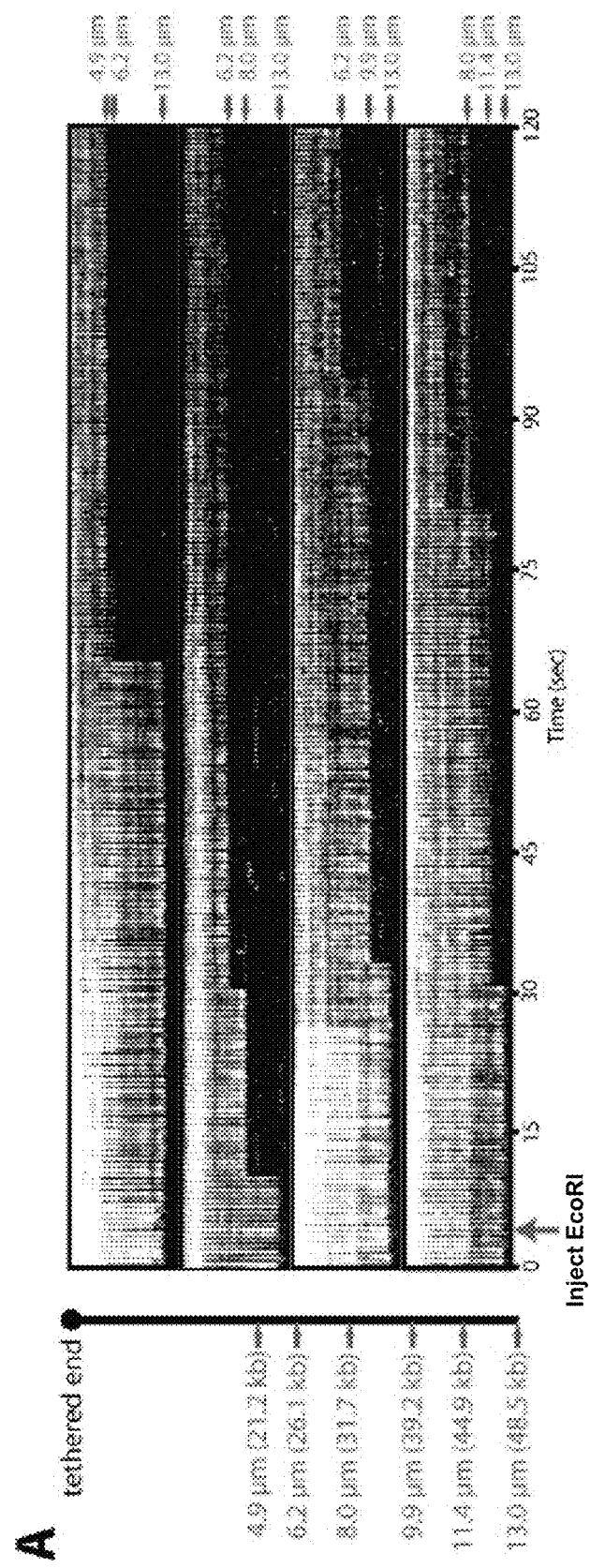
FIG. 27 shows photographic images of dynamic optical restriction mapping with EcoRI and BamHI. Kymograms in FIGS. 27A-B show representative examples of real time restriction digests of the λ phage genome using either EcoRI or BamHI. A schematic of λ is shown at the left; the tethered end of the DNA is indicated as are the predicted cleavage sites in kilobases (kb) and the observed fragment lengths in micrometers (μm).
Figure 27B:
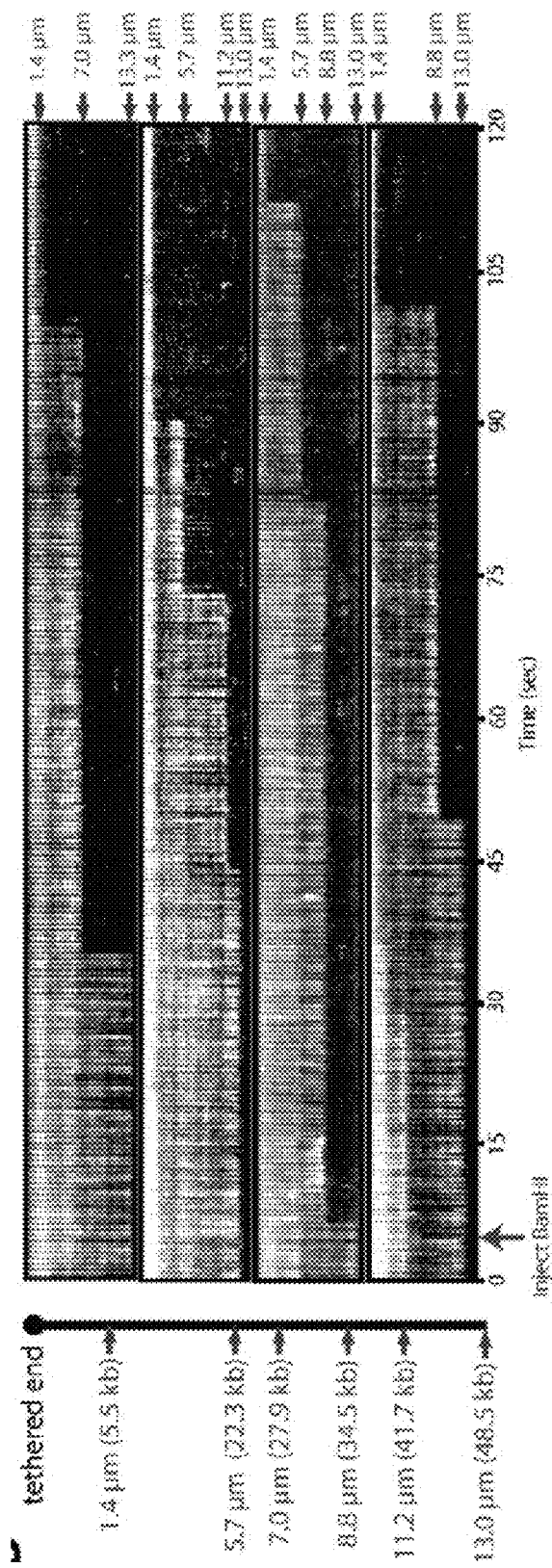

As shown above, these non-linear, geometric barrier patterns permit studies of even relatively small DNA fragments by eliminating their lateral mobility along the barrier edges. We have also demonstrated that we can load the geometric nanowells with single DNA molecules. In previous work we have shown that the design of the curtains also yields DNA molecules that are all aligned with the same sequence orientation based upon the location of the biotin tag at a specific end of the DNA. As a consequence of this consistent alignment, complete restriction digest of the DNA molecules within the curtain yields identical, tethered fragments whose lengths correspond to the furthest upstream cleavage site. Complete digests at high concentrations of restriction enzyme cannot be used to identify multiple sites cleaved by the same restriction enzyme because the downstream DNA is flushed from the sample chamber as soon as the DNA is cleaved. As shown above, restriction digests done at low concentrations of enzyme can reveal stochastic cleavage events, which could be used to reveal all of the fragments corresponding to each of these intermediate lengths. However, this is only true if the digest is viewed in real time, and sufficient numbers of molecules are observed to detect all sites, and the cleavage rate is slower than the data acquisition frequency. If these criteria are met, then following each individual cleavage event, the downstream fragment will be immediately flushed from the sample chamber by buffer flow, leaving behind the intact biotinylated fragment whose shortened length would correspond to the location of the cleavage site. This can happen repeatedly on the same DNA until that particular molecule is cleaved at the furthest upstream site relative to the anchored end of the DNA. The large number of DNA molecules that can be viewed with these DNA curtains makes it possible to detect all of the potential sites within the DNA, and the geometric nanowells prevent the DNA molecules from slipping back and forth after they are cleaved. Eventually all of the DNA molecules will be cut to a final length corresponding to the furthest upstream restriction site. We refer to this real time digest as dynamic optical restriction mapping and an example of such an assay is shown in FIG. 27A-B, using the restriction enzymes EcoRI and BamHI, respectively. These kymograms were selected because they provide examples where each of the five EcoRI sites or five BamHI sites can be identified. The total time required for this digest was just under 120 s. This assay is not possible with smooth barrier designs because the DNA molecules start to rapidly slip back and forth as the fragment lengths become shorter and shorter, thus interfering with measurements of the same DNA molecule over time. Thus this real time dynamic optical restriction mapping assay is greatly facilitated when used in combination with barrier patterns comprised of the geometric nanowells.

Example 10

High-Throughput Single-Molecule Imaging Reveals Intrinsic Nucleosome Landscapes

Nucleosomes are the fundamental unit of organization in eukaryotic chromatin and contribute to all aspects of DNA metabolism. The importance of chromatin structure has driven efforts to establish computational methods for predicting genome-wide nucleosome distributions based on intrinsic sequence preferences. Here we use high-throughput single-molecule imaging of nanofabricated DNA curtains to directly determine intrinsic energy landscapes for nucleosome deposition on model substrates. We then ask whether in silico predictions accurately reflect course-grain features of the experimentally derived intrinsic energy landscapes. Our results show that nucleosome distribution patterns were anticorrelated with predictions from the widely cited model of Segal et al[D1], but were strongly correlated with the more recent model of Field et al[D2]. Without being bound by theory, these findings reinforce that DNA contains intrinsic positioning information necessary for dictating distributions of canonical nucleosomes, and indicate that exclusionary sequences play a dominant role in this process. We also demonstrate that intrinsic landscapes are largely independent of constituent histone identity, and nucleosomes containing variant histones H2AZ or CenH3 are well correlated with patterns observed for canonical nucleosomes, indicating they are subject to similar thermodynamic principles despite disparate in vivo distributions. However, the non-histone protein Scm3 drastically alters the intrinsic landscape, enabling centromeric nucleosomes to overcome exclusionary effects of poly(dA-dT)-rich sequences. Finally, we show that cis-regulatory sequences in human DNA coincide with peaks in the intrinsic landscape, whereas valleys correspond to non-regulatory regions, and we present evidence arguing that patterns of nucleosome deposition in vertebrate genomes are influenced by both extrinsic factors and possible intrinsic sequence elements not yet accounted for by current theory.

Figure 47:
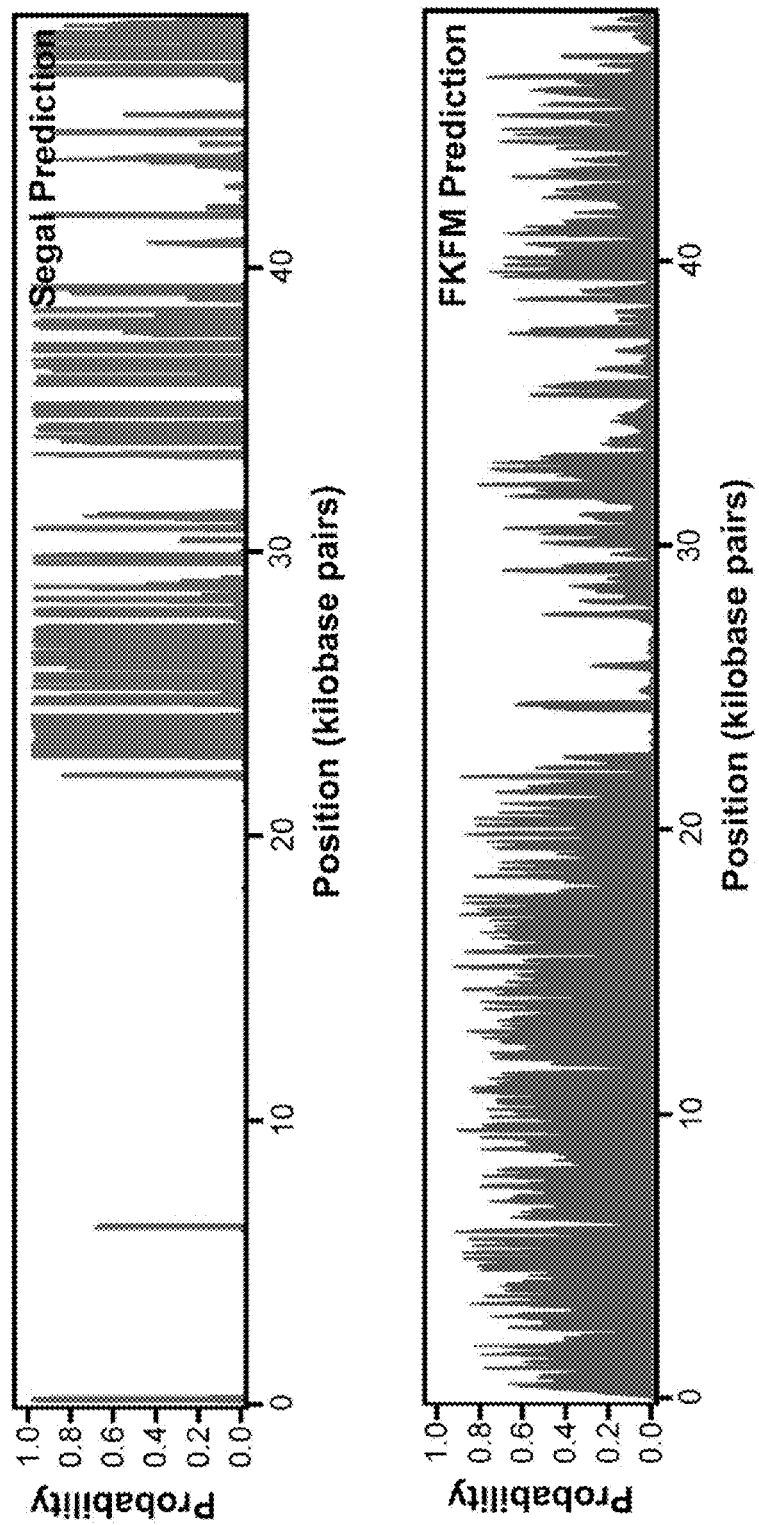
FIG. 47 are graphs that represent theoretical nucleosome distributions as reported by Segal et al. Nature. 442, 772-778 (2006) and Field et al. PLoS Comput Biol. 4, e1000216 (2008).

The distribution of nucleosomes throughout the genome has profound consequences for DNA transcription, repair, and chromosome segregation[D3-5]. Nucleosomes consist of ~147-base pairs (bp) of DNA wrapped in ~1.7 turns around an octamer containing two of each histone H2A, H2B, H3, and H4[D5,D6]. There has been tremendous interest in developing in silico models of genome-wide nucleosome positions, the first of which came from Segal et al.,[D1] and calculated probabilistic nucleosome distributions based upon the universal preference of nucleosomes for bendable DNA containing AA/TT/AT dinucleotides with 10-bp periodicities in counter-phase with GC dinucleotides[D3,D7] (see also FIG. 47). Without being bound by theory, this supported the idea of a "second genetic code", which asserts that genomes intrinsically encode information dictating nucleosome distributions, and posits that extrinsic factors, such as chromatin remodeling proteins, play a limited role in establishing steady-state positions. However, without being bound by theory, accumulating evidence demonstrates exclusion signals, such as poly(dA-dT), also influence nucleosome distribution[D5,D8-10], yet these sequences were unaccounted for in the original Segal predictions. A more recent model from Segal and colleagues, which shall be referred to as the Field, Kaplan & Fondufe-Mittendorf (FKFM) model, used ~2000-fold more sequence information from isolated nucleosomes to train the pattern matching algorithm and also included exclusion effects from motifs enriched in linker DNA[D2] (see also FIG. 47).

Figure 28:
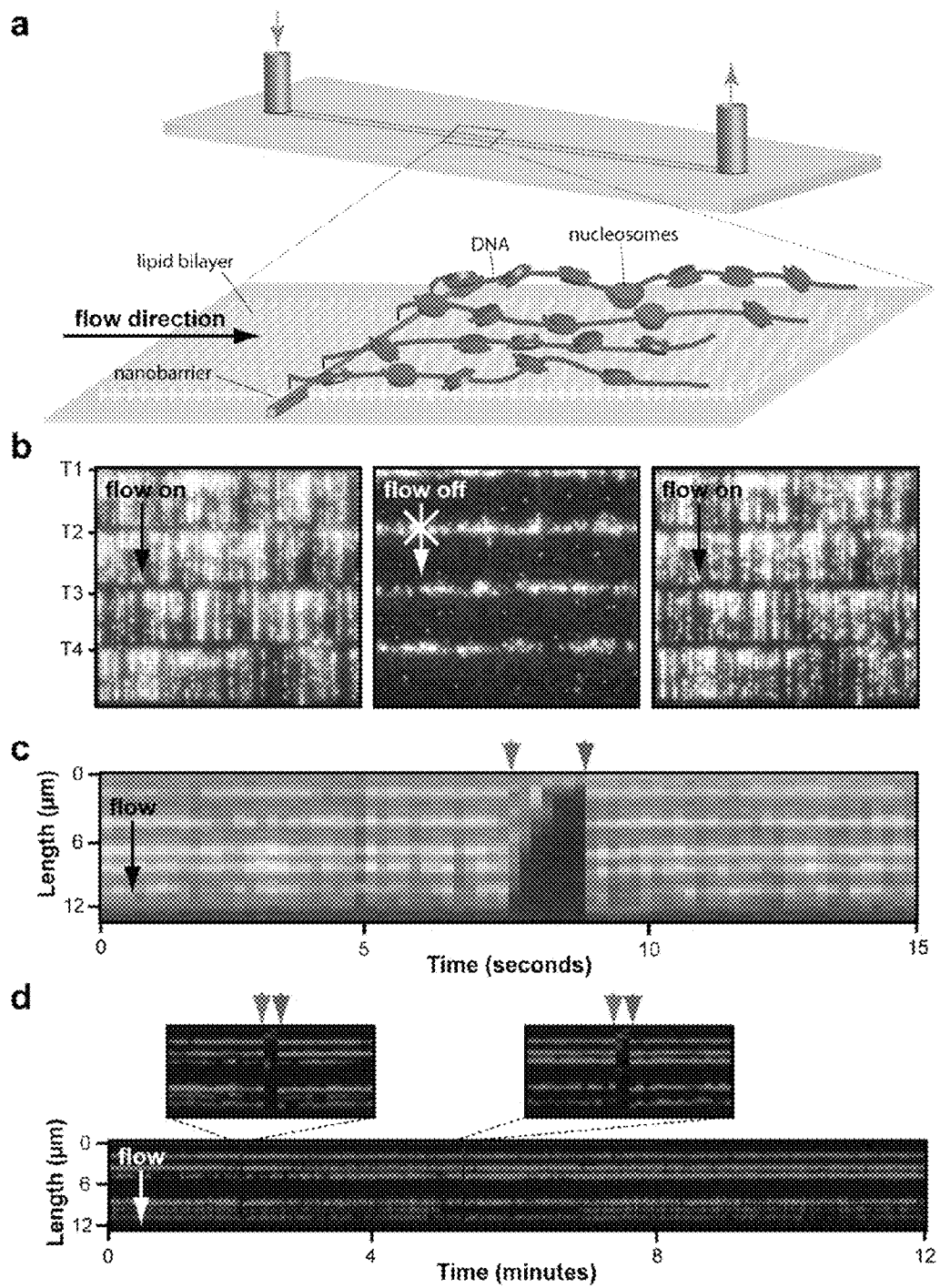
FIG. 28 depicts the visualization of fluorescently tagged recombinant nucleosomes on DNA curtains.
Figure 29A:
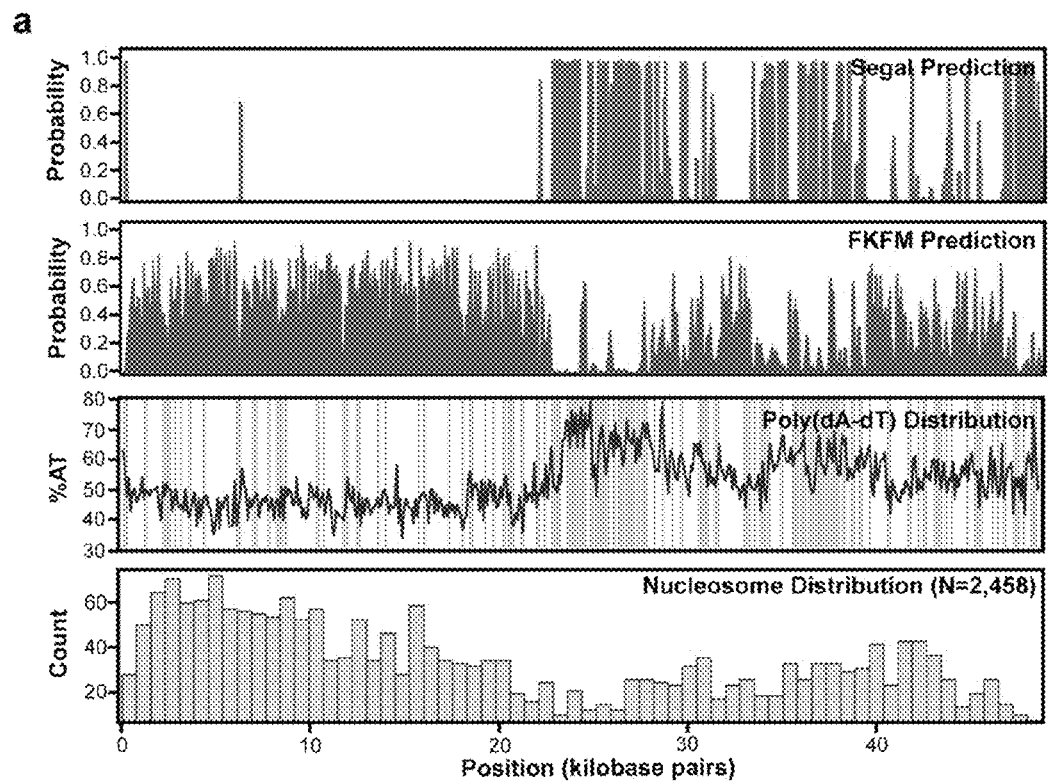
FIG. 29A shows graphs depicting the predicted and observed nucleosome distribution patterns on bacteriophage λ-DNA. The nucleosome distributions predicted by the Segal (magenta) and FKFM (green) models for λ-DNA are shown. The AT-content of the λ is shown (blue line; calculated with a 100-bp window) superimposed with the distribution of poly (dA-dT) tracts ≥5-mers (gray bars), which are asymmetrically distributed and comprise 3.2% of the phage genome. The observed nucleosome distribution is shown in the lower panel, and is comprised of data from both canonical nucleosomes and nucleosomes bearing H2AZ (FIG. 38A-B). The theoretical data is shown at 1-bp resolution, and the observed data is compiled into 758-bp bins.
Figure 29B:
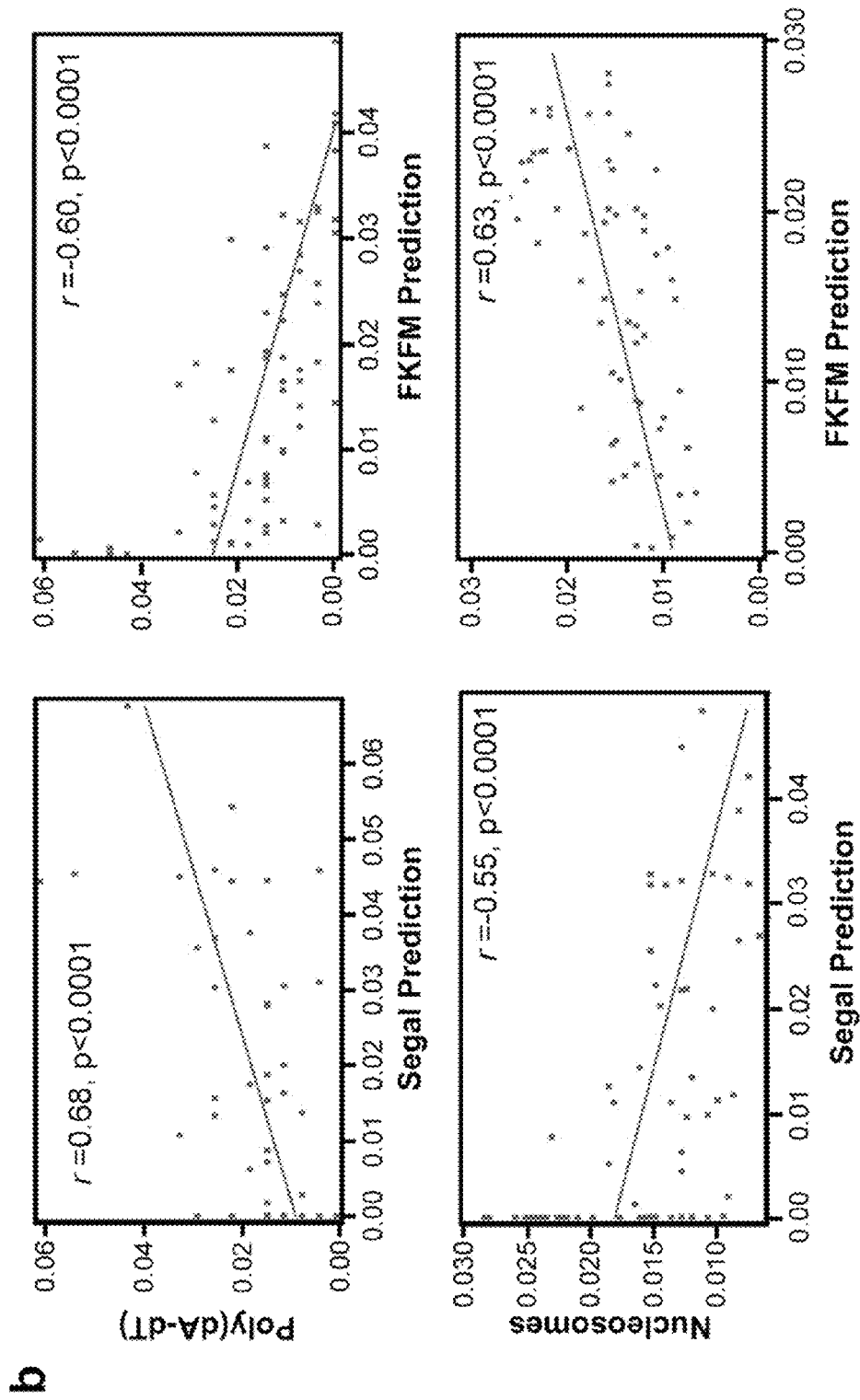
FIG. 29B are graphs showing Pearson correlation analysis of the poly(dA-dT) distribution and the observed nucleosome distribution compared to the Segal and FKFM predictions.
Figure 32:
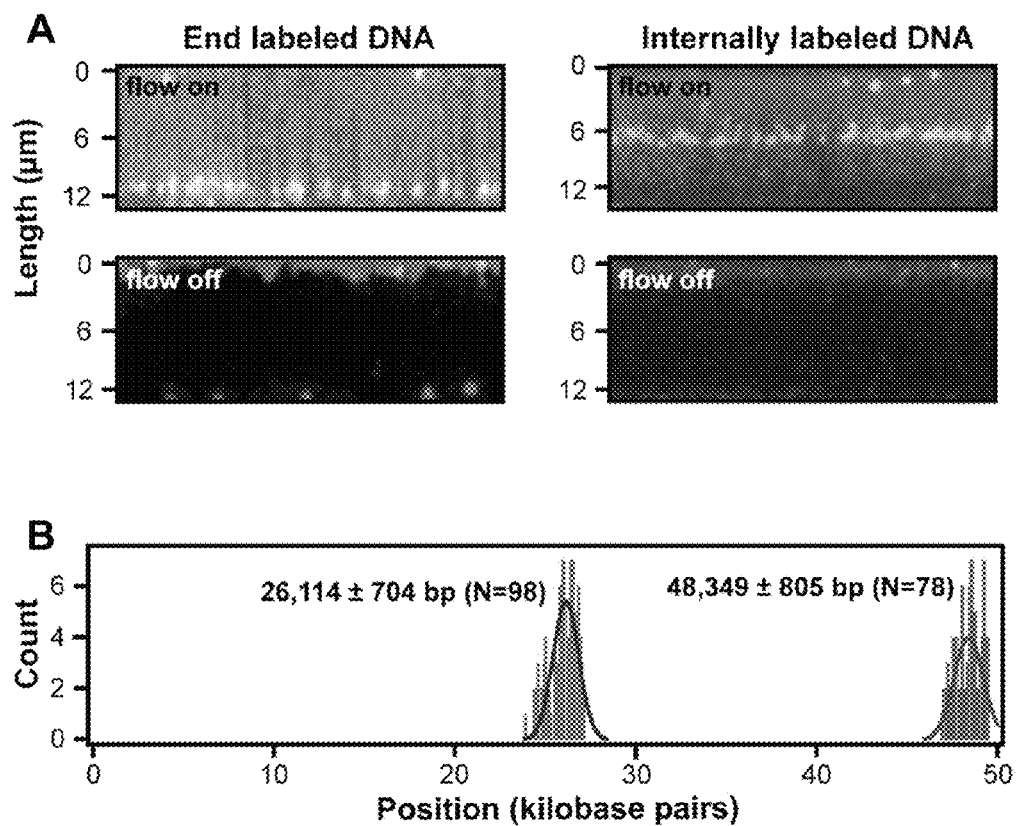
FIG. 32 represents determining target site distribution patterns with single molecule population measurements of DNA curtains.
Figure 34A:
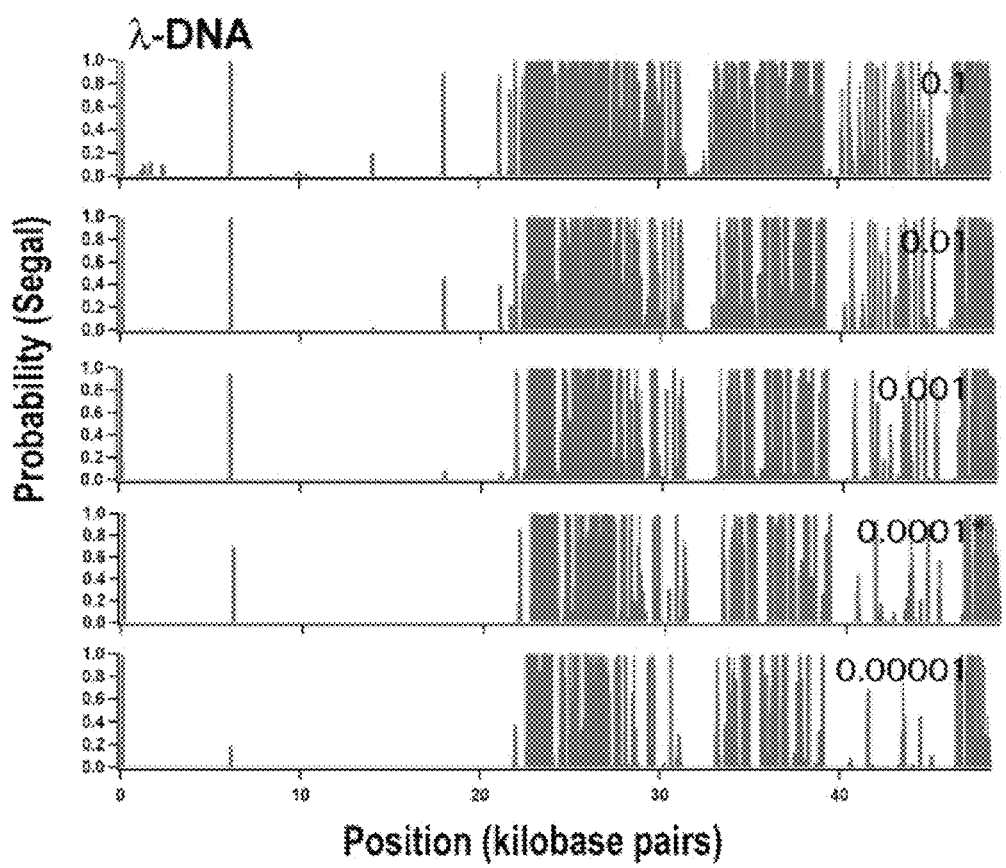
FIG. 34A demonstrates predicted distributions at differing nucleosome concentrations. The Segal algorithm contains concentration parameters for adjusting the nucleosome density on the DNA.
Figure 34B:
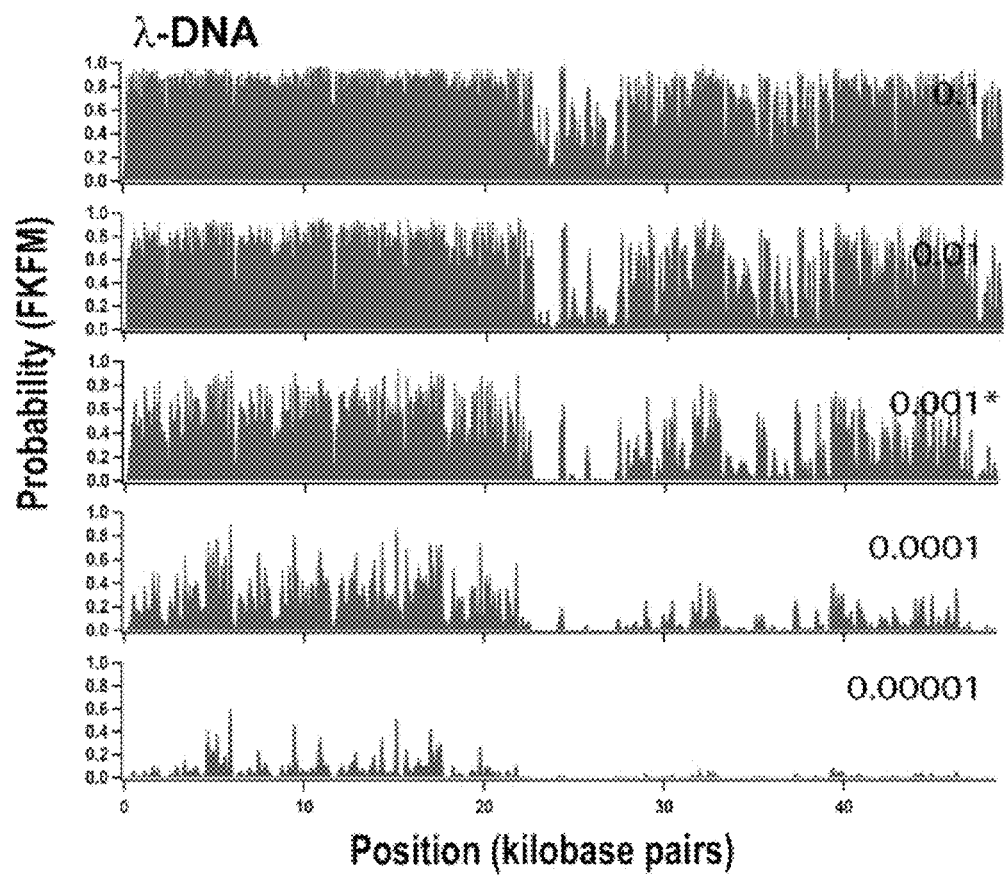
FIG. 34B demonstrates the predicted distributions at differing nucleosome concentrations. The FKFM algorithm contains concentration parameters for adjusting the nucleosome density on the DNA.
Figure 35:
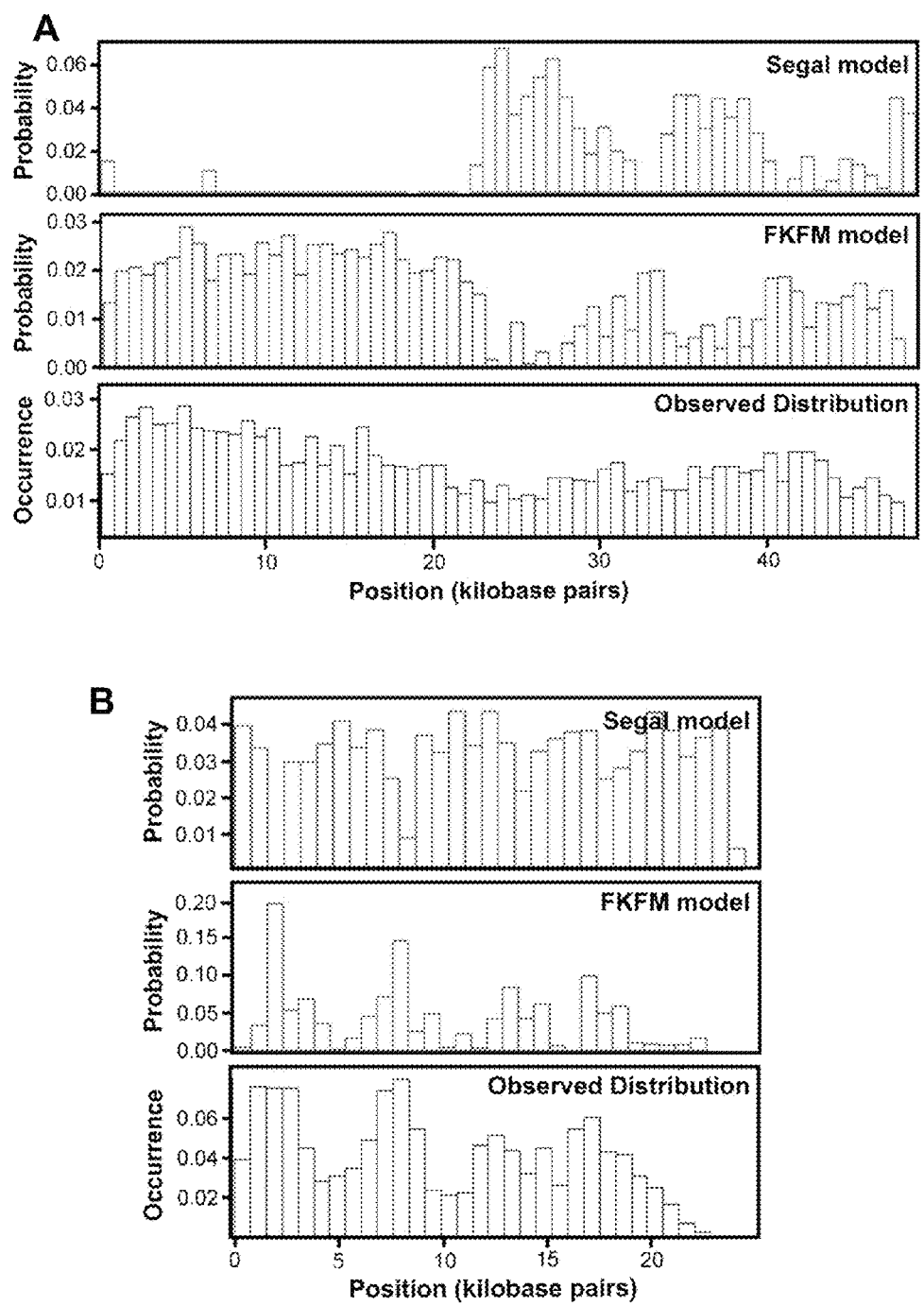
FIG. 35 shows graphs of the predicted distribution analysis and observed data binned at same resolution.
Figure 36:
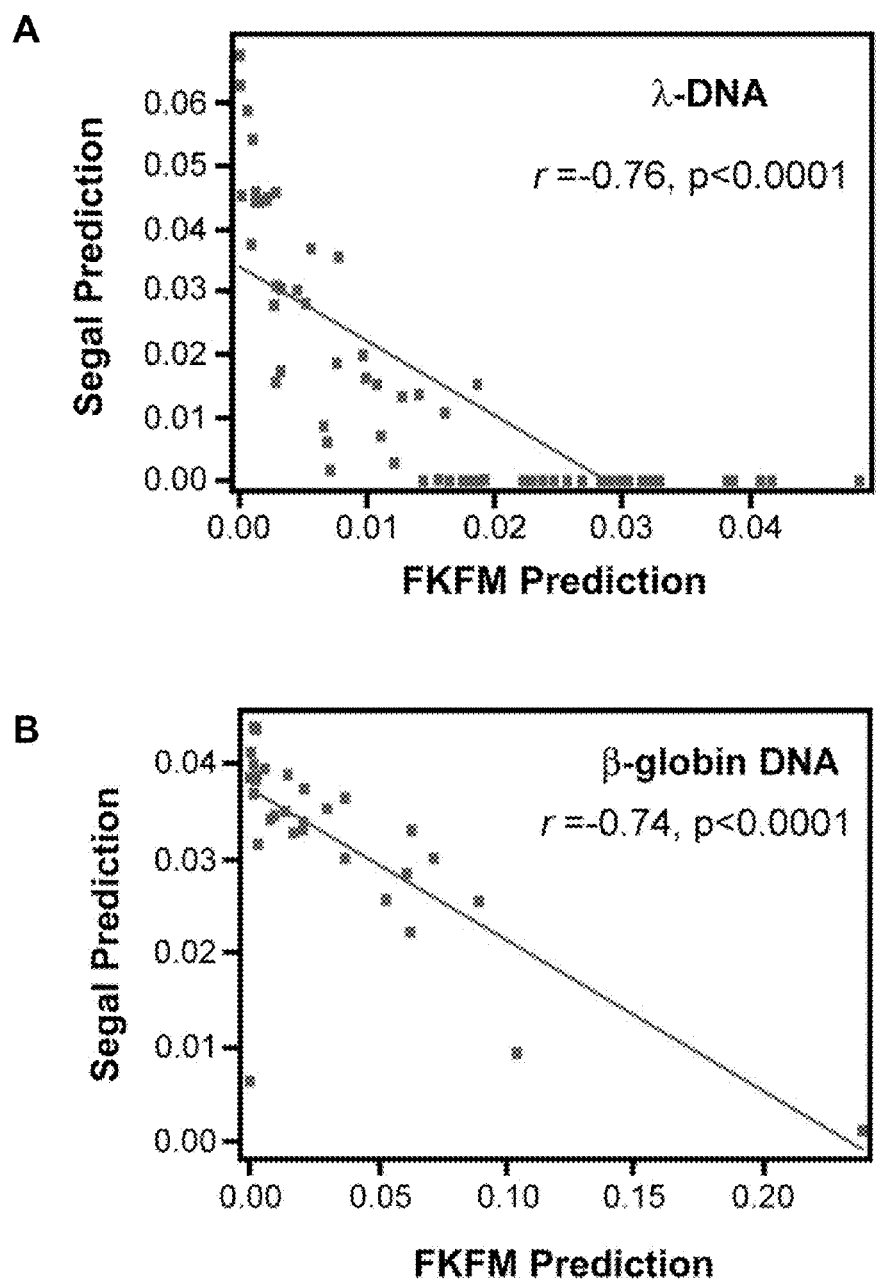
FIG. 36 shows graphs of the anticorrelation of the predictive algorithms. Correlation analysis of the Segal and FKMK predictions relative to one another for λ-DNA (FIG. 36A) and the human β-globin DNA fragment (FIG. 36B).
Figure 37:
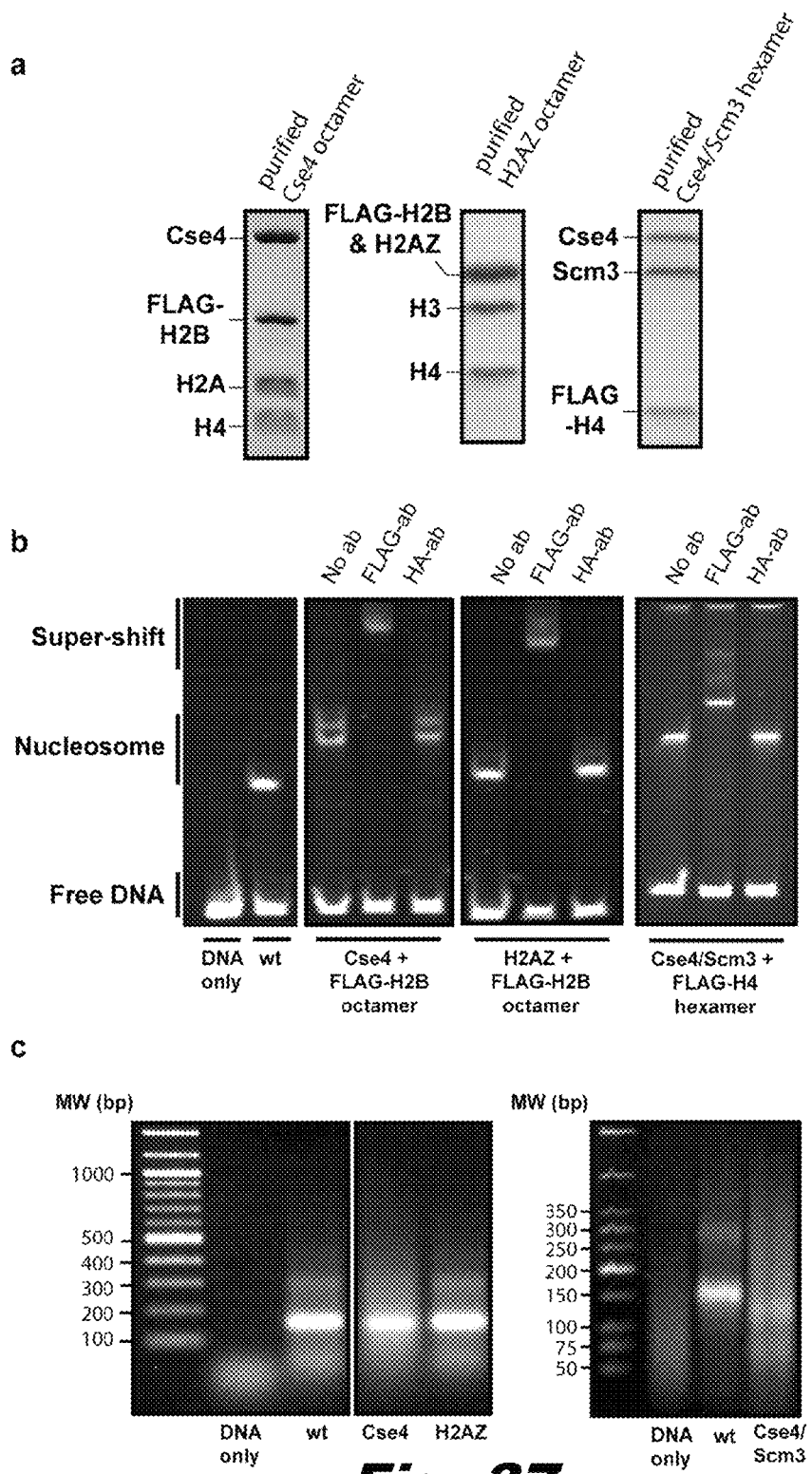
FIG. 37 shows photographic images of blots used in the characterization of nucleosomes harboring the histone variants.
Figure 38A:
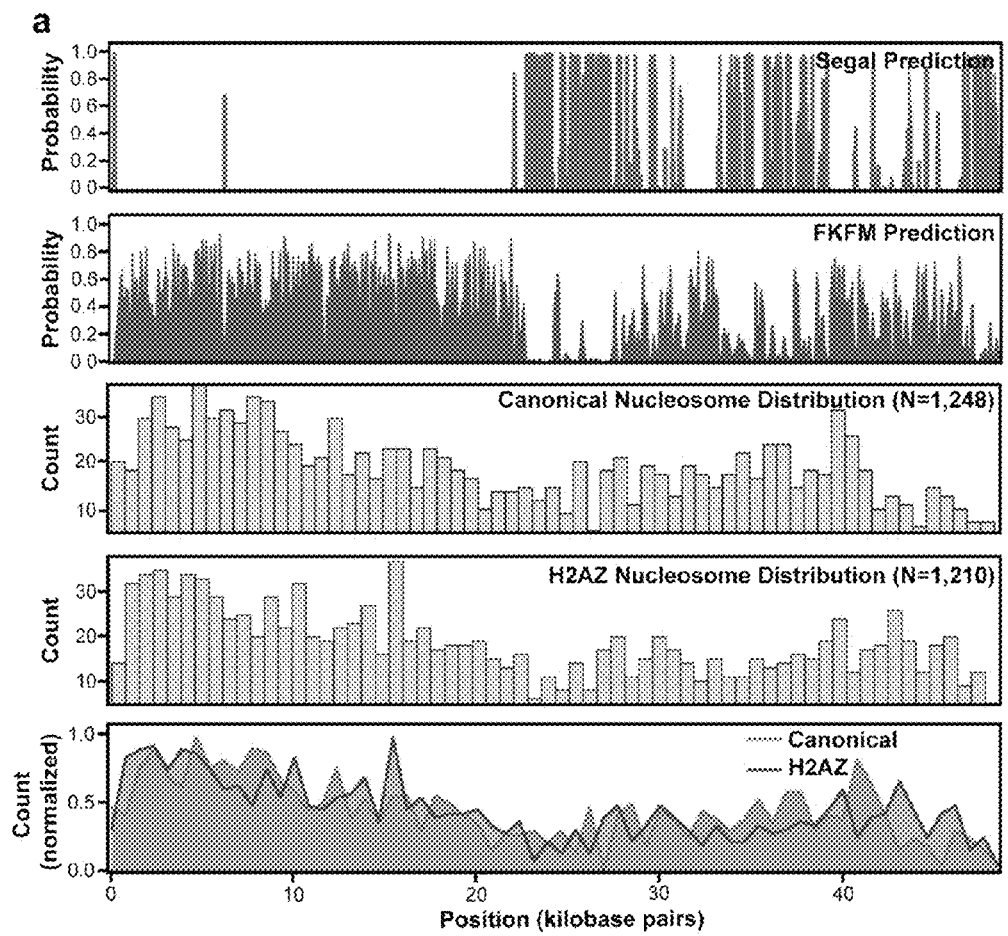
FIG. 38A shows graphs of a comparison of canonical and H2AZ nucleosomes. The graphs depict the Segal and FKFM predictions for λ-DNA along with the distribution histograms for canonical and H2AZ-containing nucleosomes, and the overlaid data sets.
Figure 38B:
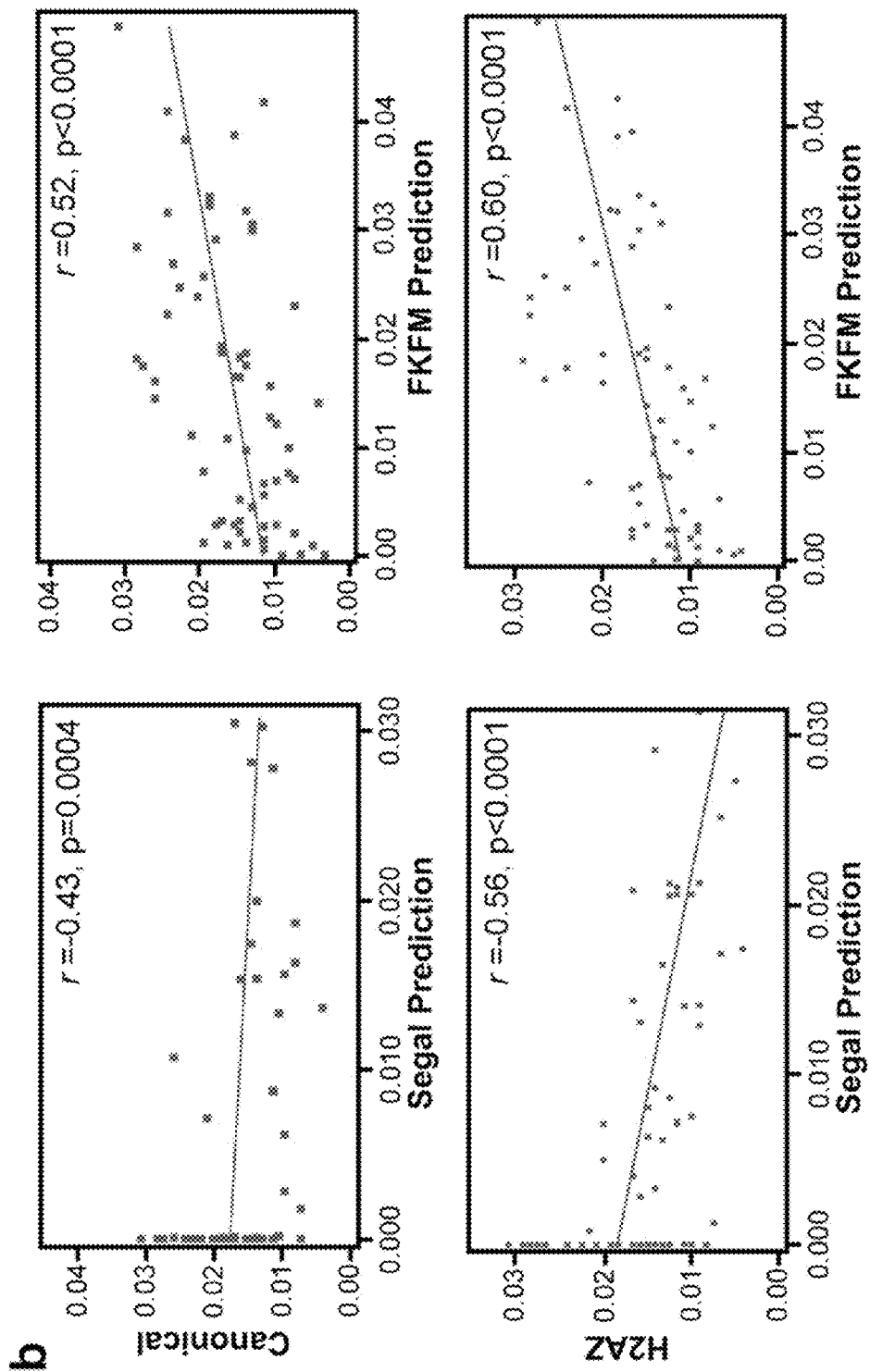
FIG. 38B shows graphs of a comparison of canonical and H2AZ nucleosomes. The graphs demonstrate the correlation between the observed distributions and the theoretical predictions from the two models.

The relative performance of these models as general tools for predicting intrinsic landscapes has yet to be thoroughly explored, prompting us to ask whether we could verify the predictions by high-throughput single-molecule imaging with total internal reflection fluorescence microscopy. For this assay, DNA is anchored to a lipid bilayer on the surface of a microfluidic chamber and hydrodynamic force is used to align thousands of molecules into curtains along nanofabricated barriers where they are viewed in real-time (FIG. 28A and FIG. 32)[D11]. To make curtains with nucleosomes, recombinant S. cerevisiae octamers containing FLAG-H2B were deposited onto biotinylated λ-DNA by salt dialysis (FIG. 33), which recapitulates thermodynamically favorable distributions[D5,D12], and nucleosomes were labeled in situ with anti-FLAG quantum dots (QDs; FIG. 28B). Transient termination of hydrodynamic force provoked entropic collapse of the curtains, causing the DNA and nucleosomes to drift outside the detection volume defined by the evanescent field, verifying the molecules were anchored only via the biotin tag (FIG. 28B-D). For distribution analysis, conditions were selected to yield ~5 nucleosomes per DNA, equivalent to ~1.5% coverage of the 48.5-kb substrate, and time courses confirmed the nucleosomes did not move or dissociate during the experiments (FIG. 28B-D).

λ-DNA is not subject to evolutionary pressure to position nucleosomes, but analysis of the phage genome revealed an advantage for its use as a model substrate: the Segal and FKFM models yielded strikingly dissimilar predictions for the nucleosome distribution patterns (FIG. 29A, FIG. 34A-B, and FIG. 35A). Pearson correlation analysis revealed these predictions were actually anticorrelated ($r=-0.76$, $p<0.0001$; FIG. 36). The contrasting predictions are attributed to exclusionary sequences, as evidenced by the observation that the Segal model was correlated with poly(dA-dT) tracts ($r=0.60$, $p<0.0001$), whereas the FKFM model was anticorrelated with these same features ($r=-0.68$, $p<0.0001$; FIG. 29B). The different distributions generated by the two models provided a means for evaluating their relative performance. To test the predictions we measured the locations of 1,248 canonical nucleosomes and 1,210 nucleosomes containing the histone variant H2AZ (N=2,458 total; FIG. 29, and FIGS. 37-38); a histogram of these positions represents a course-grained profile of the thermodynamically favored intrinsic energy landscape for nucleosome deposition (FIG. 29A). The observed nucleosome distribution was anticorrelated with both the Segal prediction ($r=-0.55$, $p<0.0001$; FIG. 29B) and the poly (dA-dT) distribution ($r=-0.32$, $p<0.01$), but bore a remarkable resemblance to the FKFM prediction ($r=0.63$, $p<0.0001$; FIG. 29A-B, and FIG. 35). These results highlight limitations of the original Segal model, but support the refined FKFM model as a general means for predicting intrinsic energy landscapes of nucleosome binding sites. The fact that an algorithm trained with sequences derived from S. cerevisiae could predict the intrinsic landscape of λ-DNA further demonstrates that steady-state nucleosome positions in yeast are dictated primarily through intrinsic sequence effects.

Information within eukaryotic genomes is enriched through targeted deposition of histone variants. Histone H2AZ is a conserved lineage of H2A that influences gene regulation[D13-18]. CenH3 (Cse4 in yeast) is an H3-variant that serves as a centromere-specific epigenetic marker[D19-21]. Cse4 can replace CenH3 in human centromeres, indicating a high degree of functional conservation[D22]. In vivo deposition of H2AZ and CenH3 requires extrinsic factors[D4,D21,D23], but it remains unclear whether variants are subject to the same energetic landscapes that dictate favorable binding by canonical nucleosomes. Nucleosomes bearing H2AZ displayed the same distribution trends as canonical nucleosomes, demonstrating that H2AZ does not alter thermodynamic sequence preferences (FIG. 29, and FIGS. 37-38). The intrinsic landscape is intriguing for Cse4, which binds poly(dA-dT)-rich CEN DNA in vivo, and forms an unusual hexasome wherein H2A/H2B is replaced with the non-histone protein Scm3[D21]. If centromeric nucleosomes obey the same principles as canonical nucleosomes with respect to site preferences, then the in vitro distributions should be similar.

Figure 30A:
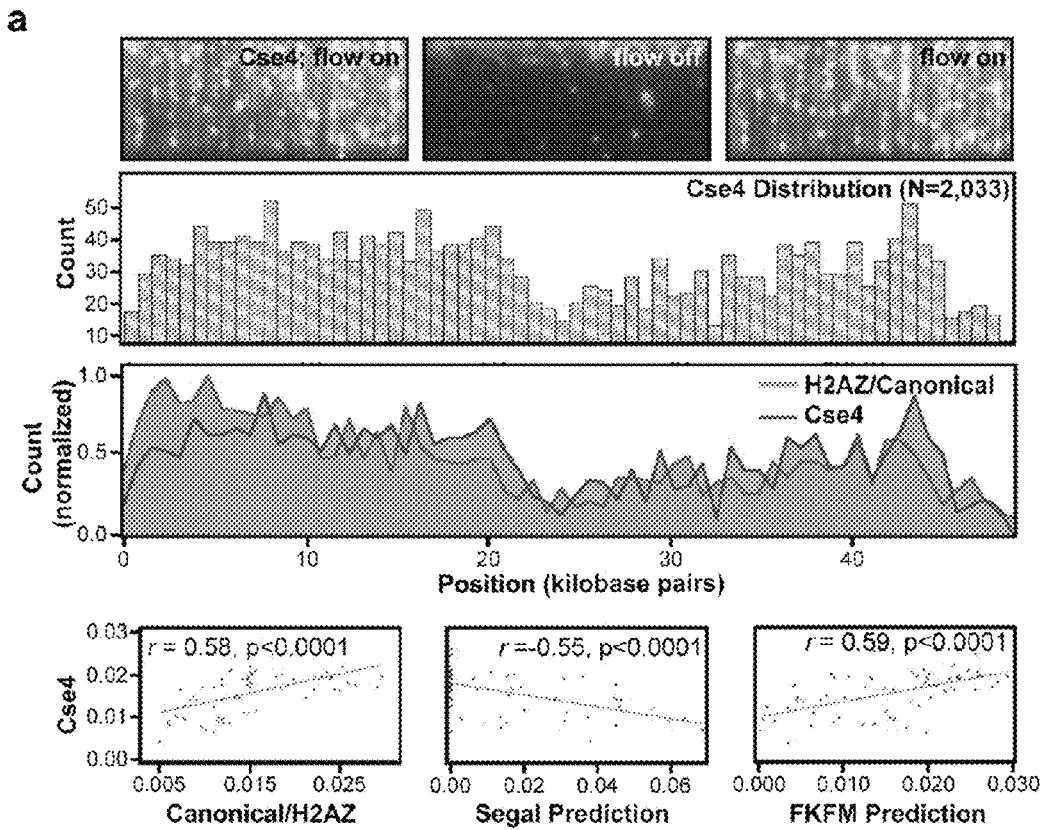
FIG. 30A represents thermodynamic landscapes for centromeric nucleosomes. Photographic images are shown in the presence and absence of buffer flow (1$^{st}$ row); population distribution histograms are depicted in the 2$^{nd}$ row; graphs of overlays with the canonical/H2AZ distributions are shown in the 3$^{rd}$ row; and graphs showing a correlation analysis for nucleosomes bearing Cse4 are shown in the 4$^{th}$ row.
Figure 30B:
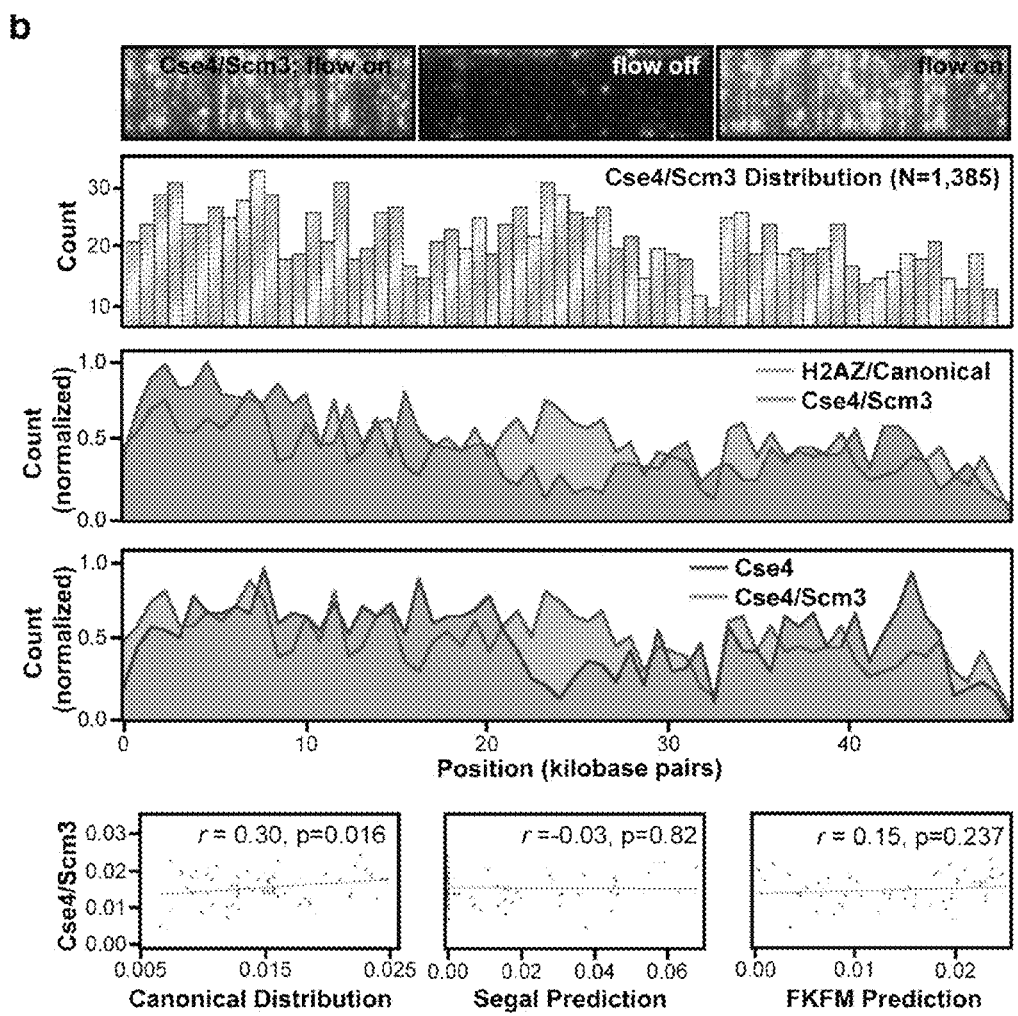
FIG. 30B represents thermodynamic landscapes for centromeric nucleosomes. Photographic images are shown in the presence and absence of buffer flow (1$^{st}$ row); population distribution histograms are depicted in the 2$^{nd}$ row; graphs of overlays with the canonical/H2AZ and Cse4 distributions are shown in the 3$^{rd}$ and 4$^{th}$ rows, respectively; and graphs showing a correlation analysis for nucleosomes bearing Cse4/Scm3 are shown in the 5$^{th}$ row.

Alternatively, if centromeric nucleosomes do not obey the same thermodynamic principles, then they should exhibit distinct distribution patterns. As shown in FIG. 30A, Cse4 did cause ~7% of the total nucleosomes to redistribution away from the left 10-kb of the λ-DNA (FIG. 30A), reflecting a subtle perturbation of the intrinsic landscape. However, the overall distribution of Cse4-nucleosomes (N=2,033) was still correlated with that of the canonical nucleosomes (r=0.58, p<0.0001), was correlated with the FKFM prediction (r=0.59, p<0.0001), and was anticorrelated with the Segal prediction (r=−0.55, p<0.0001). These findings demonstrate that Cse4 alone does not drastically alter the intrinsic landscape, which is reasonable from a physical perspective given that ~1.7 turns of DNA still wrap around octamers harboring the centromeric H3-variant (FIG. 37C). In contrast, nucleosomes containing both Cse4 and Scm3 displayed an altered landscape, which was not significantly correlated with either theoretical model (FIG. 30B), or with the canonical/H2AZ distribution (r=0.30, p=0.016; FIG. 30B). Nor was the Cse4/Scm3 distribution significantly correlated with the Cse4-octamer distribution (r=0.31, p=0.013) or the poly(dA-dT) tracts (r=0.11, p=0.387). All other nucleosomes displayed reduced occupancy within the poly(dA-dT)-rich center of λ-DNA (FIG. 29A and FIG. 30A), but this aversion was relieved by Scm3 (FIG. 30B), suggesting that Scm3 alters the mechanism of DNA binding. This conclusion is supported by the finding that nucleosomes bearing Scm3 display an altered MNase footprint (FIG. 37). Without being bound by theory, these findings support the idea that poly(dA-dT)-rich CEN sequences in S. cerevisiae have evolved in part to exclude normal octameric nucleosomes, while Scm3 abrogates this inhibition, thus ensuring a unique centromeric landmark for kinetocore assembly.

Figure 31:
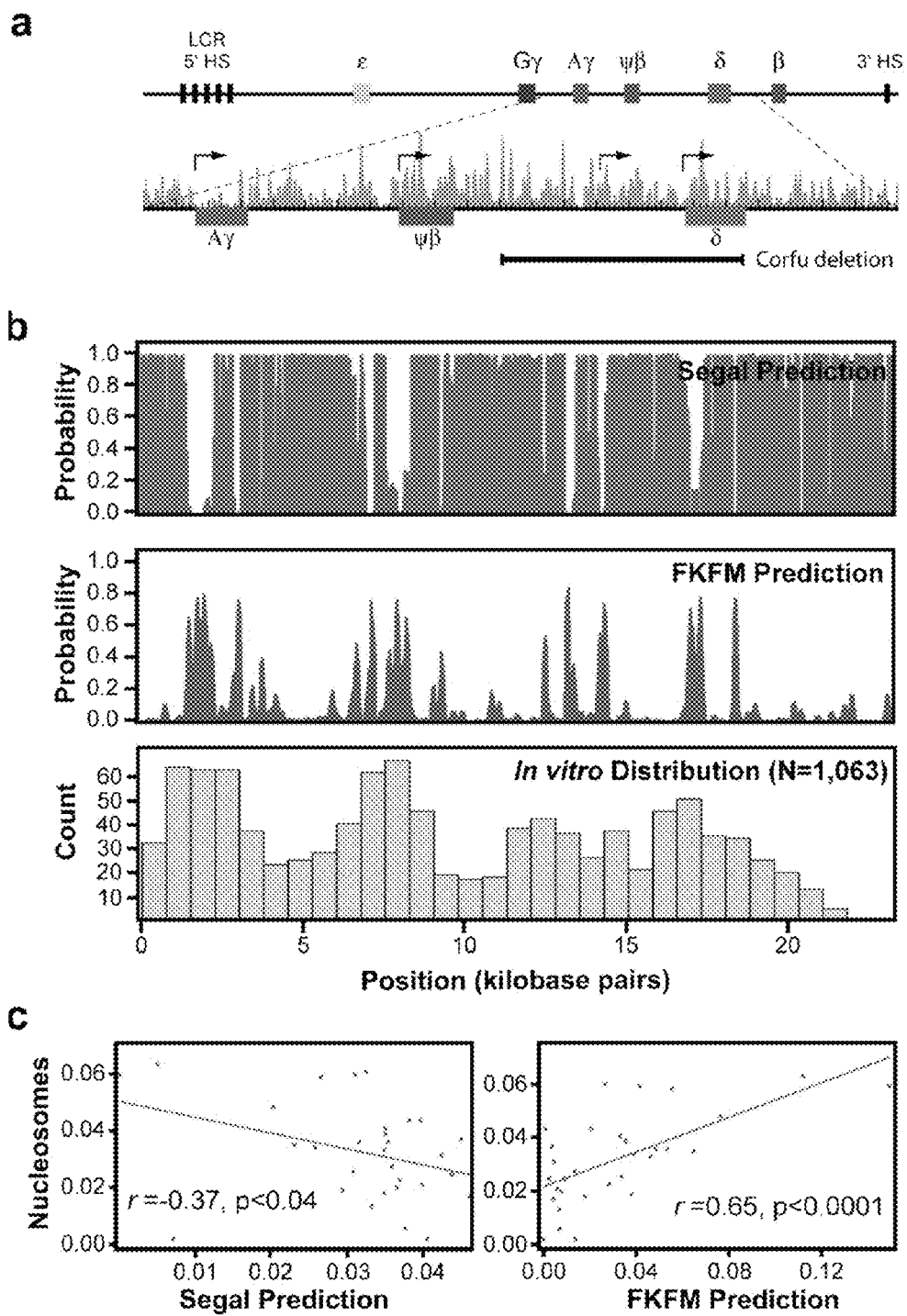
FIG. 31 shows examples where the predicted locations are binned to the same resolution as the experimental data.

All of the work described above utilized phage λ DNA as a simple model substrate. To determine the intrinsic landscape of a more complex eukaryotic substrate we tested a 23-kb fragment from the human β-globin locus (FIG. 31A). Comparison of the two theoretical distributions for this substrate revealed they were again anticorrelated (r=−0.74, p<0.0001; FIG. 31A; FIG. 36). While β-globin DNA lacks the fortuitous asymmetry of λ-phage, the FKFM model still predicts four prominent clusters of positioned nucleosomes that should be discernable in the course-grained landscape obtained from the in vitro data (FIG. 31A, FIG. 35B). As shown in FIG. 31C, the distribution of nucleosomes (N=1,063) bound to the β-globin substrate was weakly anticorrelated with the Segal prediction (r=−0.37, p=0.04), but was correlated with the FKFM prediction (r=0.65, p<0.0001). The agreement between our data and the theoretical prediction was good along the left half of the molecule, suggesting nucleosomes obey similar thermodynamic rules, as defined by the FKFM model, regardless of the origin of the DNA. The intrinsic profile along the right half of the β-globin DNA was somewhat broader (FIG. 35), which implies the existence of additional features in human DNA unaccounted for by current theory. Notably, every peak within the intrinsic landscape coincided with regulatory sequences, including the promoter-proximal regions of the Aγ- and δ-globin genes, and the non-coding ψβ-globin gene. An additional peak in the intrinsic landscape encompassed an intergenic developmental stage-specific promoter ~2.6-kb upstream from the δ-globin gene within a region containing binding sites for the repressor BCL11A, which is necessary for silencing the fetal γ-globin genes during globin gene switching and is deleted in patients with Corfu δβ-thalassemia (FIG. 31A-B)[D24-26].

In contrast, valleys within the intrinsic landscape corresponded to non-transcribed and non-regulatory DNA. This data reveals that cis-regulatory regions within the human β-globin locus are poised with thermodynamically favored nucleosome-binding sites. Without being bound by theory, this evolutionarily-driven architecture has arisen because precise nucleosome positioning within regulatory sequences can be much more critical compared to other areas of the genome[D13,D27,D28]. It remains to be determined whether this organizational relationship is a general trend defining the intrinsic landscape of eukaryotic DNA. Interestingly, the locations of nucleosomes across the β-globin locus have been mapped in CD4+ T cells[D29], but there was no obvious correlation between these positions and the theoretical FKFM prediction (FIG. 31A-B). The in vivo nucleosome distribution also did not fully coincide with the course-grain features of the experimentally observed intrinsic landscape, although the promoter proximal regions of the ψβ- and δ-globin genes were occupied by positioned nucleosomes based on the intrinsic landscape (FIG. 31A-B). However, the in vivo data were paradoxically dissimilar with the experimentally defined intrinsic landscape in the region encompassing the Aγ-globin gene, illustrating that thermodynamically favored sequences alone can not predict nucleosome occupancy within the human genome. Therefore extrinsic factors must play a more prevalent role for establishing in vivo nucleosome distribution patterns in the human genome.

Methods

Histones were expressed in E. coli, purified from inclusion bodies and reconstituted as described (FIG. 33)[D30]. H2AZ was cloned into pET-100/D-TOPO and purified using the same procedure (FIG. 37)[D30]. Cse4 was purified and reconstituted as described (FIG. 37)[D21]. Scm3 remained soluble after cell lysis and was ammonium sulfate precipitated (45% saturation), resuspended in unfolding buffer (7 M guanidinium-HCl, 1 M NaCl, 50 mM Tris-HCl [pH 7.8], 1 mM EDTA, 1 mM DTT) and dialyzed against urea buffer (7 M urea, 1 M NaCl, 10 mM Tris-HCl [pH 7.8], 1 mM EDTA, 5 mM β-mercaptoethanol). Scm3 was purified on Ni-NTA agarose in urea buffer, eluted with 200 mM imidazole, and dialysed against 10 mM Tris-HCl [pH 7.8] plus 5 mM β-mercaptoethanol, followed by 10 mM Tris-HCl [pH 7.8], then lyophilized and stored at −20° C. Nucleosomes were deposited onto DNA by salt dialysis (FIG. 33, FIG. 37), and the DNA was assembled into curtains as described$^{D11}$. Nucleosomes were labeled with 2 nM QDs (Invitrogen, 705 nm emission) conjugated to anti-FLAG antibodies (Sigma). Illumination was by a 488-nm laser (Coherent, Sapphire-CDHR), images were collected using a water immersion objective (Nikon, 1.2 NA Plan Apo, 60×). YOYO1 and QD emissions were separated using a dichroic mirror (630 nm DCXR, Chroma Technologies) and recorded with an EMCCD (Photometrics, Cascade 512B). Images for position analysis were acquired at a flow rate of 0.4 ml/min in 40 mM Tris-HCl [pH 7.8], 1 mM DTT, and 0.2 mg/ml BSA. Flow was transiently paused to exclude non-specifically bound QDs from analysis. Only full-length DNA molecules well resolved from adjacent neighboring molecules were used for distribution measurements. Nucleosome position measurements and statistical analysis were performed using Igor Pro. All correlation trends were cross-validated on a random subset comprised of half the experimental data.

Nanofabricated DNA Curtains.

Electron-beam lithography was used to nanofabricate chromium diffusion barriers on the fused silica surface of a microfluidic sample chamber. λ-DNA molecules stained with YOYO1 (green) were then anchored via a biotin-neutravidin linkage to a fluid lipid bilayer deposited on the surface of the slide. Application of buffer flow aligns the DNA molecules along the leading edges of the nanofabricated barriers and extends the DNA parallel to the sample chamber surface, confining the molecules within the excitation volume defined by the penetration depth of the evanescent field. When buffer flow is transiently paused the DNA molecules collapse due to entropic forces and move away from the surface of the sample chamber demonstrating that the molecules do not interact nonspecifically with the lipid bilayer.

Visualizing DNA Curtains and Fluorescent Nucleosomes.

A YOYO1-stained DNA curtain (green) was assembled as described, with the exception that the DNA was pre-bound by nucleosomes deposited through salt dialysis. The nucleosomes were labeled in situ using fluorescent quantum dots (magenta). When buffer flow is transiently paused, the nucleosome-bound DNA molecules collapse due to entropic forces and move away from the surface of the sample chamber demonstrating that the molecules do not interact nonspecifically with the lipid bilayer and verifying that the nucleosomes are bound to DNA.

REFERENCES

[D1] E. Segal, Y. Fondufe-Mittendorf, L. Chen et al., A genomic code for nucleosome positioning. Nature. 442, 772-778 (2006).

[D2] Y. Field, N. Kaplan, Y. Fondufe-Mittendorf et al., Distinct modes of regulation by chromatin encoded through nucleosome positioning signals. PLoS Comput Biol. 4, e1000216 (2008).

[D3] O. J. Rando and K. Ahmad, Rules and regulation in the primary structure of chromatin. Curr Opin Cell Biol. 19, 250-256 (2007).

[D4] C. A. Morris and D. Moazed, Centromere assembly and propagation. Cell. 128, 647-650 (2007).

[D5] J. Widom, Structure, dynamics, and function of chromatin in vitro. Annu Rev Biophys Biomol Struct. 27, 285-327 (1998).

[D6] K. Luger, A. W. Mäder, R. K. Richmond et al., Crystal structure of the nucleosome core particle at 2.8 A resolution. Nature. 389, 251-260 (1997).

[D7] S. C. Satchwell, H. R. Drew, and A. A. Travers, Sequence periodicities in chicken nucleosome core DNA. J Mol. Biol. 191, 659-675 (1986).

[D8] K. Struhl, Naturally occurring poly(dA-dT) sequences are upstream promoter elements for constitutive transcription in yeast. Proc Natl Acad Sci USA. 82, 8419-8423 (1985).

[D9] G. C. Yuan, Y. J. Liu, M. F. Dion et al., Genome-scale identification of nucleosome positions in *S. cerevisiae*. Science. 309, 626-630 (2005).

[D10] W. Lee, D. Tillo, N. Bray et al., A high-resolution atlas of nucleosome occupancy in yeast. Nat. Genet. 39, 1235-1244 (2007).

[D11] T. Fazio, M. L. Visnapuu, S. Wind et al., DNA curtains and nanoscale curtain rods: high-throughput tools for single molecule imaging. Langmuir. 24, 10524-10531 (2008).

[D12] E. A. Sekinger, Z. Moqtaderi, and K. Struhl, Intrinsic histone-DNA interactions and low nucleosome density are important for preferential accessibility of promoter regions in yeast. Mol. Cell. 18, 735-748 (2005).

[D13] I. Albert, T. N. Mavrich, L. P. Tomsho et al., Translational and rotational settings of H2A.Z nucleosomes across the *Saccharomyces cerevisiae* genome. Nature. 446, 572-576 (2007).

[D14] M. P. Creyghton, S. Markoulaki, S. S. Levine et al., H2AZ is enriched at polycomb complex target genes in ES cells and is necessary for lineage commitment. Cell. 135, 649-661 (2008).

[D15] M. D. Meneghini, M. Wu, and H. D. Madhani, Conserved histone variant H2A.Z protects euchromatin from the ectopic spread of silent heterochromatin. Cell. 112, 725-736 (2003).

[D16] R. M. Raisner, P. D. Hartley, M. D. Meneghini et al., Histone variant H2A.Z marks the 5' ends of both active and inactive genes in euchromatin. Cell. 123, 233-248 (2005).

[D17] H. Zhang, D. N. Roberts, and B. R. Cairns, Genome-wide dynamics of Htzl, a histone H2A variant that poises repressed/basal promoters for activation through histone loss. Cell. 123, 219-231 (2005).

[D18] D. Zilberman, D. Coleman-Derr, T. Ballinger et al., Histone H2A.Z and DNA methylation are mutually antagonistic chromatin marks. Nature. 456, 125-129 (2008).

[D19] B. E. Black, D. R. Foltz, S. Chakravarthy et al., Structural determinants for generating centromeric chromatin. Nature. 430, 578-582 (2004).

[D20] P. B. Meluh, P. Yang, L. Glowczewski et al., Cse4p is a component of the core centromere of *Saccharomyces cerevisiae*. Cell. 94, 607-613 (1998).

[D21] G. Mizuguchi, H. Xiao, J. Wisniewski et al., Nonhistone Scm3 and histones CenH3-H4 assemble the core of centromere-specific nucleosomes. Cell. 129, 1153-1164 (2007).

[D22] G. Wieland, S. Orthaus, S. Ohndorf et al., Functional complementation of human centromere protein A (CENP-A) by Cse4p from *Saccharomyces cerevisiae*. Mol Cell Biol. 24, 6620-6630 (2004).

[D23] G. Mizuguchi, X. Shen, J. Landry et al., ATP-driven exchange of histone H2AZ variant catalyzed by SWR1 chromatin remodeling complex. Science. 303, 343-348 (2004).

[D24] J. Gribnau, K. Diderich, S. Pruzina et al., Intergenic transcription and developmental remodeling of chromatin subdomains in the human beta-globin locus. Mol. Cell. 5, 377-386 (2000).

[D25] A. Bank, Regulation of human fetal hemoglobin: new players, new complexities. Blood. 107, 435-443 (2006).

[D26] V. G. Sankaran, T. F. Menne, J. Xu et al., Human fetal hemoglobin expression is regulated by the developmental stage-specific repressor BCL11A. Science. 322, 1839-1842 (2008).

[D27] M. G. Guenther, S. S. Levine, L. A. Boyer et al., A chromatin landmark and transcription initiation at most promoters in human cells. Cell. 130, 77-88 (2007).

[D28] T. N. Mavrich, C. Jiang, I. P. Ioshikhes et al., Nucleosome organization in the *Drosophila* genome. Nature. 453, 358-362 (2008).

[D29] D. E. Schones, K. Cui, S. Cuddapah et al., Dynamic regulation of nucleosome positioning in the human genome. Cell. 132, 887-898 (2008).

[D30] J. Wittmeyer, A. Saha, and B. Cairns, DNA translocation and nucleosome remodeling assays by the RSC chromatin remodeling complex. Methods Enzymol. 377, 322-343 (2004).

Example 11

Nanofabricated Racks of Aligned and Anchored DNA Molecules for Imaging Individual Protein-DNA Interactions Single molecule studies of biological macromolecules can benefit from new approaches that facilitate experimental design and data acquisition. Here we develop new strategies to construct molecular curtains of DNA in which the substrates are aligned with respect to one another and maintained in an extended configuration. Importantly, both ends of the DNA are anchored to the surface of a microfluidic sample chamber that is otherwise coated with an inert lipid bilayer. This is accomplished through the use of nanofabricated racks of metallic barrier patterns with two distinct functional elements. Linear barriers to lipid diffusion are first used to align the DNA. Pentagons coated with antibodies then provide solid anchor points for the free ends of the aligned DNA molecules. These devices enable the alignment and anchoring of hundreds of individual DNA molecules, which can then be visualized using total internal reflection fluorescent microscopy under conditions that do not require continuous application of buffer flow to stretch the DNA. This offers the potential for imaging and data acquisition without perturbing the behavior of the proteins under investigation by eliminating the need for an externally applied hydrodynamic force. We provide a demonstration that these DNA racks can be used in a 1D diffusion assay that monitors the motion of quantum dot tagged proteins along DNA.

Introduction

Dynamic interactions between proteins and DNA underlie many biological processes, and as such are the subject of intense investigation. Many laboratories are now tackling these problems using new experimental methods that enable the visualization of DNA molecules or protein-DNA complexes at the single-molecule level in real time, and the information garnered from these experiments is being used to build detailed mechanistic models of many different types of reactions[E1-4]. Similarly, micro- and nanoscale devices are becoming increasingly powerful tools for the manipulation and analysis of individual DNA molecules[E5-7]. However, one major drawback of many single-molecule techniques is that they are inherently designed to probe individual reactions, and as a consequence it can be challenging to gather statistically relevant data. This difficulty is often compounded by the fact that these experiments are technically demanding. Therefore it is advantageous to establish new approaches that can increase throughput capacity of single-molecule methods, while at the same time making these approaches both easier and more readily applicable to biological reactions involving different types of DNA transactions.

In an effort to help make single-molecule imaging techniques more accessible we have integrated nanoscale engineering, microfluidics, and lipid bilayer-coated surfaces with single molecule optical microscopy to develop high-throughput methods for making molecular curtains comprised of thousands of individual DNA molecules[E8-10]. A key aspect of these experimental platforms is that they utilize inert lipid bilayers to passivate the fused silica surface of a microfluidic sample chamber. Artificial lipid membranes deposited on solid supports have proven useful for many types of biochemical studies[E13-15]. An important aspect of artificial membranes is that the chemical characteristics of the bilayer can be readily controlled through careful selection of the constituent lipids[E11,E13]. In addition, artificial membranes is that they can be partitioned with chemical or mechanical barriers[E12,E16,E17], and the distributions of molecules anchored to lipids can also be manipulated using photochemical modulation, electrical fields, or hydrodynamic force[E18-21]. Taken together, the aforementioned features suggested the potential for controlling the organization of molecules anchored to lipid membranes, and accordingly we have demonstrated that mechanical barriers that disrupt the continuity of lipid bilayers can be used to control the two-dimensional organization of DNA molecules anchored to a surface[E8-10]. This controlled organization is accomplished by first coating a sample chamber surface with a bilayer containing a small fraction of biotinylated head groups, and DNA molecules are anchored by one end to the bilayer via a biotin-neutravidin linkage[E8-10]. The lipid-tethered DNA molecules are assembled into molecular curtains by pushing them to the leading edge of either micro- or nano-scale lipid diffusion barriers through the application of a hydrodynamic force. We have demonstrated that microscale barriers to lipid diffusion made by manually etching a fused silica surface with a diamond-tipped scribe could be used to align hundreds of lipid-tethered DNA molecules, and we refer to these as DNA curtains[E10,E22-25]. More recently we have we have employed electron-beam (ebeam) lithography to fabricate barriers with nanoscale dimensions, which allows for much more precise control over both the location and lateral distribution of the DNA molecules within the curtains[E8,E9]. These nanofabricated DNA curtains permit simultaneous visualization of thousands of individual DNA molecules that are perfectly aligned with respect to one another, and can be used for massively parallel data acquisition from thousands of individual protein-DNA complexes in real time using a robust experimental platform that is amenable to a wide variety of biological applications. We have also shown that these DNA curtains are advantageous for studying protein-DNA interactions at the single molecule level, and we have applied these tools to biological systems such as nucleosomes and chromatin remodeling, homologous DNA recombination, and post-replicative mismatch repair[E22-26].

Our previous DNA curtain designs required continuous application of a hydrodynamic force during data collection because just one end of the DNA is anchored to the lipid bilayer. If buffer flow is terminated the DNA does not remain stretched, and as a consequence it can not be visualized along its full contour length because it drifts outside of the detection volume defined by the penetration depth of the evanescent field. The need for buffer flow is not problematic for many types of measurements, however, it can potentially impact the behavior of bound proteins or protein complexes, and the magnitude of this impact can scale in proportion to the hydrodynamic radius of the molecules under observation[E27,E28]. The influence of buffer flow is especially apparent during measurements involving proteins that slide on DNA by one-dimensional diffusion, because an applied flow force can strongly bias the direction that the sliding proteins travel along the DNA[E27].

Here we sought to develop new procedures for making curtains of aligned DNA molecules that were held in an extended configuration anchored by both ends to the surface of a microfluidic sample chamber and suspended above an inert bilayer. These double-tethered curtains of DNA are specifically intended for use in experiments designed to look at passive protein motion along DNA molecules. To achieve this design this we have developed new patterns of metallic barriers with made using either electron-beam or nanoimprint lithography. These metallic patterns incorporate both linear barriers to lipid diffusion and arrayed pentagons, and together these distinct functional elements serve to align and tether long molecules of DNA. The DNA molecules are first anchored by one end to a fluid lipid bilayer via a biotin-neutravidin interaction, and initially aligned with one another by using hydrodynamic force to push them into the linear barriers. The arrayed pentagons serve as solid anchor points positioned at a defined distance downstream from the linear barriers and are coated with antibodies directed against either digoxigenin or bromodeoxyuridine, which are covalently attached to the free ends of the DNA molecules. Importantly, once linked to the surface, the DNA molecules are maintained in an extended state suspended above an inert lipid bilayer and remain confined within the detection volume defined by the penetration depth of the evanescent field, allowing for continuous observation along their full contour length, even in the absence of an applied hydrodynamic force.

Materials and Methods

Electron Beam Lithography.

Fused silica slides were cleaned in NanoStrip solution (CyanTek Corp, Fremont, Calif.) for 20 minutes, then rinsed with acetone and isopropanol and dried with $N_2$. The slides were spin-coated with a bilayer of polymethylmethacrylate (PMMA), molecular weight 25K, 3% in anisole and 495K, 1.5% in anisole (MicroChem, Newton, Mass.), followed by a layer of Aquasave conducting polymer (Mitsubishi Rayon). Each layer was spun at 4,000 rpm for 45 seconds using a ramp rate of 300 rpm/s. Polygon patterns and linear barriers were written by Ebeam lithography using an FEI Sirion scanning electron microscope equipped with a pattern generator and lithography control system (J. C. Nabity, Inc., Bozeman, Mont.). After patterning, Aquasave was rinsed off with deionized water. Resist was developed using a 3:1 solution of isopropanol to methyl isobutyl ketone (MIBK) for 1 minute with ultrasonic agitation at 5° C. The substrate was then rinsed in isopropanol and dried with $N_2$. A 15-20 nm layer of gold atop a 3-5 nm adhesion layer of either chromium or titanium was deposited using a Semicore electron beam evaporator. Liftoff was effected at 80° C. in a 9:1 ratio of methylene chloride to acetone. Alternatively, barriers were made out of just a 15-20 nm layer of chromium, as previously described[E8,E9]. Following liftoff, samples were rinsed with acetone to remove stray chromium flakes and dried with $N_2$. Barriers were imaged using a Hitachi 4700 scanning electron microscope and a PSIA XE-100 Scanning Probe Microscope in noncontact mode. Optical images of the barriers were taken with a Nikon Eclipse ME600.

Nanoimprint Lithography.

Nanoimprint masters were fabricated using electron beam lithography, liftoff, and inductively-coupled plasma etching. Briefly, a bilayer of poly-methyl methacrylate (PMMA, 25K and 495K) was spun onto a silicon wafer with a thin coating of silicon dioxide. Patterns were written by an FEI Sirion SEM outfitted with a Nabity Nanopattern Generation System, then developed in a mixture of isopropanol: methyl isobutyl ketone (3:1) at 5° C. in a bath sonicator. Samples were rinsed with isopropanol and dried with $N_2$. A Semicore Ebeam evaporator was used to evaporate 20 nm Cr onto the masters. Liftoff was performed in acetone at 65° C. The patterned masters were plasma-etched to a depth of 100 nm in a mixture of $C_4F_8$:$O_2$ (9:1) for 90 seconds at a power of 300 W using an Oxford ICP etch tool. Nanoimprint masters were coated with a fluorinated self-assembled monolayer (Nanonex, Princeton, N.J.) to prevent adhesion between the master and resist.

To make nanoimprinted barriers, PMMA 35K (Microresist Technologies, Germany) was spin-coated on a fused silica microscope slide and baked on a hotplate for 5 min. at 180° C. Nanoimprint was performed in two stages: a 2-min. pre-imprint phase with a pressure of 120-psi and pre-temp. of 120° C., followed by a 5-min. imprint phase with a pressure of 480-psi and temp. of 190° C. This heated PMMA well above its glass transition temp. and allowed it to conform to the mold. After imprinting, a de-scum process was done to remove ~10 nm of residual PMMA. De-scum was done in an inductively coupled plasma under $CHF_3$:$O_2$ (1:1) and a power of 200 W for 40 seconds total (two iterations of 20 seconds). After descum, 15-20 nm of Cr was evaporated on the samples and liftoff was performed in acetone at 65° C. for several hours, followed by bath sonication to remove stray metal flakes. Nanopatterned slides were then rinsed in acetone and dried with $N_2$.

Lipid Bilayers and DNA Curtains.

The flowcells were assembled from fused silica slides (G. Finkenbeiner, Inc.) with chromium nanoscale diffusion barriers. Inlet and outlet ports were made by boring through the slide with a high-speed precision drill press equipped with a diamond-tipped bit (1.4 mm O.D.; Kassoy). The slides were cleaned by successive immersion in 2% (v/v) Hellmanex, 1 M NaOH, and 100% MeOH. The slides were rinsed with filtered sterile water between each wash and stored in 100% MeOH until use. Prior to assembly, the slides were dried under a stream of nitrogen and baked in a vacuum oven for at least 1 hour. A sample chamber was prepared from a borosilicate glass coverslip (Fisher Scientific) and double-sided tape (~25 μm thick, 3M). Inlet and outlet ports (Upchurch Scientific) were attached with hot-melt adhesive (SureBonder glue sticks, FPC Corporation). The total volume of the sample chambers was ~4 μl. A syringe pump (Kd Scientific) and actuated injection valves (Upchurch Scientific) were used to control sample delivery, buffer selection and flow rate. The flowcell and prism were mounted in a custom-built heater with computer-controlled feedback regulation to control the temperature of the sample from between 25-37° C. (±0.1° C.), as necessary. After each use, the slides were soaked in MeOH to remove the ports and tape, rinsed with water, washed briefly (15-20 minutes) with Nanostrip, and rinsed with water. This procedure was sufficient to clean the slide surfaces for reuse, and each slide could be used multiple times without degrading the quality of the optical surface or the metallic patterns.

DNA curtains were constructed as described[E8,E9], with the exception of additional steps necessary for anchoring the second end of the DNA. All lipids were purchased from Avanti Polar Lipids and liposomes were prepared as previously described. In brief, a mixture of DOPC (1,2-dioleoyl-sn-glycero-phosphocholine), 0.5% biotinylated-DPPE (1,2-dipalmitoyl-sn-glycero-3-phosphoethanolamine-N-(cap biotinyl)), and 8-10% mPEG 550-PE (1,2-dioleoyl-sn-glycero-3-phosphoethanolamine-N-[methoxy(polyethylene glycol)-550]). The mPEG is does not affect bilayer formation or assembly of the DNA curtains, but rather serves to further passivated the surface against nonspecific adsorption of quantum dots (which we use in our studies of protein-DNA interactions). Liposomes were applied to the sample chamber in three injections of 200 µl followed by 5 minute incubations. Excess liposomes were flushed away with 1 ml of buffer A, which contained 10 mM Tris-HCl (pH 7.8) plus 100 mM NaCl, and the bilayer was incubated for an addition 30 minutes. Buffer A plus 25 µg/ml anti-DIG Fab (Roche), anti-fluorescein (Sigma), or anti-BrdU IgG (Sigma) was then injected into the sample chamber and incubated for 30 minutes. The sample chamber was then flushed with 1 ml of buffer B, which contained 40 mM Tris-HCl (pH 7.8), 1 mM DTT, 1 mM $MgCl_2$, and 0.2 mg/ml BSA, and incubated for an additional 5 minutes. 1 ml of buffer A containing Neutravidin (330 nM) was then injected into the sample chamber and incubated for 20 minutes. The flowcell was then rinsed with 3 ml of buffer B to remove any unbound Neutravidin. 1 ml of λ-DNA (20 pM) labeled at one end with biotin and at the other end with either digoxigenin, fluorescein or bromodeoxyuridine (as indicated) and pre-stained with 1-2 nM YOYO1 was injected into the sample chamber in five 200-µl aliquots, with a 2-3 minute incubation period following each injection. The DNA was then aligned at the linear barriers using a flow rate of 0.02 ml/min, and this rate was then increased to 2-3 ml/min to anchor the second end of the DNA molecules.

DNA Substrates.

The DNA substrates were made by ligating oligonucleotides to the 12 nucleotide overhangs at the end of the λ phage genome (48.5 kb). Ligation mixes (1 ml total volume) contained 4 nM λ DNA (Invitrogen), 1 µM biotinylated oligonucleotiode (5'-pAGG TCG CCG CCC [BioTEG]-3' (SEQ ID NO: 1)), 1 µM fluorescein labeled oligonucleotide (or DIG labeled oligonucleotide; 5'-pGGG CGG CGA CCT [fluor]-3' (SEQ ID NO: 6) or 5'-pGGG CGG CGA CCT [DIG]-3' (SEQ ID NO: 3)), and 1× ligase buffer (NEB). The reaction mix was warmed to 65° C. for 10 minutes and then cooled slowly to room temperature. After cooling, ligase was added (T4 DNA ligase (400 U/µl) or Taq ligase (40 U/µl); NEB) and the mixture was incubated overnight at 42° C. Reactions performed with T4 ligase were then heat inactivated at 65° C. for 10 minutes, and the ligated DNA products were purified over a Sephacryl S200HR column (GE Healthcare) run in 10 mM Tris-HCl (pH 7.8), 1 mM EDTA, plus 150 mM NaCl. The purified DNA was stored at −20° C.

For inserting a DIG labeled oligonucleotide complementary to position 26,151-26,166 on λ 500 ul of DNA (200 pM; labeled at the ends with biotin and fluorescein (as described above)) was incubated for 2 hours with the nicking enzymes Nb.BsmI and Nt.BstNBI (50 units each; NEB) at 55° C. in buffer containing 10 mM Tris-HCl (pH 7.8), 10 mM $MgCl_2$, 150 mM NaCl. Subsequently, 1 uM of oligonucleotide (5'-pCAT TCT TGA GTC CAA TTT TT[DIG]-3'(SEQ ID NO: 4)) was added to the solution along with 10 mM EDTA and the mixture was incubated at 55° C. for 20 minutes and then allowed to slowly cool to room temperature over the course of an hour. ATP was added to a final concentration of 1 mM along with 2,000 units of T4 ligase and an additional 10 mM $MgCl_2$. The reaction was then incubated at room temp. for 90 min. Additional EDTA ($C_f$=20 mM) was added to the solution and the nicking enzymes and ligase were heat denatured at 80° C. for 20 min.

For inserting an oligonucleotide at position 33,779-33,791 on λ 500 µl DNA (200 pM; labeled at the ends with biotin and fuorescein (as described above)) was incubated for 2 hours with the nicking enzyme Nt.BstNBI (50 units; NEB) at 55° C. in buffer containing 10 mM Tris-HCl (pH 7.8), 10 mM $MgCl_2$, 150 mM NaCl. The enzyme was heat denatured by incubation at 80° C. for 20 minutes. 1 µM of oligonucleotide (5'-pTTC AGA GTC TGA CTT TT[DIG]-3' (SEQ ID NO: 5)) was added to the solution and the mixture was incubated at 55° C. for 20 minutes then cooled slowly to room temperature over the course of 1 hr. ATP was then added to a final concentration of 1 mM along with 2,000 units of T4 ligase, and the reaction was incubated at room temperature for 90 min. The ligase was then heat denatured by incubation at 65° C. for 20 minutes.

TIRFM and 1D Diffusion Assays.

The basic design of the microscope used in this study has been previously described[E10]. In brief, the system is built around a Nikon TE2000U inverted microscope with a custom-made illumination system. For this study, a 488 nm, 200 mW diode-pumped solid-state laser (Coherent, Sapphire-CDHR) was used as the excitation source. The laser was attenuated as necessary with a neutral density filter and centered over the DNA curtain by means of a remotely operated mirror (New Focus). The beam intensity at the face of the prism was ~10-15 mW. Images were detected with a back-illuminated EMCCD detector (Photometrics, Cascade 512B). TIRFM images were collected using a 60× water immersion objective lens (Nikon, 1.2 NA Plan Apo), unless otherwise indicated.

Results

Design Elements of the DNA Rack.

Here we expand on our previous work and demonstrate the development of new barrier patterns, which we call DNA "racks", that can be used to make DNA curtains in which both ends of the molecules are anchored to the flowcell surface. An overview of the general design is presented in FIG. 18 and utilizes a combination of two distinct pattern elements, as described below. In principle, one end of the DNA is first anchored via a biotin-neutravidin interaction to a supported lipid bilayer coating the surface of the sample chamber (FIG. 18B-C). In the absence of a hydrodynamic force the molecules are randomly distributed on the surface, but lie primarily outside of the detection volume defined by the penetration depth of the evanescent field (~150-200 nm). Application of flow pushes the DNA through the sample chamber with one end remaining anchored to the bilayer. The first pattern elements are linear barriers to lipid diffusion, which are oriented perpendicular to the direction of flow at strategic locations in the path of the DNA (FIG. 18B-C); these linear barriers are designed to halt the movement of the lipid-tethered DNA molecules causing them to accumulate at leading edge of the barriers where they then extend parallel to the surface. The second elements of the pattern are a series of arrayed pentagons positioned behind the linear barriers and separated from one another by small channels. The non-linear, geometric shape of the pentagons is intended to act as a funnel and direct any lipid-tethered DNA molecules through the channels so that they do not accumulate at the leading edge of the pentagons, but rather are pushed along the surface until they encounter the next successive linear barrier in the pattern. The distance between the linear barriers and the pentagons is optimized for the length of the DNA to be used for the experiments. The pentagons themselves present a large surface that can be coated with antibodies directed against digoxigenin (DIG), which is covalently linked to the ends of the DNA opposite the ends bearing the biotin tag. When the DIG-coupled DNA end encounters the antibody-coated pentagons they should become immobilized, and the DNA should remain stretched parallel to the surface even when no buffer is being pushed through the sample chamber.

Figure 39:
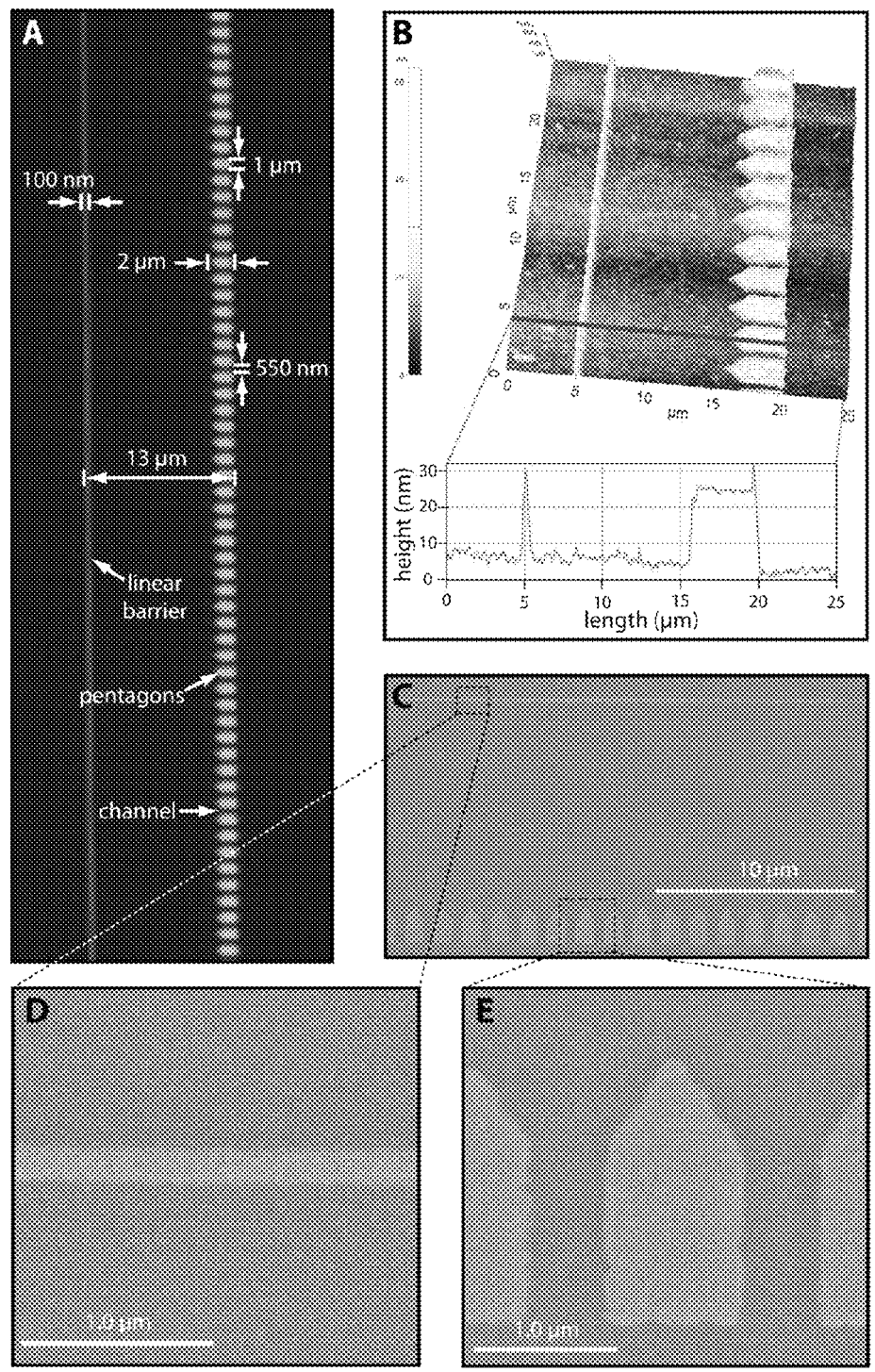
FIG. 39 represents the nanofabrication and characterization of the DNA rack elements.

The barrier patterns necessary to achieve the desired design features were made by either Ebeam lithography as previously described[E8,E9], or by nanoimprint lithography[E29,E30]. FIG. 39 shows the characterization of a DNA rack made by Ebeam lithography and highlights specific features of the pattern geometry deemed critical for its function. FIG. 39A shows an optical image of the overall pattern design, including the dimensions of critical pattern parameters. FIG. 39B shows measurements of these parameters using atomic force microscopy (AFM). FIG. 39C shows characterization of the patterns with scanning electron microscopy (SEM). As demonstrated from these images, the height of the patterns elements was on the order of 20 nm, the width of the channels was 500 nm, and the optimal distance between the leading edge of the linear barriers and the back of the pentagon array was ~13 µm (see below). This distance was specifically selected for use with λ-DNA, which is 48,502 base pairs with a fully extended contour length of approximately 16.5 µm, thus 11-13 µm would correspond to a mean extended length of ~65-79% that of the full contour length, respectively.

Assembly and Characterization of Double-Tethered DNA Curtains.

The overall design of the DNA rack relies upon the selective, but nonspecific adsorption of antibodies to the relatively large exposed surface of the metallic pentagons, and the antibodies should not interact with the inert lipid bilayer. All nanofabricated elements of the pattern are made of the same material, therefore the antibodies could potentially bind both the linear barriers as well as the pentagons. However, each pentagon has a surface area of 1.55 µm$^2$ and for each 260 µm long linear barrier there are 167 pentagons. This corresponds to a total surface area of 372 µm$^2$ for the pentagons compared to just 36 µm$^2$ for the entire linear barrier. The smaller total surface area of the linear barriers should ensure adsorption of more antibody to the much larger area encompassed by the pentagons.

Figure 40:
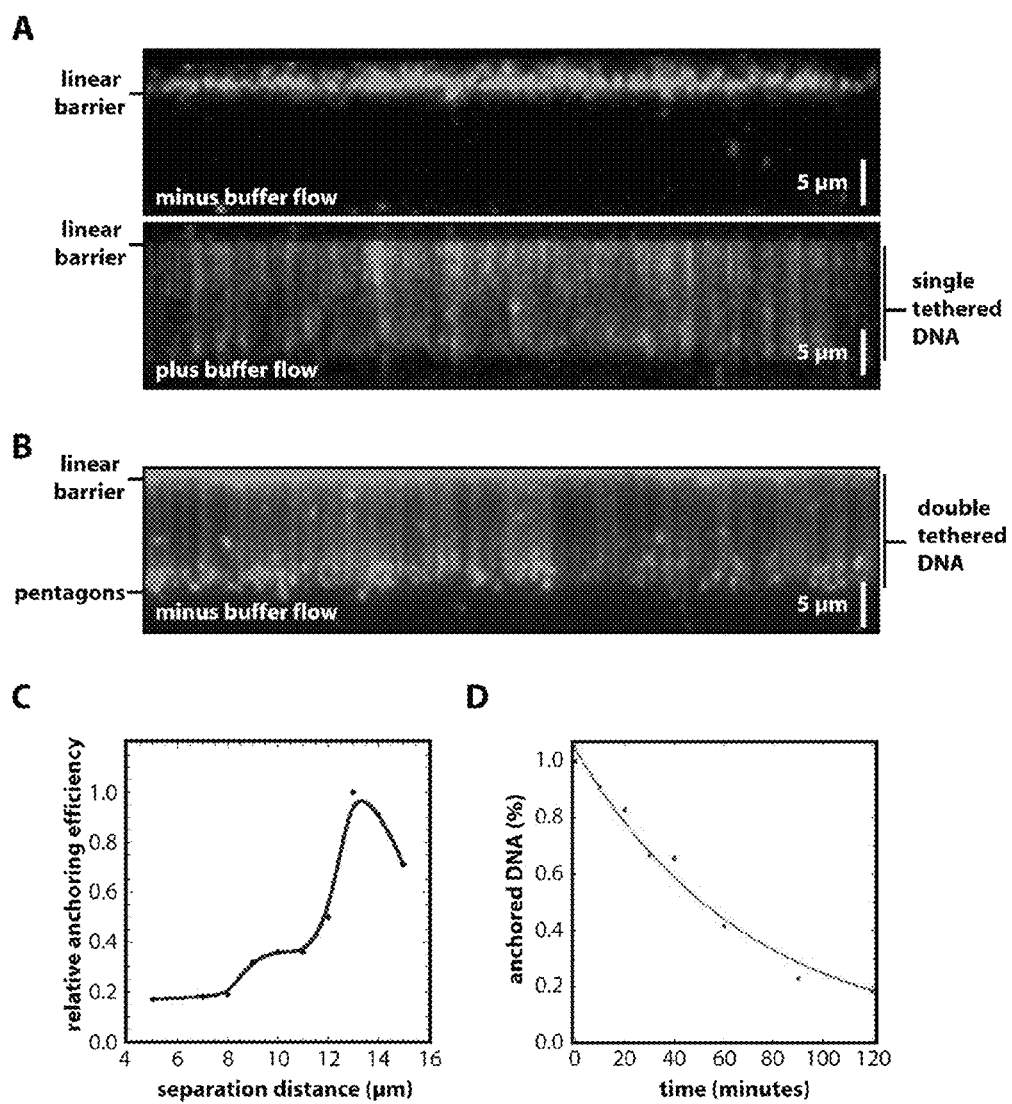
FIG. 40 represents curtains of double-tethered DNA. Curtains of double-tethered DNA.

To assemble the DNA curtains, the surface of the flowcell was first coated with a lipid bilayer, as previously described[E8,E9], with the exception that BSA was omitted from all buffers used prior to deposition of the antibody. Once the bilayer was assembled on the surface, anti-DIG Fab fragments or anti-fluorescein IgG was injected into the sample chamber where they were allowed to adhere nonspecifically to the exposed metal barriers. Following a brief incubation, the free antibody was rinsed from the flowcell and replaced with buffer containing 0.2 mg/ml BSA, which served as a nonspecific blocking agent to passivate any remaining exposed surfaces. DNA stained with the fluorescent intercalating dye YOYO1 was then injected into the sample chamber, incubated briefly without buffer flow, and then buffer flow was applied to push the anchored molecules into the linear barriers. Buffer flow was then terminated and the anchored DNA molecules imaged by TIRFM. As shown in FIG. 40, this procedure yielded curtains of DNA molecules that remained fully extended and visible even though no buffer was flowing through the sample chamber. Any DNA molecules that failed to become anchored by the DIG-labeled end remained near the linear barriers, but only the ends of the molecules could be observed rather than their full contour lengths. These single-tethered DNA molecules gradually diffused away from the barrier edges and could also be pushed away from the barrier edge by reversing the direction of buffer flow (FIG. 40), but the double-tethered DNA molecules remained anchored to their original locations, providing additional conformation that the molecules making up the curtain are anchored in the desired configuration.

The number of DNA molecules at each of the different barrier locations was proportional to the distance between the adjacent linear barriers. The number of double tethered DNA molecules decreased slowly over time, with a half-life of >1 hour for the DIG-labeled molecules. Finally, control experiments verified that the presence of both the DIG labeled and the Fab fragments were necessary for efficiently anchoring the two ends of the DNA. Approximately 70% of the anchored DNA could be attributed to specific antibody:hapten interactions, with the remaining 30% due to nonspecific anchoring of the DNA ends to the antibody-coated pentagons. Similar double-tethered DNA curtains could be made using substrates that were end-labeled with either a single bromodeoxyuridine (BrdU) or fluorescein moiety, and pentagons coated with anti-BrdU or anti-fluorescein antibodies (see below), respectively. The half-life of the fluorescein-anchored DNA was comparable to that of the DIG-anchored DNA. However, the BrdU-anchored DNA molecules had a greater tendency to dissociate from the pentagons, displaying a half-life on the order of just a few minutes.

Defined Orientation of the DNA.

Figure 41C:
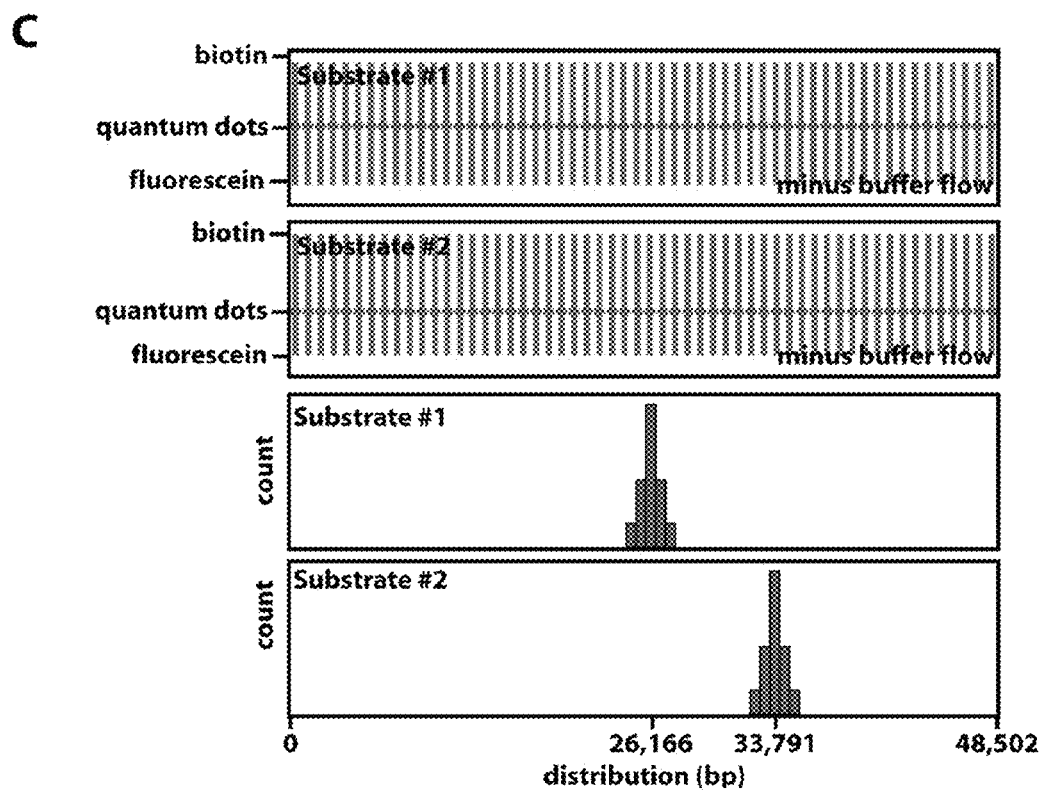
FIG. 41C shows the same type of analysis except that the DNA molecules are anchored to the surface via both ends: the biotin tagged end is coupled to the bilayer and aligned along the barriers, and the fluorescein tagged end is anchored to the antibody-coated polygons. As with the single tethered DNA, the locations of the quantum dots are mapped in the lower panels.

The differential chemistries used to anchor the two ends of the DNA were predicted to define the orientation of the molecules within the curtains. Specifically, the biotinylated end should be anchored at the edge of the linear barrier and the other end should be at the pentagons, and based on this design all of the molecules should be in the exact same orientation. If the DNA molecules were aligned as expected, then a fluorophore located at a single specific site within the DNA and offset from its center should appear as a fluorescent "line" spanning the DNA curtain. The line should be oriented perpendicular to the long axis of the extended DNA molecules and should coincide precisely with the know location of the fluorescent tag. In contrast, if the DNA molecules were randomly oriented, then the fluorescent tags should appear as two lines demarking each of the two possible orientations of the DNA. To confirm that the DNA was oriented correctly, the molecules were labeled at the free ends with fluorescein, and labeled at a specific internal position with DIG. The internal labels were made using an oligonucleotide replacement strategy wherein the DNA was nicked at specific sites with a nicking endonuclease and short ssDNA fragments flanked by the resulting nicks were replaced with a DIG-tagged oligonucleotide (see Materials and Methods). Experiments with DNA curtains anchored by a single end confirmed that the fluorescent tags were present at a single location within the DNA molecules as dictated by the sequences of the oligonucleotides (FIG. 41A). The double-tethered curtains were then assembled using pentagons coated with anti-BrdU antibodies, and after assembly the DIG tags with labeled with anti-DIG coated Qdots. As shown in FIG. 41B, the anti-DIG Qdots were all aligned with one another, confirming the orientation of the DNA molecules. These results demonstrate that the DNA molecules anchored to the surface via the rack elements were all in the same orientation, as defined by the distinct function groups at the opposing ends of the DNA.

Imaging Proteins Sliding on the DNA.

Many biological reactions are dependent upon protein motion along DNA, and these processes often involve passive diffusion[E27]. The primary motivation for development of these double-tethered DNA curtains was for use in experiments designed to visualize motion of proteins along DNA. We have previously demonstrated that the protein complex Msh2-Msh6 can diffuse in one-dimension along duplex DNA[E22]. Msh2-Msh6 is an essential component of the post-replicative mismatch repair machinery and is responsible for locating and initiating repair of biosynthetic DNA replication errors. Our initial studies with Msh2-Msh6 relied upon DNA molecules that were tethered by either end to neutravidin nonspecifically absorbed to a fused silica surface that was otherwise coated with a lipid bilayer. With this approach we would obtain only 10-30 DNA molecules per flowcell that were suitable for making diffusion measurements. These double tethered DNA molecules were randomly distributed and had to be manually located before use by visually scanning the entire surface, making these 1D-diffusion measurements technically demanding and time consuming. As shown above, using the engineered surfaces we can now visualize thousands of molecules per flowcell. Here we demonstrate that these anchored curtains of DNA are suitable for visualizing protein-DNA interactions.

Figure 42:
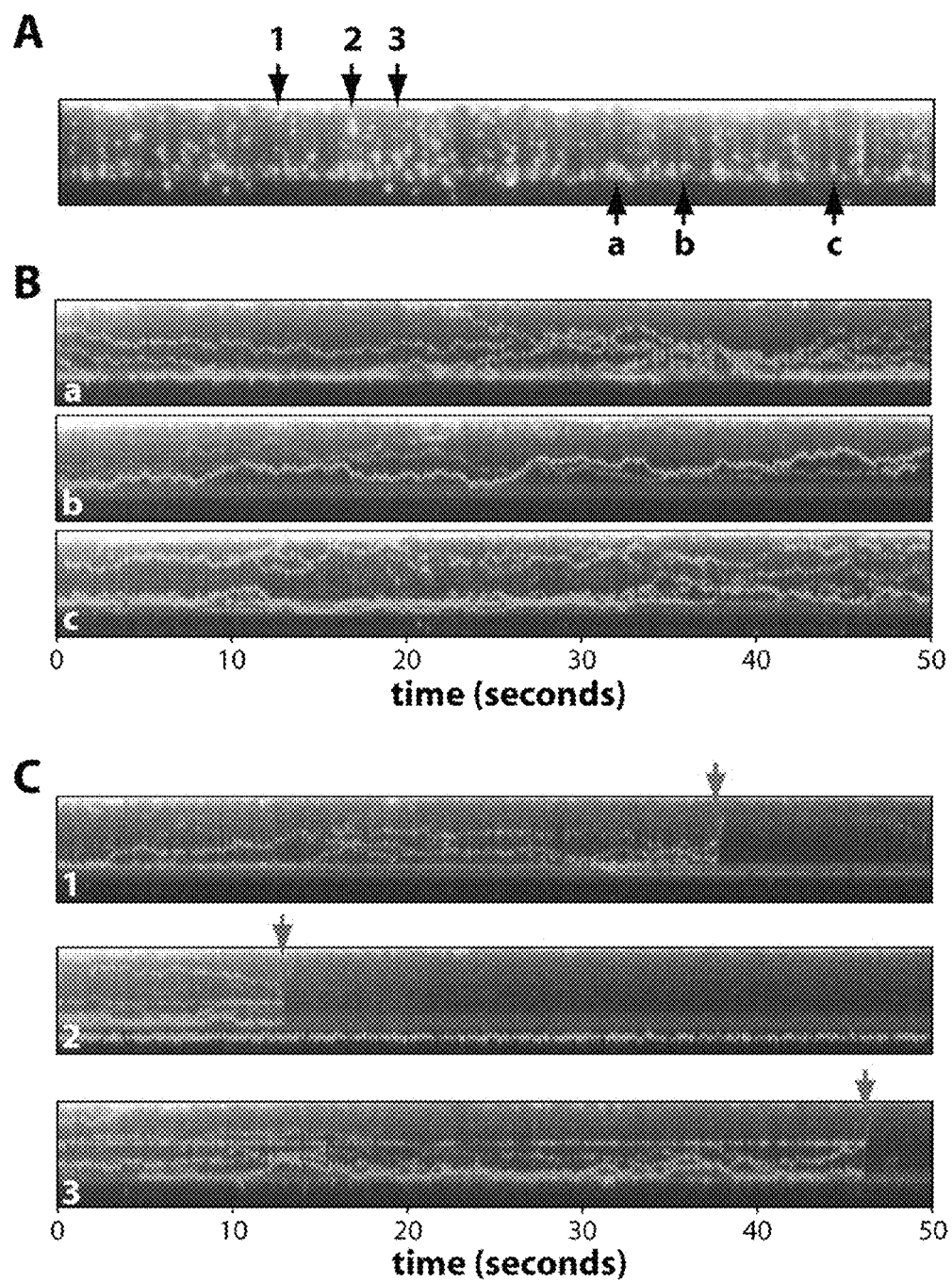
FIG. 42 demonstrates using DNA racks to visualize 1D protein diffusion.

To determine whether the DNA racks could be used to study 1D-diffusion of proteins along DNA we used the mismatch repair protein Mlh1, and it was labeled with a single quantum dot via a FLAG epitope tag; complete analysis of quantum dot-tagged Mlh1 will be presented elsewhere. The labeled proteins were injected into a flowcell containing a curtain of double tethered DNA molecules and videos were collected over a 60-second period. As shown in FIG. 42A, we could readily detect binding of Mlh1 to the DNA molecules that were aligned and anchored on the surface. There were 79 DNA molecules and 235 DNA-bound proteins observed in this single field-of-view, illustrating the dramatic improvement of this approach compared to our previous technique for making double-tethered DNA molecules[E22,E23]. The proteins bound to the DNA rapidly diffused along the DNA molecules, and this motion was revealed in kymograms made from representative examples of molecules within the DNA curtains (FIG. 42B).

If protein bound molecules were nonspecifically linked to the sample chamber surface along its contour length, rather than suspended above the inert bilayer, then they should remain in view even if the DNA breaks or otherwise detaches from one of its anchor points. In contrast, if the proteins only interacted with the DNA, then detachment of the DNA should cause the molecules to retract away from the surface and disappear from view. As shown in FIG. 42C, when the DNA molecules randomly detached from the surface the proteins immediately disappeared from view as they drifted outside the detection volume define by the penetration depth of the evanescent field. This data demonstrates that the fluorescently tagged proteins were bound to the DNA, the DNA molecules only interacted with the sample chamber surface through their anchored ends, and neither the quantum dot-tagged protein nor the DNA interacted nonspecifically with the lipid bilayer.

Discussion

Single molecule studies offer many unique opportunities to probe biological reactions in ways not possible through conventional biochemical or biophysical approaches. We are developing new techniques for controlling the spatial organization of surface anchored DNA molecules within the confines of a microfluidic sample chamber. Procedures for anchoring numerous, long DNA molecules to surfaces are present in the literature[E31-36]. However, none of these methods offers the ability to patterns hundreds of DNA molecules all aligned in the same orientation using an experimental platform that is both compatible with protein biochemistry and single-molecule fluorescence imaging. Our unique approaches are based upon surface engineering techniques that enable us to control the distribution of DNA substrates with micro- and nanoscale precision. Here we build upon our previous work by using direct-write Ebeam or nanoimprint lithography to fabricate arrays of diffusion barriers followed by pentagonal anchor points, which together utilize different functional features to anchor curtains of DNA by both ends on the surface of a microfluidic sample chamber. We refer to these patterned surfaces as DNA "racks" because the DNA is stretched out and anchored to the flowcell surface where they can be viewed by TIRFM. An important aspect of these devices is that the fused silica surface is coated with a supported lipid bilayer, and the DNA molecules are suspended above this bilayer, ensuring that they are maintained within an inert microenvironment compatible with a range of biological molecules. We have demonstrated that these tools can be used along with wide-field TIRF microscopy to visualize hundreds of individual, perfectly aligned DNA molecules, all of which are arranged in the same orientation and anchored by both ends to the sample chamber surface. As with our previous nanofabricated devices, this new approach is simple and robust, the flowcells are reusable, the barriers themselves are uniform, and they do not compromise the optical quality of the fused silica or interfere with signal detection.

As a first conceptual demonstration, we show here that the curtains of double-tethered DNA can be used to image 1D-diffusion of DNA-binding proteins. Our previous approach to these experiments relied upon DNA that was randomly anchored to a surface via biotin-neutravidin interactions, which yielded no more than 1-3 molecules of DNA per field-of-view, and there were just ~10-30 double-tethered DNA molecules present over the entire surface of the flowcell. Moreover, the prior studies showed that the orientation of DNA could not be defined because the molecules were anchored with biotin located at either end of the DNA. Therefore, the molecules were randomly oriented on the flowcell surface, making it difficult to locate and compare different DNA molecules to one another in order to dissect sequence specific events. While this original approached proved useful for our initial studies, it was tedious and remained challenging to collect sufficient data for thorough analysis. As demonstrated here, we are now able to visualize on the order of one hundred DNA molecules per field-of-view, thousands of molecules are present on the surface of a flowcell, and all the DNA molecules are aligned in the exact same orientation, which will make 1D diffusion measurements and molecule-to-molecule comparisons straightforward for future work.

REFERENCES

E1. Bustamante, C.; Bryant, Z.; Smith, S. B., Nature 2003, 421, 423-7.
E2. Cairns, B. R., Nat Struct Mol Biol 2007, 14, 989-96.
E3. Zlatanova, J.; van Holde, K., Mol Cell 2006, 24, 317-29.
E4. van Oijen, A. M., Biopolymers 2007, 85, 144-53.
E5. Riehn, R.; Austin, R. H.; Sturm, J. C., Nano Lett 2006, 6, 1973-6.
E6. Riehn, R.; Lu, M.; Wang, Y. M.; Lim, S. F.; Cox, E. C.; Austin, R. H., Proc Natl Acad Sci USA 2005, 102, 10012-6.
E7. Tegenfeldt, J. O.; Prinz, C.; Cao, H.; Huang, R. L.; Austin, R. H.; Chou, S. Y.; Cox, E. C.; Sturm, J. C., Anal Bioanal Chem 2004, 378, 1678-92.
E8. Fazio, T.; Visnapuu, M. L.; Wind, S.; Greene, E. C., Langmuir 2008, 24, 10524-31.
E9. Visnapuu, M. L.; Fazio, T.; Wind, S.; Greene, E. C., Langmuir 2008, 24, 11293-9.
E10. Granéli, A.; Yeykal, C.; Prasad, T. K.; Greene, E. C., Langmuir 2006, 22, 292-299.

E11. Sackmann, E., Science 1996, 271, 43-48.

E12. Groves, J.; Boxer, S., Acc Chem Res 2002 March, 35, 149-57.

E13. Chan, Y. H.; Boxer, S. G., Curr Opin Chem Biol 2007, 11, 581-7.

E14. Perez, T. D.; Nelson, W. J.; Boxer, S. G.; Kam, L., Langmuir 2005, 21, 11963-8.

E15. Floyd, D. L.; Ragains, J. R.; Skehel, J. J.; Harrison, S. C.; van Oijen, A. M., Proc Natl Acad Sci USA 2008, 105, 15382-7.

E16. Cremer, P. S.; Boxer, S. G., J. Phys. Chem. B 1999, 103, 2554-2559.

E17. Groves, J. T.; Boxer, S. G., Acc Chem Res 2002, 35, 149-57.

E18. Tanaka, M.; Hermann, J.; Haase, I.; Fischer, M.; Boxer, S. G., Langmuir 2007, 23, 5638-5644.

E19. Groves, J. T.; Boxer, S. G.; McConnell, H. M., Proc Natl Acad Sci USA 1997, 94, 13390-5.

E20. Jackson, B. L.; Nye, J. A.; Groves, J. T., Langmuir 2008, 24, 6189-93.

E21. Groves, J. T.; Ulman, N.; Boxer, S. G., Science 1997, 275, 651-3.

E22. Gorman, J.; Chowdhury, A.; Surtees, J. A.; Shimada, J.; Reichman, D. R.; Alani, E.; Greene, E. C., Mol Cell 2007, 28, 359-70.

E23. Granéli, A.; Yeykal, C.; Robertson, R. B.; Greene, E. C., Proceedings of the National Academy of Sciences, USA 2006, 103, 1221-1226.

E24. Prasad, T. K.; Robertson, R. B.; Visnapuu, M. L.; Chi, P.; Sung, P.; Greene, E. C., J Mol Biol 2007, 369, 940-53.

E25. Prasad, T. K.; Yeykal, C.; Greene, E. C., Journal of Molecular Biology 2006, 363, 713-728.

E26. Visnapuu, M. L.; Greene, E. C., Submitted 2009.

E27. Gorman, J.; Greene, E. C., Nat Struct Mol Biol 2008, 15, 768-74.

E28. Tafvizi, A.; Huang, F.; Leith, J. S.; Fersht, A. R.; Mirny, L. A.; van Oijen, A. M., Biophys J 2008, 95, L01-3.

E29. Chou, S. Y.; Krauss, P. R.; Renstrom, P. J., Science 1996, 272, 85-87.

E30. Gao, H.; Tan, H.; Zhang, W.; Morton, K.; Chou, S. Y., Nano Lett 2006, 6, 2438-41.

E31. Lebofsky, R.; Bensimon, A., Briefings in functional genomics and proteomics 2003, 1, 385-396.

E32. Kabata, H.; Kurosawa, O.; Arai, I.; Washizu, M.; Margarson, S. A.; Glass, R. E.; Shimamoto, N., Science 1993, 262, 1561-1563.

E33. Guan, J.; Lee, L. J., Proceedings of the National Academy of Sciences, USA 2005, 102, 18321-18325.

E34. Kim, S.; Blainey, P. C.; Schroeder, C. M.; Xie, S. X., Nature methods 2007, 4, 397-399.

E35. Assi, F.; Jenks, R.; Yang, J.; Love, C.; Prentiss, M., Journal of Applied Physics 2002, 92, 5584-5586.

E36. Lin, J.; Qi, R.; Aston, C.; Jing, J.; Anantharaman, T. S.; Mishra, B.; White, O.; Daly, M. J.; Minton, K. W.; Venter, J. C.; Schwartz, D. C., Science 1999, 285, 1558-1562.

E37. Washizu, M.; Kurosawa, O.; Arai, I.; Suzuki, S.; Shimamoto, N., IEEE Trans. Ind. Appl. 1995, 31, 447-456.

E38. Dimalanta, E. T.; Lim, A.; Runnheim, R.; Lamers, C.; Churas, C.; Forrest, D. K.; de Pablo, J. J.; Graham, M. D.; Coppersmith, S. N.; Goldstein, S.; Schwartz, D. C., Analytical Chemistry 2004, 76, 5293-5301.

Example 12

Reversible Anchoring of DNA Along its Contour to the Sample Chamber Surface

Lipid bilayers, DNA curtains, and DNA substrates were prepared as described in the Examples above.

DNA is attached to lipid bilayer as shown in FIG. 43A. DNA is then aligned at the diffusion barrier edge (for example, a linear diffusion barrier or a non-linear, geometric diffusion barrier) using either a hydrodynamic force or and electric field (FIG. 43B). A calcium solution of about 1 mM is then injected into the flow cell. The DNA becomes reversibly anchored to the lipid bilayer throughout the DNA's entire contour length (FIG. 43C). The following calcium concentration can also be used, for example, a calcium concentration of at least about 0.5 mM, at least about 1 mM, at least about 1.5 mM, at least about 2 mM, at least about 2.5 mM, at least about 3 mM, at least about 3.5 mM, at least about 4 mM, at least about 4.5 mM, at least about 5 mM, at least about 5.5 mM, at least about 6 mM, at least about 6.5 mM, at least about 7 mM, at least about 7.5 mM, at least about 8 mM, at least about 8.5 mM, at least about 9 mM, at least about 9.5 mM, at least about 10 mM, or at least about 10.5 mM.

Some advantages of using this system are as follows: the need for a second barrier surface for anchoring DNA molecule is eliminated; the DNA remains anchored when flow is reduced or eliminated; Anchoring of DNA is completely reversible upon washing the flowcell with buffer lacking calcium; and the system would enable manipulation and/or collections of fragment after cleavage with a restriction enzyme.

Example 13

Non-Destructive Mapping of DNA Molecules

Lipid bilayers, DNA curtains, and DNA substrates were prepared as described in the Examples above.

A sample of homogeneous DNA molecules is attached to lipid bilayer as shown in FIG. 44A. Fluorescently tagged oligonucleotides or PNAs (protein-nucleic acids) directed against specific target sequences can be hybridized to DNA molecules aligned at the edge of a diffusion barrier (for example a linear diffusion barrier or a non-linear, geometric diffusion barrier) using either a hydrodynamic force or and electric field (FIG. 44B). An advantage of using this system includes course mapping of DNA for genomics applications which can be carried out without the requirement for cutting the DNA. This type of mapping technology is being used by others, but not in the context of a DNA curtain. The DNA curtain design (top view, FIG. 44B) offers two potential benefits over what is being practiced: (1) easier data analysis because DNA molecules are aligned; and (2) the DNA can be collected after analysis by cleaving it with a restriction enzyme. For example, one could design a single, specific cut site right at the point of attachment. No other single molecule DNA mapping technique allows the user to harvest the DNA after analysis.

A sample of heterogeneous DNA molecules (for example, a heterogeneous preparation of genomic DNA) can be attached to lipid bilayer as shown in FIG. 45A. Fluorescently tagged oligonucleotides or PNAs (protein-nucleic acids) directed against specific target sequences can be hybridized to DNA molecules aligned at the edge of a diffusion barrier (for example a linear diffusion barrier or a non-linear, geometric diffusion barrier) using either a hydrodynamic force or and electric field (FIG. 45B). Individual DNA molecules can then be designated or numbered, and from the organization scheme of these DNA molecules, a DNA map can be generated based on overlapping signals (FIG. 45B, top view). An example of a DNA map is seen in FIG. 45C. An advantage of using this system includes course mapping of DNA for genomics applications which can be carried out without the requirement for cutting the DNA. Specifically, this system allows the mapping of more complex mixtures of genomic DNA. One would need to prepare clean samples of genomic DNA comprised of fragments that could range in size from ~10-300 kb. One would also have to ensure that the DNA is labeled at ONE end (not both ends) with a tag (such as biotin or another tag used in the art). This would allow for the DNA molecule to be anchored to the surface, and is not trivial for heterogeneous DNA samples have different ends sequences.

Example 14

Single-Molecule Imaging Reveals Mechanisms of Protein Disruption by a DNA Translocase In physiological settings nucleic acid translocases must act on substrates occupied by other proteins, and an increasingly appreciated role of translocases is to catalyze protein displacement from RNA and DNA[F1,F2,F3,F4]. However, little is known regarding the inevitable collisions that must occur, and the fate of protein obstacles and the mechanisms by which they are evicted from DNA remain unexplored. Here we sought to establish the mechanistic basis for protein displacement from DNA using RecBCD as a model system. Using nanofabricated curtains of DNA and multi-color single-molecule microscopy, we visualized collisions between a model translocase and different DNA-bound proteins in real time. We show that the DNA translocase RecBCD can disrupt core RNA polymerase (RNAP), holoenzyme, stalled elongation complexes, and transcribing RNAP in either head-to-head or head-to-tail orientations, as well as EcoRI$^{E111Q}$, lac repressor and even nucleosomes. RecBCD did not pause during collisions and often pushed proteins thousands of base-pairs before evicting them from DNA. We conclude that RecBCD overwhelms obstacles through direct transduction of chemomechanical force with no need for specific protein-protein interactions, and that proteins can be removed from DNA through active disruption mechanisms that act on a transition state intermediate as they are pushed from one nonspecific site to the next.

RecBCD is a heterotrimeric translocase involved in initiating homologous recombination and processing stalled replication forks[F5,F6]. RecB is a 3'→5' SF1A helicase and contains a nuclease domain for DNA processing; RecD is a 5'→3' SF1B helicase; RecC holds the complex together and coordinates the response to cis-acting Chi sequences (5'-dGCTG-GTGG-3' [SEQ ID NO: 7]). RecD is the lead motor before Chi, RecB is the lead motor after Chi, and Chi-recognition is accompanied by a reduced rate of translocation corresponding to the slower velocity of RecB[F7,F8]. Chi prompts RecBCD to process DNA, yielding 3' ssDNA overhangs onto which RecA is loaded[F7,F8].

Figure 67:
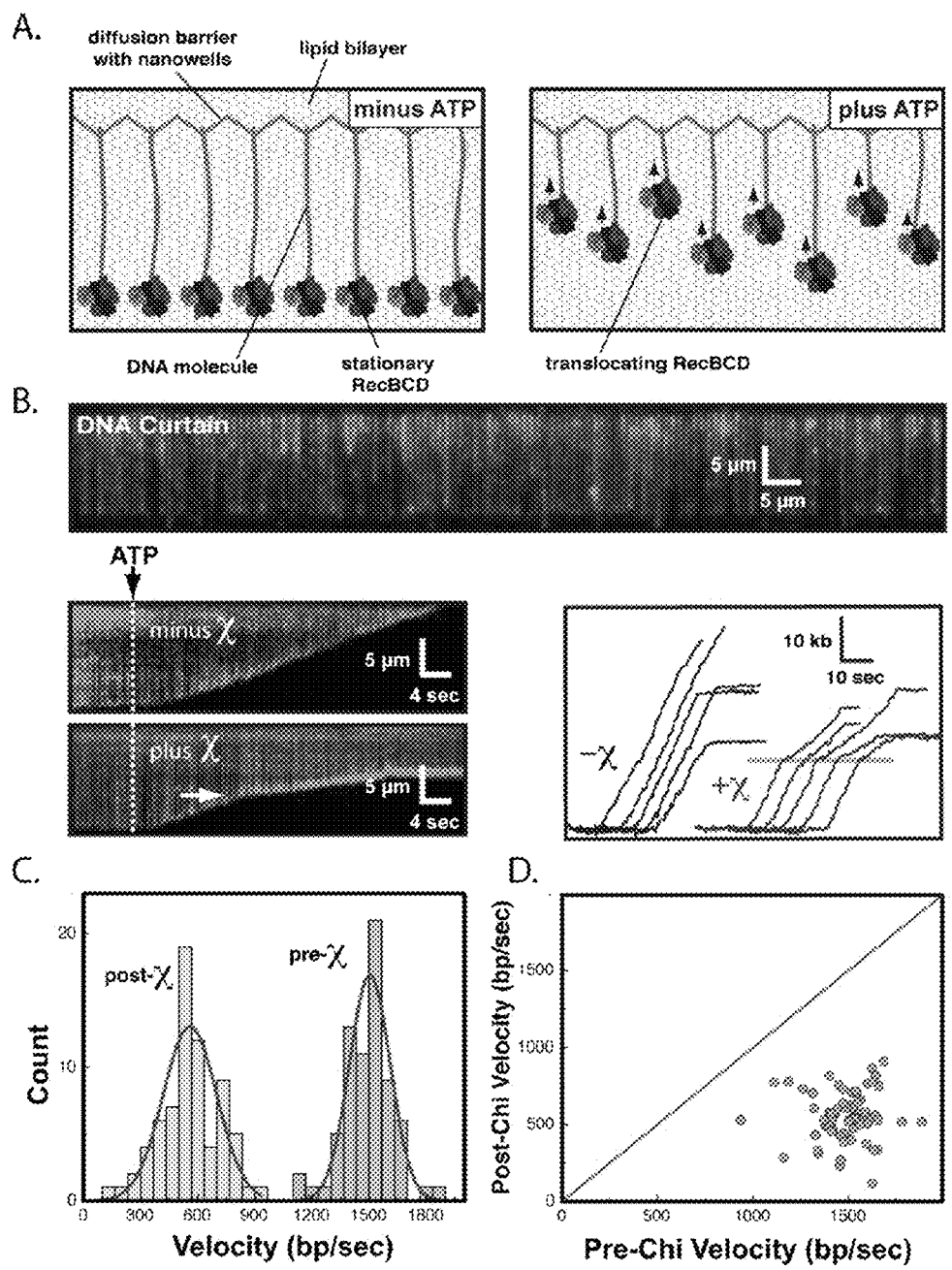
FIG. 67 shows RecBCD translocation on DNA curtains.

We monitored RecBCD activity using total internal reflection fluorescence microscopy (TIRFM) and a DNA curtain assay that allows us to visualize hundreds of aligned molecules (FIG. 67)[9]. When assayed on DNA curtains, RecBCD displayed rapid translocation (1,484±167 bp sec$^{-1}$, 37° C., 1 mM ATP, N=100; FIG. 67B-C), high processivity (36,000±12,500 bp), and also decreased velocity in response to Chi (549±155 bp sec$^{-1}$, 37° C., 1 mM ATP, N=100; FIG. 67), in agreement with previous studies[F6,F7].

E. coli contains ~2,000 molecules of RNA polymerase, and ≥65% of these are bound to the bacterial chromosome[F10], making it one of the most commonly encountered obstacles in physiological settings. RNAP is of special interest because it is a high-affinity DNA-binding protein ($K_d$≈10 pM and $K_d$≈100 pM for λ$P_R$ and λ$P_L$, respectively) and powerful translocase capable of moving under an applied load of ~14-25 pN[F11]. RNAP survives encounters with replication forks[F12,F13,F14] and stalls fork progression in head-on collisions[F15,F16] arguing that RNAP is among the most formidable roadblocks encountered in vivo. During replication restart RecBCD translocates towards OriC, therefore most collisions with RNAP will occur in a head-on orientation, suggesting that to survive these encounters RecBCD would need to exert more force than a replisome.

Figure 69:
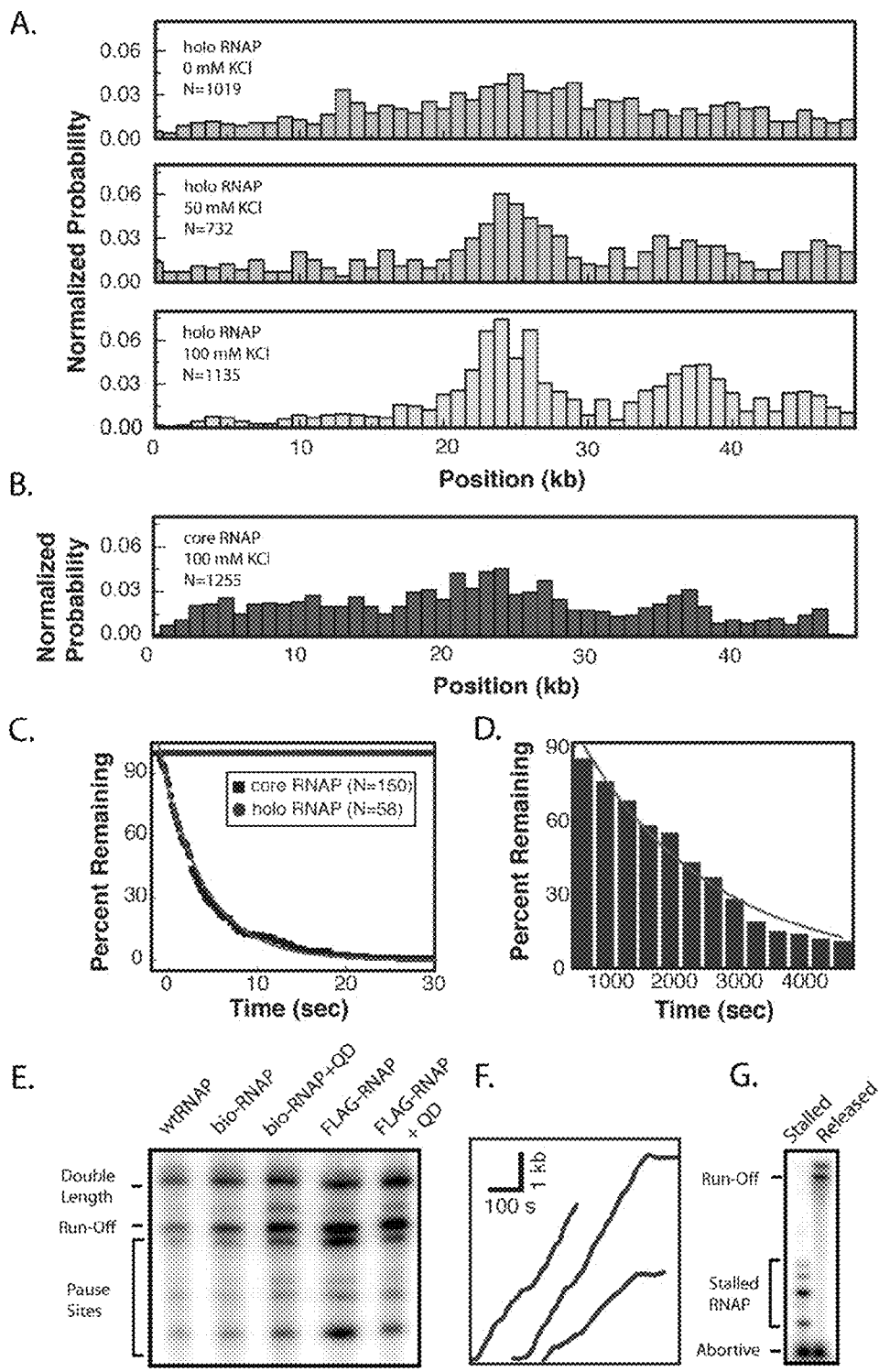
FIG. 69 shows single molecule and bulk characterization of RNAP.

We used quantum dots (QDs) to fluorescently label RNAP (See Methods). The binding distribution of QD-RNAP holoenzyme overlapped with known promoters (FIG. 63A), promoter targeting was σ$^{F70}$-dependent, and promoter-bound holoenzymes were highly stable ($t_{1/2}$=23.2±1.42 min, N=58; FIGS. 69A-C). Core QD-RNAP dissociated when challenged with heparin ($t_{1/2}$=3.4±0.03 sec, N=150), whereas promoter-bound holoenzyme was heparin-resistant ($t_{1/2}$>>6.7 min, N=58), confirming open complex formation (FIGS. 69C-D). Bulk assays verified QD-RNAP produced transcripts (FIG. 69E), and single molecule assays revealed a transcription velocity of 15.7±8.6 bp sec$^{-1}$ (N=20, 25° C., 250 µM of each rNTP; FIG. 69F).

Figure 63:
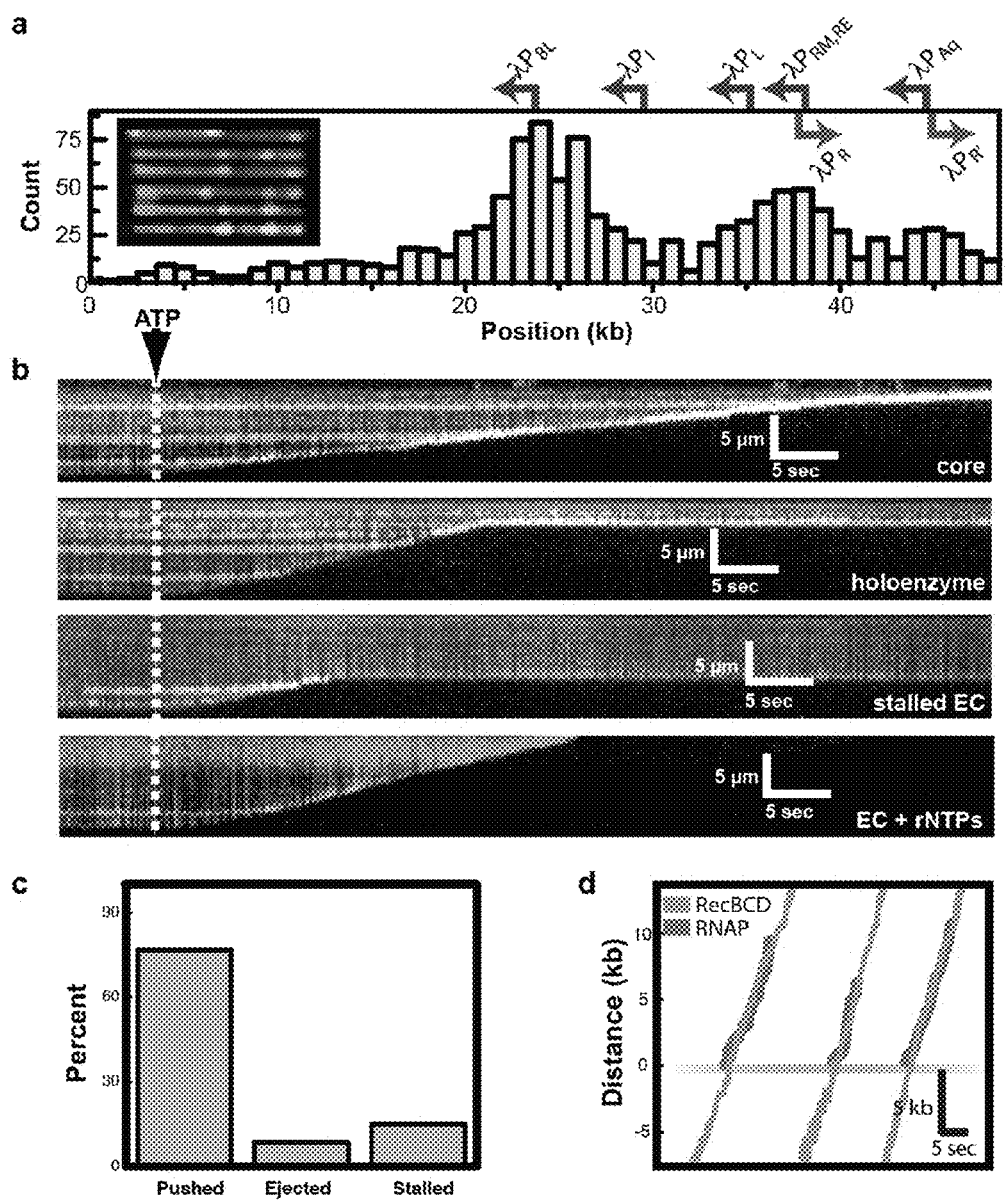
FIG. 63 shows that RecBCD removes RNAP from DNA.
Figure 70C:
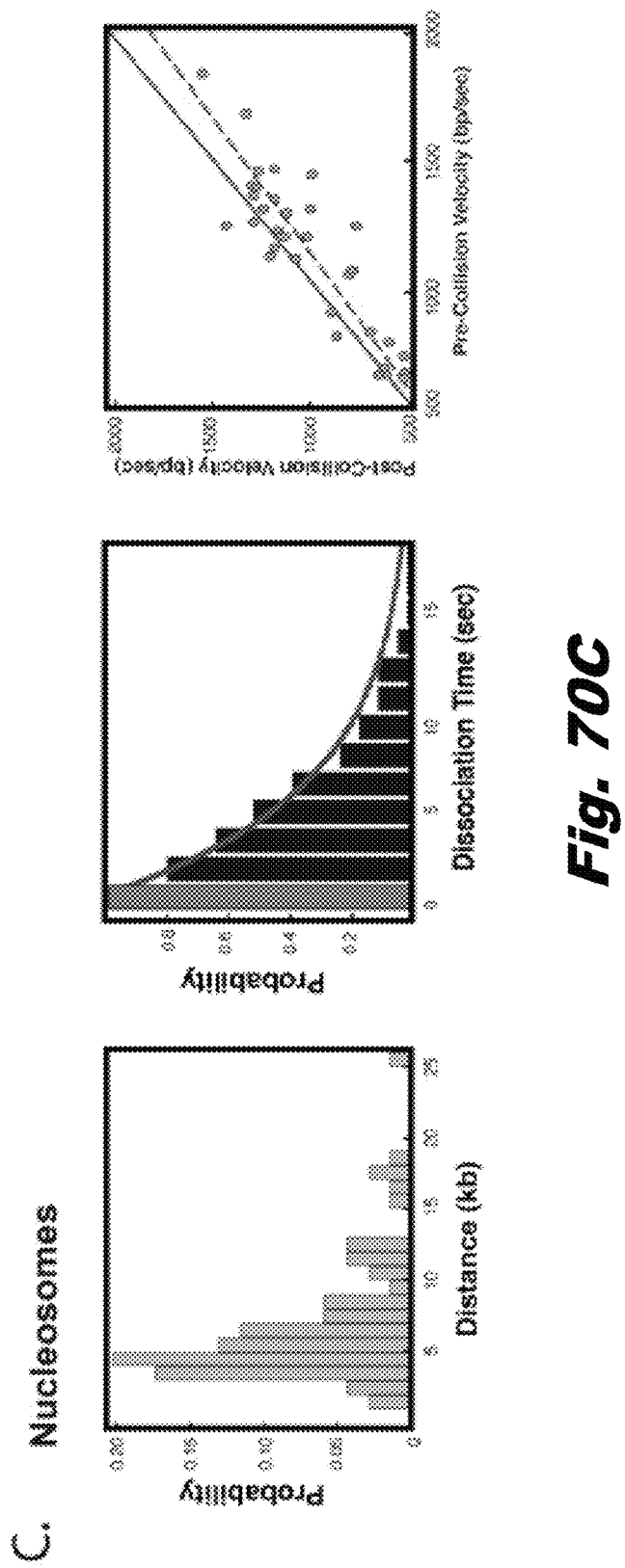
FIG. 70C shows graphs of nucleosome collisions. Left, middle, and right panels show nucleosome pushing distances, lifetimes, and a scatter plot with pre- and post-collision RecBCD velocities, respectively. The points cluster below the reference line (m=1), and a linear fit to the data (dashed red line) yields a slope of m=0.90±0.04 ($R^2$=0.82), corresponding to a statistically significant 10% reduction in RecBCD velocity while pushing nucleosomes (t-test, p=0.0005).
Figure 71:
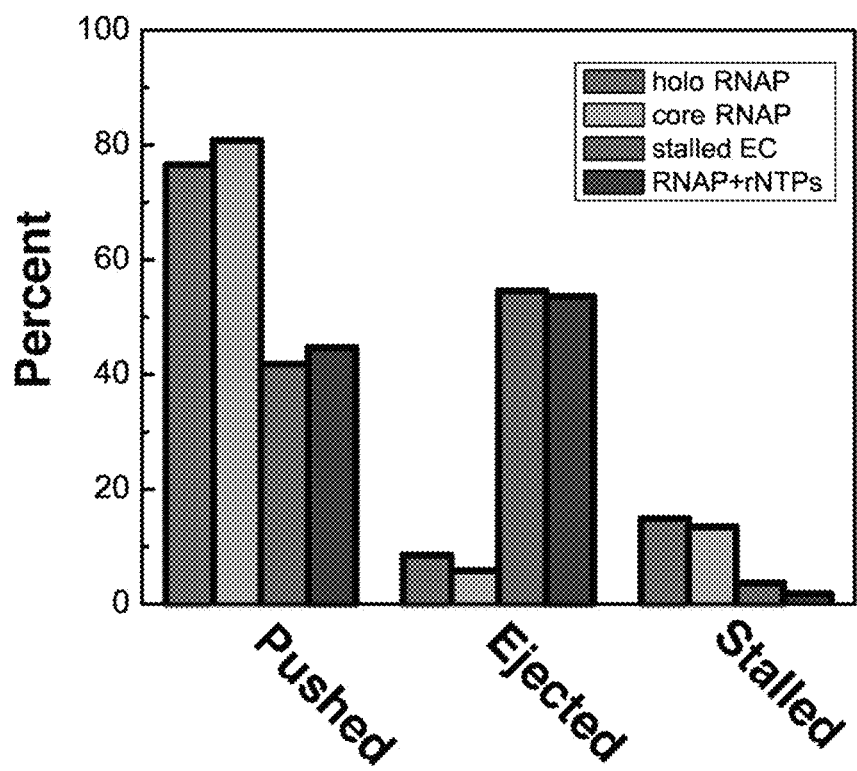
FIG. 71 is a graph of the analysis of collisions between RecBCD and various forms of RNAP. Comparison of RecBCD-induced sliding and ejection behavior of various RNAP species. Stalled and elongating complexes are evicted more readily without sliding compared to holo and core RNAPs. At least fifty collisions were observed between RecBCD and each different type of RNAP complex.
Figure 72:
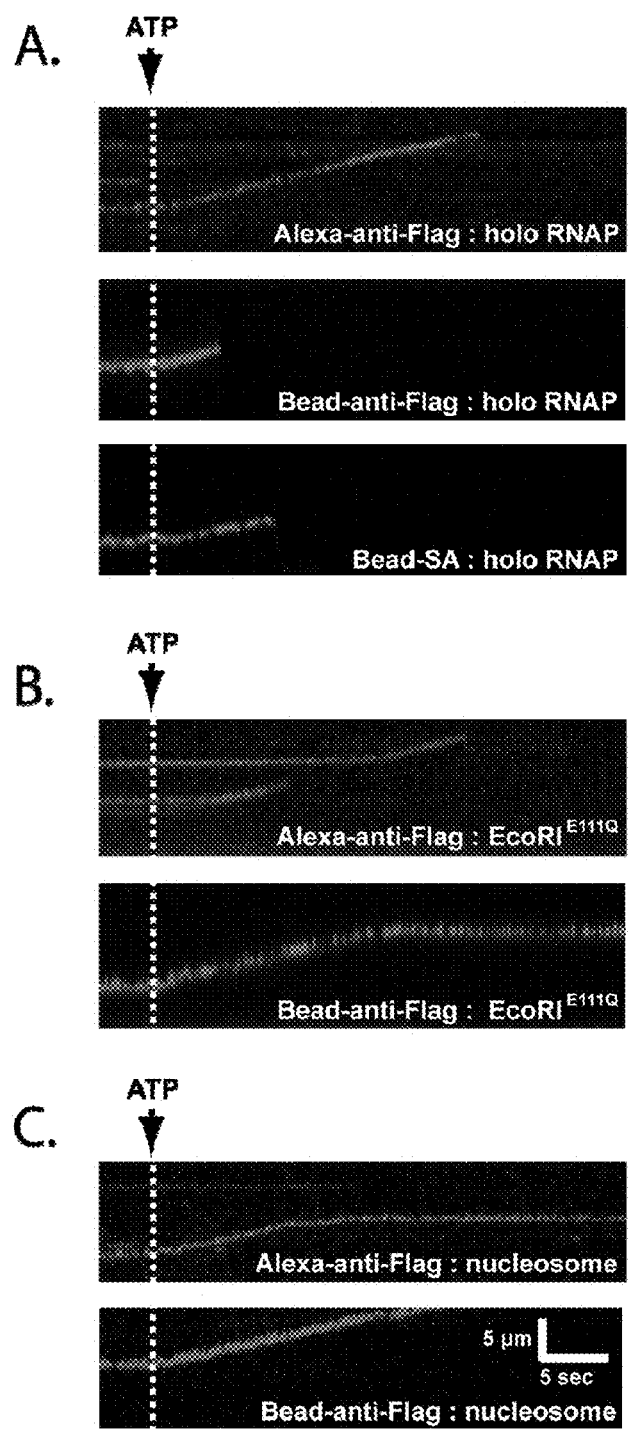
Figure 73:
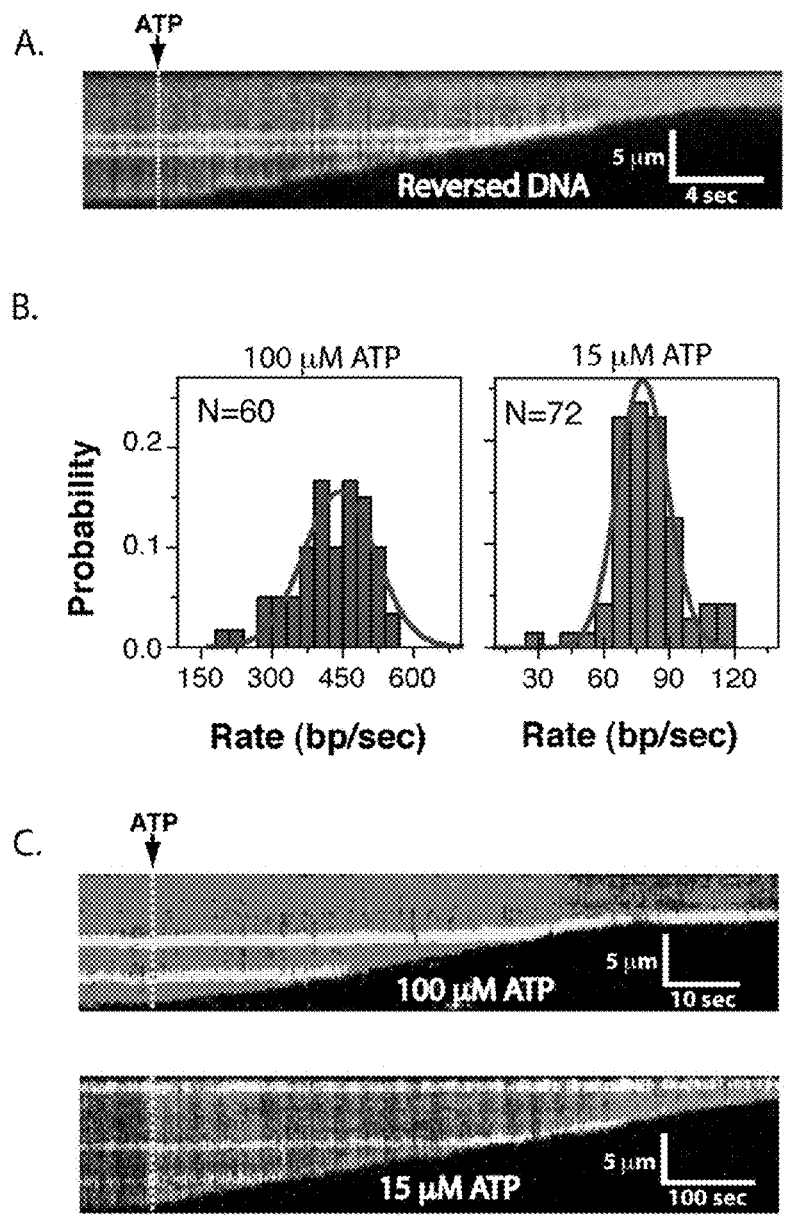
FIG. 73 shows reversed DNA orientation and low velocity collisions.

When RecBCD collided with RNAP, the polymerase was rapidly ejected from DNA ($t_{1/2}$=2.4±0.13 sec; FIG. 63B). Remarkably, RNAP could be pushed long distances (10,460±7,690 bp, N=44; FIG. 63 & FIG. 70), and RecBCD could disrupt core, holoenzyme, stalled elongation complexes (ECs), and active ECs (FIG. 63B & FIG. 71). Out of 47 collisions with QD-RNAP holoenzyme, 15% (7/47) immediately stalled RecBCD, 8.5% (4/47) resulted in dissociation of RNAP with no sliding, 76.5% (36/47) of RNAP was pushed and 71% of pushed molecules were eventually ejected (FIG. 63C). The population of RNAP molecules that was directly ejected from the DNA increased ~5-fold for stalled and active elongation complexes (FIG. 71). RecBCD also pushed and evicted RNAP labeled with 40-nm fluorescent beads or Alexa Fluor 488-IgG, arguing against nonspecific interactions between RecBCD and the QDs (FIG. 72A). RecBCD did not slow or pause upon colliding with RNAP (FIG. 63D & FIG. 70A), nor was there any reduction in processivity compared to naked DNA (29,000±15,500 bp). Similar outcomes were observed before and after Chi, indicating that RecBCD could dislodge RNAP regardless of whether RecB or RecD was the lead motor. We could unambiguously assign the orientation of RNAP at λ$P_{BL}$, (FIG. 63A & FIG. 69F), and RecBCD dislodged RNAP bound at λ$P_{BL}$ during collisions in either direction (FIG. 63B & FIG. 73). RecBCD also pushed and ejected RNAP bound at all other locations regardless of DNA orientation (FIG. 63B). RecBCD even dislodged RNAP at lower velocities (446±192 bp sec$^{-1}$, 122±128 bp sec$^{-1}$, and 78±27 bp sec$^{-1}$, at 100 µM, 25 µM and 15 µM ATP, respectively; FIG. 73), indicating proteins could be dislodged even under sub-optimal translocation conditions. We conclude that RecBCD disrupts RNAP regardless of orientation, transcriptional status, or translocation velocity.

We next asked whether RecBCD could dislodge other proteins. EcoRI$^{E111Q}$ is a catalytically inactive version of EcoRI, which has high affinity ($K_d$≈2.5 fM) for cognate sites and even binds tightly to nonspecific DNA ($K_d$≈4.8 pM)[F17]. EcoRI$^{E111Q}$ can halt E. coli RNA polymerase[F18,F19], T7 and SP6 RNA polymerases[F20], SV40 large T-antigen, UvrD, DnaB, and Dda helicases, SV40 replication forks[F21], and E. coli replication forks[F4]. EcoRI withstands up to ~20-40 pN[F22], and EcoRI$^{E111Q}$ binds cognate sites ~3000-fold stronger than wild-type EcoRI ($K_d$≈6.7 pM)[F17], thus we infer the catalytic mutant can resist at least as much force as the wild-type protein. Lac repressor (LacI) is representative of a large family of bacterial transcription factors that has served as a paradigm for transcriptional regulation and protein-DNA interactions. LacI binds tightly to specific sites ($K_d$=10 fM for a 21-bp symmetric operator)[F23], but binds weakly to nonspecific DNA ($K_d$≥1 nM)[F24] and slides rapidly along nonspecific DNA rather than remaining at fixed locations[F25,F26]. LacI blocks RNAP and replication forks both in vitro and in vivo[F18], highlighting this protein as a potent and physiologically relevant barrier to translocase progression.

Figure 64:
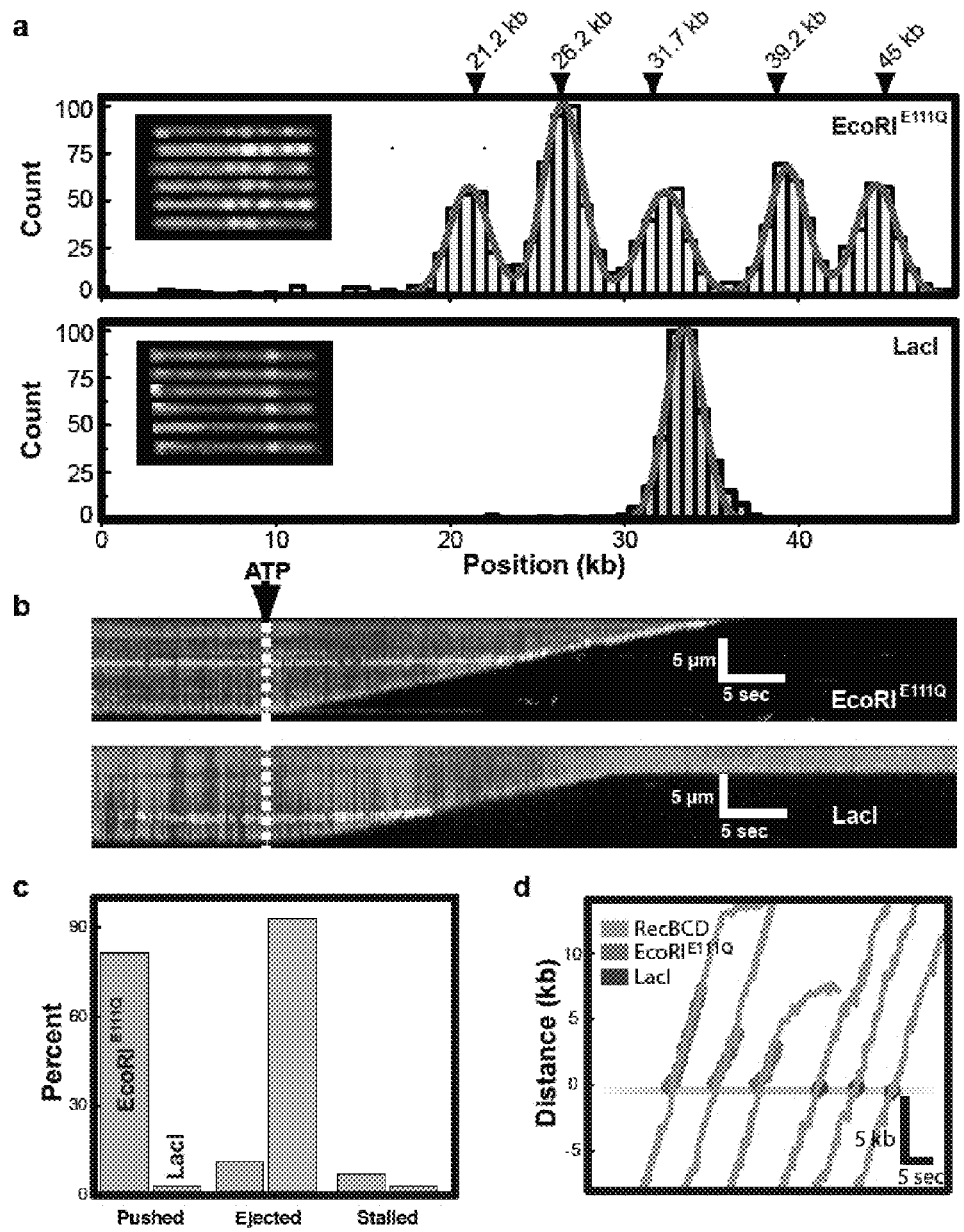
FIG. 64 shows the disruption of EcoRI$^{E111Q}$ and lac repressor by RecBCD.
Figure 75:
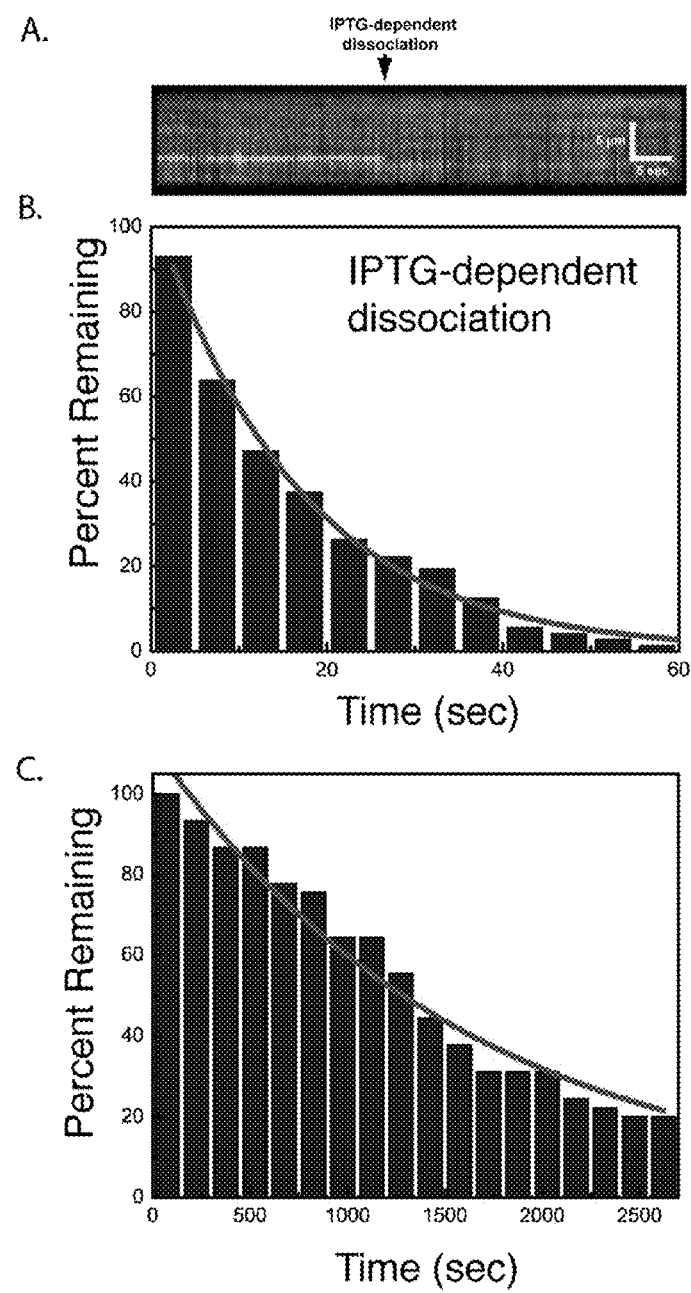
FIG. 75 shows the characterization of lac repressor.
Figure 76:
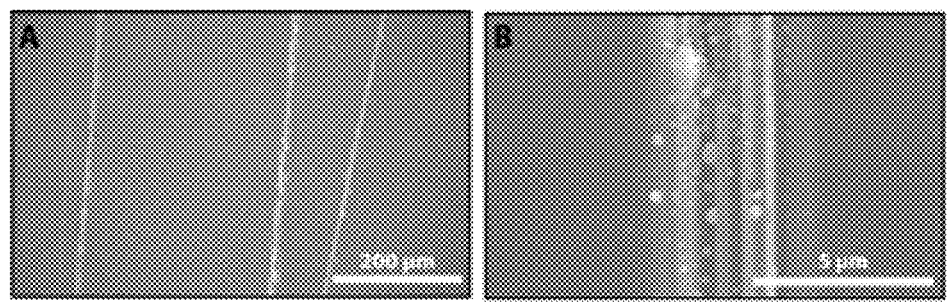
FIG. 76 shows DNA curtains made with manually etched barriers.
Figure 77:
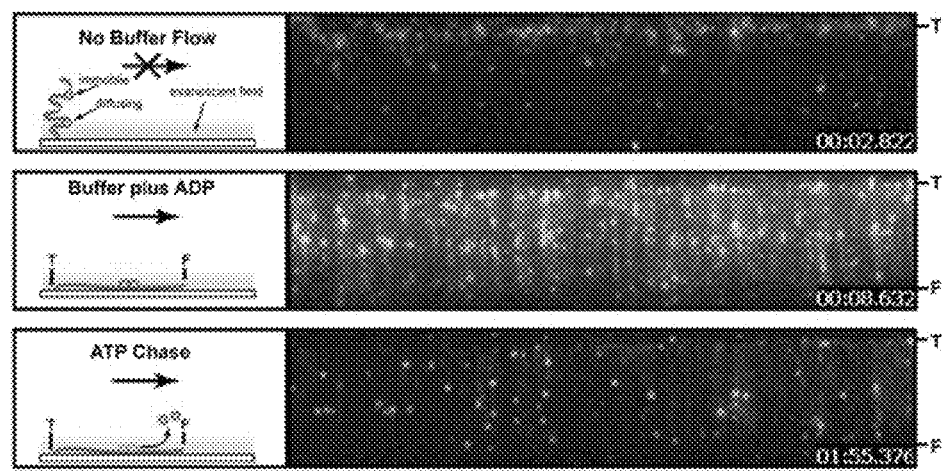
FIG. 77 shows ATP-triggered release of Msh2-Msh6 from DNA aligned at a manually etched barrier. (A) Shows the assay used to probe the effects of ATP on the immobile population of Msh2-Msh6. The proteins are red and the DNA is green. The DNA is tethered to the surface by only one end ("T") and the free end ("F") is only observed when flow is applied. Flow is from top to bottom in each panel and the distance between T and F is ~13 μm. The upper panel shows the field after transiently pausing buffer flow (Flow ON/OFF control) and the cartoon at the left depicts the behavior of the molecules the absence of flow. The middle panel shows the same field after resuming flow. Each red spot in the image corresponds to at least one Msh2-Msh6 complex, and there are 274 identifiable red spots in this experiment and 124 DNA molecules. The lower panel shows the same DNA molecules after the injection of 2 mM ATP.
Figure 78:
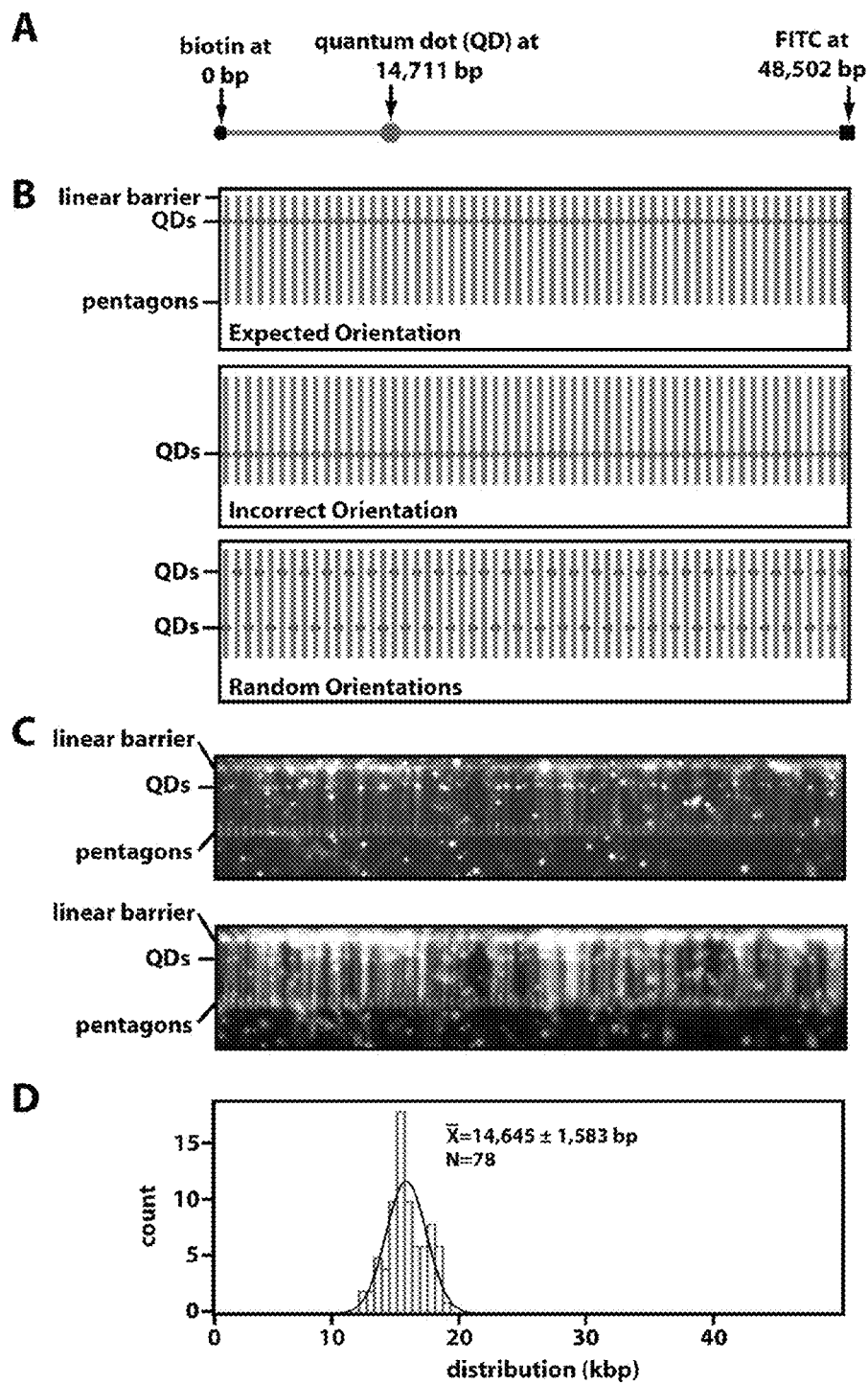
FIG. 78 shows the defined orientation of the DNA molecules.

EcoRI$^{E111Q}$ and LacI were labeled with QDs (See Methods). QD-EcoRI$^{E111Q}$ and QD-LacI were targeted to the correct locations on the DNA substrates (FIG. 64A & FIG. 74), and QD-LacI was rapidly released from DNA with IPTG, as expected (FIG. 75). When RecBCD collided with EcoRI$^{E111Q}$ it pushed the proteins 13,000±9,100 bp (N=70), before ejecting them from DNA (FIGS. 64B-C). In contrast, LacI was immediately ejected, and was not pushed within our resolution limits (FIGS. 64B-D). There was no change in velocity or processivity upon colliding with either protein (FIGS. 64B, 64D & FIG. 70). Out of 70 collisions with QD-EcoRI$^{E111Q}$, 11.2% (5/70) stalled the translocase, 11.4% (8/70) resulted in immediate dissociation of EcoRI$^{E111Q}$ with no detectable sliding, 81.4% (57/70) of EcoRI$^{E111Q}$ was pushed along DNA and 92% of pushed molecules were eventually ejected (FIG. 64C). Out of 30 collisions with LacI, 3.3% (1/30) stalled the translocase, 93.3% (28/30) resulted in immediate dissociation of LacI with no detectable sliding, and 3.3% (1/30) exhibited sliding before dissociation (FIG. 64C). A greater fraction of LacI might slide, but if so, the sliding events fall below our resolution limits. Control experiments confirmed RecBCD disrupted EcoRI$^{E111Q}$ labeled with fluorescent beads or Alexa Fluor 488 (FIG. 72). As with RNAP, RecBCD could strip EcoRI$^{E111Q}$ after Chi, and RecBCD also disrupted EcoRI$^{E111Q}$ and LacI during low velocity collisions. These findings confirm that RecBCD readily displaces tightly bound proteins from DNA.

In eukaryotes, nucleosomes are the most frequently encountered DNA-bound obstacles. Replisomes, transcription machinery, and ATP-dependent chromatin remodelers all act through mechanisms requiring force generation, and the response of nucleosomes to these forces remains a long standing question in chromatin biology. Heterologous systems have revealed fundamental principles underlying these processes[F27,F28]: experiments with SP6 RNAP provided a theoretical framework for nucleosome repositioning[F27]; and studies with phage T4 proteins were among the first to address the fate of nucleosomes during replication[F28]. Eukaryotic translocases exert forces in the same net direction as RecBCD, and RecBCD can unwind nucleosome-bound DNA[F29], arguing that it can serve as a good protein-based force probe for studying the fate of nucleosomes when rammed by a translocase.

Figure 65:
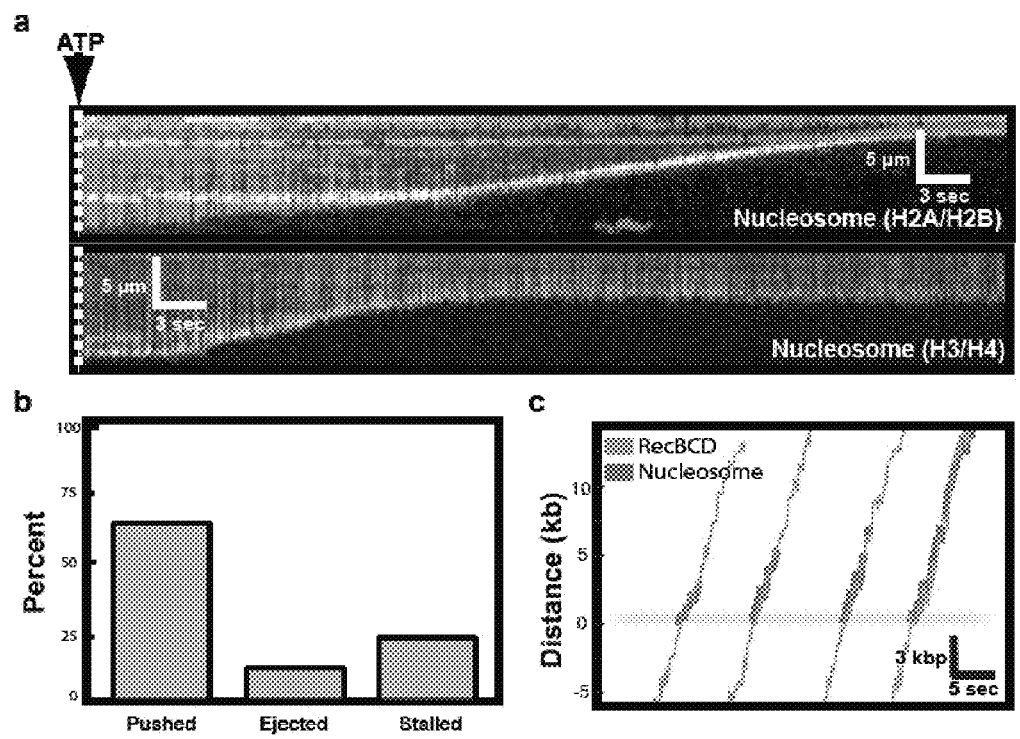
FIG. 65 shows that nucleosomes can be pushed along DNA.

Recombinant nucleosomes were deposited on DNA curtains by salt dialysis, as described[F9]. Remarkably, RecBCD could push nucleosomes (7,311±5,373 bp, N=75; FIG. 65), and similar results were obtained with fluorescently labeled H2A/H2B or H3/H4 (FIG. 65A). Control experiments demonstrated that RecBCD could also push nucleosomes labeled with either fluorescent beads or Alexa Fluor 488 (FIG. 72C). Out of 357 collisions with QD-nucleosomes, 24% (84/357) immediately stalled RecBCD, 11% (40/357) resulted in direct nucleosome ejection, 65% (233/357) led to sliding (FIG. 65B) and ~50% of these were eventually ejected ($t_{1/2}$=3.93±0.21 sec; FIG. 65B & FIG. 70C). Nucleosomes reduced the processivity of RecBCD to 14,000±7,000 bp, as anticipated[F29], and a larger fraction of these collisions caused the translocase to stall (24%) compared to RNAP (15% stall), EcoRI$^{E111Q}$ (7% stall) and LacI (3.3% stall). Fewer of the pushed nucleosomes (50%) were subsequently ejected from the DNA compared to the other roadblock proteins, and there was a 10% reduction (t-test, p=0.0005) in velocity while pushing nucleosomes (FIG. 65C & FIG. 70C). These results demonstrate that intact nucleosomes can be pushed along DNA as theoretically predicted[F30], but indicated that RecBCD had more difficulty pushing and evicting nucleosomes compared to the other protein roadblocks. The finding that RecBCD pushes and evicts nucleosomes also rules out mechanisms requiring species-specific protein-protein interactions.

Protein disruption mechanisms can be described by at least four models, which differ in the nature of mobile intermediates and the stage of the chemomechanical cycle during which the proteins dissociate (FIG. 66A). For the first model, passive release, the proteins (S) are dislodged from a high-affinity specific site, and then pushed from one sequential nonspecific site to the next. Subsequent dissociation occurs spontaneously simply because the proteins are bound to lower-affinity nonspecific DNA (N). This model assumes the proteins have similar low affinities for all nonspecific sites sampled, and predicts that the observed rates of RecBCD-induced dissociation ($k_{off,obs}$) would be similar to spontaneous dissociation from nonspecific DNA in the absence of RecBCD ($k_{off,obs} \approx k_{off,N}$). This model also predicts that the distance (d) over which proteins are pushed will be dictated by their affinity for nonspecific DNA, and will be proportional to velocity (V), such that faster translocation will lead to longer distances and slower translocation will yield shorter distances.

The second model, preferred site release, accounts for a scenario where proteins encounter rare sequences of exceptionally low-affinity (N') such that they preferentially dissociate from these sites ($k_{off,N'} \gg k_{off,N}$).

In the third model, structural disruption, translocase collisions alter the conformation of the proteins (e.g. by permanently rupturing a subset of protein-DNA contacts), such that they persist as structurally perturbed complexes (X) after displacement from the high-affinity site. In this scenario, the mobile intermediates have a characteristic lifetime ($\tau_x$) dictated by their weakened affinity for DNA, and this lifetime should be insensitive to translocation velocity. Therefore, the distance (d) over which proteins are pushed will be proportional to velocity (V), and faster translocation will lead to longer distances whereas slower translocation will yield shorter distances. The most important feature of this model, which distinguishes it from all of the other models, is that the structurally disrupted proteins are more weakly bound to DNA specifically as a consequence of the collision, such that the observed rate of RecBCD-induced dissociation ($k_{off,obs}$) would be greater than the rate of spontaneous dissociation from nonspecific DNA ($k_{off,obs} \approx k_{off,X} \gg k_{off,N}$).

The fourth model, transition state ejection, is characterized by a series of tightly bound nonspecific complexes (N) that must pass through a weakly bound transition state (T) as they are pushed from one position to the next. This model predicts that dissociation occurs predominantly during the transition state ($k_{off,T} \gg k_{off,N}$). The time required to pass through the transition state during one round of the chemomechanical cycle is equivalent to the time required for the translocase to take a single step ($k_{step}$), which is a fixed intrinsic value independent of ATP concentration. This relationship can be rationalized by considering that the velocity of RecBCD can be controlled by modulating ATP concentration (see below), with slower velocities manifesting from longer dwell times between steps while awaiting new ATP, rather than from changes in $k_{step}$. Therefore the time it takes the roadblock to pass through the transition state during a single step will be independent of ATP concentration, whereas the cumulative time spent in the transition state will increase linearly with step number (n) irrespective of the overall observed translocation velocity. The probability of dissociation will then increase with step number, the observed lifetimes will be inversely proportional to velocity, and the total distance the proteins are pushed before dissociation will be independent of velocity (i.e. the roadblocks will be pushed similar distances regardless of how fast the translocase moves).

Each aforementioned model makes distinct predictions that can be experimentally evaluated. This evaluation is made easier for RNAP, EcoRI$^{E111Q}$, and nucleosomes because these proteins were pushed long distances (LacI is considered separately below). We first measured dissociation of these proteins from specific and nonspecific sites in the absence of RecBCD (Supplementary Information), and compared these results to RecBCD-induced rates of dissociation (FIG. 66B). RNAP, EcoRI$^{E111Q}$, and nucleosomes all bind tightly to nonspecific DNA, and RecBCD-induced dissociation was ≥200-fold faster than spontaneous dissociation from nonspecific sites, which is inconsistent with passive release. We next analyzed pushing trajectories to determine if there was any evidence supporting preferred site release. Comparison of these trajectories revealed that RecBCD-induced dissociation of all three roadblock proteins occurred at random locations (FIG. 66C), arguing against preferred site release. To distinguish between structural disruption and transition state eviction we compared protein lifetimes and pushing distances at four different translocation velocities (FIG. 66D). Remarkably, a 3.3-fold decrease in RecBCD velocity (446±192 bp sec$^{-1}$ at 100 μM ATP) led to a 1.5-, 7.0-, and 3.4-fold increase in the post-collision half-life of EcoRI$^{E111Q}$, RNAP, and nucleosomes, respectively, while the distribution of distances over which the proteins were pushed remained largely unaltered (FIG. 66F & Table 1).

any evidence for a structural disruption mechanism of eviction, this does not rule out the possibility that EcoRI$^{E111Q}$, RNAP, and nucleosomes are structurally altered when acted upon by RecBCD. However, if they are structurally perturbed, this alone does not result in their eventual dissociation from DNA.

LacI differs from the other roadblocks in that it was immediately evicted from DNA, and the RecBCD-induced dissociation rate was comparable to the rate of spontaneous dissociation from nonspecific sites (FIG. 66B), which would seem consistent with a passive release model. However, with current resolution limits we cannot completely rule out other mechanisms, and future studies will be necessary to fully address this issue. Importantly, RNAP, EcoRI$^{E111Q}$, and nucleosomes all bind tightly to nonspecific DNA, whereas LacI binds much more weakly to nonspecific sequences (FIG. 66B), suggesting that LacI is released more rapidly from DNA after the collisions due to its weaker affinity for nonspecific sites. This result demonstrates that the roadblock proteins and the nature of their interactions with nonspecific DNA are critical contributing factors to the outcome of the collisions.

This leaves the question of how much force RecBCD exerts, and how much is sufficient to disrupt obstacles. While our experiments do not yield a direct read out of force, we can safely conclude that the force exerted by RecBCD is sufficient to overcome RNAP, EcoRI$^{E111Q}$, LacI and nucleosomes. Our work has revealed unprecedented details of protein collisions on DNA and provides new insights into how translocases can disrupt nucleoprotein complexes. Given the flexibility of our experimental platform, we anticipate these studies can be extended to other translocases and roadblock proteins, and it will be important to determine whether the mechanistic concepts developed here apply to different types of collisions between proteins on DNA

TABLE 1

Collision Data at Different RecBCD Velocities.

| [ATP] (μM) | EcoRI$^{E111Q}$ | | holo RNAP | | Nucleosomes | |
|---|---|---|---|---|---|---|
| | Sliding Dist. (kb) | $t_{1/2}$ (sec) | Sliding Dist. (kb) | $t_{1/2}$ (sec) | Sliding Dist. (kb) | $t_{1/2}$ (sec) |
| 15 | 10.2 ± 8.4 | 95 ± 3 | 17.2 ± 12.7 | 226 ± 5.3 | 10.7 ± 6.2 | 89 ± 3.6 |
| | (N = 62) | (N = 45) | (N = 51) | (N = 30) | (N = 63) | (N = 24) |
| 25 | 13.5 ± 9 | 75 ± 1.3 | 18.4 ± 12.4 | 90 ± 2.2 | 8.9 ± 5.6 | 42 ± 2.8 |
| | (N = 54) | (N = 47) | (N = 39) | (N = 38) | (N = 64) | (N = 23) |
| 100 | 9.1 ± 6 | 4 ± 0.2 | 12 ± 9.3 | 17 ± 1 | 8.7 ± 4.7 | 12.5 ± 0.4 |
| | (N = 55) | (N = 40) | (N = 65) | (N = 45) | (N = 65) | (N = 32) |
| 1000 | 13 ± 9.1 | 2.7 ± 0.1 | 10.5 ± 7.7 | 2.4 ± 0.1 | 7.3 ± 5.4 | 3.7 ± 0.1 |
| | (N = 48) | (N = 45) | (N = 44) | (N = 35) | (N = 75) | (N = 33) |

Half-lives are reported in seconds (sec) and pushing distances are reported in kilobases (kb) at each of the four different ATP concentrations tested. See FIG. 5d-e for a graphical representation of the data.

This effect was even more obvious at 15 μM ATP, where a 19-fold decrease in RecBCD velocity (78±27 bp sec$^{-1}$) led to a 36-, 93-, and 24-fold increase in post-collision half-life of EcoRI$^{E111Q}$, RNAP, and nucleosomes, respectively, while pushing distances were either unaltered or increased compared to the faster velocities. These results indicated that dissociation was dictated by the number of steps the proteins were forced to take rather than the cumulative time it took to be pushed a given distance, which is most consistent with transition state ejection. While our experiments did not reveal

REFERENCES

[F1] Jankowsky, E., Gross, C., Shuman, S. & Pyle, A. Active disruption of an RNA-protein interaction by a DExH/D RNA helicase. Science 291, 121-125 (2001).

[F2] Marquis, K. et al. SpoIIIE strips proteins off the DNA during chromosome translocation. Genes Dev 22, 1786-1795 (2008).

[F3] Krejci, L. et al. DNA helicase Srs2 disrupts the Rad51 presynaptic filament. Nature 423, 305-309 (2003).

[F4] Guy, C. et al. Rep provides a second motor at the replisome to promote duplication of protein-bound DNA. Mol Cell 36, 654-666 (2009).

[F5] Singleton, M., Dillingham, M., Gaudier, M., Kowalczykowski, S. & Wigley, D. Crystal structure of RecBCD enzyme reveals a machine for processing DNA breaks. *Nature* 432, 187-193 (2004).

[F6] Bianco, P. et al. Processive translocation and DNA unwinding by individual RecBCD enzyme molecules. *Nature* 409, 374-378 (2001).

[F7] Spies, M., Amitani, I., Baskin, R. & Kowalczykowski, S. RecBCD enzyme switches lead motor subunits in response to chi recognition. *Cell* 131, 694-705 (2007).

[F8] Taylor, A. & Smith, G. RecBCD enzyme is a DNA helicase with fast and slow motors of opposite polarity. *Nature* 423, 889-893 (2003).

[F9] Visnapuu, M.-L. & Greene, E. Single-molecule imaging of DNA curtains reveals intrinsic energy landscapes for nucleosome deposition. *Nat Struct Mol Biol* 16, 1056-1062 (2009).

[F10] Ishihama, A. Functional modulation of *Escherichia coli* RNA polymerase. *Annu Rev Microbiol* 54, 499-518 (2000).

[F11] Herbert, K., Greenleaf, W. & Block, S. Single-molecule studies of RNA polymerase: motoring along. *Annu Rev Biochem* 77, 149-176 (2008).

[F12] Liu, B., Wong, M. & Alberts, B. A transcribing RNA polymerase molecule survives DNA replication without aborting its growing RNA chain. *Proc Natl Acad Sci USA* 91, 10660-10664 (1994).

[F13] Liu, B., Wong, M., Tinker, R., Geiduschek, E. & Alberts, B. The DNA replication fork can pass RNA polymerase without displacing the nascent transcript. *Nature* 366, 33-39 (1993).

[F14] Liu, B. & Alberts, B. Head-on collision between a DNA replication apparatus and RNA polymerase transcription complex. *Science* 267, 1131-1137 (1995).

[F15] Pomerantz, R. & O'Donnell, M. The replisome uses mRNA as a primer after colliding with RNA polymerase. *Nature* 456, 762-766 (2008).

[F16] Pomerantz, R. & O'Donnell, M. Direct restart of a replication fork stalled by a head-on RNA polymerase. *Science* 327, 590-592 (2010).

[F17] Wright, D., King, K. & Modrich, P. The negative charge of Glu-111 is required to activate the cleavage center of EcoRI endonuclease. *J Biol Chem* 264, 11816-11821 (1989).

[F18] Epshtein, V., Toulmé, F., Rahmouni, A., Borukhov, S. & Nudler, E. Transcription through the roadblocks: the role of RNA polymerase cooperation. *EMBO J* 22, 4719-4727 (2003).

[F19] Nudler, E., Kashlev, M., Nikiforov, V. & Goldfarb, A. Coupling between transcription termination and RNA polymerase inchworming *Cell* 81, 351-357 (1995).

[F20] Pavco, P. & Steege, D. Characterization of elongating T7 and SP6 RNA polymerases and their response to a roadblock generated by a site-specific DNA binding protein. *Nucleic Acids Res* 19, 4639-4646 (1991).

[F21] Byrd, A. & Raney, K. Displacement of a DNA binding protein by Dda helicase. *Nucleic Acids Res* 34, 3020-3029 (2006).

[F22] Noom, M., van den Broek, B., van Mameren, J. & Wuite, G. Visualizing single DNA-bound proteins using DNA as a scanning probe. *Nat Methods* 4, 1031-1036 (2007).

[F23] Sadler, J., Sasmor, H. & Betz, J. A perfectly symmetric lac operator binds the lac repressor very tightly. *Proc Natl Acad Sci USA* 80, 6785-6789 (1983).

[F24] Lin, S. & Riggs, A. Lac repressor binding to DNA not containing the lac operator and to synthetic poly dAT. *Nature* 228, 1184-1186 (1970).

[F25] Elf, J., Li, G.-W. & Xie, X. Probing transcription factor dynamics at the single-molecule level in a living cell. *Science* 316, 1191-1194 (2007).

[F26] Wang, Y. M., Austin, R. H. & Cox, E. C. Single molecule measurements of repressor protein 1D diffusion on DNA. *Phys Rev Lett* 97, 048302 (2006).

[F27] Studitsky, V., Clark, D. & Felsenfeld, G. Overcoming a nucleosomal barrier to transcription. *Cell* 83, 19-27 (1995).

[F28] Bonne-Andrea, C., Wong, M. & Alberts, B. In vitro replication through nucleosomes without histone displacement. *Nature* 343, 719-726 (1990).

[F29] Eggleston, A., O'Neill, T., Bradbury, E. & Kowalczykowski, S. Unwinding of nucleosomal DNA by a DNA helicase. *J Biol Chem* 270, 2024-2031 (1995).

[F30] Mollazadeh-Beidokhti, L., Deseigne, J., Lacoste, D., Mohammad-Rafiee, F. & Schiessl, H. Stochastic model for nucleosome sliding under an external force. *Phys Rev E Stat Nonlin Soft Matter Phys* 79, 031922 (2009).

Materials and Methods

Summary.

We conducted TIRFM experiments on a home-built microscope using nanofabricated DNA curtains, as previously described[F9]. For all initial experiments, and for all kymograms shown in the manuscript, we used YOYO1 to stain the DNA. YOYO1 does not affect the translocation rate or processivity of RecBCD[F6], nor did it affect the binding distributions of RNAP, EcoRI[E111Q], or nucleosomes. In the presence of YOYO1 the roadblocks showed the same general response to collisions with RecBCD, with identical distributions of ejection, stalling, and pushing (and pushing velocities) seen ±YOYO1. However, YOYO1 reduced the distance obstacles were pushed by 20-30% compared to minus YOYO1 reactions. Therefore all sliding distances and half-lives reported in the manuscript correspond to values measured in the absence of YOYO1. Sliding distances are only reported for roadblocks that did not encounter any other QD-tagged proteins as they were pushed along the DNA. This ensures that each analyzed collision/dissociation event only involved a single QD-tagged protein. Many reactions were observed in which multiple QD-tagged roadblocks were pushed into one another, but in these cases we could not determine the order in which each QD-protein was displaced from the DNA, and therefore could not measure sliding distances. For categorizing the event type distributions we defined "sliding" as any QD-tagged roadblock that moved more than 0.53 μm (1,950 bp), and anything less than this was scored as a direct dissociation event.

Protein Cloning and Purification.

RecBCD was purified from *E. coli* JM109 co-transformed with plasmids pPB800 and pPB520, which were a generous gift from Dr. Jeff Gelles (Brandeis University)[G1,G2] Cells were grown in 2YT in the presence of 34 μg ml$^{-1}$ chloramphenicol and 50 μg ml$^{-1}$ carbenicillin. The cells were grown to an $OD_{600}$~0.6, induced with IPTG, collected 4 hours after induction, resuspended in buffer R (50 mM Tris-HCl pH 7.5, 0.1 mM PMSF, 10% sucrose), and lysed by freezing and sonication[G1]. The lysate was clarified by high-speed centrifugation and fractionated with 0.282 g ml$^{-1}$ ammonium sulfate. The precipitated protein was recovered by centrifugation at 20,000 g for 20 mM. The pellet was resuspended in buffer A (20 mM Tris-HCl [pH 7.5], 0.1 mM DTT, 0.1 mM EDTA) and loaded onto a 5 ml HiTrap Q FF column (GE Healthcare). The protein was eluted with a gradient to 100% buffer B (20 mM Tris-HCl [pH 7.5], 0.1 mM DTT, 0.1 mM EDTA, 1 M NaCl). The protein-containing fraction were diluted with buffer A to a final NaCl concentration of less than 0.1 M, and loaded onto a HiPrep Heparin 16/10 FF column (GE Healthcare). The protein was eluted with a gradient to 50% buffer B, loaded directly onto a Mono Q 5/50 GL column, and eluted with a gradient to 100% buffer B. The pooled protein fractions were loaded onto a HiPrep 16/60 Sephacryl S-300 HR column (GE Healthcare). Following purification, the protein was dialyzed into storage buffer (50 mM Tris-HCl [pH 7.5], 0.1 M NaCl, 0.1 mM EDTA, 1 mM DTT, 50% glycerol) and stored at −20° C. Care was taken to minimize exposure of the protein to high NaCl concentrations to avoid dissociation of the RecD subunit[G3]. Protein concentration was determined using $\epsilon_{280}=4\times 10^5$ $M^{-1}$ $cm^{-1}$ [G3]. An 8% SDS-PAGE gel stained with SafeStain (Invitrogen) indicated that the preparation was >95% pure with a 1:1:1 ratio for the three protein components. Exonuclease and DNA-dependent ATPase activities were assayed for the wild type protein (see below)[G1,G3,G4].

Wild-type EcoRI was purchased from New England Biolabs. Constructs encoding the hydrolytically defective EcoRI$^{E111Q}$ were also used[G5,G6]. For overexpression and purification the gene for EcoRI$^{E111Q}$ was sub-cloned into the pTXB3 vector (New England Biolabs), generating vector pTXBERI. To prepare EcoRI$^{E111Q}$ with a triple FLAG epitope tag repeat, the EcoRI$^{E111Q}$ gene was PCR amplified with oligos IF01 and IF02 (see Table 2).

gation and loaded onto a chitin binding domain column according to the manufacturer suggested protocol (New England Biolabs). The column was washed with 20 column volumes of washing buffer W (20 mM Tris-HCl [pH 8.5] and 0.5 M NaCl). The intein-CBD tag was cleaved by flushing the column with buffer W supplemented with 50 mM DTT and incubating overnight at 4° C. Protein-containing fractions were pooled, dialyzed into storage buffer (40 mM Tris-HCl [pH 7.5], 300 mM NaCl, 10 mM 2-Mercaptoethanol, 0.1 mM EDTA, 50% Glycerol, 0.15% Triton X-100), and stored at −20° C.

Wild-type RNA polymerase holo- and core-enzymes were purchased from Epicentre Biotechnologies, which were used in bulk experiments as controls. The single molecule experiments used either FLAG tagged RNAP or biotinylated RNAP. RNA polymerase containing an N-terminal 6-His (SEQ ID NO: 12) and C-terminal triple FLAG tagged a-subunit were prepared from constructs described in[G7]. Plasmid p706a[G7] was digested with BsiWI and XhoI and ligated with oligos 1F03 and 1F04 (see Table 2). The resulting plasmid, p706a-3FL, was transformed into HMS174 (DE3) pLysS cells. The 6His-tagged ("6His" disclosed as SEQ ID NO: 12) RNA polymerase was purified as described previously[G7-G9]. Prior

TABLE 2

Oligonucleotides.

| SEQ ID NO: | Name | Sequence |
|---|---|---|
| 8 | IF01 | CGGCATCAGGCCATGGATTACAAAGATGACGACGATAAGGATTACAAAGATGACGACGAT AAGGATTACAAAGATGACGACGATAAGGCTGCCGCAATGTCTAATAAAAAACAGTC |
| 9 | IF02 | TTTATAGCTCTTCCGCACTTAGATGTAAGCTG |
| 10 | IF03 | [P] GTACGATTACAAAGATGACGACGATAAGGATTACAAAGATGACGACGATAAGGATTA CAAAGATGACGACGATAAGTAAC |
| 11 | IF04 | [P] TCGAGTTACTTATCGTCGTCATCTTTGTAATCCTTATCGTCGTCATCTTTGTAATCC TTATCGTCGTCATCTTTGTAATC |
| 13 | IF05 | [P] TCGAAGCTGGTGGACTAGTAGCTGCTGGTGGTTAATTAACTGCTGGTGGA |
| 14 | IF06 | [P] CTAGTCCACCAGCAGTTAATTAACCACCAGCAGCTACTAGTCCACCAGCT |
| 15 | IF07 | [P] AGGTCGCCGCCC [B] |
| 16 | IF08 | [P] GGGCGGCGACCT [B] |
| 17 | IF09 | TCAGATCTCTCACCTACCAAAC |
| 18 | IF10 | AGGGCGGTTAACTGGTTTTG |
| 19 | IF11 | CTCAGATTTCATGAAACCAGTAACGTTATACG |
| 20 | IF12 | ACTCTACTAGTGTCATCTCCCGTGATGCACGCATCGATTAACTGCCCGCTTTCCAGTC |
| 21 | IF13 | [P] TCGAATGTGTGGAATTGTGAGCGCTCACAATTCCACACAACTAGTATGAGCTTAATT AAA |
| 22 | IF14 | [P] CTAGTTTAATTAAGCTCATACTAGTTGTGTGGAATTGTGAGCGCTCACAATTCCACA CAT |

† Phosphates at 5' positions are marked with a [P].
Biotin at the 3' end is marked with a [B].

The PCR amplicon was digested with SapI and NcoI (New England Biolabs) and ligated into pTXB3 to generate plasmid pTXBERI-3FL. The plasmid was transformed into HMS174 DE3 (pLysS) cells. The cells were grown to an $OD_{600}$~0.6 in the presence of 34 µg ml$^{-1}$ chloramphenicol and 50 µg ml$^{-1}$ carbenicillin, induced with IPTG, collected 4 hours after induction, resuspended in buffer R, and lysed by freezing and sonication. The lysate was clarified by high-speed centrifuto separation of the holo- and core enzymes on a MonoQ column[G9], an additional HisTrap column was used to separate the FLAG tagged from wild-type proteins[G7]. Experiments employing a biotinylated RNA polymerase were purified from a construct described in[G10]. Cells harboring a chromosomal copy of the E. coli RNA polymerase with an in vivo biotynilation peptide on the C-terminus of the β' subunit were purified as described[G8,G9] and the core and holoenzyme fractions were separated on a MonoQ column[G9]. Protein activity for all RNAP constructs was assayed by in vitro transcription runoff assays (see below).

Nucleosomes where prepared as described[G11]. Histones (H2A, H2B, H3, H4 and 3×FLAG-H3) were expressed in *E. coli*, purified from inclusion bodies and reconstituted as described[G12]. In brief, inclusion bodies were resuspended in unfolding buffer (7 M guanidinium-HCl, 1 M NaCl, 50 mM Tris-HCl [pH 7.8], 1 mM EDTA, 1 mM DTT), dialyzed against urea buffer (7 M urea, 10 mM Tris-HCl [pH 7.8], 1 mM EDTA, 5 mM β-mercaptoethanol and 100 mM NaCl for H2A, H2B, 3×FLAG-H3 or 200 mM NaCl for H3, H4), then loaded onto tandem HiTrap Q and SP columns (GE Healthcare). 3×FLAG-H2B was expressed in *E. coli*, precipitated from cell lysate in 50% $NH_3SO_4$, dialyzed against urea buffer and 100 mM NaCl and loaded onto HiTrap SP column (GE Healthcare). Histones were eluted from the SP column with a 100-400 mM NaCl gradient for H2A, H2B, and 3×FLAG-H2B and 3×FLAG-H3 and a 200-500 mM NaCl gradient for H3 and H4. Purified histones were dialyzed against 10 mM Tris-HCl [pH 7.8] plus 5 mM β-mercaptoethanol, followed by 10 mM Tris-HCl [pH 7.8], then lyophilized and stored at −20° C. Lyophilized histones were unfolded in 7 M guanidinium-HCl, 50 mM Tris-HCl [pH 7.8] plus 10 mM DTT, combined at equimolar ratios, and dialyzed into 2 M NaCl, 20 mM Tris-HCl [pH 7.8], 1 mM EDTA, 5 mM β-mercaptoethanol with several buffer changes over 48 hours. Reconstituted octamers were purified by gel filtration and deposited onto DNA by salt dialysis[G12,G13].

Wild-type LacI was PCR amplified for plasmid pTYB21 (New England Bioloabs) using oligos IF11 and IF12 and sub-cloned into pTXB3, generating pTXLACI. A $FLAG_6$ epitope tag was introduced at the C-terminus by ligating oligos encoding FLAG repeats at the C-terminal ClaI restriction site to generated pTXLACI-6FL. Plasmids encoding either wt or FLAG-labeled LacI were transformed into BL21 (DE3) cells, grown to $OD_{600}$~0.6 in the presence of 50 µml$^{-1}$ carbenicillin, and induced with 2.5 mM IPTG. After a three-hour induction, the cells were harvested and purified using the same protocol as for EcoRI (see above).

Bulk Characterization of RecBCD.

RecBCD activity was verified using ATPase reactions under the same buffer conditions as the single-molecule flow-cell assay. Reaction mixtures containing 1.5 nM (in molecules; 3 nM in DNA ends) λ-DNA (New England Biolabs), 0.1 µM [α-$^{32}$P]ATP, 1 mM ATP, 40 mM Tris-HCl [pH 8], 2 mM $MgCl_2$, 0.2 µg µl$^{-1}$ BSA, and 1 mM DTT. For the time courses, reactions contained 0.1 nM RecBCD and were terminated with the addition of EDTA to a final concentration of 80 mM after incubations for the indicated periods (FIG. 67). Reaction products were resolved by thin layer chromatography on PEI-cellulose (Sigma Aldrich) run in 0.5 M formic acid with 0.5 M LiCl. Products were detected with a PhosphorImager, and analysis was done with ImageQuant 5.2 software.

Exonuclease assays were carried out essentially as described previously[G14] and confirmed the proteins were fully active. Under reaction conditions were [ATP]<<[$Mg^{2+}$], RecBCD nuclease activity produces short oligonucleotide products that can be separated from intact duplex DNA by trichloroacetic (TCA) acid precipitation[G14,G15]. Exonuclease activity was followed by observing the time dependent release of radio-labeled oligonucleotides that remain soluble after TCA precipitation. Substrate DNA was produced by PCR amplifying a 965 bp region of λ-DNA (primers: 5'-GCTGGCTGACATTTTCGGTGC-3' [SEQ ID NO: 23] and 5'-GCCACGCCCATTAGTGAAACG-3' [SEQ ID NO: 24]) using Pfu DNA polymerase (Stratagene) as described by the manufacturer with the addition of 1 µCi [α-$^{32}$P]dATP. The PCR product was purified with a Qiagen MinElute kit, and the concentration quantified by UV-VIS, assuming one $OD_{260}$ unit is 50 µg ml$^{-1}$ for dsDNA. The specific activity of the dsDNA was determined to be 356,000 cpm nmol$^{-1}$ using liquid scintillation counting.

Reactions containing 50 mM Tris HCl [pH 8.5], 10 mM $MgCl_2$, 40 µM ATP, 40 µM dsDNA (in nucleotides), 0.67 mM DTT, and 0.2 µg µl$^{-1}$ BSA were pre-incubated at 37° C. for several minutes. Reactions were initiated by addition of RecBCD (in reaction buffer minus DNA and ATP) to a final concentration of 0.1 nM. At the indicated time points, 20 µL aliquots were withdrawn and quenched by adding 100 µL of 10% ice-cold TCA and 5 µL of 0.5 mg ml$^{-1}$ sheared salmon sperm DNA (Ambion). The quenched aliquots were kept on ice for at least ten minutes, and undigested DNA collected as an invisible pellet by centrifugation at ~14,000 rcf for 10 minutes at 4° C. Following centrifugation, 110 µL of the supernatant was added to 5 mL of scintillation counting fluid (Fisher Scientific) and quantified by liquid scintillation counting. All measurements were performed at least three times. Control experiments containing all components except ATP indicated no nuclease activity.

Bulk Characterization of RNA Polymerase.

RNA polymerase run-off transcription assays were performed to ensure that the introduction of an epitope tag and QD labeling did not adversely affect enzymatic activity (FIG. 68). A 467 bp segment of λ-DNA containing the $λP_L$ promoter was amplified by PCR using cloned Pfu DNA polymerase (Stratagene) and primers IF09 and IF10. The amplicon was purified with a QIAGEN PCR purification kit[G16]. Transcription assays were carried out in 25 µl reactions containing transcription buffer (40 mM Tris-HCl [pH 8.0], 150 mM KCl, 10 mM $MgCl_2$, 250 µM each rNTP) supplemented with 0.5 µCi [α-$^{32}$P]ATP, 40 U SUPERase•In RNAse inhibitor (Ambion), 40 nM dsDNA template, and 20 nM holo-RNA polymerase. When indicated, QDs were added to a final concentration of 40 nM. The reaction was incubated for 1 hr at 37° C. Reactions were centrifuged through a NucAway desalting column (Ambion) and mixed with 2×RNA loading dye solution (Fermentas). Transcription products were resolved on 6% polyacrylamide-urea gels (Invitrogen). Gels were run at room temperature for 1 hr (constant voltage, 175V) in 1×TBE running buffer. The expected transcription products[G16] were detected with a Typhoon PhosphorImager (GE), and analysis was done with ImageQuant 5.2 software.

Single-turnover transcription experiments were performed on stalled RNAP elongation complexes to determine the percent of stalled polymerases that can re-initiate transcription[G17]. Stalled complexes were prepared by incubating 20 nM holo RNAP with 40 nM dsDNA template in transcription buffer supplemented with 40 U SUPERase•In RNAse inhibitor, 150 µM ApU (RiboMed), 0.5 µCi [α-$^{32}$P]ATP and 25 µM each of rATP, rCTP, rGTP. The reaction was incubated for ten minutes at 37° C. Half of the reaction was quenched with EDTA to 25 mM and kept on ice. The second half-reaction was rapidly supplemented with 0.1 mg/ml heparin and 250 µM each of rATP, rCTP, rGTP, rUTP. After a five minute incubation at 37° C., transcription products were resolved on an 18% polyacrylamide-urea gel (Invitrogen). Gels were run at room temperature for 1:45 hr (constant voltage, 175V) in 1×TBE running buffer and analyzed as above. All transcription reactions were repeated at least three times.

Bulk Characterization of EcoRI$^{E111Q}$.

EcoRI digestion protection assays were performed essentially as described[G18]. λ-DNA (1.5 nM; five EcoRI sites) was incubated with 30 nM EcoRI$^{E111Q}$ (concentration in dimers) in binding buffer (25 mM Tris-Cl [pH 8.0], 150 mM NaCl, 1 mM DTT, 0.2 µg µl$^{-1}$ BSA, 10 mM MgCl$_2$) for 30 minutes on ice, followed by 2 minutes at 37° C. Where indicated, QDots were included as a two-fold excess over EcoRI$^{E111Q}$ dimers. DNA-EcoRI$^{E111Q}$ complexes were challenged with 10 U µl$^{-1}$ wtEcoRI (New England Biolabs) for 5-60 minutes at 37° C. Reactions were stopped with 20 mM EDTA, 0.5% SDS and deproteinized with 1 mg ml$^{-1}$ Proteinase K for 30 minutes at 50° C. The products were run at 80V on a 0.6%, room temperature agarose gel, stained with ethidium bromide, and imaged on a UV trans-illuminator (SynGene). Time-courses were in agreement with previously published results[G18]. All assays were repeated at least three times.

DNA Substrates for Single Molecule Experiments.

Most experiments used bacteriophage λ (48,502 bp) lacking a Chi-sequence. To determine whether RecBCD could strip obstacles when RecB was the lead motor a triple Chi-sequence[G19] was cloned into bacteriophage λ. In vitro, RecBCD recognizes each Chi-sequence with a 30% probability[G20] and a triple Chi-sequence repeat was previously shown to be recognized by 90% of translocating RecBCD molecules[G19]. Phage DNA harboring the cI857 and S7 mutations (New England Biolabs) was digested with XhoI and NheI and ligated with oligos IF05 and IF06 (Table S2), which abolish both cut sites. The ligated product was digested again with XhoI and NheI prior to phage DNA packaging according to the manufacturer supplied protocol (EpiCentre). Individual phage plaques were screened for the insert by PCR and confirmed by DNA sequencing. Phage particles were isolated from heat-inducible *E. coli* lysogens and the DNA containing the Chi locus was purified with a commercial phage DNA extraction kit (Qiagen). The final DNA construct containing Chi was 47,321 bp.

For experiments with LacI-RecBCD collisions, a single high-affinity "ideal" LacO sequence[G21] was introduced into λ-phage by ligating the complimentary oligonucleotides IF13 and IF14 between XhoI and NheI restriction sites, as described above. The final DNA construct containing LacO was 47,331 bp.

Phage DNA with a biotinylated cos end was prepared according to previously published protocols[G22]. Briefly, the cos end was annealed with oligos IF07 or IF08 (Table 2), ligated and filtered over an Sephacryl S-200 HR column (GE Healthcare) to remove excess oligonucleotide and ligation reaction components.

Quantum Dot Preparation.

Streptavidin-quantum dots (QDs) were purchased from Invitrogen. To prepare antibody labeled QDs, amine-functionalized QDs were labeled with affinity purified, reduced anti-FLAG antibodies (Sigma-Aldrich) using SMCC (succinimidyl 4-[N-maleimidomethyl]cyclohexane-1-carboxylate). The resulting QD-antibody conjugates were then purified over a Superdex 200 10/300 GL gel filtration column (GE Healthcare), and were stored in PBS [pH 7.4] at 4° C. Although the manufacturer-reported antibody:QD ratio is ~4:1, the percentage of QDs with an active antibody may be substantially lower[G23]. There may be "dark" proteins that are not coupled to QDs or QDs that are not fluorescent[G24]. The presence of dark QDs or unlabeled proteins would increase the total number of RecBCD-roadblock collisions, but those involving dark roadblocks would not be observed. The possible presence of dark roadblocks does not affect any of our conclusions.

Nanofabrication, Flowcells, Lipid Bilayers, and DNA Curtains.

A complete description of the DNA curtains made with nanofabricated diffusion barriers containing geometric nanowells can be found in Visnapuu et al., 2008[G25]. In brief, fused silica slides (G. Finkenbeiner, Inc.) were cleaned in NanoStrip solution (CyanTek Corp, Fremont, Calif.) for 20 minutes, rinsed with acetone and isopropanol and dried with N$_2$. Slides were spin-coated with a bilayer of polymethylmethacrylate (PMMA; 25K and 495K; MicroChem, Newton, Mass.), followed by a layer of Aquasave (Mitsubishi Rayon). Patterns were written with a FEI Sirion scanning electron microscope (J. C. Nabity, Inc., Bozeman, Mont.). Aquasave was removed with deionized water and resist was developed using isopropanol:methyl isobutyl ketone (3:1) for 1 minute with ultrasonic agitation at 5° C. The substrate was rinsed in isopropanol and dried with N$_2$. Barriers were made with a 15-20 nm layer of chromium (Cr), and following liftoff, samples were rinsed with acetone and dried with N$_2$, as described[G25].

Inlet and outlet ports were made by boring through the slide with a precision drill press equipped with a diamond-tipped bit (1.4 mm O.D.; Kassoy). The slides were cleaned by successive immersion in 2% (v/v) Hellmanex, 1 M NaOH, and 100% MeOH. Slides were rinsed with MilliQ™ between each wash and stored in 100% MeOH until use. Prior to assembly, slides were dried under a stream of nitrogen and baked in a vacuum oven for at least 1 hour. A sample chamber was prepared from a borosilicate glass coverslip (Fisher Scientific) and double-sided tape (~100 µm thick, 3M). Ports (Upchurch Scientific) were attached with hot-melt adhesive (SureBonder glue sticks, FPC Corp.). The total volume of the sample chambers was ~14 µl. A syringe pump (Kd Scientific) and actuated injection valves (Upchurch Scientific) were used to control sample delivery. The flowcell and prism were mounted in a custom-built heater with computer-controlled feedback regulation.

Lipids were purchased from Avanti Polar Lipids and liposomes were prepared as previously described[G25]. In brief, a mixture of DOPC (1,2-dioleoyl-sn-glycero-phosphocholine), 0.5% biotinylated-DPPE (1,2-dipalmitoyl-sn-glycero-3-phosphoethanolamine-N-(cap biotinyl)), and 8% mPEG 2000-DOPE (1,2-dioleoyl-sn-glycero-3-phosphoethanolamine-N-[methoxy(polyethylene glycol)-2000]). The mPEG prevented nonspecific adsorption of QDs. Liposomes were applied to the sample chamber for 30 minutes. Excess liposomes were removed with buffer containing 10 mM Tris-HCl [pH 7.8] and 100 mM NaCl. The sample chamber was then flushed with buffer A (40 mM Tris-HCl [pH 7.8], 1 mM DTT, and 1 mM MgCl$_2$) plus 0.2 mg ml$^{-1}$ BSA for 5 minutes. Streptavidin (0.02 mg ml$^{-1}$) in buffer A was injected into the sample chamber and incubated for 20 minutes. After rinsing with additional buffer A plus 0.2 mg ml$^{-1}$ BSA, λ-DNA (15-20 pM) labeled at one end with biotin and pre-stained with 0.5 nM YOYO1 was injected into the chamber, incubated for 10 minutes, and unbound DNA was removed by flushing with buffer at 0.1 ml min$^{-1}$. Application of flow aligned the DNA molecules along the diffusion barriers, pushed them into the nanowells, and stretched the molecules parallel to the sample chamber surface. We could readily distinguish nanowells harboring 1 DNA from those containing 2 or more molecules based on YOYO1 signal intensity[G25], and RecBCD translocation data were only collected from nanowells containing single full-length DNA molecules (see below).

Single Molecule Assays.

DNA curtains without any roadblock proteins were assembled on nanofabricated silica slides as described herein. (See also Fazio et al., Langmuir. 2008 Sep. 16; 24(18):10524-31). RecBCD was diluted to 20 nM in imaging (IM) buffer (40 mM Tris-HCl [pH 8.0], 2 mM MgCl$_2$, 1 mM DTT, 0.5 nM YOYO1 (Invitrogen), 50 mM β-mercaptoethanol, 1.4 mM glucose, glucose oxidase and catalase)[G26], and injected slowly (70 μl min$^{-1}$) into the flowcell over the course of several minutes. After excess RecBCD was washed out, the flow rate was increased to 400 μl min$^{-1}$, and data acquisition was initiated. At this flow rate, the DNA was approximately 80% extended relative to its full contour length (see below). A hundred frames were acquired prior to switching to digestion buffer (IM buffer supplemented with 1 mM ATP, unless otherwise indicated). Upon ATP injection, RecBCD begins to unwind and nucleolytically degrade dsDNA, leading to a reduction in DNA length and concomitant ejection of YOYO1, and the time-dependent DNA length is used as a readout of RecBCD translocation (see below)[G27,G28]. All experiments were conducted at 37° C.

DNA curtains with stationary holo- or core-RNA polymerase enzymes were prepared using biotinylated RNAP. The biotinylated polymerase was incubated with a five-fold molar excess of Streptavidin-conjugated QDs on ice for ~15 minutes. After labeling, the reaction was diluted to 1 nM RNA polymerase (5 nM QDs) with RNAP Buffer (40 mM Tris [pH 8.0], 100 mM KCl, 2 mM MgCl$_2$, 1 mM DTT, 0.2 mg ml$^{-1}$ BSA) supplemented with ~10 μM free biotin to block remaining streptavidin sites on the quantum dots. Prior to QD-RNAP injection, remaining biotin-binding sites on the flowcell surface-immobilized streptavidin were blocked by incubating the flowcell in imaging buffer containing ~10 μM free biotin. Control experiments indicated that all free flowcell streptavidin sites were blocked by biotin. QD-RNA polymerase was injected into the flowcell at 70 μl min$^{-1}$ in RNAP buffer over the course of several minutes. Inclusion of free biotin in the flow buffer further prevented potential interactions between the biotinylated enzyme and lipid-bound streptavidin. After all free RNA polymerase and biotin were flushed out of the sample chamber, flow was switched to IM buffer for further RecBCD experiments. Reactions with FLAG-tagged RNAP were carried out by pre-incubating 20 μl of ~150 pM λ-DNA with 1 μl of 100 nM FLAG-RNAP in RNAP buffer for 10 minutes at 37° C. The reaction was diluted to a total volume of 1 ml with RNAP buffer, injected into the flowcell, and incubated 5 minutes at room temperature, allowing the biotinylated ends to attach to the streptavidin on the lipid bilayer surface. Excess DNA and RNAP were flushed out and the FLAG-tagged proteins were labeled in situ by flushing 700 μl of 1 nM anti-FLAG QDs through the flowcell in IM buffer. The use of FLAG-tagged RNAP eliminated the need to block the sample chamber surface with free biotin.

Experiments involving transcribing RNA polymerase molecules were carried out using the FLAG-tagged construct. Stalled elongation complexes were prepared on λ-DNA as described[G7,G8]. Briefly, holo-RNA polymerase was diluted to 15 nM in 20 μl of Buffer T (10 mM Tris [pH 8.0], 100 mM KCl, 10 mM MgCl$_2$, 1 mM DTT) supplemented with 150 pM λ-DNA, 150 μM ApU, 25 μM rATP, 25 μM rGTP, and 25 μM rCTP for 10 minutes. After incubation, the reaction was diluted to a total volume of 1 ml with RNAP buffer supplemented with 0.2 mg ml$^{-1}$ heparin, injected into the flowcell, and incubated 5 minutes at room temperature. Heparin effectively competes for DNA binding, dissociating all RNAP complexes that are bound at nonspecific λ-DNA sites (see FIG. 68)[G29]. Free proteins and rNTPs were washed out and the DNA-bound RNA polymerases were labeled in situ with anti-FLAG QDs as described above. Active elongation complexes were prepared from stalled ECs by injecting buffer T supplemented with 250 μM CTP, GTP, UTP, and 1 mM ATP (to maintain consistent RecBCD velocity).

For DNA curtain assays using EcoRI$^{E111Q}$, 20 μl of ~150 pM λ-DNA (750 pM EcoRI sites) was incubated with 1 μl of 100 nM EcoRI$^{E111Q}$ (concentration in dimers) in EcoRI Buffer (10 mM Tris-HCl [pH 8.0], 150 mM NaCl, 10 mM MgCl$_2$, 0.2 mg ml$^{-1}$ BSA) for 30 minutes on ice, followed by 5 minutes at 37° C. The reaction was diluted to a total volume of 1 ml with EcoRI buffer, injected into the flowcell, and incubated 5 minutes at room temperature allowing the biotinylated DNA ends to attach to the streptavidin on the lipid bilayer surface. Excess DNA and EcoRI$^{E111Q}$ were flushed out and the FLAG tagged proteins were labeled in situ as described above.

DNA curtains with specifically-bound LacI were constructed as for EcoRI$^{E111Q}$ above. λ-DNA containing LacO (20 μl of ~150 pM DNA) was incubated with 1 μl of 50 nM LacI (concentration in dimers) in LacI Buffer (10 mM Tris-HCl [pH 8.0], 150 mM NaCl, 1 mM EDTA, 0.2 mg ml$^{-1}$ BSA) for 5 minutes at 37° C. The reaction was diluted to a total volume of 1 ml with LacI buffer. After the DNA curtain was constructed and excess protein and DNA flushed out of the flowcell, LacI was labeled with antiFLAG QDs in situ.

Control experiments with LacI incubated with wild type λ-DNA (lacking a LacO sequence) indicated that the enzyme bound the non-specific DNA transiently and rapidly dissociated from the DNA in the presence of buffer flow. Lifetimes of non-specific LacI-DNA complexes were estimated by incubating FLAG-LacI with a five-fold excess of antiFlag-QDs and injecting the enzyme into flow-cells with pre-formed wild type λ-DNA curtains. The reaction buffer, flow rate and illumination conditions were identical to those used for RecBCD digest experiments. Under these conditions, we observed a number of transient and DNA-specific LacI binding events (N=445) that lasted 0.2-5 seconds. A histogram of 445 LacI-DNA association events (data not shown) was fit with an exponential lifetime of 0.24 seconds, but since the majority of observed events lasted one frame (0.2 seconds), we report an upper bound of 300 msec for the non-specific half-life.

Nucleosome-bound DNA curtains were constructed as described previously[G11] and the nucleosomes were labeled in situ by flowing 700 μl of 2 nM antiFLAG QDs through the flowcell in IM buffer. Nucleosome collision experiments were conducted as described above for RNAP EcoRI$^{E111Q}$ and LacI.

Single Molecule Data Collection and Analysis.

The custom-built total internal reflection microscope used in this study has been described previously[G25,G30] Streams of 1000-3000 images were acquired at 5.0 Hz using a 200-millisecond integration time. For RecBCD experiments at lower ATP concentrations and roadblock dissociation measurements, the laser beam was shuttered for up to two seconds between individual 200 ms exposures. All data were collected using NIS-Elements software (Nikon) and saved as uncompressed, 16-bit TIFF files. A Dual-View image-splitting device (Optical Insights) with a dichroic mirror (630 DCXR, Chroma Technologies) was used for two-color detection. This set-up allowed us to simultaneously image the $\lambda_{em}$=705 nm QD-protein complexes and YOYO-stained DNA ($\lambda_{em}$=509 nm) on separate halves of the same CCD chip. Alignment of red and green channels was performed during post-processing (ImageJ software with "Align RGB Planes" plug-in) using dark signal from the nanofabricated barriers as a reference. Alignment was confirmed by observing fluorescent signals from surface imperfections that were occasionally observed in both channels. Aligned images were pseudo-colored and digitally recombined in ImageJ.

DNA length tracking for experiments involving RecBCD collisions with RNAP or EcoRI$^{E111Q}$ were performed using an automated algorithm (MATLAB) that iteratively fit the intensity profiles of individual YOYO-stained DNA molecules according to equation (1):

$$I(x) = \frac{A}{2}\text{erfc}\left(\frac{-(x_c - x)}{w}\right) + I_0 \tag{1}$$

where I(x) is the intensity of the YOYO1 signal at pixel x, A is the amplitude, $I_0$ is the intensity offset, $x_c$ is the center, and w the width of the complimentary error function defined by:

$$\text{erfc}(x) = \frac{2}{\sqrt{\pi}}\int_x^\infty e^{-t^2}\,dt$$

To improve signal-to-noise, the intensity profile for each DNA molecule, I(x), was computed by averaging the fluorescent signal from a fifty pixel long and two pixel wide region-of-interest that captured the most intense YOYO fluorescence. The algorithm described by equation (1) tracks the position of the free DNA end, as the surface-tethered DNA end is stationary at the diffusion barrier. The total length of the DNA molecule was defined as the distance between the tethered DNA end, $x_T$, and the free DNA end, $x_F = x_c + w$.

In experiments studying RecBCD collisions with nucleosomes, DNA length tracking was performed using a custom algorithm (IgorPro) that iteratively fit the images of individual YOYO-stained DNA molecules according to the equation (2):

$$I(x, y) = I_0 + A\frac{e^{\left(\frac{-(x-x_c)^2}{w^2}\right)}}{\left(1 + e^{\frac{(y_{min}-y)}{w}}\right)\left(1 + e^{\frac{(y-y_{max})}{w}}\right)} \tag{2}$$

Where I(x,y) is the YOYO1 intensity at pixel position (x,y). A is the amplitude, $I_0$ is the background intensity, $x_c$ is the center of the DNA, $y_{min}$ and $y_{max}$ are the top and bottom edges of the DNA, and w is the width of the point spread function.

For both cases, the conversion factor from pixels to base pairs for each flowcell was obtained by averaging the observed length of at least five full-length, undigested DNA molecules and dividing by the known number of base pairs. This conversion factor was computed for every flowcell prior to injection of RecBCD under the same imaging conditions. We restricted data analysis to individual DNA molecules that are full length at the start of the experiment, and are clearly separated from neighboring DNA. The resolution of the DNA tracking algorithm was estimated by tracking several hundred frames of full-length λ-DNA molecules under the same conditions as used for single molecule RecBCD digestion experiments. The fluctuations in the measured DNA length set a resolution of ~1,000 by for full-length λ-DNA.

QD-tagged proteins were tracked as described previously using an automated algorithm (MATLAB or IgorPro)$^{G11,G22}$. Briefly, the x and y positions of the point-spread function were fit to a 2D-Gaussian function in conjunction with a region-of-interest mask. Both the x-coordinates (i.e. perpendicular to the long axis of the DNA) and y-coordinates (i.e. parallel to the long axis of the DNA molecules) were recorded for each tracked particle. All RecBCD velocity histograms were fit to a Gaussian function using Origin Pro (OriginLabs, Inc.) and the reported values for the means and standard deviations were determined directly from the Gaussian fits to the data. Roadblock dissociation histograms were fit to a single exponential decay in Origin Pro and the reported values are for the half-life and standard fit error.

For all initial experiments, and for all kymograms shown in the manuscript, YOYO1 was used to stain the DNA and locate the curtains. YOYO1 did not affect the translocation rate or processivity of RecBCD, and did not affect the binding distributions of RNAP, EcoRI$^{E111Q}$, or nucleosomes. In the presence of YOYO1 the roadblocks showed the same general response to collisions with RecBCD as seen in the absence of YOYO1. However, when YOYO1 was present the overall distance that the obstacles were pushed was reduced compared to minus YOYO1 reactions, yielding values of 6720±4800, 6670±4390, and 6265±3555 base pairs for RNAP, EcoRI$^{E111Q}$, and nucleosomes respectively. The reduction in sliding distance, and the similarity of the three values suggests that the YOYO1 was inducing DNA damage (possible nicks) or otherwise perturbing the nucleoprotein complexes, and that the distances over which the obstacles were pushed were limited by the presence of the YOYO1 dye. Therefore all sliding distances and half-lives reported in the main manuscript correspond to values that were measured in the absence of any YOYO1.

Sliding distances were only reported for QD-tagged roadblocks that were pushed along the DNA and did not encounter any other QD-tagged proteins as they moved along the DNA. This ensures that each analyzed collision/dissociation event only involved a single QD-tagged protein. Many reactions were observed in which multiple QD-tagged roadblocks were pushed into one another, but in these cases we could not definitely determine the order in which each different QD-protein was eventually displaced from the DNA, and therefore could not measure sliding distances. Finally, for categorizing the event type distributions we defined "sliding" as any QD-tagged roadblock that moved more than 0.53 µm (approximately 1,950 bp), and anything less than this was scored as a direct dissociation event.

Polystyrene Bead and Alexa Fluor Dye Experiments.

Streptavidin-labeled 40-nm far-red fluorescent TransFluo-Spheres (488/645) were purchased from Invitrogen (Cat. No. T-10711). To prepare antibody labeled microspheres, 30 µL of 66 nM biotinylated monoclonal anti-FLAG antibodies (Sigma-Aldrich) in conjugation buffer (40 mM Tris-HCl [pH 8.0], 1 mM MgCl$_2$, 1 mM DTT, 0.2 mg/ml BSA) were incubated with 30 µL of TransFluoSpheres at stock concentration (0.5% solids) for 20 minutes on ice. The microsphere-antibody complexes were isolated from free antibodies by centrifugation at 16,100 RCF for 20 minutes at 4° C. The flowcell surface was blocked with 0.1× saturated biotin solution (C$_f$≈0.1 mM biotin) in conjugation buffer. The pelleted microsphere-anti-FLAG conjugates were diluted to 100 µl of 1M buffer and injected into flowcells that contained DNA curtains with pre-bound roadblock proteins as described for the QD labeling experiments. For experiments with biotinylated RNA polymerase, the bead-enzyme complexes was prepared as described above and injected into flow-cells with pre-formed DNA at a slow rate (0.05 ml/min) to facilitate binding of RNAP to the DNA curtain.

The Alexa 488 dye-labeled anti-FLAG antibodies were prepared according to the manufacturer's protocol (Invitrogen; Cat. No. A-20181). In brief, amine-reactive Alexa-Fluor 488 was reacted with monoclonal anti-FLAG antibody (Sigma-Aldrich) and purified on a size exclusion spin column. Labeling efficiency was calculated according to the manufacture's recommendation: Moles dye per mole protein=A494/(71,000×(M)), where 71,000 cm$^{-1}$M$^{-1}$ is the molar extinction coefficient of the Alexa Fluor 488 dye at 494 nm, and (M)=[A280−(A494×0.11)]/203,000, where 203,000 cm$^{-1}$M$^{-1}$ is the molar extinction coefficient of the antibody at 280 nm and 0.11 is a correction factor that accounts for the fluorophore's contribution to the absorbance at 280 nm. This calculation yielded a value of ~5 Alexa Fluor 488 dyes per antibody. The fluorescent antibodies were diluted to 5 nM in 1 ml of IM buffer and injected into the flowcell that contained DNA curtains with pre-bound roadblock proteins as described for the QD experiments. Single molecule RecBCD collision experiments were conducted with the bead- and Alexa-labeled roadblock proteins as described above for the QD-labeled roadblock proteins.

REFERENCES

[G1] Dohoney, K. M. & Gelles, J. Chi-sequence recognition and DNA translocation by single RecBCD helicase/nuclease molecules. *Nature* 409, 370-374 (2001).

[G2] Boehmer, P. E. & Emmerson, P. T. *Escherichia coli* RecBCD enzyme: inducible overproduction and reconstitution of the ATP-dependent deoxyribonuclease from purified subunits. *Gene* 102 (1991).

[G3] Roman, L. J. & Kowalczykowski, S. C. Characterization of the adenosinetriphosphatase activity of the *Escherichia coli* RecBCD enzyme: relationship of ATP hydrolysis to the unwinding of duplex DNA. *Biochemistry* 28, 2873-2881 (1989).

[G4] Roman, L. J. & Kowalczykowski, S. C. Characterization of the helicase activity of the *Escherichia coli* RecBCD enzyme using a novel helicase assay. Biochemistry 28, 2863-2873 (1989).

[G5] Wright, D. J., King, K. & Modrich, P. The negative charge of Glu-111 is required to activate the cleavage center of EcoRI endonuclease. *J Biol Chem* 264, 11816-11821 (1989).

[G6] King, K., Benkovic, S. J. & Modrich, P. Glu-111 is required for activation of the DNA cleavage center of EcoRI endonuclease. *J Biol Chem* 264, 11807-11815 (1989).

[G7] Adelman, K. et al. Single molecule analysis of RNA polymerase elongation reveals uniform kinetic behavior. *Proc Natl Acad Sci USA* 99, 13538-13543 (2002).

[G8] Nudler, E., Gusarov, I. & Bar-Nahum, G. Methods of Walking with the RNA Polymerase. *Methods Enzymol* 371, 160-169 (2003).

[G9] Hager, D. A., Jin, D. J. & Burgess, R. R. Use of Mono Q high-resolution ion-exchange chromatography to obtain highly pure and active *Escherichia coli* RNA polymerase. *Biochemistry* 29, 7890-7894 (1990).

[G10] Shaevitz, J. W., Abbondanzieri, E. A., Landick, R. & Block, S. M. Backtracking by single RNA polymerase molecules observed at near-base-pair resolution. *Nature* 426, 684-687 (2003).

[G11] Visnapuu, M. L. & Greene, E. C. Single-molecule imaging of DNA curtains reveals intrinsic energy landscapes for nucleosome deposition. *Nat Struct Mol Bio* 16, 1056-1075 (2009).

[G12] Thastrom, A., Lowary, P. T. & Widom, J. Measurement of histone-DNA interaction free energy in nucleosomes. *Methods* 33, 33-44 (2004).

[G13] Luger, K., Rechsteiner, T. J. & Richmond, T. J. Preparation of nucleosome core particle from recombinant histones. *Methods Enzymol* 304, 3-19 (1999).

[G14] Julin, D. A. Detection and quantitation of RecBCD enzyme (Exonuclease V) activity. *Methods Mol Biol* 152, 91-105 (2000).

[G15] Eichler, D. C. & Lehman, I. R. On the role of ATP in phosphodiester bond hydrolysis catalyzed by the recBC deoxyribonuclease of *Escherichia coli*. *J Biol Chem* 252, 499-503 (1977).

[G16] Washburn, R. S., Wang, Y. & Gottesman, M. E. Role of *E. coli* transcription-repair coupling factor Mfd in Nun-mediated transcription termination. *J Mol Biol* 329, 655-662 (2003).

[G17] Levin, J., Krummel, B. & Chamberlin, M. Isolation and properties of transcribing ternary complexes of *Escherichia coli* RNA polymerase positioned at a single template base. *J Mol Biol* 196, 85-100 (1987).

[G18] Pluciennik, A. & Modrich, P. Protein roadblocks and helix discontinuities are barriers to the initiation of mismatch repair. *Proc Natl Acad Sci USA* 104, 12709-12713 (2007).

[G19] Spies, M., Amitani, I., Baskin, R. J. & Kowalczykowski, S. C. RecBCD enzyme switches lead motor subunits in response to chi recognition. *Cell* 131, 694-705 (2007).

[G20] Anderson, D. G., Churchill, J. J. & Kowalczykowski, S. C. Chi-activated RecBCD enzyme possesses 5'→3' nucleolytic activity, but RecBC enzyme does not: evidence suggesting that the alteration induced by Chi is not simply ejection of the RecD subunit. *Genes Cells* 2, 117-128 (1997).

[G21] Sadler, J., Sasmor, H. & Betz, J. A perfectly symmetric lac operator binds the lac repressor very tightly. *Proc Natl Acad Sci USA* 80, 6785-6789 (1983).

[G22] Gorman, J. et al. Dynamic basis for one-dimensional DNA scanning by the mismatch repair complex Msh2-Msh6. *Mol Cell* 28, 359-370 (2007).

[G23] Pathak, S., Davidson, M. C. & Silva, G. A. Characterization of the functional binding properties of antibody conjugated quantum dots. *Nano Lett* 7, 1839-1845 (2007).

[G24] Yao, J., Larson, D. R., Vishwasrao, H. D., Zipfel, W. R. & Webb, W. W. Blinking and nonradiant dark fraction of water-soluble quantum dots in aqueous solution. *Proc Natl Acad Sci USA* 102, 14284-14289 (2005).

[G25] Visnapuu, M. L., Fazio, T., Wind, S. & Greene, E. C. Parallel arrays of geometric nanowells for assembling curtains of DNA with controlled lateral dispersion. *Langmuir: the ACS journal of surfaces and colloids* 24, 11293-11299 (2008).

[G26] Rasnik, I., McKinney, S. A. & Ha, T. Nonblinking and long-lasting single-molecule fluorescence imaging. *Nat Methods* 3, 891-893 (2006).

[G27] Bianco, P. et al. Processive translocation and DNA unwinding by individual RecBCD enzyme molecules. *Nature* 409, 374-378 (2001).

[G28] Spies, M., Amitani, I., Baskin, R. & Kowalczykowski, S. RecBCD enzyme switches lead motor subunits in response to chi recognition. *Cell* 131, 694-705 (2007).

[G29] Lozinski, T., Bolewska, K. & Wierzchowski, K. L. Equivalence of Mg2+ and Na+ ions in salt dependence of the equilibrium binding and dissociation rate constants of *Escherichia coli* RNA polymerase open complex. *Biophys Chem* 142, 65-75 (2009).

[G30] Graneli, A., Yeykal, C. C., Prasad, T. K. & Greene, E. C. Organized arrays of individual DNA molecules tethered to supported lipid bilayers. *Langmuir* 22, 292-299 (2006).

Example 15

Visualizing 1D-Diffusion of Eukaryotic DNA Repair Factors Along a Chromatin Lattice DNA-binding proteins survey genomes for targets using facilitated diffusion, which typically includes a one-dimensional (1D) scanning component for sampling local regions. Eukaryotic proteins must accomplish this task while navigating through chromatin. Yet it is unknown whether nucleosomes disrupt 1D scanning, or whether eukaryotic DNA-binding factors can circumnavigate nucleosomes without falling off DNA. Here we use single-molecule microscopy in conjunction with nanofabricated curtains of DNA to show that the post-replicative mismatch repair (MMR) protein complex Mlh1-Pms1 diffuses in 1D along DNA via a hopping/stepping mechanism and readily bypasses nucleosomes. This is the first experimental demonstration that a passively diffusing protein can traverse stationary obstacles. In contrast, Msh2-Msh6, an MMR protein complex that slides while maintaining continuous contact with DNA, experiences a boundary upon encountering nucleosomes. These differences reveal important mechanistic constraints impacting intranuclear trafficking of DNA-binding proteins.

Virtually all DNA-binding proteins must use some form of facilitated diffusion (e.g. hopping, jumping, sliding and/or intersegmental transfer) to scan the genome and locate targets[H1-H4]. The advent of single molecule imaging has led to a resurgence of interest in facilitated diffusion, and an emerging consensus agrees that many proteins can scan DNA via one-dimensional (1D) diffusion where the proteins undergo a random walk while moving laterally along the helix[H2-H7]. However, all of these studies have been limited to naked DNA substrates, which do not resemble the crowded environments that would be encountered in vivo, leaving the role of 1D-diffusion in question under physiologically relevant settings[H3,H4,H7]. In eukaryotes, these processes must occur within the context of chromatin, which has the potential to hinder protein mobility[H3,H4,H7,H8]. Motor proteins, such as RNA polymerase and other DNA translocases, solve this problem by using the chemomechanical energy derived from nucleotide hydrolysis to push their way through nucleosome obstacles[H3,H4,H7,H8]. However, most DNA binding proteins, such as transcription factors or DNA-repair proteins, cannot mechanically disrupt nucleosomes, therefore other mechanisms must come into play if these proteins are to scan chromatin. Whether or not proteins can circumnavigate nucleosomes without dissociating from DNA remains an unresolved issue with direct bearing on how all eukaryotic DNA-binding proteins are trafficked throughout the nucleus[H3,H4,H7,H8]. This problem led us to ask whether eukaryotic proteins that diffuse in 1D along DNA could circumnavigate individual nucleosomes and travel along nucleosomal arrays, and if so, what mechanistic principles affect mobility along chromatin.

We have chosen the post-replicative mismatch repair (MMR) protein complexes Msh2-Msh6 and Mlh1-Pms1 as model systems for studying the physical basis of facilitated diffusion. MMR is a ubiquitous repair pathway that corrects errors (mismatches and small insertion/deletion loops) left behind by the replication machine[H11-H13]. Defects in MMR lead to elevated mutation rates, are linked to hereditary nonpolyposis colon cancer (HNPCC), and are associated with many sporadic tumors[H12]. Msh2-Msh6 and Mlh1-Pms1 are DNA-binding proteins required for MMR. During MMR, Msh2-Msh6 must locate lesions and also helps identify nearby signals differentiating parental and nascent DNA strands, whereas Mlh1-Pms1 must locate lesion-bound Msh2-Msh6, and then coordinates downstream steps in the reaction. Although Msh2-Msh6 and Mlh1-Pms1 are both ATPases, neither uses ATP for generating chemomechanical force, rather nucleotide binding and hydrolysis are thought to serve as signaling mechanisms for coordinating the various stages of repair by regulating protein-protein interactions in the case of Mlh1-Pms1 or protein-DNA interactions with Msh2-Msh6[H11,H13]. These or closely related protein complexes are also involved in mitotic and meiotic recombination, triplet-repeat expansion, class-switch recombination, somatic hypermutation, and DNA-damage signaling checkpoints[H11]. All known functions of Msh2-Msh6 and Mlh1-Pms1 require targeting to specific structures within the genome, and the later stages of the MMR reaction involved in strand discrimination are also thought to involve 1D movement along DNA[H11-H13], making these protein complexes good candidates as model systems for single molecule studies of facilitated diffusion.

Results

Experimental Approach for Visualizing Protein-DNA Interactions.

Figure 84:
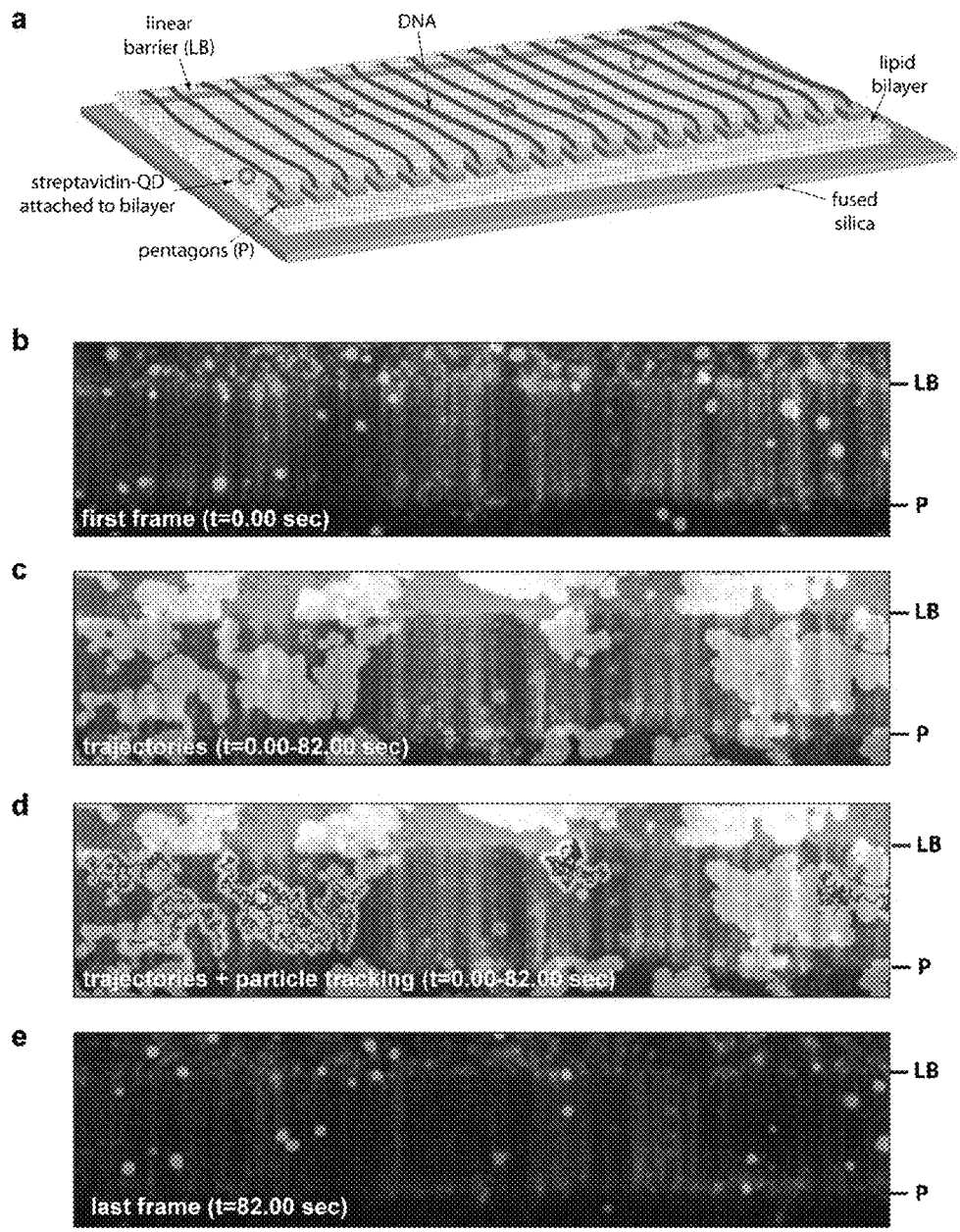
FIG. 84 shows that DNA curtains provide sufficient clearance for free passage of QDs.

Using total internal reflection fluorescent microscopy (TIRFM) we have previously demonstrated that Msh2-Msh6 moves on DNA via a sliding mechanism consistent with a model where it tracks the phosphate backbone[H14]. To determine whether Mlh1-Pms1 also moves on DNA, the proteins (FIG. 79A) were engineered with epitope tags (FLAG and/or HA), and labeled with antibody-coupled quantum dots (QDs). Gel shift and nitrocellulose filter-binding assays confirmed labeling specificity, and demonstrated that labeling did not disrupt DNA binding activity (FIGS. 80A-C). For TIRFM, we used microfluidic devices with hybrid surfaces comprised of fluid lipid bilayers and nanofabricated metallic barrier patterns made by electron-beam lithography[H15]. The DNA substrates (λ-DNA, 48,502 bp) were anchored by one end to the bilayer through a biotin-streptavidin linkage, and hydrodynamic force was then used to push the DNA and align it along the leading edges of nanofabricated barriers to lipid diffusion (FIG. 79A)[H15]. The second end of the DNA was then anchored to antibody-coated pentagons positioned downstream from the linear barriers (FIG. 79A)[H15]. This strategy yields "double-tethered" curtains of DNA in which the individual DNA molecules are suspended above a lipid bilayer and anchored by both ends such that they can be viewed across their entire contour length by TIRFM in the absence of a perturbing hydrodynamic flow (FIGS. 79B-C, FIG. 84).

Mlh1-Pms1 Binds and Diffuses on DNA Using a Stepping or Hopping Mechanism.

Figure 79:
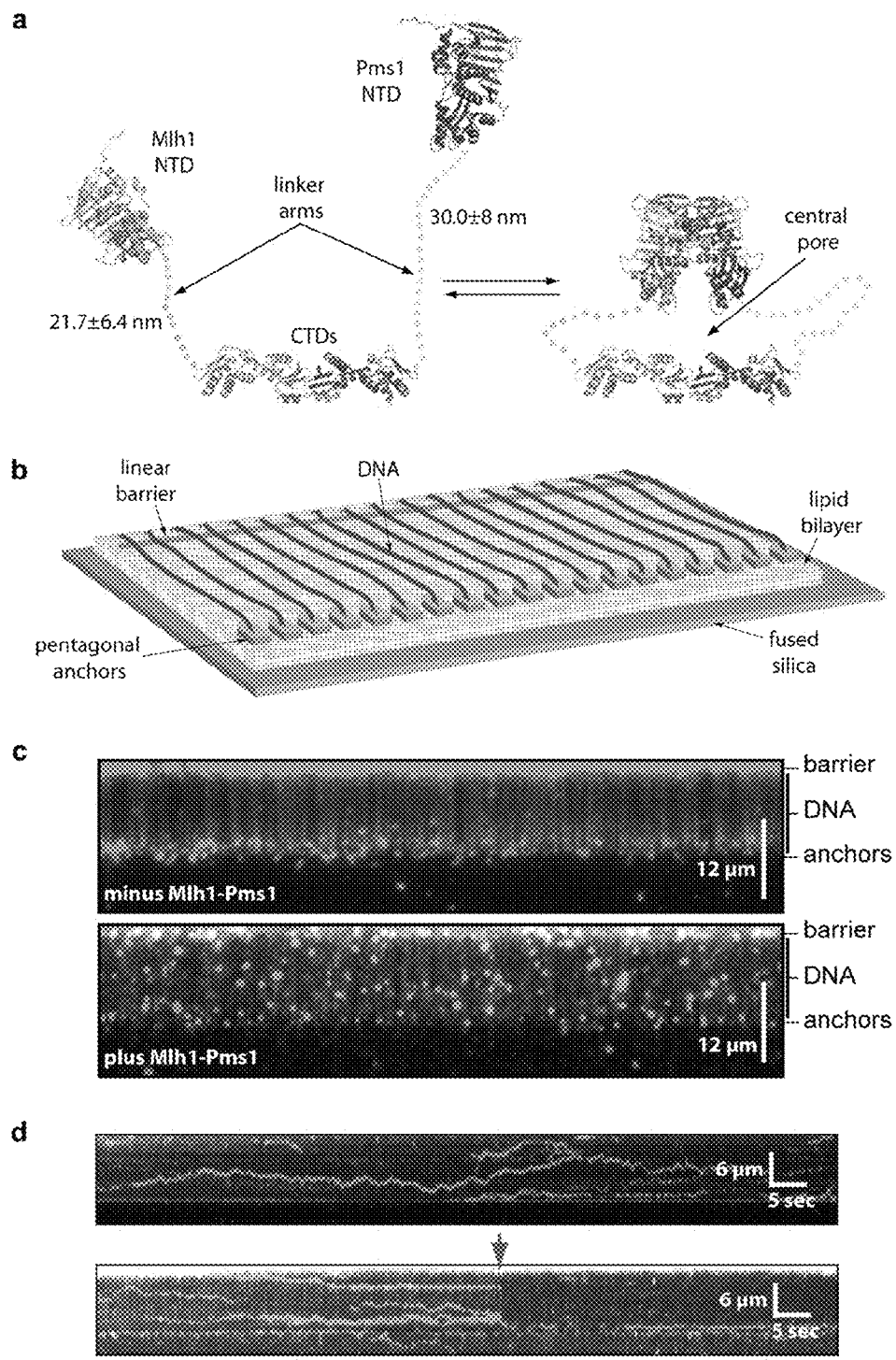
FIG. 79 shows nanofabricated racks of DNA for visualizing 1D diffusion of Mlh1-Pms1.
Figure 80:
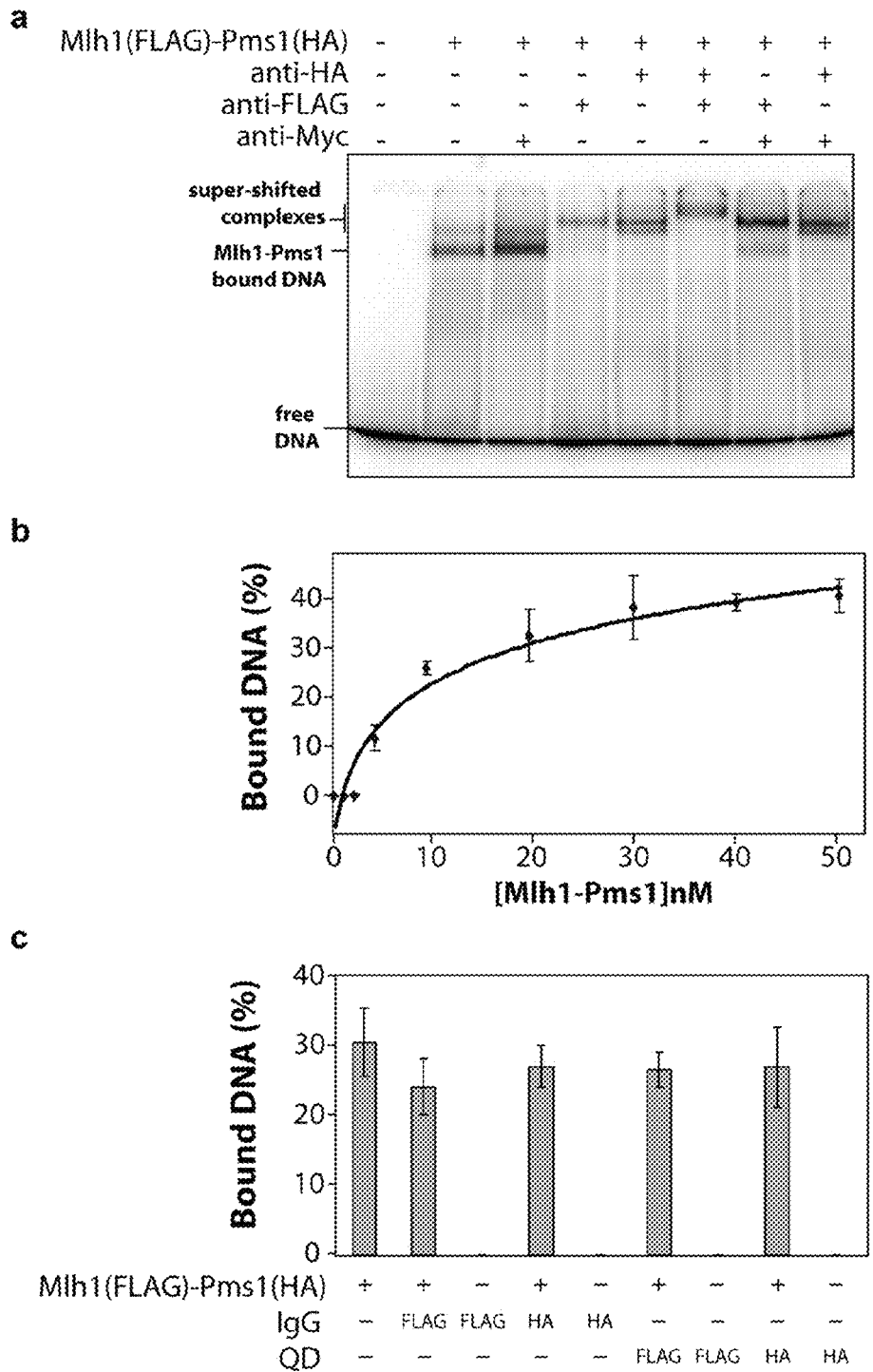
FIG. 80 shows DNA-binding activity of fluorescently tagged Mlh1-Pms1.

When imaged by TIRFM, Mlh1-Pms1 co-localized with DNA (FIG. 79C), and ≥95% of the DNA-bound proteins moved rapidly back and forth along the DNA molecules (FIG. 79D, Table 3).

TABLE 3

Binding and Movement of Proteins to DNA.

| | |
|---|---|
| Stuck to barrier | 127[†] |
| Stuck to bilayer | 14[†] |
| Bound to DNA | 203 |
| Stationary on DNA | 32 |
| stationary, not blinking | (25)[†] |
| stationary, blinking | (7) |
| Moving on DNA | 172[§] |
| not blinking | (27)[†] |
| too many collisions | (75) |
| lifetime too short | (48) |

TABLE 3-continued

Binding and Movement of Proteins to DNA.

| trackable | (22)‡ |
|---|---|
| Total QDs | 344 |

†Excluded from further consideration.
‡Trackable complexes over 250 consecutive frames and did not collide with other proteins.
§The percent of DNA-bound complexes that are moving is equal to the number of DNA bound complexes that were moving (145) divided by the total number of DNA-bound complexes (152) and yields a value of 95.4%. This calculation excludes any QDs that were not blinking Two-color labeling experiments revealed that most (98.4%) of the complexes were single heterodimers under the conditions used for these experiments. Mlh1-Pms1 often remained bound to the DNA for several minutes without dissociating (FIG. 79C), consistent with bulk biochemical studies[H16]. Analysis of the motion revealed linear MSD plots, as expected for 1D-diffusion (FIG. 81A)[H5,H1-H4], yielding a mean diffusion coefficient of $D_{1d}$=0.143±0.29 μm² sec⁻¹ (N=25) at 150 mM NaCl and 1 mM MgCl₂ (FIG. 81B). 1D-diffusion was observed ±ADP, ATP, and ATPγS (FIG. 81B), and the differences in the diffusion coefficients measured under the different nucleotide conditions were statistically insignificant (student t-test, p≥01). These results indicate that nucleotide binding and hydrolysis were unnecessary for movement, consistent with the notion that nucleotide binding is primarily involved in promoting protein-protein interactions or structural rearrangements with little impact on DNA-binding[H11,H13,H17].

Figure 81:
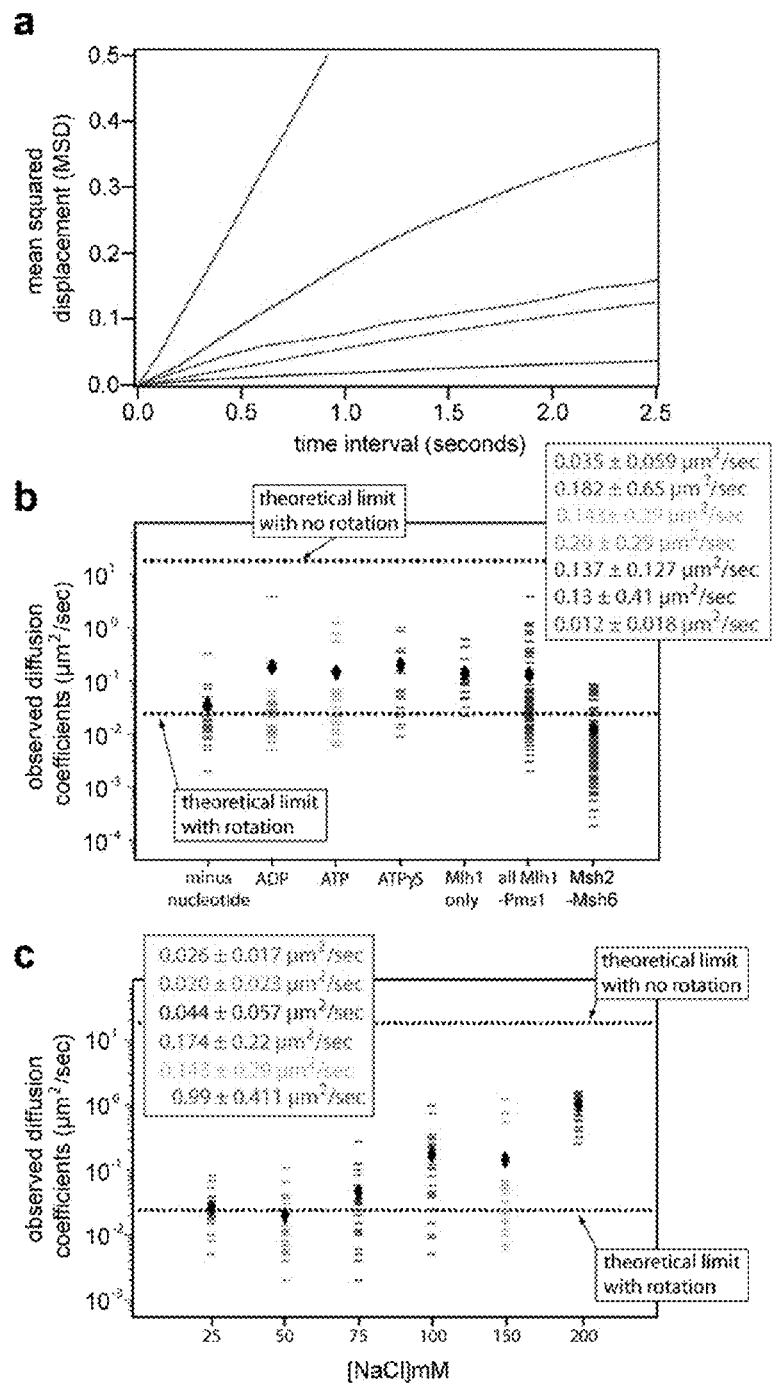
FIG. 81 shows a quantitative analysis of Mlh1-Pms1 diffusion.
Figure 85:
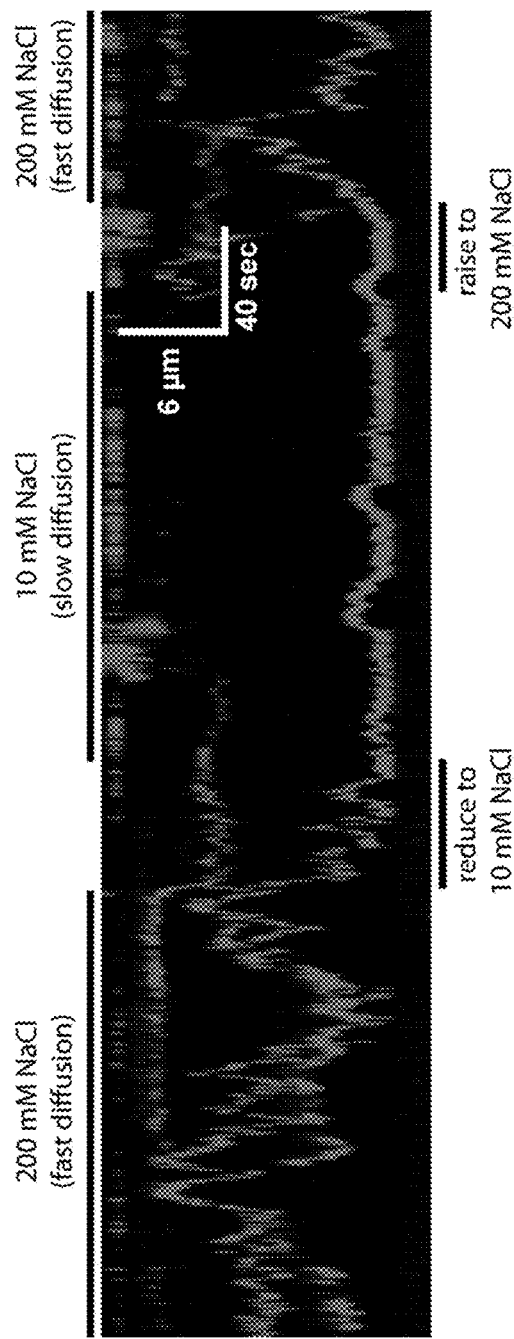
FIG. 85 shows salt-dependence of Mlh1-Pms1 1D diffusion. Mlh1-Pms1 was bound to a double-tethered DNA molecule at 200 mM NaCl and allowed to diffuse in the absence of buffer flow. At the 160-second time point (first arrowhead) the flow chamber was gently washed with buffer containing 10 mM NaCl. The wash was completed at the 232-second time point (second arrowhead) and Mlh1-Pms1 was monitored in the absence of buffer flow. A second wash was initiated at 360-seconds ($3^{rd}$ arrowhead) to raise the NaCl concentration back up to 200 mM, and this was completed at 420-seconds (fourth arrowhead). Buffer flow was then terminated and diffusion was allowed to proceed in the absence of flow. As shown here, the movement of Mlh1-Pms1 was highly dependent upon the concentration of NaCl, and the protein complex rapidly diffuses at high salt ($D_{1d}$=0.310 $\mu m^2$ $sec^{-1}$ at 200 mM NaCl), but diffuses much more slowly when the salt was reduced ($D_{1d}$=0.021 $\mu m^2$ $sec^{-1}$ at 10 mM NaCl; corresponding to a 14-fold decrease in the diffusion coefficient), and then begins rapid diffusion once the salt concentration was increased again ($D_{1d}$=0.281 $\mu m^2$ $sec^{-1}$ at 200 mM NaCl).

Mlh1-Pms1 diffusion coefficients were an order of magnitude greater (student t-test, p<0.0001) than Msh2-Msh6 under physiological salt concentrations (0.143±0.29 μm² sec⁻¹ vs. 0.009±0.011 μm² sec⁻¹ at 150 mM NaCl; FIG. 81B)[H14], suggesting the possibility that the two complexes might move via different mechanisms. Potential mechanisms for diffusive motion along DNA include hopping, jumping, sliding or intersegmental transfer. The structure of Mlh1-Pms1 (FIG. 79A)[H17-H20] also suggested a possible "stepping" mechanism, which is virtually identical to hopping, with the N-terminal and/or C-terminal domains (NTD and CTD) acting as DNA-binding domains that independently hop while connected by flexible linkers. Jumping would yield punctuate kymograms as a consequence of repeated dissociation and rebinding events, and cannot account for the continuous motion that predominated the diffusion trajectories; the stretched DNA configuration makes intersegmental transfer involving DNA-looping unlikely; and the 38-fold increase (student t-test, p<0.0001) in the diffusion coefficient measured over a range of salt concentrations argues against sliding ($D_{1d}$=0.026±0.017 μm² sec⁻¹ vs. 0.99±0.411 μm² sec⁻¹, at 25 and 200 mM NaCl, respectively; FIG. 81C, and FIG. 85), but is consistent with a hopping and/or stepping mechanism[H5,H21]. In contrast to Mlh1-Pms1, we have previously shown that the diffusion coefficient of Msh2-Msh6 does not vary over the same range of NaCl concentrations (see supplementary FIG. 3a from ref H14), which is most consistent with a sliding mechanism[H14]. We conclude that while Msh2-Msh6 and Mlh1-Pms1 both travel along DNA via 1D diffusion, they do so using different mechanisms: Msh2-Msh6 slides while in continuous contact with the phosphate backbone, whereas Mlh1-Pms1 hops or steps as it moves back and forth along DNA.

Mlh1-Pms1 Exhibits Properties Consistent with Ring-Like Architecture.

Figure 82:
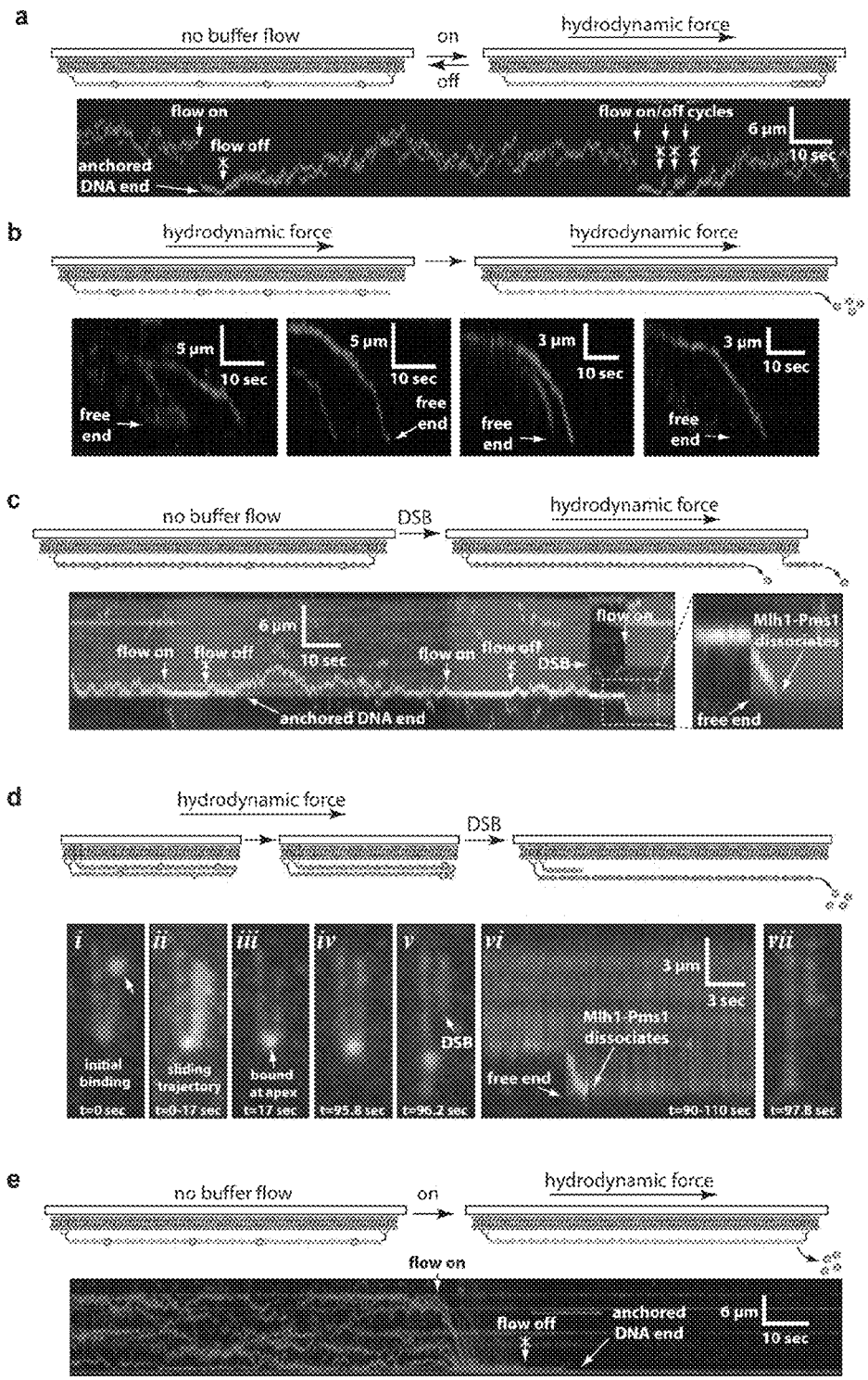
FIG. 82 shows end-dependent dissociation of Mlh1-Pms1 from DNA.

The Mlh1-Pms1 heterodimer is maintained through protein-protein interactions between the CTDs, and the NTDs and CTDs are separated by very long linker arms (FIG. 79A)[H17,H22]. It has been previously hypothesized that this structural organization allows Mlh1-Pms1 and related proteins to adopt a ring-like architecture, which would enable them to encircle DNA (FIG. 79A)[H19]. This type of topological binding mechanism makes several specific experimentally testable predictions, as follows: (i) dissociation from DNA should occur preferentially from the free ends of linear DNA molecules; (ii) protein dissociation should be prevented if the DNA ends are sterically occluded; (iii) dissociation should be less prevalent from internal positions; and (iv) an intact heterodimer would be necessary for stable DNA-binding activity and for end-dependent dissociation. We first asked whether Mlh1-Pms1 preferentially dissociated from DNA ends (FIGS. 82A-D). When hydrodynamic force (~100 fN) was used to push Mlh1-Pms1, most complexes (>95%) did not dissociate upon encountering anchored (i.e. sterically blocked) DNA ends (FIG. 82A; $N_{dis}/N_{tot}$=1/23 [dissociated/total pushed to DNA ends]), nor did Mlh1-Pms1 dissociate from the apex of looped DNA (FIG. 82D; $N_{dis}/N_{tot}$=0/4). In contrast, Mlh1-Pms1 immediately dissociated from free ends of "single-tethered" DNA (FIG. 82B; $N_{dis}/N_{tot}$=880/1000), and from free ends of photo-chemically induced double-stranded breaks (DSB; FIGS. 82C-D; $N_{dis}/N_{tot}$=14/14). Mlh1 alone can exist as monomers or dimers ($K_d$ of 3.14±0.19 μM), but the Mlh1-NTDs do not self-associate[H22]. Mlh1 alone could bind DNA (FIG. 82E), exhibiting a diffusion coefficient 6.9-fold greater (p<0.0001) than Mlh1-Pms1 under the same conditions ($D_{1d}$=0.137±0.127 μm² sec⁻¹, N=25, vs. 0.020±0.023 μm² sec⁻¹, N=25, respectively, at 50 mM NaCl; Mlh1 binding was not detected at higher ionic strengths), indicating Pms1 was not essential for binding or diffusion. However, when flow was applied, Mlh1 moved rapidly down the DNA and >80% dissociated from the anchored DNA ends (FIG. 82E; $N_{dis}/N_{tot}$=285/350); this finding was strikingly different from results with the intact heterodimer, indicating that the presence of Pms1 was necessary to observe end-dependent dissociation. Finally, we engineered TEV cleavage sites into the linker of Mlh1 and Pms1, and proteolytic cleavage of one or both linker arms abolished detectable DNA-binding activity (FIG. 86), highlighting the importance of the linker arms for DNA-binding. We conclude that formation of an intact Mlh1-Pms1 heterodimer stabilizes the DNA-bound complex, and that the heterodimer preferentially dissociates from DNA ends. These experimental findings are all consistent with predictions for the previously proposed mechanism where Mlh1-Pms1 can adopt a ring-like architecture that wraps around DNA, although we are careful note that we do not yet know structural details of the wrapped complex.

Molecules of Mlh1-Pms1 can Bypass One Another while Traveling Along the Same DNA.

Figure 87:
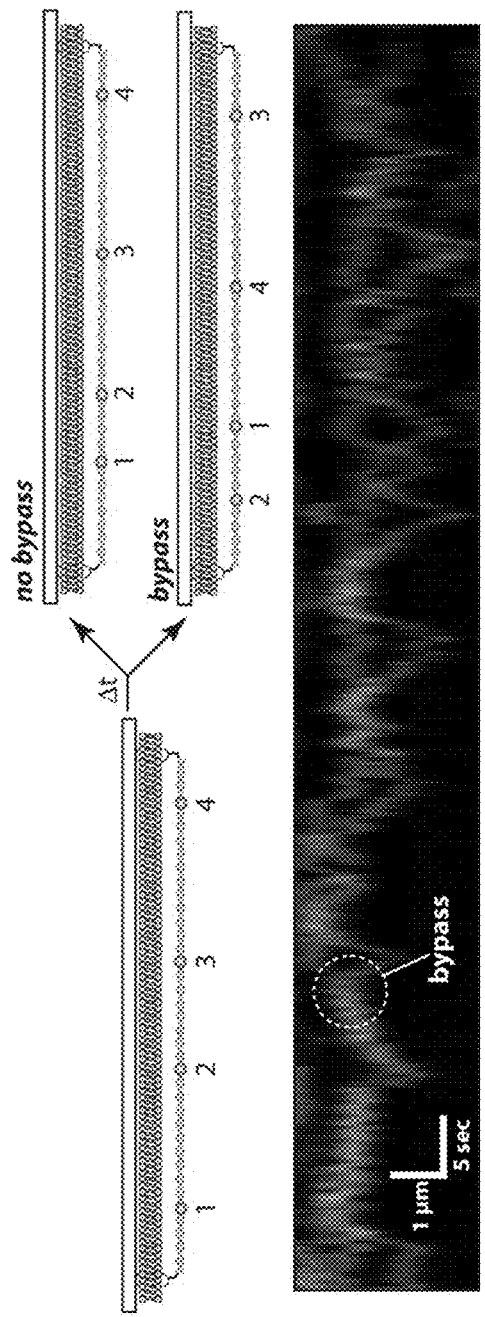
FIG. 87 shows that Mlh1-Pms1 complexes can occasionally bypass one another while traveling along the same DNA. Two Mlh1-Pms1 molecules are bound to the same DNA and each is labeled with a different colored QD (either green or magenta). An example of a bypass event is highlighted. We observed a total of 5 bypass events out of ~50 pairs of colliding magenta and green Mlh1-Pms1 complexes.

We have previously shown that Msh2-Msh6 complexes traveling on the same molecule cannot pass one another, arguing that the proteins maintain continuous close contact with the DNA, which is consistent with a sliding mechanism[H14]. In contrast, two-color labeling experiments revealed that Mlh1-Pms1 complexes could bypass one another as they traveled along the same DNA molecule (FIG. 87), which is only consistent with a hopping/stepping mechanism wherein the individual hops or steps span distances comparable to or greater than the dimensions of the QD-tagged proteins. Closed ring-like architecture is difficult to reconcile with the observed protein bypass, and would require two Mlh1-Pms1 complexes to thread through one another as they moved along the DNA. A threading mechanism specifically predicts that Mlh1-Pms1 would be unable to bypass obstacles larger than the internal diameter of the large central pore formed the protein complex. Alternatively, bypass could also be accomplished through transient ring opening, whereupon the proteins could simple step past one another in an open configuration. This type of open stepping mechanism predicts that Mlh1-Pms1 would be capable of bypassing obstacles larger than the internal diameter of the protein ring. Given the combined length of the Mlh1-Pms1 linker arms (51.7±14.6 nm)$^{H17}$, the corresponding maximal diameter of the central pore would be 16.5±4.6 nm in diameter, which is too small to accommodate passage of a QD (~20-nm dia.), ruling out a threading mechanism for obstacle bypass. We conclude that Mlh1-Pms1 most likely bypasses obstacles by stepping over them in an open ring configuration, implying that the protein is capable of transitioning back and forth between an open and closed conformation.

Mlh1-Pms1 can Traverse Nucleosomes while Undergoing 1D Diffusion.

Figure 83:
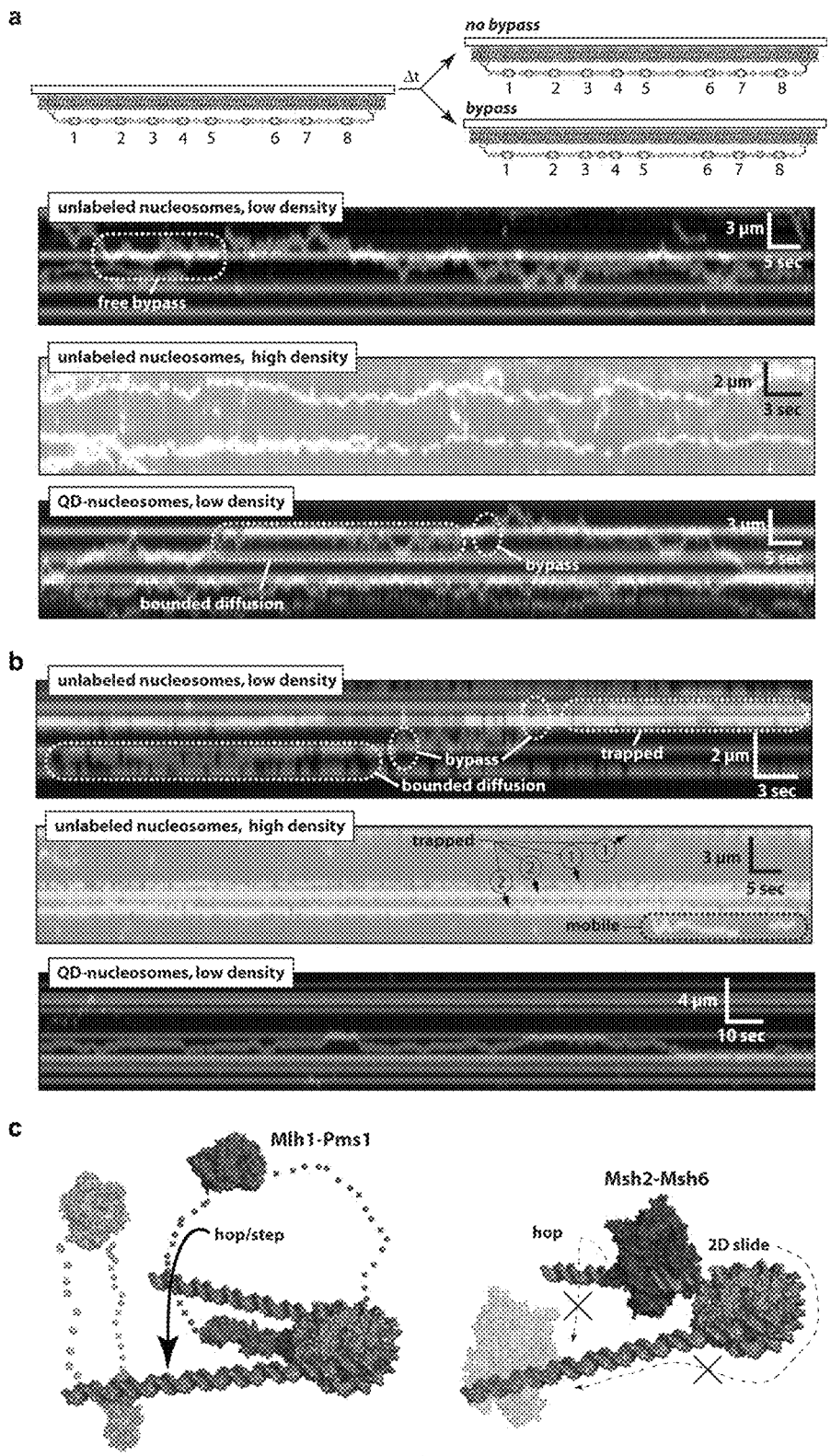
FIG. 83 shows diffusion of Mlh1-Pms1 and Msh2-Msh6 along nucleosome-bound DNA.

The finding that Mlh1-Pms1 complexes could bypass one another suggested that these proteins might be able to undergo 1D diffusion on crowded DNA substrates, similar to what would be found in an in vivo environment. Therefore we next asked whether MMR proteins could traverse nucleosomes, which are anticipated to be the most abundant obstacles encountered in eukaryotes. For these experiments unlabeled, recombinant nucleosomes were deposited onto the DNA substrates by salt dialysis at a ratio of either ~5-10 or ~80-100 nucleosomes per DNA molecule$^{H23}$. The Mlh1-Pms1 diffusion measurements were performed as described above, and the nucleosomes were then located by labeling with QDs after the diffusion measurements were completed (Supplementary Information). As shown in FIG. 83, Mlh1-Pms1 still diffused on nucleosome-bound DNA ($D_{1d}$=0.027±0.021 µm$^2$ sec$^{-1}$, N=26), and repeatedly bypassed unlabeled nucleosomes (~10-nm dia.), exhibiting no evident boundary effects upon colliding with single nucleosomes (FIG. 83A, upper panel; N>1,000 Mlh1-Pms1 complexes, each giving rise to multiple bypass events). Mlh1-Pms1 also moved freely along DNA bound by up to ~80-100 unlabeled nucleosomes (FIG. 83A, middle panel; $D_{1d}$=0.034±0.018 µm$^2$ sec$^{-1}$, N=25), providing an unequivocal demonstration that nucleosomes do not prevent 1D-diffusion of Mlh1-Pms1. We conclude Mlh1-Pms1 can travel along a simple chromatin lattice by 1D diffusion while bypassing protein obstacles at it travels along the DNA (FIG. 83C). As indicated above, for all of these experiments the nucleosomes were labeled only after making the diffusion measurements to ensure that the large QDs would not interfere with Mlh1-Pms1 movement. However, Mlh1-Pms1 could also bypass QD-labeled nucleosomes (N=63 Mlh1-Pms1 complexes, each yielding multiple bypass events), although in this case Mlh1-Pms1 exhibited characteristics of bounded diffusion upon colliding with the QD-nucleosomes with the large QD-nucleosomes acting as semi-penetrable barriers (FIG. 83A, lower panel). Given the large diameter of the QD-nucleosome (≥30-nm) compared to the size of Mlh1-Pms1, we conclude that nucleosome bypass must occur via a stepping mechanism where the protein transiently adopts an open ring configuration. These results provide the first experimental demonstration that a protein undergoing 1D diffusion can circumnavigate protein obstacles that lie in its path.

The Diffusion of Msh2-Msh6 is Highly Restricted by Nucleosomes.

In striking contrast to Mlh1-Pms1, the movement of Msh2-Msh6 past unlabeled nucleosomes was highly restricted, exhibiting characteristics of bounded diffusion with nucleosomes acting as semi-penetrable barriers, and Msh2-Msh6 typically became trapped between nucleosomes (FIG. 83B, upper and middle panels). On higher-density nucleosome arrays (~80-100 nucleosomes per 48.5 kb DNA substrate) most molecules of Msh2-Msh6 were immobile or oscillated within tightly confined regions (N=964/1000), and displayed little evidence of free 1D-diffusion within our detection limits ($D_{1d}$≤1×10$^{-4}$ µm$^2$ sec$^{-1}$). A small subpopulation of Msh2-Msh6 remained mobile on the high-density arrays (N=36/1000; 3.6%), suggesting they were bound in an alternate conformation. In further contrast to Mlh1-Pms1, Msh2-Msh6 never bypassed QD-tagged nucleosomes (FIG. 83B, lower panel), indicating that large obstacles (≥30-nm dia.) present insurmountable barriers, which is fully consistent with expectations based on the structure of Msh2-Msh6, which wraps around DNA making intimate contacts with the phosphate backbone over nearly 1.5 turns of helix$^{H24}$, and is also consistent with a continuous sliding mechanism that does not involve extensive hopping$^{H14}$. Rare nucleosome bypass by Msh2-Msh6 might occur through occasional hopping events, or through limited excursions into 2D-sliding where Msh2-Msh6 maintains contact with the DNA without tracking the helical pitch of the phosphate backbone (FIG. 83C) H6, H8. In either case, the mechanism does not permit efficient mobility of Msh2-Msh6 along the higher density nucleosome arrays; this conclusion agrees with bulk biochemical studies showing that nucleosomes or other stationary obstacles can trap Msh2-Msh6 (or its homologs) on DNA$^{H25-H28}$.

Discussion

Intranuclear trafficking of all DNA-binding proteins is governed by facilitated diffusion. Theoretical descriptions and bulk measurements of facilitated diffusion have long been reported in the literature beginning with the classical studies of lac repressor$^{H29-H32}$, and more recently with NMR experiments of transcription factors$^{H33-H35}$, but direct measurements of diffusion have only recently become possible through development of new single molecule techniques$^{H5,H6,H14,H36-H38}$. Together these studies support an emerging consensus that many DNA-binding proteins can travel long distances along DNA by 1D diffusion in vitro. However, the validity of this conclusion with respect to physiological settings remains unclear, despite years of experimental and theoretical efforts, specifically because it remains unknown whether or how 1D diffusion can occur in the presence of nucleosomes and other nucleoprotein structures$^{H1,H3,H4,H7,H8,H39,H40}$. Here we sought to resolve this issue by using single molecule imaging, nanofabricated curtains of "double tethered" DNA molecules, and MMR proteins as model systems for facilitated diffusion.

We have demonstrated that both Msh2-Msh6 and Mlh1-Pms1 can diffuse in 1D along DNA, but do so using very different mechanisms. Mlh1-Pms1 hops or steps along the DNA, but Msh2-Msh6 moves predominantly by sliding along the DNA while remaining in continuous close contact with the phosphate backbone. The functional consequences of these mechanistic differences are that Mlh1-Pms1 can readily traverse nucleosomes and travel along chromatin whereas Msh2-Msh6 cannot. These results provide an unambiguous demonstration that 1D diffusion can occur on crowded DNA substrates in the presence of protein obstacles, and that the ability to bypass obstacles is dependent upon the how the protein in question diffuses along DNA. We anticipate that these behaviors displayed by Mlh1-Pms1 and Msh2-Msh6 in response to collisions with nucleosomes will reflect general mechanistic attributes of their respective modes of 1D-diffusion, which in principle will apply to any proteins that diffuse on DNA (e.g. DNA repair proteins, transcription factors, etc.): proteins that track the phosphate backbone while sliding along DNA will experience a barrier upon encountering obstacles and must either disengage the DNA and enter a 2D- or 3D-mode of diffusion to continue searching for targets, or the DNA must be cleared of obstacles before hand to allow unhindered access to the DNA (see below); in contrast, proteins that do not track the backbone can traverse obstacles without experiencing significant boundary effects.

The different modes of diffusion found for Msh2-Msh6 and Mlh1-Pms1 also impose specific constraints on the mechanisms of MMR. Msh2-Msh6 is the first to arrive at lesions, and helps identify nearby signals differentiating the parental and nascent DNA strands. Many models for strand discrimination invoke 1D-movement of Msh2-Msh6 along DNA, and even transient loss of contact with the DNA during this second phase of the reaction could compromise repair[H11-13]. Nucleosomes, or other DNA-binding proteins, have the potential to thwart Msh2-Msh6 and a single nucleosome deposited near a lesion could render it irreparable, suggesting regions in need of repair must be kept free from obstacles. Replication forks disrupt nucleosomes, leaving stretches of naked DNA in their wake[H41]. While speculative, if Msh2-Msh6 were restricted to the region behind the fork, possibly through direct association with PCNA, then it would be free to scan newly replicated, naked DNA[H14,H42,H43]. Mlh1-Pms1 is thought to arrive later than Msh2-Msh6[H11,H13], implying it must survey the entire genome for lesion-bound Msh2-Msh6 without the benefit of confined searches in regions already cleared by a replication fork. The ability of Mlh1-Pms1 to hop or step along DNA and freely traverse nucleosomes ensures it could efficiently bypass stationary obstacles while searching the genome for its binding targets.

Methods

Mlh1-Pms1 Expression, Purification, and Characterization.

Mlh1-Pms1 was expressed and purified using pMH1 (GAL1-MLH1-VMA-CBD, 2μ, TRP1) and pMH8 (GAL10-PMS1, 2μ, LEU2) vectors transformed into the S. cerevisiae strain BJ2168[H16]. Mlh1-Pms1 complexes containing FLAG, HA, and/or TEV tags were purified from BJ2168 containing the relevant pMH1 and pMH8 derivatives described in the Supplemental Information. All Mlh1-Pms1 constructs were functional for mismatch repair in vivo.

Single-Molecule Imaging.

The TIRFM system, particle tracking, and data analysis have been described[H14]. Unless otherwise indicated, data were collected using DNA molecules anchored with nanofabricated patterns made by electron-beam lithography[H15]. QDs were prepared using a protocol that yields 0.076±0.014 epitope-binding sites per QD (i.e. approximately 1 in 13 QDs has ½ of a functional IgG)[H44]. Assuming the conjugation reaction is a Poisson process, the probability of a QD having two or three epitope binding sites is P=0.0027 and P=7.02× $10^{-5}$, respectively. FLAG-tagged Mlh1-Pms1 (30-250 nM) was mixed with 2-fold molar excess anti-FLAG QDs in buffer containing 40 mM Tris-HCl [pH 7.7], 150 mM NaCl, ±1 mM $MgCl_2$, 1 mM DTT, and 0.4 mg ml$^{-1}$ BSA, and incubated for 15-20 minutes on ice. Reactions were diluted 10-fold (3-25 nM Mlh1-Pms1) prior to injection. Crosslinking assays verified Mlh1-Pms1 did not dissociate to monomers under dilute conditions (not shown). TIRFM experiments were done using 40 mM Tris-HCl [pH 7.7], 150 mM NaCl (unless otherwise indicated), ±1 mM $MgCl_2$, 1 mM DTT, 0.4 mg ml$^{-1}$ BSA, 140 mM β-mercaptoethanol, ±1 mM nucleotide (ADP, ATP or ATPγS, as indicated). Labeled proteins were injected into the sample chamber, unbound proteins were quickly flushed away, and flow was terminated prior to data acquisition. YOYO1 (0.5 nM; Invitrogen) and an $O_2$ scavenging system [glucose oxidase (34 units ml$^{-1}$), catalase (520 units ml$^{-1}$), and 1% glucose (w/v)] was included in reactions requiring fluorescent DNA. Bulk experiments verified that YOYO1 and the $O_2$ scavenging system did not affect Mlh1-Pms1 DNA binding activity. Recombinant histones were purified from E. coli, reconstituted into octamers, and deposited on the DNA as described[H23].

REFERENCES

H1. von Hippel, P. & Berg, O. Facilitated target location in biological systems. J Biol Chem 264, 675-8 (1989).

H2. Elf, J., Li, G.-W. & Xie, X. Probing transcription factor dynamics at the single-molecule level in a living cell. Science 316, 1191-1194 (2007).

H3. Hager, G., McNally, J. & Misteli, T. Transcription dynamics. Mol Cell 35, 741-53 (2009).

H4. Li, G.-W., Berg, O. & Elf, J. Effects of macromolecular crowding and DNA looping on gene regulation kinetics. Nature Physics 5, 294-297 (2009).

H5. Blainey, P. C., van Oijen, A. M., Banerjee, A., Verdine, G. L. & Xie, X. S. A base-excision DNA-repair protein finds intrahelical lesion bases by fast sliding in contact with DNA. Proc Natl Acad Sci USA 103, 5752-7 (2006).

H6. Gorman, J. & Greene, E. C. Visualizing one-dimensional diffusion of proteins along DNA. Nat Struct Mol Biol 15, 768-774 (2008).

H7. Gorski, S., Dundr, M. & Misteli, T. The road much traveled: trafficking in the cell nucleus. Curr Opin Cell Biol 18, 284-90 (2006).

H8. Kampmann, M. Facilitated diffusion in chromatin lattices: mechanistic diversity and regulatory potential. Mol Micro 57, 889-899 (2005).

H9. Hodges, C., Bintu, L., Lubkowska, L., Kashlev, M. & Bustamante, C. Nucleosomal fluctuations govern the transcription dynamics of RNA polymerase II. Science 325, 626-8 (2009).

H10. Studitsky, V., Clark, D. & Felsenfeld, G. Overcoming a nucleosomal barrier to transcription. Cell 83, 19-27 (1995).

H11. Jiricny, J. The multifaceted mismatch-repair system. Nat Rev Mol Cell Biol 7, 335-346 (2006).

H12. Modrich, P. Mechanisms in eukaryotic mismatch repair. J Biol Chem 281, 30305-9 (2006).

H13. Kunkel, T. A. & Erie, D. A. DNA mismatch repair. Annu Rev Biochem 74, 681-710 (2005).

H14. Gorman, J. et al. Dynamic basis for one-dimensional DNA scanning by the mismatch repair complex Msh2-Msh6. Mol Cell 28, 359-70 (2007).

H15. Gorman, J., Fazio, T., Wang, F., Wind, S. & Greene, E. Nanofabricated racks of aligned and anchored DNA substrates for single-molecule imaging. Langmuir 26, 1372-9 (2010).

H16. Hall, M. C., Wang, H., Erie, D. A. & Kunkel, T. A. High affinity cooperative DNA binding by the yeast Mlh1-Pms1 heterodimer. J Mol Biol 312, 637-647 (2001).

H17. Sacho, E. J., Kadyrov, F. A., Modrich, P., Kunkel, T. A. & Erie, D. A. Direct visualization of asymmetric adenine-nucleotide-induced conformational changes in MutL alpha. Mol Cell 29, 112-21 (2008).

H18. Guarné, A., Junop, M. & Yang, W. Structure and function of the N-terminal 40 kDa fragment of human PMS2: a monomeric GHL ATPase. EMBO J 20, 5521-31 (2001).

H19. Guarné, A. et al. Structure of the MutL C-terminal domain: a model of intact MutL and its roles in mismatch repair. EMBO J 23, 4134-45 (2004).

H20. Kosinski, J., Steindorf, I., Bujnicki, J., Giron-Monzon, L. & Friedhoff, P. Analysis of the quaternary structure of the MutL C-terminal domain. *J Mol Biol* 351, 895-909 (2005).

H21. Komazin-Meredith, G., Mirchev, R., Golan, D., van Oijen, A. & Coen, D. Hopping of a processivity factor on DNA revealed by single-molecule assays of diffusion. *Proc Natl Acad Sci USA* 105, 10721-10726 (2008).

H22. Hall, M. C. et al. DNA binding by yeast Mlh1 and Pms1: implications for DNA mismatch repair. *Nuc Acids Res* 31, 2025-2034 (2003).

H23. Visnapuu, M.-L. & Greene, E. Single-molecule imaging of DNA curtains reveals intrinsic energy landscapes for nucleosome deposition. *Nat Struct Mol Biol* 16, 1056-1062 (2009).

H24. Warren, J. J. et al. Structure of the human MutSalpha DNA lesion recognition complex. *Mol Cell* 26, 579-92 (2007).

H25. Li, F., Tian, L., Gu, L. & Li, G. Evidence that nucleosomes inhibit mismatch repair in eukaryotic cells. *J Biol Chem* 284, 33056-61 (2009).

H26. Gradia, S. et al. hMSH2-hMSH6 forms a hydrolysis-independent sliding clamp on mismatched DNA. *Mol Cell* 3, 255-261 (1999).

H27. Pluciennik, A. & Modrich, P. Protein roadblocks and helix discontinuities are barriers to the initiation of mismatch repair. *Proc Natl Acad Sci USA* 104, 12709-13 (2007).

H28. Mendillo, M. L., Mazur, D. J. & Kolodner, R. D. Analysis of the interaction between the *Saccharomyces cerevisiae* MSH2-MSH6 and MLH1-PMS1 complexes with DNA using a reversible DNA end-blocking system. *J Biol Chem* 280, 22245-57 (2005).

H29. Berg, O., Winter, R. & von Hippel, P. Diffusion-driven mechanisms of protein translocation on nucleic acids. 1. Models and theory. *Biochemistry* 20, 6929-48 (1981).

H30. Winter, R., Berg, O. & von Hippel, P. Diffusion-driven mechanisms of protein translocation on nucleic acids. 3. The *Escherichia coli* lac repressor-operator interaction: kinetic measurements and conclusions. *Biochemistry* 20, 6961-77 (1981).

H31. Winter, R. & von Hippel, P. Diffusion-driven mechanisms of protein translocation on nucleic acids. 2. The *Escherichia coli* repressor-operator interaction: equilibrium measurements. *Biochemistry* 20, 6948-60 (1981).

H32. Riggs, A., Bourgeois, S. & Cohn, M. The lac repressor-operator interaction. 3. Kinetic studies. *J Mol Biol* 53, 401-17 (1970).

H33. Doucleff, M. & Clore, G. Global jumping and domain-specific intersegment transfer between DNA cognate sites of the multidomain transcription factor Oct-1. *Proc Natl Acad Sci USA* 105, 13871-6 (2008).

H34. Iwahara, J. & Clore, G. Direct observation of enhanced translocation of a homeodomain between DNA cognate sites by NMR exchange spectroscopy. *J Am Chem Soc* 128, 404-5 (2006).

H35. Iwahara, J., Zweckstetter, M. & Clore, G. NMR structural and kinetic characterization of a homeodomain diffusing and hopping on nonspecific DNA. *Proc Natl Acad Sci USA* 103, 15062-7 (2006).

H36. Roy, R., Kozlov, A., Lohman, T. & Ha, T. SSB protein diffusion on single-stranded DNA stimulates RecA filament formation. *Nature* 461, 1092-7 (2009).

H37. Liu, S., Abbondanzieri, E., Rausch, J., Le Grice, S. & Zhuang, X. Slide into action: dynamic shuttling of HIV reverse transcriptase on nucleic acid substrates. *Science* 322, 1092-7 (2008).

H38. Tafvizi, A. et al. Tumor suppressor p53 slides on DNA with low friction and high stability. *Biophys J* 95, L01-3 (2008).

H39. Halford, S. & Szczelkun, M. How to get from A to B: strategies for analysing protein motion on DNA. *Eur Biophys J* 31, 257-67 (2002).

H40. Mirny, L. et al. How a protein searches for its site on DNA: the mechanism of facilitated diffusion. *J Physics A* 42, 434013 (2009).

H41. Groth, A., Rocha, W., Verreault, A. & Almouzni, G. Chromatin challenges during DNA replication and repair. *Cell* 128, 721-733 (2007).

H42. Umar, A. et al. Requirement for PCNA in DNA mismatch repair at a step preceding DNA resynthesis. *Cell* 87, 65-73 (1996).

H43. Kolodner, R. D., Mendillo, M. L. & Putnam, C. D. Coupling distant sites in DNA during mismatch repair. *Proc Natl Acad Sci USA* 104, 12953-12954 (2007).

H44. Pathak, S., Davidson, M. & Silva, G. Characterization of the functional binding properties of antibody conjugated quantum dots. *Nano Letters* 7, 1839-1845 (2007).

H45. Bagchi, B., Blainey, P. C. & Xie, X. S. Diffusion Constant of a Nonspecifically Bound Protein Undergoing Curvilinear Motion along DNA. *J Phys Chem B* (2008).

H46. Luger, K., Mäder, A., Richmond, R., Sargent, D. & Richmond, T. Crystal structure of the nucleosome core particle at 2.8 A resolution. *Nature* 389, 251-60 (1997).

Supplemental Discussion

Mechanisms of Facilitated Diffusion and Effects of Salt.

Proteins that hop cycle rapidly between a free and a bound state, and increasing ionic strength increases the lifetime of unbound intermediate while decreasing the lifetime of the bound intermediate, hence increasing the overall observed rate of travel (Berg et al., Biochemistry, 1981; Blainey et al., PNAS, 2006; Kochaniak, et al., J. Biol. Chem., 2008; Komazin-Meredith, et al., PNAS, 2008). Stepping can be considered virtually identical to hopping, with the exception that at least two separate parts of the protein must cycle between free and bound states (i.e. hop). The effect of salt on a stepping process would be similar to that which is observed for a simpler hopping mechanism and would lead to an apparent overall increase in the rate of travel along the DNA. It is important to note that different forms of facilitated diffusion are not mutually exclusive, and for example the bound states that exist during a hopping/stepping mechanism may in fact slide on DNA (Givaty & Levy, J. Mol. Biol., 2009). Nevertheless, our data indicate that Msh2-Msh6 moves predominantly by sliding, and Mlh1-Pms1 moves predominantly by hopping/stepping. The functional consequence of this difference is that Mlh1-Pms1 can readily traverse nucleosomes and chromatin, whereas Msh2-Msh6 cannot.

Jumping is distinct from hopping/stepping, in that it is an uncorrelated search involving a free 3D diffusion component enabling the protein to move long distances between each independent jumping event (von Hippel & Berg, J. Biol. Chem. 1989). Similar to hopping/stepping, jumping frequency would also increase at higher ionic strengths, which in the case of jumping would lead to increased dissociation of the protein from the DNA, and single molecule experiments done in the presence of buffer flow induce dissociation of jumping proteins, as the free state is readily pushed away from the DNA and irretrievably lost to solution. We do not completely rule out the possibility that occasional jumping is a potential mechanism that could contribute to Mlh1-Pms1 movement. However, in a single molecule assay, jumping would appear as the sudden disappearance of a protein followed by its near immediate reappearance at a distant location or even on a different DNA molecule (Bonnet et al., Nucleic Acids Res. 2008). The vast majority of the diffusion trajectories observed for Mlh1-Pms1 involved continuous 1D motion along the DNA, which is only consistent with a correlated scanning mechanism (i.e. sliding and/or hopping/stepping), but inconsistent with extensive jumping. Moreover, extensive jumping is inconsistent with the end-dependent DNA dissociation observed for Mlh1-Pms1 and the wrapped DNA-binding topology that we propose as an explanation for the end-dependent dissociation.

Supplemental Methods

Mlh1-Pms1 Cloning and Characterization.

Plasmids containing tagged MLH1 under the native MLH1 promoter were created by overlap-extension PCR as derivatives of pEAA213 (Heck et al. 2006): pEAA373 contains a FLAG-tag (underlined) flanked on either side by three alanines (AAADYKDDDKAAA [SEQ ID NO: 25]) and inserted immediately after amino acid 448T of MLH1; pEAA516 contains a TEV site (underlined) flanked on either side by three alanines (AAAENLYFQSAAA [SEQ ID NO: 26]) inserted immediately after amino acid 448T and the FLAG-tag inserted immediately after amino acid 499Y of MLH1. For expression, the tagged MLH1 constructs were sub-cloned into pMH1, and purified as described (Hall and Kunkel, 2001). Sub-cloning from pEAA373 and pEAA516 into pMH1 created pEAE267 and pEAE295, respectively. For tagged PMS1, pEAE296 was created as a derivative of pMH8 by overlap-extension PCR and included a HA-tag (underlined) flanked by three alanine residues (AAA YPYDVPDYAAAA [SEQ ID NO: 27]) inserted after amino acid D565 of PMS1. For complementation, the epitope-tag from pEAE296 was sub-cloned into pEAA238 (Heck et al., 2006), which has PMS1 under its native promoter, and then cloned into pEAA248, which is the same as pEAA238 but contains the URA3 selectable marker, to create pEAA517. All clones were sequenced (Cornell BioResource Center), and additional details on vector construction will be provided upon request.

MLH1 constructs were tested in vivo for the mlh1Δ mutator phenotype in ARS-CEN LEU2 vectors containing MLH1 expressed from its native promoter. The HA-tagged PMS1 was tested in vivo for the pms1Δ mutator phenotype (Heck et al., 2006). To test complementation, the semiquantitative canavanine resistance assay was used to measure mutation rates in the S288c strains EAY874 (MATα, leu2-3,112, trp1-289, ura3::argD, cyhS, mlh1Δ::KanMX4) and EAY1087 (MATα, ura3-52, leu2Δ1, trp1Δ63, his3Δ200, lys2Δ202, pms1Δ::KanMX4). EAY874 strains containing pRS415 (mutant control), pEAA213 (wild-type control) or pEAA373, pEAA515 and pEAA516 (epitope-tagged MLH1) were streaked on leucine dropout plates to obtain single colonies. EAY310 strains containing pRS416 (mutant control), pEAA248 (wild-type control) and pEAA517 (HA-PMS1) were streaked onto uracil dropout plates to obtain single colonies. 35 independent colonies from each strain were patched onto appropriate dropout plates containing L-canavanine (60 mg $L^{-1}$) and incubated for 3 days at 30° C. The number of canavanine-resistant papillations in each patch was counted and the median number for each strain was used for comparison. All tested derivatives of MLH1 and PMS1 conferred mutation frequencies indistinguishable from wild-type in contrast to the 10-fold higher frequency found in the corresponding null strains carrying an empty vector.

Ensemble Characterization of Mlh-Pms1 DNA-Binding Activity.

Protein concentrations were determined by Bradford assay using BSA as a standard. Gel mobility shift assays with oligonucleotide substrates were performed as described (Kijas et al., 2003). Binding reactions were performed at room temperature (RT) for 5 minutes in 15 μl reactions containing 60 nM (5'-$^{32}$P)-end labeled 40 bp substrate, 120 nM Mlh1-Pms1, 25 mM Hepes [pH, 7.6], 40 μml$^{-1}$ BSA, 1 mM DTT, 50 mM NaCl, and 8% (w/v) sucrose. In super-shift experiments, either 0.65 μg of FLAG antibody (Sigma Cat. No. F3165) or 3.25 μg of HA antibody (Sigma Cat. No. H3663) were pre-incubated with Mlh1-Pms1 on ice for 30 min prior to the addition of DNA substrates. Samples were loaded on 4% (w/v) non-denaturing polyacrylamide gels containing 0.5× TBE and electrophoresed at 130 V for 1 hour at RT. Gels were dried on 3mM Whatman paper and visualized by Phosphor-Imaging. Analysis was done using ImageJ. The 40 bp substrate was created by annealing S1 (5'dACC GAA TTC TGA CTT GCT AGG ACA TCT TTG CCC ACG TTG A [SEQ ID NO: 28]) and S2 (5'dTCA ACG TGG GCA AAG ATG TCC TAG CAA GTC AGA ATT CGG T [SEQ ID NO: 29]) (Integrated DNA Technologies; Surtees and Alani, 2006).

Nitrocellulose filter binding assays were performed as described (Chi and Kolodner, 1994). Briefly, nitrocellulose filters (BA85, 0.45 μm, 25 mm, Whatman Schleicher & Schuell) were pre-soaked in 0.5 M KOH for 20 minutes, rinsed thoroughly with sterile deionized distilled water, washed once with reaction buffer (25 mM Hepes [pH 7.6], 0.01 mM EDTA) and stored in same buffer prior to use. The 3 kb plasmid (pEAO242) was linearized with NcoI followed by treatment with calf intestinal phosphatase (CIP; New England Biolabs). CIP-treated DNA was purified (QIAquick; Qiagen) and end-labeled with T4 polynucleotide kinase and [γ-$^{32}$P]ATP, followed by heat inactivation and removal of unincorporated nucleotides, as described by the manufacturer (New England Biolabs). Binding reactions (30 μl) were performed in buffer supplemented with 1 mM DTT and 40 μg ml$^{-1}$ BSA without EDTA, and included 100 pM of 5'$^{32}$P-labeled 3 kb linear plasmid. Mlh1-Pms1 was incubated with 40 nM IgG or IgG coupled QDs (as indicated) on ice for 30 minutes. Binding reactions were incubated at RT for 10 minutes, and filtration was performed on a Hoefer filter manifold (FH225V, Hoefer Scientific). Binding reactions were added to 2.5 ml of ice-cold reaction buffer overlaying nitrocellulose filters and passed through with a flow rate of ~2.5 ml min$^{-1}$. Dried filters were placed in 5 ml of Ecoscint scintillant (National Diagnostics) and the bound radioactivity measured in a Beckman LS 5000 scintillation counter. Background was determined in reactions without protein and was typically around 1-5% of total radioactivity. Percent DNA binding was determined by dividing the background subtracted count for each filter by the total radioactivity per reaction.

TEV Cleavage Assays.

3 μg of Mlh1-Pms1 was incubated with 0.03 μg of TEV protease in 15 μl reactions containing 25 mM Hepes [pH 7.6], 1 mM DTT, and 40 μg ml$^{-1}$ BSA. TEV protease was a generous gift from Dr. Ailong Ke (Cornell). TEV cleaved proteins were assayed for DNA binding activity using gel shift assays, as described above. To confirm TEV cleavage, samples were incubated at 30° C. for 30 minutes, after which 7.5 μl of 3×SDS-loading buffer (0.195 M Tris [pH 6.8], 30% glycerol, 3% β-mercaptoethanol, 6% SDS) was added to each and samples were boiled for 3 minutes. Samples were analyzed by 10% SDS-PAGE and stained with Coomassie blue (see FIG. 80C).

Construction of DNA Substrates for TIRFM.

DNA substrates were made by ligating oligonucleotides to the 12-nucleotide overhangs at the end of the λ-DNA. Oligonucleotides were purchased from Operon Technologies and gel purified prior to use. Ligation mixes (1 ml total volume)

contained 4 nM λ-DNA (Invitrogen), 1 µM biotinylated oligonucleotiode (5'-pAGGT CGCCGCCC[BioTEG]-3' [SEQ ID NO: 30]), 1 µM DIG (digoxigenin) or FITC (fluorescein isothiocyanate) labeled oligonucleotide (5'-pGGG CGG CGA CCT[DIG]-3' (SEQ ID NO: 31) or 5'-pGGG CGG CGA CCT[FITC]-3' [SEQ ID NO: 32]), and 1x ligase buffer (New England Biolabs). The reaction mix was warmed to 65° C. for 10 minutes and then cooled slowly to RT. After cooling, ligase was added (T4 DNA ligase (400 units µl$^{-1}$) or Taq ligase (40 units µl$^{-1}$; New England Biolabs) and the mixture was incubated overnight at 42° C. Reactions performed with T4 ligase were heat inactivated at 65° C. for 10 minutes, and ligated DNA products were purified over a Sephacryl S200HR column (GE Healthcare) run in 10 mM Tris-HCl [pH 7.8], 1 mM EDTA, plus 150 mM NaCl. Purified DNA was stored at −20° C.

Quantum Dots.

QDs were prepared by following the manufacturer's recommended protocol, as described in Gorman et al., 2007 and Pathak et al., 2007 (Qdot® 585 Antibody Conjugation Kit, Cat. No. Q22011MP, and Qdot® 705 Antibody Conjugation Kit, Cat. No. Q22061MP; Invitrogen). In brief, QDs (4 µM) were activated with 1 mM SMCC (succinimidyl 4-[N-maleimidomethyl]cyclohexane-1-carboxylate) for 1 hour at RT, yielding maleimide functional groups on the QD surface. Antibodies (1 mg ml$^{-1}$ in PBS; Sigma Cat. No. H3663 and F3165, for anti-HA and anti-FLAG, respectively) were reduced with 20 mM DTT for 30 minutes at RT, which cleaves disulfide bonds between heavy chains generating free thiols that can be coupled the maleimide-QDs. Reduced IgG was purified on a NAP-5 column and then mixed with the maleimide activated QDs for 1 hour at RT. Reactions were quenched with 100 µM β-mercaptoethanol for 30 minutes at RT, and the resulting antibody-QD conjugates were purified over a Superdex 200 10/300 GL gel filtration column (GE Healthcare) run in PBS to remove unreacted IgG. Purified conjugates were stored in PBS [pH 7.4] plus 0.1 mg ml$^{-1}$ acetylated BSA at 4° C.

Individual QDs blink and this well-known phenomenon enables one to distinguish single vs. multiple QDs (M. Dahan et al., Science, 2003; J. Yao et al., PNAS, 2005; Q. Zhang et al., Science, 2009). In our experiments a non-blinking QD signal could arise from either QD aggregation or protein aggregation, therefore any QDs that did not blink were discarded from analysis, ensuring all reported data arose from single fluorescent molecules. Apparent differences in signal intensities within the kymograms can arise from several sources, including: normal variations in QD fluorescence; variations in QDs blinking frequency; stationary QDs are brighter because their signal is confined to a fixed location during frame acquisition; nonblinking signals are brighter because they arise from multiple QDs; and some faint signals in the kymograms arise from "bleed-through" of signal from QD-proteins bound to an adjacent DNA in the curtain. These variations are expected, and we have confined our analysis and calculations to blinking QDs to ensure we are monitoring single fluorescent molecules.

Two-Color Labeling to Assess the Oligomeric State of Mlh1-Pms1.

Two-color QD labeling experiments (as described in S. L. Reck-Peterson et al., Cell, 2006) were used to assess whether the Mlh1-Pms1 complexes under investigation were consistent with single heterodimers or higher order oligomers. In brief, we premixed equimolar amounts of anti-FLAG green QDs (Qdot® 585) and anti-FLAG magenta QDs (Qdot® 705), and then used this two-color mixture to label Mlh1 (FLAG)-Pms1. Heterodimeric Mlh1(FLAG)-Pms1 contains just one FLAG epitope, and therefore could only be labeled with one QD (either green OR magenta, but not both). Whereas higher order oligomers would contain multiple FLAG tags (the exact number of FLAG tags would scale in proportion to the number of Mlh1-Pms1 subunits within the oligomer) and therefore could be labeled with two or more QDs, leading to colocalization of both green and magenta QDs. These two-color colocalization experiments revealed that 94.8% (N=1,254/1,323) of the proteins were either only green or only magenta, arguing that most Mlh1-Pms1 complexes contained only a single FLAG epitope. This result is consistent with a heterodimeric Mlh1-Pms1 complex, but inconsistent with the formation of larger Mlh1-Pms1 oligomers at the low protein concentrations used for our diffusion experiments.

Double-Tethered DNA Curtains.

A complete description of the double-tethered DNA curtains can be found in Gorman et al., 2010. Fused silica slides (G. Finkenbeiner, Inc.) were cleaned in NanoStrip solution (CyanTek Corp, Fremont, Calif.) for 20 minutes, rinsed with acetone and isopropanol and dried with $N_2$. Slides were spin-coated with a bilayer of polymethylmethacrylate (PMMA; 25K and 495K; MicroChem, Newton, Mass.), followed by a layer of Aquasave (Mitsubishi Rayon). Patterns were written with a FEI Sirion scanning electron microscope (J. C. Nabity, Inc., Bozeman, Mont.). Aquasave was removed with deionized water and resist was developed using isopropanol:methyl isobutyl ketone (3:1) for 1 minute with ultrasonic agitation at 5° C. The substrate was rinsed in isopropanol and dried with $N_2$. Barriers were made with a 15-20 nm layer of chromium (Cr), and following liftoff, samples were rinsed with acetone and dried with $N_2$, as described (Gorman, et al., 2010).

Inlet and outlet ports were made by boring through the slide with a precision drill press equipped with a diamond-tipped bit (1.4 mm O.D.; Kassoy). The slides were cleaned by successive immersion in 2% (v/v) Hellmanex, 1 M NaOH, and 100% MeOH. Slides were rinsed with MilliQ™ between each wash and stored in 100% MeOH until use. Prior to assembly, slides were dried under a stream of nitrogen and baked in a vacuum oven for at least 1 hour. A sample chamber was prepared from a borosilicate glass coverslip (Fisher Scientific) and double-sided tape (~100 µm thick, 3M). Ports (Upchurch Scientific) were attached with hot-melt adhesive (SureBonder glue sticks, FPC Corp.). The total volume of the sample chambers was ~13 µl. A syringe pump (Kd Scientific) and actuated injection valves (Upchurch Scientific) were used to control sample delivery. The flowcell and prism were mounted in a custom-built heater with computer-controlled feedback regulation.

Lipids were purchased from Avanti Polar Lipids and liposomes were prepared as previously described (Gorman et al., 2010). In brief, a mixture of DOPC (1,2-dioleoyl-sn-glycero-phosphocholine), 0.5% biotinylated-DPPE (1,2-dipalmitoyl-sn-glycero-3-phosphoethanolamine-N-(cap biotinyl)), and 8% mPEG 550-DOPE (1,2-dioleoyl-sn-glycero-3-phospho-ethanolamine-N-[methoxy(polyethylene glycol)-550]). The mPEG prevented nonspecific adsorption of QDs. Liposomes were applied to the sample chamber for 15 minutes. Excess liposomes were removed with buffer containing 10 mM Tris-HCl [pH 7.8] and 100 mM NaCl. The flowcell was then rinsed with the same buffer and incubated for 30 minutes. 30 µg ml$^{-1}$ anti-DIG Fab (Roche Cat. No. 1214667001) or anti-FITC (Invitrogen Cat. No. 71-1900) was injected into the chamber and incubated for 20 minutes. The sample chamber was then flushed with buffer A (40 mM Tris-HCl [pH 7.8], 1 mM DTT, and 1 mM $MgCl_2$) plus and 0.2 mg ml$^{-1}$ BSA for 5 minutes.

Streptavidin (0.02 mg ml$^{-1}$) in buffer A was injected into the sample chamber and incubated for 20 minutes. After rinsing with additional buffer A plus 0.2 mg ml$^{-1}$ BSA, λ-DNA (15-20 pM) labeled at one end with biotin and at the other end with DIG or FITC and pre-stained with 0.5 nM YOYO1 was injected into the chamber, incubated for 10 minutes, and unbound DNA was removed by flushing with buffer at 0.1 ml min$^{-1}$. Application of flow aligned the DNA molecules along the diffusion barriers, and stretched the molecules so the free ends could attach to the pentagons.

Using Hydrodynamic Force to Push Proteins.

All experiments where proteins were pushed along DNA by hydrodynamic force were done at a flow rate of 0.5 ml min$^{-1}$. When considering flow through a channel in which the height (h) is much less than the width (w), one can use the Navier-Stokes equations to determine the flow profile v(y) obtained when a pressure difference is applied between the two ends of the channel. In this case the top and bottom surfaces of the flowcell chamber create a drag on the buffer that results in a parabolic flow where the velocity of the buffer at a distance y from the surface can be described by the equation:

$$v(y) = \frac{4v_m}{h^2}(hy - y^2),$$

where $v_m$ is the maximum velocity in the middle of the channel (Berg 1993). The maximum velocity can be determined by reasoning that the volume of total fluid passing through the channel per unit of time equals:

$$w\int_0^h v(y)\partial y = \frac{2}{3}whv_m.$$

With the velocity obtained from the above equations the force acting upon a molecule can then be determined by Stokes law which states that to move a molecule of radius a at a velocity of $v_d$ in buffer of a viscosity η the force required is equal to:

$$F = 6\pi\eta a v_d$$

We approximated the distance y from the surface to be 100 nm and the radius of the protein-QD complex to be 13 nm. The height of a typical channel was measured to be 100 μm and the width of the channel was measured to be 4,500 μm. The resulting calculated force applied to a protein-QD complex at a buffer flow of 0.5 ml min$^{-1}$ is approximately 25 fN. At 200 nm from the surface this theoretical value increases to approximately 50 fN.

We then determined the force acting on a complex experimentally and compared these experimental results to the above theoretical calculations. The drift velocity of a particle is equal to the force exerted on that molecule (F) divided by the drag coefficient of the molecule (f) (Berg 1993):

$$v_d = \frac{F}{f}$$

The diffusion coefficient (D) of a molecule is also determined by this drag coefficient:

$$D = \frac{kT}{f}$$

We were therefore able to calculate the force applied to a single Mlh1-QD complex on DNA by first determining its diffusion coefficient and subsequently pushing the molecule with buffer flow and tracking the movement to determine its drift velocity. Using these values we determined the actual force on the molecule to be 100 fN, which is in close agreement to the theoretical values calculated above. Importantly, this experimental method implicitly includes the drag components from the hydrodynamic radius of the complex as well as the protein DNA interaction, without needing to determine these components directly, and also makes no assumptions regarding the distance of the protein from the surface.

Experiments with Chromatin Substrates.

Nucleosomes were prepared as described (Visnapuu & Greene, 2009). Histones (H2A, FLAG-H2B, H3, and H4) were expressed in E. coli, purified from inclusion bodies and reconstituted as described (Wittmeyer et al., 2004). In brief, inclusion bodies were resuspended in unfolding buffer (7 M guanidinium-HCl, 1 M NaCl, 50 mM Tris-HCl [pH 7.8], 1 mM EDTA, 1 mM DTT), dialyzed against urea buffer (7 M urea, 1 M NaCl, 10 mM Tris-HCl [pH 7.8], 1 mM EDTA, 5 mM β-mercaptoethanol), then loaded onto tandem HiTrap Q and SP columns (GE Healthcare). Histones were eluted from the SP column with a 100-400 mM NaCl gradient for H2A and FLAG-H2B and a 200-500 mM NaCl gradient for H3 and H4. Purified histones were dialysed against 10 mM Tris-HCl [pH 7.8] plus 5 mM β-mercaptoethanol, followed by 10 mM Tris-HCl [pH 7.8], then lyophilized and stored at -20° C. Lyophilized histones were unfolded in 7M guanidinium-HCl, 1 M NaCl, 50 mM Tris-HCl [pH 7.8] plus 10 mM DTT, combined at equimolar ratios, and dialyzed into 2 M NaCl, 20 mM Tris-HCl [pH 7.8], 1 mM EDTA, 5 mM β-mercaptoethanol with several buffer changes over 48 hours. Reconstituted octamers were purified by gel filtration and deposited onto DNA by salt dialysis (Luger et al., 1999, Thåströmet al., 2004).

The FLAG-tagged nucleosomes were labeled with 0.5 nM QDs (QD 585, Invitrogen) conjugated to anti-FLAG antibodies (Sigma). Nucleosome labeling was done in situ as described (Visnapuu & Greene, 2009), either before or after the injection of Mlh1-Pms1, as indicated (see FIG. 82). For experiments with unlabeled nucleosomes, we first conducted the diffusion experiment using QD-Mlh1-Pms1 (QD 705, Invitrogen), in buffer containing 40 mM Tris-HCl [pH 7.7], 150 mM NaCl, ±1 mM ATP, O mM Mg$^{2+}$, 1 mM DTT, and 0.4 mg ml$^{-1}$ BSA. Mg$^{2+}$ induces condensation of the chromatin substrates by promoting nucleosome-nucleosome interactions, and for this reason was omitted from the diffusion experiments. Mlh1-Pms1 was then flushed from the chamber with 300 mM NaCl (which does not disrupt the nucleosomes; M-L.V and E.C.G, unpublished, Burton et al., 1978, and Park et al., 2004) and the nucleosomes were then located by labeling with QDs (QD 705, Invitrogen). The QD signal from the labeled nucleosomes was then pseudocolored and superimposed on the kymograms of Mlh1-Pms1 diffusion (see FIGS. 82A-B, upper and middle panels). For reactions with labeled nucleosomes, the nucleosomes were labeled in situ with anti-FLAG QDs (QD 585, Invitrogen), then QD-Mlh1-Pms1 (QD 705, Invitrogen) was injected into the sample chamber and the signal from the different colored QDs was collected concurrently; signal gaps in the real time data correspond to QD blinking (see FIGS. 82A-B, lower panels).

The chromatin diffusion experiments with Msh2-Msh6 were conducted essentially the same as with Mlh1-Pms1, in buffer containing 40 mM Tris-HCl [pH 7.7], 50 mM NaCl, 1 mM ADP, 1 mM DTT, and 0.4 mg ml$^{-1}$ BSA. ATP was omitted to prevent ATP-triggered protein dissociation, and the salt concentration was kept at 50 mM NaCl to increase the half-life of the bound state in order to evaluate whether it was able to pass nucleosomes (Gorman et al., 2007). Under identical reaction conditions, in the absence of nucleosomes, many molecules (48%, N=380) of Msh2-Msh6 reversibly enter a nondiffusive state (immobile) thought to mimic a pseudo-damage recognition complex, and the remaining Msh2-Msh6 complexes remain mobile (52%, N=412; Gorman et al., 2007). In the presence of high-density nucleosomes (~80-100 nucleosomes per DNA molecule), the fraction of immobile molecules increases from 48% to 96.4%, and we attribute this increase to Msh2-Msh6 molecules that are now trapped between nucleosomes and incapable of diffusing on DNA.

Data Analysis.

All diffusion coefficients represent the mean±standard deviation of ≥25 particle tracking measurements and were calculated from MSD plots as described in Gorman et al., 2007. Traces were used to calculate diffusion coefficients only if the QDs could be tracked over ≥250 consecutive frames (50 seconds), only QDs that blinked were used for tracking (verifying they were single QDs), and traces were excluded if collisions between two or more proteins prevented accurate tracking. We can calculate diffusion coefficients using fewer than 250 consecutive frames, but the variance and error in the resulting data begins to increase significantly. Trajectories where the proteins approached to within 500-nm of one another were also excluded from the diffusion coefficient calculations as a quality control measure because error in the tracking algorithm increases below this distance. Two closely approaching QDs can be optically resolved from one another at distances >10 nm (Lacoste et al., PNAS, 2000; Lagerholm et al., Biophysics J., 2006), but as indicated above, as a quality control measure we excluded any traces where proteins approached to within 500 nm of one another to ensure uniform accuracy in the particle tracking data.

Diffusion coefficients were calculated from the tracking data as previously described (Gorman et al., Mol. Cell, 2006). In brief, the movement of each protein complex in the y-direction (parallel to the long axis of the DNA) was then analyzed to calculate the mean squared displacement (MSD) using:

$$MSD(n\Delta T) = \sum_{i=0}^{N} (Y_{i+n} - Y_i)^2 / (N+1)$$

where nΔT=10% of the total diffusion time (to minimize errors due to sampling size) (Qian, et al, 1991). Using the MSD information, the diffusion coefficient for each protein complex was calculated by:

$$D(t) = MSD(t)/2t$$

where D(t) is the diffusion coefficient for time interval t (Qian, et al., 1991; Berg, 1993). For the linear MSD traces, the diffusion coefficients were calculated from direct fits to the entire plot. For nonlinear MSD plots the diffusion coefficients were estimated from the initial slope of the curve and this slope is not appreciably affected by nondiffusive behavior or bounded diffusion (Kusimi et al., 1993; Saxton and Jacobson, 1997). The 1D-diffusion coefficients display a lognormal distribution, which likely arises due to the roughness of the energy landscape (Gorman et al., Mol. Cell, 2007), and where indicated student t-tests were performed on the natural logarithm (1n) of the diffusion coefficients to obtain p-values for statistical comparisons of the data.

The particle-tracking algorithm used to monitor the movement of Msh2-Msh6 and Mlh1-Pms1 simultaneously records its position in the y-direction (parallel to the long axis of the DNA) and in the x-direction (perpendicular to the long axis of the DNA). The values obtained for the x-direction primarily reflect the thermal motions of the DNA molecules. All of the tracked proteins displayed x-direction fluctuations ranging between ±50-250 nanometers (with a mean of ±80 nm), which is an order of magnitude below the motions observed along the helical axis (i.e. the y-direction) of the DNA. DNAs more flexible than this were occasionally observed, but they were omitted from the analysis because their flexibility caused the bound fluorescent Msh2-Msh6 to fluctuate too much within the evanescent field making them impossible to track accurately (although qualitatively they displayed exactly the same diffusive behavior). The transverse fluctuations of the DNA and the temporal resolution of our detection system impose a lower limit of >1×10$^{-4}$ μm$^2$ sec$^{-1}$ for the diffusion coefficients that can be measured (anything slower than this will look like a stationary particle), but this lower limit is well below any values reported in our study.

SUPPLEMENTAL REFERENCES

Bagchi, B., Blainey, P. C., and Xie, X. S. Diffusion constant of a nonspecifically bound protein undergoing curvilinear motion along DNA. *Journal of Physical Chemistry B* 112, 6282-4 (2008).

Berg, H. C. (1993). Random walks in biology (Princeton University Press, Princeton).

Berg O. G., Winter R. B., von Hippel, P. H. Diffusion-driven mechanisms of protein translocation on nucleic acids. I. Models and theory. *Biochemistry* 20, 6929-48 (1981).

Bonnet, I., Biebricher, A., Potré, P-L., Loverdo, C., Bénichou, O., Voituriez, R., Escudé, C., Wende, W., Pingoud, A., and Desbiolles, P. Sliding and jumping of single EcoRV restriction enzymes on non-cognate DNA. *Nucleic Acids Research* 36, 4118-27 (2008).

Burton, D. R., Butler, M. J., Hyde, J. E., Phillips, D., Skidmore, C. J., and Walker, I. O. The interaction of core histones with DNA: equilibrium binding studies. *Nucleic Acids Research* 5, 3643-63 (1978).

Chi, N. W. and Kolodner, R. D. Purification and characterization of Mlh1, a yeast mitochondrial protein that binds to DNA mismatches. *Journal of Biological Chemistry* 269, 29984-92 (1994).

Dahan, M., Levi, S., Luccardini, C., Rostaing, P., Riveau, B., and Tiller, A. Diffusion dynamics of glycine receptors revealed by single-quantum dot tracking. *Science* 302, 442-445 (2003).

Givaty, O., and Levy, J. Protein sliding along DNA: dynamics and structural characterization. *Journal of Molecular Biology* 385, 1087-1097 (2009).

Gorman, J., Chowdhury, A., Surtees, J., Shimada, J., Reichman, D. R., and Greene, E. C. Dynamic basis for one-dimensional DNA scanning by the mismatch repair complex Msh2-Msh6. *Molecular Cell* 28, 359-370 (2007).

Gorman, J., Fazio, T. Wang, F. Wind, S., and Greene, E. C. Nanofabricated racks of aligned and anchored DNA substrates for single-molecule imaging. *Langmuir* 26, 1372-9 (2010).

Hall, M. C. and Kunkel, T. A. Purification of eukaryotic MutL homologs from *Saccharomyces cerevisiae* using self-affinity technology. *Protein expression and purification* 21, 333-342 (2001).

Heck, J. A., Gresham, D., Botstein, D., and Alani, E. Accumulation of recessive lethal mutations in *Saccharomyces cerevisiae* mlh1 mismatch repair mutants is not associated with gross chromosomal rearrangements. *Genetics* 174, 519-523 (2006).

Kijas, A. W., Studamire, B., and Alani, E. Msh2 separation of function mutations confer defects in the initiation steps of mismatch repair. *Journal of Molecular Biology* 331, 123-38 (2003).

Kochaniak, A. B., Habuchi, S., Loparo, J. J., Chang, D. J., Cimprich, K. A., Wlater, J. C., and van Oijen, A. M. Proliferating cell nuclear antigen uses two distinct modes to move along DNA. *Journal of Biological Chemistry* 283, 13310-9 (2008).

Komazin-Meredith, G., Mirchev, R., Golan, D. E., van Oijen, A. M., and Coen, D. M. Hopping of a processivity factor on DNA revealed by single-molecule assays of diffusion. *Proceedings of the National Academy of Science USA* 105, 10721-6 (2008).

Kusimi, A., Sako, Y., and Yamamoto, M. Confined lateral diffusion of membrane receptors as studied by single particle tracking (nanovid microscopy). Effects of calcium-induced differentiation in cultured epithelial cells. *Biophysical Journal* 65, 2021-40 (1993).

Lacoste, T. D., Michalet, X., Pinaud, F., Chemla, D. S., Alivisatos, A. P., and Weiss, S. Ultrahigh-resolution multicolor colocalization of single fluorescent probes. *Proceedings of the National Academy of Science USA* 97, 9461-6 (2000).

Lagerholm, B. C., Averett, L., Weinreb, G. E., Jacobson, K., and Thompson, N. L. Analysis method for measuring submicroscopic distances with blinking quantum dots. *Biophysical Journal* 91, 3050-60 (2006).

Luger, K., Rechsteiner, T. J., and Richmond, T. J. Preparation of nucleosome core particle from recombinant histones. *Methods in Enzymology* 304, 3-19 (1999).

Park, Y-J., Dyer, P. N., Tremethick, D. J., and Luger, K. A new fluorescence resonance energy transfer approach demonstrates that the histone variant H2AZ stabilizes the histone octamer within the nucleosome. *Journal of Biological Chemistry* 279, 24274-82 (2004).

Pathak, S., Davidson, M. C., and Silva, G. A. Characterization of the functional binding properties of antibody conjugated quantum dots. *Nano Letters* 7, 1839-1845 (2007).

Qian, H., Sheetz, M. P., and Elson, E. L. Single particle tracking. *Biophysical Journal* 60, 910-921 (1991).

Reck-Peterson, S. L., Yildiz, A., Carter, A. P., Gennerich, A., Zhang, N., and Vale, R. D. Single-molecule analysis of dynein processivity and stepping behavior. *Cell* 126, 335-348 (2006).

Saxton, M. J. and Jacobson, K. Single-particle tracking: applications to membrane dynamics. *Annual Review of Biophysics and Biomolecular Structure* 26, 373-399 (1997).

Surtees, J. and Alani, E. Mismatch repair factor Msh2-Msh3 binds and alters the conformation of branched DNA structures predicted to form during genetic recombination. *Journal of Molecular Biology* 360, 523-36 (2006).

Thåström, A., Lowary, P. T, and Widom, J. Measurement of histone-DNA interaction free energy in nucleosomes. *Methods* 33, 33-44 (2004).

Visnapuu, M-L., and Greene, E. C. Single-molecule imaging of DNA curtains reveals intrinsic energy landscapes for nucleosome deposition. *Nature Structural and Molecular Biology* 16, 1056-62 (2009).

von Hippel, P. H. and Berg, O. G. Facilitated target location in biological systems. *Journal of Biological Chemistry* 264, 675-8 (1989).

Wittmeyer, J., Saha, A., and Cairns, B. DNA translocation and nucleosome remodeling assays by the RSC chromatin remodeling complex. *Methods in Enzymology* 377, 322-343 (2004).

Yao, J., Larson, D. R., Vishwasrao, H. D., Zipfel, W. R., and Webb, W. W. Blinking and nonradiant dark fraction of water-soluble quantum dots in aqueous solution. *Proceedings of the National Academy of Science USA* 102, 14284-9 (2005).

Zhang, Q., Li, Y., and Tsien, R. W. The dynamic control of kiss-and-run and vesicular reuse probed with single nanoparticles. *Science* 323, 1448-53 (2009).

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. An array comprising:
    a) a solid support, wherein the solid support comprises an elevated non-linear geometric barrier and wherein the elevated non-linear geometric barrier comprises a repetitive triangular wave;
    b) a fluid lipid bilayer disposed on the solid support wherein the fluid lipid bilayer does not traverse or coat the elevated non-linear geometric barrier;
    c) at least one nucleic acid molecule; and
    d) a linkage for attaching the nucleic acid molecule to the fluid lipid bilayer, wherein the elevated non-linear geometric barrier serves to diminish nucleic acid slippage.

2. The array of claim 1, wherein the elevated non-linear geometric barrier comprises a nanometer-scale mechanical barrier, a chemical barrier, a protein barrier, or a combination thereof.

3. The array of claim 2, wherein the chemical elevated non-linear geometric barrier comprises a metal, a metal oxide, or a combination thereof.

4. The array of claim 3, wherein the metal comprises chromium, aluminum, gold, or titanium.

5. The array of claim 3, wherein the metal oxide comprises chromium oxide, aluminum oxide, or titanium oxide.

6. The array of claim 1, wherein the elevated non-linear geometric barrier forms a nanowell by connecting vertices of the repetitive triangular waves of the elevated non-linear geometric barrier.

7. The array of claim 1, further comprising neutravidin and biotin linkages for attaching the nucleic acid molecule to the fluid lipid bilayer.

8. The array of claim 1, wherein the nucleic acid molecule is aligned along the elevated non-linear geometric barrier through application of a hydrodynamic force, an electrophoretic force, or a combination thereof.

9. The array of claim 1, wherein the elevated non-linear geometric barrier controls the lateral displacement of the nucleic acid molecule(s).

10. The array of claim 1, wherein the elevated non-linear geometric barrier is generated by nanofabrication.

11. The array of claim 10, wherein nanofabrication comprises electron-beam lithography, nanoimprint lithography, or photolithography.

12. The array of claim 1, wherein one end of the nucleic acid molecule is attached to the fluid lipid bilayer by a linkage.

13. The array of claim 12, wherein the nucleic acid molecule is reversibly attached to the fluid lipid bilayer along its contour.

14. The array of claim 1, wherein both ends of the nucleic acid molecule are attached to the fluid lipid bilayer by a linkage.

15. The array of claim 14, wherein the ends of the nucleic acid molecule are each attached to the fluid lipid bilayer by different linkages.

16. The array of claim 1, wherein the nucleic acid molecule is a DNA molecule.

17. The array of claim 16, wherein the DNA molecule comprises from about 20 to about 100,000 base pairs.

18. The array of claim 1, wherein the nucleic acid molecule is coupled to a label.

19. The array of claim 18, wherein the label is a fluorescent label.

20. The array of claim 1, wherein the solid support comprises SiO2.

21. The array of claim 1, wherein the fluid lipid bilayer comprises zwitterionic lipids.

22. A microfluidic flowcell comprising the array of claim 1.

23. The microfluidic flowcell of claim 22 further comprising a staging area, a bifurcated nanochannel, at least one pair of parallel channels, at least one pore, or a combination thereof.

24. The microfluidic flowcell of claim 22, wherein the nucleic acid molecule of claim 1 is aligned along the non-linear geometric barrier through application of a hydrodynamic force, an electrophoretic force, or a combination thereof.

25. The microfluidic flowcell of claim 24, wherein the hydrodynamic force is tangential, perpendicular, or a combination thereof, with respect to the non-linear geometric barrier.

26. The microfluidic flowcell of claim 24, wherein the electrophoretic force is tangential, perpendicular, or a combination thereof, with respect to the non-linear geometric barrier.

27. A method for identifying a nucleic acid sequence that disrupts an interaction between a nucleic acid molecule and a polypeptide, the method comprising:
  a) providing a first array of claim 1, wherein the first array comprises a first population of identical nucleic acid molecules, and wherein the nucleic acid molecules are coupled to a first fluorescent label;
  b) providing a second array of claim 1, wherein the second array comprises a second population of identical nucleic acid molecules, wherein the nucleic acid molecules are coupled to the first fluorescent label, and wherein the second population of nucleic acid molecules differ from the first population of nucleic acid molecules by at least one nucleotide;
  c) contacting a polypeptide to the arrays, wherein the polypeptide is coupled to a second fluorescent label that permits visualization of the polypeptide; and
  d) determining whether the first population of nucleic acid molecules and the second population of nucleic acid molecules interact with the polypeptide, wherein localization of the polypeptide anywhere along the length of the first population of nucleic acid molecules is indicative of an interaction between the first population and the polypeptide, and wherein an absence of localization of the polypeptide along the length of the second population of nucleic acid molecules is indicative that the second population comprises a nucleic acid sequence that disrupts the interaction between the first nucleic acid molecule and the polypeptide.

28. A method for mapping a nucleic acid molecule, the method comprising:
  a) providing the array of claim 1, wherein the nucleic acid molecule is a DNA molecule coupled to a fluorescent label that permits visualization of the DNA molecule;
  b) applying a hydrodynamic force or an electrophoretic force tangential to the surface of the support to align the DNA molecule in a desired orientation;
  c) visualizing the length of the DNA molecule; d) contacting a restriction enzyme to the DNA molecule; and
  e) determining the changes in the length of the DNA molecule following the contacting step.

29. A method for reversibly attaching a nucleic acid molecule along its contour to a lipid bilayer, the method comprising:
  a) providing the array of claim 1, wherein the nucleic acid is a DNA molecule coupled to a first fluorescent label that permits visualization of the DNA molecule;
  b) applying a hydrodynamic force or an electrophoretic force tangential to the surface of the support to align the DNA molecule in a desired orientation;
  c) adding an effective concentration of calcium to the buffer flow, wherein the calcium concentration is at least about 1 mM; and
  d) washing away the calcium from the buffer.

* * * * *

SEQUENCE LISTING

```
<160> NUMBER OF SEQ ID NOS: 32

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-A
<220> FEATURE:
<221> NAME/KEY: modified_base
<222> LOCATION: (12)..(12)
<223> OTHER INFORMATION: C-Biotin triethylene glycol
```

```
<400> SEQUENCE: 1
aggtcgccgc cc                                                          12

<210> SEQ ID NO 2
<211> LENGTH: 13
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-G
<220> FEATURE:
<221> NAME/KEY: modified_base
<222> LOCATION: (13)..(13)
<223> OTHER INFORMATION: Bromodeoxyuridine

<400> SEQUENCE: 2
gggcggcgac ctn                                                         13

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-G
<220> FEATURE:
<221> NAME/KEY: modified_base
<222> LOCATION: (12)..(12)
<223> OTHER INFORMATION: T-Digoxigenin

<400> SEQUENCE: 3
gggcggcgac ct                                                          12

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-C
<220> FEATURE:
<221> NAME/KEY: modified_base
<222> LOCATION: (20)..(20)
<223> OTHER INFORMATION: T-Digoxigenin

<400> SEQUENCE: 4
cattcttgag tccaattttt                                                  20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(1)
<223> OTHER INFORMATION: Phospho-T
<220> FEATURE:
<221> NAME/KEY: modified_base
<222> LOCATION: (17)..(17)
<223> OTHER INFORMATION: T-Digoxigenin

<400> SEQUENCE: 5
ttcagagtct gactttt                                                    17

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-G
<220> FEATURE:
<221> NAME/KEY: modified_base
<222> LOCATION: (12)..(12)
<223> OTHER INFORMATION: T-fluorescein

<400> SEQUENCE: 6
gggcggcgac ct                                                         12

<210> SEQ ID NO 7
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 gctggtgg                                                               8

<210> SEQ ID NO 8
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cggcatcagg ccatggatta caaagatgac gacgataagg attacaaaga tgacgacgat      60
aaggattaca agatgacga cgataaggct gccgcaatgt ctaataaaaa acagtc         116

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttatagctc ttccgcactt agatgtaagc tg                                   32

<210> SEQ ID NO 10
<211> LENGTH: 80
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-G

<400> SEQUENCE: 10
gtacgattac aaagatgacg acgataagga ttacaaagat gacgacgata aggattacaa    60
agatgacgac gataagtaac                                                80

<210> SEQ ID NO 11
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-T

<400> SEQUENCE: 11
tcgagttact tatcgtcgtc atctttgtaa tccttatcgt cgtcatcttt gtaatcctta    60
tcgtcgtcat ctttgtaatc                                                80

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-T

<400> SEQUENCE: 13
tcgaagctgg tggactagta gctgctggtg gttaattaac tgctggtgga               50

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-C

<400> SEQUENCE: 14
```
ctagtccacc agcagttaat taaccaccag cagctactag tccaccagct                50

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-A
<220> FEATURE:
<221> NAME/KEY: modified_base
<222> LOCATION: (12)..(12)
<223> OTHER INFORMATION: C-Biotin

<400> SEQUENCE: 15
aggtcgccgc cc                                                         12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-G
<220> FEATURE:
<221> NAME/KEY: modified_base
<222> LOCATION: (12)..(12)
<223> OTHER INFORMATION: T-Biotin

<400> SEQUENCE: 16
gggcggcgac ct                                                         12

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcagatctct cacctaccaa ac                                              22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agggcggtta actggttttg                                                 20

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctcagatttc atgaaaccag taacgttata cg                                    32

<210> SEQ ID NO 20
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
actctactag tgtcatctcc cgtgatgcac gcatcgatta actgcccgct ttccagtc        58

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-T

<400> SEQUENCE: 21
tcgaatgtgt ggaattgtga gcgctcacaa ttccacacaa ctagtatgag cttaattaaa      60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-C

<400> SEQUENCE: 22
ctagtttaat taagctcata ctagttgtgt ggaattgtga gcgctcacaa ttccacacat      60

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctggctgac attttcggtg c                                                21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccacgccca ttagtgaaac g                                                21

<210> SEQ ID NO 25

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Ala Asp Tyr Lys Asp Asp Lys Ala Ala Ala
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Ala Ala Glu Asn Leu Tyr Phe Gln Ser Ala Ala Ala
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Ala Tyr Pro Tyr Asp Val Pro Asp Tyr Ala Ala Ala Ala
1               5                   10                  15

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
accgaattct gacttgctag gacatctttg cccacgttga                              40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tcaacgtggg caaagatgtc ctagcaagtc agaattcggt                              40

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-A
<220> FEATURE:
```

```
<221> NAME/KEY: modified_base
<222> LOCATION: (12)..(12)
<223> OTHER INFORMATION: C-Biotin triethylene glycol

<400> SEQUENCE: 30
aggtcgccgc cc                                                              12

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-G
<220> FEATURE:
<221> NAME/KEY: modified_base
<222> LOCATION: (12)..(12)
<223> OTHER INFORMATION: T-Digoxigenin

<400> SEQUENCE: 31
gggcggcgac ct                                                              12

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phospho-G
<220> FEATURE:
<221> NAME/KEY: modified_base
<222> LOCATION: (12)..(12)
<223> OTHER INFORMATION: T-FITC

<400> SEQUENCE: 32
gggcggcgac ct                                                              12
```